US009999687B2

(12) United States Patent
Rajopadhye et al.

(10) Patent No.: US 9,999,687 B2
(45) Date of Patent: Jun. 19, 2018

(54) FLUORESCENT IMAGING AGENTS

(71) Applicant: VisEn Medical, Inc., Waltham, MA (US)

(72) Inventors: Milind Rajopadhye, Westford, MA (US); Kevin Groves, Arlington, MA (US); Dorin V. Preda, Medford, MA (US)

(73) Assignee: VisEn Medical, Inc., Waltham, MA (US)

( * ) Notice: Subject to any disclaimer, the term of this patent is extended or adjusted under 35 U.S.C. 154(b) by 0 days. days.

(21) Appl. No.: 15/250,038

(22) Filed: Aug. 29, 2016

(65) Prior Publication Data

US 2017/0119908 A1    May 4, 2017

Related U.S. Application Data

(62) Division of application No. 14/457,064, filed on Aug. 11, 2014, now Pat. No. 9,427,481, which is a division of application No. 12/355,777, filed on Jan. 17, 2009, now Pat. No. 8,815,214.

(60) Provisional application No. 61/022,024, filed on Jan. 18, 2008.

(51) Int. Cl.
| | |
|---|---|
| *A61K 38/00* | (2006.01) |
| *A61K 49/00* | (2006.01) |
| *C09B 23/01* | (2006.01) |
| *C09B 23/08* | (2006.01) |
| *C07K 5/11* | (2006.01) |
| *C07K 7/06* | (2006.01) |
| *C07K 7/64* | (2006.01) |
| *A61K 47/65* | (2017.01) |

(52) U.S. Cl.
CPC .......... *A61K 49/0032* (2013.01); *A61K 47/65* (2017.08); *A61K 49/0056* (2013.01); *C07K 5/1019* (2013.01); *C07K 7/06* (2013.01); *C07K 7/64* (2013.01); *C09B 23/0008* (2013.01); *C09B 23/083* (2013.01); *C09B 23/086* (2013.01)

(58) Field of Classification Search
CPC ............ A61K 49/0032; A61K 49/0056; C07K 5/1019; C07K 7/06; C07K 7/64; C09B 23/083
See application file for complete search history.

(56) References Cited

U.S. PATENT DOCUMENTS

| | | | |
|---|---|---|---|
| 4,281,645 A | 8/1981 | Jobsis | |
| 4,321,930 A | 3/1982 | Jobsis et al. | |
| 4,647,447 A | 3/1987 | Gries et al. | |
| 4,945,239 A | 7/1990 | Wist et al. | |
| 4,947,850 A | 8/1990 | Vanderkooi et al. | |
| 4,981,977 A | 1/1991 | Southwick et al. | |
| 5,090,415 A | 2/1992 | Yamashita et al. | |
| 5,136,373 A | 8/1992 | Kamiya et al. | |
| 5,179,202 A | 1/1993 | Gross | |
| 5,186,173 A | 2/1993 | Zuckerman | |
| 5,268,486 A | 12/1993 | Waggoner et al. | |
| 5,384,241 A | 1/1995 | Kline | |
| 5,391,877 A | 2/1995 | Marks | |
| 5,403,928 A | 4/1995 | Arrhenuis | |
| 5,421,339 A | 6/1995 | Ramanujam et al. | |
| 5,486,616 A | 1/1996 | Waggoner et al. | |
| 5,569,587 A | 10/1996 | Waggoner | |
| 5,569,766 A | 10/1996 | Waggoner et al. | |
| 5,593,658 A | 1/1997 | Bogdanov et al. | |
| 5,627,027 A | 5/1997 | Waggoner | |
| 5,641,878 A | 6/1997 | Dandliker et al. | |
| 5,650,135 A | 7/1997 | Contag et al. | |
| 5,661,035 A | 8/1997 | Tsien et al. | |
| 5,677,199 A | 10/1997 | Arrhenuis | |
| 5,699,798 A | 12/1997 | Hochman et al. | |
| 5,759,781 A | 6/1998 | Ward et al. | |
| 5,808,044 A | 9/1998 | Brush et al. | |
| 5,827,190 A | 10/1998 | Palcic et al. | |
| 5,846,703 A | 12/1998 | Devlin et al. | |
| 5,865,754 A | 2/1999 | Sevick-Muraca et al. | |
| 5,876,946 A | 3/1999 | Burbaum et al. | |
| 5,877,310 A | 3/1999 | Reddington et al. | |
| 5,952,664 A | 9/1999 | Wake et al. | |
| 6,002,003 A | 12/1999 | Shen et al. | |
| 6,004,536 A | 12/1999 | Leung et al. | |
| 6,008,373 A | 12/1999 | Waggoner et al. | |
| 6,026,319 A | 2/2000 | Hayashi et al. | |

(Continued)

FOREIGN PATENT DOCUMENTS

| | | |
|---|---|---|
| EP | 1065250 | 1/2001 |
| EP | 1207385 A1 | 5/2002 |

(Continued)

OTHER PUBLICATIONS

Veronese. Peptide and protein PEGylation: a review of problems and solutions. Biomaterials, 2001. pp. 405-417.*
Abe S et al., 'Correlation of in vivo Autofluorescence Endoscopy Images with Histopathologic Findings in Stomach Cancer,' Endoscopy, Apr. 2000 (Apr. 2000), 32(4):281-6.
AC Kak and M Slaney, Principles of Computerized Tomographic Imaging, (1st Ed (electronic), 1988), WR Crone (Ed), The Institute of Electrical and Electronics Engineers Press, New York, NY (Publ), pp. 208-218, ISBN: 0-87942-198-3.
Achilefu S et al., 'Novel Receptor-Targeted Fluorescent Contrast Agents for in vivo Tumor Imaging,' Invest Radiol, Aug. 2000 (Aug. 2000), 35(8):479-85.

(Continued)

*Primary Examiner* — Marcela M Cordero Garcia
(74) *Attorney, Agent, or Firm* — Goodwin Procter LLP

(57) ABSTRACT

Provided is a family of intramolecularly quenched imaging agents for use in both in vivo and in vitro imaging that contain at least one enzymatically cleavable oligopeptide and two fluorophores or a fluorophore and a quencher. When subjected to proteolytic cleavage, at least one fluorophore is unquenched and becomes capable of producing a fluorescent signal upon excitation with light of an appropriate wavelength. Also provided are in vivo and in vitro imaging methods using such imaging agents.

13 Claims, 14 Drawing Sheets

(56) References Cited

U.S. PATENT DOCUMENTS

| | | | |
|---|---|---|---|
| 6,043,025 A | 3/2000 | Minden et al. |
| 6,081,322 A | 6/2000 | Barbour |
| 6,083,485 A | 7/2000 | Licha et al. |
| 6,083,486 A | 7/2000 | Weissleder et al. |
| 6,127,134 A | 10/2000 | Minden et al. |
| 6,130,094 A | 10/2000 | Waggoner et al. |
| 6,133,445 A | 10/2000 | Waggoner et al. |
| 6,136,612 A | 10/2000 | Della Ciana et al. |
| 6,205,347 B1 | 3/2001 | Morgan et al. |
| 6,217,847 B1 | 4/2001 | Contag et al. |
| 6,258,340 B1 | 7/2001 | Licha et al. |
| 6,268,222 B1 | 7/2001 | Chandler et al. |
| 6,304,771 B1 | 10/2001 | Yodh et al. |
| 6,377,841 B1 | 4/2002 | Lin et al. |
| 6,377,842 B1 | 4/2002 | Pogue et al. |
| 6,397,099 B1 | 5/2002 | Chance |
| 6,448,008 B1 | 9/2002 | Caputo et al. |
| 6,526,309 B1 | 2/2003 | Chance |
| 6,534,041 B1 | 3/2003 | Licha et al. |
| 6,592,847 B1 | 7/2003 | Weissleder et al. |
| 6,615,063 B1 | 9/2003 | Ntziachristos et al. |
| 6,740,755 B2 | 5/2004 | Caputo et al. |
| 6,747,159 B2 | 6/2004 | Caputo et al. |
| 6,825,928 B2 | 11/2004 | Liu et al. |
| 6,869,593 B2 | 3/2005 | Frangioni |
| 6,913,743 B2 | 7/2005 | Licha et al. |
| 6,926,885 B2 | 8/2005 | Licha et al. |
| 7,025,949 B2 | 4/2006 | Licha et al. |
| 7,374,746 B2 | 5/2008 | Frangioni |
| 7,383,076 B2 | 6/2008 | Ntziachristos et al. |
| 7,439,319 B2 | 10/2008 | Smith et al. |
| 7,445,767 B2 | 11/2008 | Licha et al. |
| 7,655,217 B2 | 2/2010 | Licha et al. |
| 7,947,256 B2 | 5/2011 | Rajopadhye et al. |
| 8,173,819 B2 | 5/2012 | Rajopadhye et al. |
| 8,182,790 B2 | 5/2012 | Lovhaug et al. |
| 8,221,721 B2 | 7/2012 | Narayanan |
| 8,420,055 B2 | 4/2013 | Gaw et al. |
| 8,455,651 B2 | 6/2013 | Rajopadhye et al. |
| 8,486,373 B2 | 7/2013 | Weissleder et al. |
| 8,685,370 B2 | 4/2014 | Rajopadhye et al. |
| 8,771,646 B2 | 7/2014 | Rajopadhye et al. |
| 8,815,214 B2 * | 8/2014 | Rajopadhye ....... A61K 49/0032 424/9.6 |
| 8,864,821 B2 | 10/2014 | Jaffer et al. |
| 9,365,721 B2 | 6/2016 | Narayanan |
| 9,427,481 B2 * | 8/2016 | Rajopadhye ....... A61K 49/0032 |
| 2001/0055567 A1 | 12/2001 | Licha et al. |
| 2002/0065421 A1 | 5/2002 | Caputo et al. |
| 2002/0156288 A1 | 10/2002 | Caputo et al. |
| 2003/0026763 A1 | 2/2003 | Licha et al. |
| 2003/0124194 A1 | 7/2003 | Gaw et al. |
| 2003/0170179 A1 | 9/2003 | Licha et al. |
| 2003/0219383 A1 | 11/2003 | Weissleder et al. |
| 2004/0028611 A1 | 2/2004 | Frangioni |
| 2005/0106106 A1 | 5/2005 | Licha et al. |
| 2005/0149877 A1 | 7/2005 | Rice et al. |
| 2005/0169843 A1 | 8/2005 | Weissleder et al. |
| 2005/0169844 A1 | 8/2005 | Licha et al. |
| 2005/0171434 A1 | 8/2005 | Madden et al. |
| 2005/0245734 A1 | 11/2005 | Caputo et al. |
| 2006/0002857 A1 | 1/2006 | Frangioni |
| 2006/0171893 A1 | 8/2006 | Zheng et al. |
| 2006/0239916 A1 | 10/2006 | Licha et al. |
| 2006/0275775 A1 | 12/2006 | Weissleder et al. |
| 2007/0036724 A1 | 2/2007 | Frangioni |
| 2008/0219933 A1 | 9/2008 | Ntziachristos et al. |
| 2008/0226562 A1 | 9/2008 | Groves et al. |
| 2008/0267883 A1 | 10/2008 | Rajopadhye et al. |
| 2008/0286207 A1 | 11/2008 | Narayanan |
| 2008/0317676 A1 | 12/2008 | Rajopadhye et al. |
| 2009/0068115 A1 | 3/2009 | Gaw et al. |
| 2009/0123383 A1 | 5/2009 | Frangioni |
| 2009/0130024 A1 | 5/2009 | Narayanan et al. |
| 2009/0208412 A1 | 8/2009 | Lovhaug et al. |
| 2009/0220430 A1 | 9/2009 | Rajopadhye et al. |
| 2010/0074847 A1 | 3/2010 | Madden et al. |
| 2010/0129293 A1 | 5/2010 | Licha et al. |
| 2010/0166659 A1 | 7/2010 | Licha et al. |
| 2010/0172841 A1 | 7/2010 | Peterson et al. |
| 2010/0189657 A1 | 7/2010 | Weissleder et al. |
| 2010/0268070 A1 | 10/2010 | Jaffer et al. |
| 2011/0152501 A1 | 6/2011 | Weissleder et al. |
| 2011/0165075 A1 | 7/2011 | Rajopadhye et al. |
| 2011/0171136 A1 | 7/2011 | Poss et al. |
| 2011/0256065 A1 | 10/2011 | Frangioni |
| 2012/0077279 A1 | 3/2012 | Wiesner et al. |
| 2012/0231972 A1 | 9/2012 | Golyshin et al. |
| 2012/0321562 A1 | 12/2012 | Rajopadhye et al. |
| 2012/0321563 A1 | 12/2012 | Groves et al. |
| 2013/0142734 A1 | 6/2013 | David |
| 2013/0169500 A1 | 7/2013 | Bilotti et al. |
| 2013/0195760 A1 | 8/2013 | Olson |
| 2013/0272967 A1 | 10/2013 | Rajopadhye et al. |
| 2014/0050662 A1 | 2/2014 | Ho |
| 2014/0314677 A1 | 10/2014 | Groves et al. |
| 2014/0348746 A1 | 11/2014 | Narayanan |
| 2015/0018517 A1 | 1/2015 | Rajopadhye et al. |
| 2015/0133773 A1 | 5/2015 | Jaffer et al. |

FOREIGN PATENT DOCUMENTS

| | | | |
|---|---|---|---|
| JP | 04-122248 A1 | 4/1992 | |
| JP | 08-131445 A1 | 5/1996 | |
| JP | 05-223738 B2 | 6/2013 | |
| WO | WO-1988/004777 A1 | 6/1988 | |
| WO | WO90/15818 * | 6/1990 | ............... C07K 5/08 |
| WO | WO-1997/040104 | 10/1997 | |
| WO | WO-1998/047538 | 10/1998 | |
| WO | WO-1999/051702 | 10/1999 | |
| WO | WO-1999/058161 A1 | 11/1999 | |
| WO | WO-2001/021624 | 3/2001 | |
| WO | WO-2002/041760 A2 | 5/2002 | |
| WO | WO-2002/056670 A2 | 7/2002 | |
| WO | WO-2003/079015 A1 | 9/2003 | |
| WO | WO-2003/102558 A1 | 12/2003 | |
| WO | WO-2004/028449 A2 | 4/2004 | |
| WO | WO-2006/054904 A2 | 5/2006 | |
| WO | WO-2006/125134 A1 | 11/2006 | |
| WO | WO-2007/008080 A2 | 1/2007 | |
| WO | WO-2007/028037 | 3/2007 | |
| WO | WO-2007/028118 | 3/2007 | |
| WO | WO-2007/028163 A1 | 3/2007 | |
| WO | WO-2007/136413 | 11/2007 | |
| WO | WO-2013/036743 A1 | 3/2013 | |
| WO | WO-2014/028057 A1 | 2/2014 | |
| WO | WO-2014/176284 A1 | 10/2014 | |
| WO | WO-2015/094111 A1 | 6/2015 | |

OTHER PUBLICATIONS

Albericio F, 'Developments in Peptide and Amide Synthesis,' Curr Opin Chem Biol, Jun. 2004 (Jun. 2004), 8(3):211-21.

Alexander W, 'Lasers Investigated as Diagnostic Tools for Breast Cancer,' J Clin Laser Med Surg, Dec. 1991 (Dec. 1991), 9(6):416-8.

Alfano RR et al., 'Advances in Optical Imaging of Biomedical Media,' Ann NY Acad Sci, May 30, 1997 (May 30, 1997), 820:248-70.

Almeida PC et al., 'Hydrolysis by Cathepsin B of Fluorescent Peptides Derived from Human Prorenin,' Hypertension, Jun. 2000 (Jun. 2000), 35(6):1278-83.

Anonymous, 'The Cleavage Specificities of Selected Enzymes and Chemicals,' ExPASy PeptideCutter Tool: Available Enzymes, SIB ExPASy Bioinformatics Resources Portal, SIB Swiss Institute of Bioinformatics, Lausanne, CH (Pub), downloaded from <http://web.expasy.org/peptide_cutter/peptidecutter+enzymes.html> on Jul. 15, 2015 (8 pages).

Ballou B et al., 'Tumor Detection and Visualization Using Cyanine Fluorochrome-Labeled Antibodies,' Biotechnol Prog, Sep.-Oct. 1997 (Sep.-Oct. 1997), 13(5):649-58.

(56) References Cited

OTHER PUBLICATIONS

Ballou B et al., 'Tumor Labeling in vivo Using Cyanine-Conjugated Monoclonal Antibodies,' Cancer Immunol Immunother, Oct. 1995 (Oct. 1995), 41(4):257-63.
Becker A et al., 'Receptor-Targeted Optical Imaging with Near-Infrared Fluorescent Ligands,' Nat Biotechnol, Apr. 2001 (Apr. 2001), 19(4):327-31.
Boas DA et al., 'Scattering of Diffuse Photon Density Waves by Spherical Inhomogeneities Within Turbid Media: Analytic Solution and Applications,' Proc Natl Acad Sci USA, May 24, 1994 (May 24, 1994), 91(11):4887-91.
Bogdanov AA Jr and Weissleder R, 'The Development of in vivo Imaging Systems to Study Gene Expression,' Trends Biotechnol, Jan. 1998 (Jan. 1998), 16(1):5-10.
Bogdanov AA Jr et al., 'Long-Circulating Blood Pool Imaging Agents,' Adv Drug Deliv Rev, Sep. 1995 (Sep. 1995), 16(2-3):335-48.
Bouteiller C et al., 'Novel Water-Soluble, Near-Infrared Cyanine Dyes: Synthesis, Spectral Properties, and Use in the Preparation of Internally Quenched Fluorescent Probes,' Bioconj Chem, May 13, 2007 (May 13, 2007), 18(4):1303-7.
Brea RJ et al., 'Controlling Multiple Fluorescent Signal Output in Cyclic Peptide-Based Supramolecular Systems,' J Am Chem Soc, Feb. 14, 2007 (Feb. 14, 2007) Jan. 23, 2007 (Jan. 23, 2007)(ePub), 129(6):1653-7.
Bugaj JE et al., 'Novel Fluorescent Contrast Agents for Optical Imaging of in vivo Tumors Based on a Receptor-Targeted Dye-Peptide Conjugate Platform,' J Biomed Opt, Apr. 2001 (Apr. 2001), 6(2):123-33.
Chance B, 'Near-Infrared Images Using Continuous, Phase-Modulated, and Pulsed Light with Quantitation of Blood and Blood Oxygenation,' Ann N Y Acad Sci, Feb. 9, 1998 (Feb. 9, 1998), 838:29-45.
Cheng X and Boas D, 'Diffuse Optical Reflection Tomography Using Continuous Wave Illumination,' Opt Express, Aug. 3, 1998 (Aug. 3, 1998), 3(3):118-23.
Cheng Z et al., 'Near-infrared Fluorescent RGD Peptides for Optical Imaging of Integrin αvβ3 Expression in Living Mice,' Bioconj Chem, Nov.-Dec. 2005, 16(6):1433-41.
Christie RJ and Grainger DW, 'Design Strategies to Improve Soluble Macromolecular Delivery Constructs,' Adv Drug Deliv Rev, Feb. 2003, 55(3):421-37.
CIPO, Examination Report for Canadian Patent Application No. 2,749,108 (Mezzetti A), dated Dec. 1, 2015 (Dec. 1, 2015), pp. 1-3.
Citrin D and Camphausen K, 'Optical Imaging of Mice in Oncologic Research,' Expert Rev Anticancer Ther, Oct. 2004 (Oct. 2004), 4(5):857-64.
Dellian M et al., 'Vascular Permeability in a Human Tumor Xenograft: Molecular Charge Dependence,' Br J Cancer, May 2000 (May 2000), 82(9):1513-8.
Denmeade SR et al., 'Specific and Efficient Peptide Substrates for Assaying the Proteolytic Activity of Prostate-Specific Antigen,' Cancer Res, Nov. 1, 1997 (Nov. 1, 1997), 57(21):4924-30.
European Patent Office, European Search Report and Search Opinion for European Patent Application No. 13185417 dated Apr. 24, 2014 (11 pages).
Flanagan JH Jr et al., 'Functionalized Tricarbocyanine Dyes as Near-Infrared Fluorescent Probes for Biomolecules,' Bioconjug Chem, Sep.-Oct. 1997 (Sep.-Oct. 1997), 8(5):751-6.
Folli S et al., 'Antibody-Indocyanin Conjugates for Immunophotodetection of Human Squamous Cell Carcinoma in Nude Mice,' Cancer Res, May 15, 1994 (May 15, 1994), 54(10):2643-9.
Folli S et al., 'Immunophotodiagnosis of Colon Carcinomas in Patients Injected with Fluoresceinated Chimeric Antibodies Against Carcinoembryonic Antigen,' Proc Natl Acad Sci USA, Sep. 1, 1992 (Sep. 1, 1992), 89(17):7973-7.
Fukumura D et al., 'Tumor Induction of VEGF Promoter Activity in Stromal Cells,' Cell, Sep. 18, 1998 (Sep. 18, 1998), 94(6):715-25.
Funovics M et al., 'Protease Sensors for Bioimaging,' Anal Bioanal Chem, Sep. 3, 2003 (Sep. 3, 2003)(ePub), 377(6):956-63.
Gahlen J et al., 'Spectrometry Supports Fluorescence Staging Laparoscopy After Intraperitoneal Aminolaevulinic Acid Lavage for Gastrointestinal Tumors,' J Photochem Photobiol B, Sep.-Oct. 1999 (Sep.-Oct. 1999), 52(1-3):131-5.
Galande AK et al., 'Fluorescence Probe with pH-Sensitive Trigger,' Bioconjug Chem, Mar.-Apr. 2006 (Mar.-Apr. 2006), 17(2):255-7.
Graves EE et al., 'Fluorescence Molecular Imaging of Small Animal Tumor Models,' Curr Mol Med, Jun. 2004 (Jun. 2004), 4(4):419-30.
Gulnik SV et al., 'Design of Sensitive Fluorogenic Substrates for Human Cathepsin D,' FEBS Lett, Aug. 18, 1997 (Aug. 18, 1997), 413(2):379-84.
Gurfinkel M et al., 'Pharmacokinetics of ICG and HPPH-car for the Detection of Normal and Tumor Tissue Using Fluorescence, Near-Infrared Reflectance Imaging: A Case Study,' Photochem Photobiol, Jul. 2000 (Jul. 2000), 72(1):94-102.
Ha T et al., 'Probing the Interaction Between Two Single Molecules: Fluorescence Resonance Energy Transfer Between a Single Donor and a Single Acceptor,' Proc Natl Acad Sci USA, Jun. 25, 1996 (Jun. 25, 1996), 93(13):6264-8.
Harris JM and Chess RB, 'Effect of Pegylation on Pharmaceuticals,' Nat Rev Drug Discov, Mar. 2003 (Mar. 2003), 2(3):214-21.
Held P, 'Peptide and Amino Acid Quantification Using UV Fluorescence in Synergy HT Multi-Mode Microplate Reader,' BioTek Applications—application Notes, Apr. 18, 2003 (Apr. 18, 2003)(ePub), BioTek Instruments, Winooski, VT (Publ), pp. 1-13, Accessed online at <http://www.biotek.com/resources/articles/peptides-amino-acids-fluorescence.html> on Jul. 15, 2015.
Hirsch FR et al., 'Early Detection of Lung Cancer: Clinical Perspectives of Recent Advances in Biology and Radiology,' Clin Cancer Res, Jan. 2001 (Jan. 2001), 7(1):5-22.
International Searching Authority, International Search Report and Written Opinion for International Patent Application No. PCT/US2009/031364 dated Sep. 15, 2009 (12 pages).
IP Australia, Patent Examination Report No. 1 for Australian Patent Application No. 2009205950 (Case T), dated May 23, 2013 (May 23, 2013), pp. 1-3.
Izuishi K et al., 'Detection of Bile Duct Cancer by Autofluorescence Cholangioscopy: A Pilot Study,' Hepatogastroenterology, Mar.-Apr. 1999 (Mar.-Apr. 1999), 46(26):804-7.
Kinstler O et al., 'Mono N-terminal Poly(ethylene glycol)-protein Conjugates,' Jun. 2002, 54(4):477-85.
Koo V et al., 'Non-Invasive in vivo Imaging in Small Animal Research,' Cell Oncol, 2006 (2006), 28(4):127-39.
Korlach J et al., 'Characterization of Lipid Bilayer Phases by Confocal Microscopy and Fluorescence Correlation Spectroscopy,' Proc Natl Acad Sci USA, Jul. 20, 1999 (Jul. 20, 1999), 96(15):8461-6.
Kriegmair M et al., '5-Aminolevulinic Acid-Induced Fluorescence Endoscopy for the Detection of Lower Urinary Tract Tumors,' Urol Int, 1999 (1999), 63(1):27-31.
Lee S et al., 'Activatable Imaging Probes with Amplified Fluorescent Signals,' Chem Commun (Camb), Jul. 25, 2008 (Jul. 25, 2008)(ePub), (36):4250-60.
Mahmood U et al., 'Near-Infrared Optical Imaging of Protease Activity for Tumor Detection,' Radiology, Dec. 1999 (Dec. 1999), 213(3):866-70.
Major AL et al., 'In vivo Fluorescence Detection of Ovarian Cancer in the NuTu-19 Epithelial Ovarian Cancer Animal Model Using 5-aminolevulinic Acid (ALA),' Gynecol Oncol, Jul. 1997 (Jul. 1997), 66(1):122-32.
Masters BR et al., 'Multiphoton Excitation Fluorescence Microscopy and Spectroscopy of in vivo Human Skin,' Biophys J, Jun. 1997 (Jun. 1997), 72(6):2405-12.
Mew D et al., 'Photoimmunotherapy: Treatment of Animal Tumors with Tumor-specific Monoclonal Antibody-Hematoporphyrin Conjugates,' J Immunol, Mar. 1983 (Mar. 1983), 130(3):1473-7.
Moats RA et al., 'A "Smart" Magnetic Resonance Imaging Agent that Reports on Specific Enzymatic Activity,' Angew Chem Int Ed Engl, Apr. 18, 1997 (Apr. 18, 1997), 36(7):726-8.

(56) References Cited

OTHER PUBLICATIONS

Monsky WL et al., 'Augmentation of Transvascular Transport of Macromolecules and Nanoparticles in Tumors Using Endothelial Growth Factor,' Cancer Res, Aug. 15, 1999 (Aug. 15, 1999), 59(16):4129-35.
Mycek MA et al., 'Colonic Polyp Differentiation Using Time-Resolved Autofluorescence Spectroscopy,' Gastrointest Endosc, Oct. 1998 (Oct. 1998), 48(4):390-4.
Neri D et al., 'Targeting by Affinity-Matured Recombinant Antibody Fragments of an Angiogenesis Associated Fibronectin Isoform,' Nat Biotechnol, Nov. 1997 (Nov. 1997), 15(12):1271-5.
Ntziachristos V et al., 'Concurrent MRI and Diffuse Optical Tomography of Breast After Indocyanine Green Enhancement,' Proc Natl Acad Sci USA, Mar. 14, 2000 (Mar. 14, 2000), 97(6):2767-72.
Ntziachristos V et al., 'Fluorescence Imaging with Near-Infrared Light: New Technological Advances that Enable in vivo Molecular Imaging,' Eur Radiol, Jul. 19, 2002 (Jul. 19, 2002)(ePub), 13(1):195-208.
Ntziachristos V et al., 'Fluorescence Molecular Tomography Resolves Protease Activity in vivo,' Nat Med, Jun. 24, 2002 (Jun. 24, 2002)(ePub), 8(7):757-60.
Ntziachristos V, 'Fluorescence Molecular Imaging,' Annu Rev Biomed Eng, 2006 (2006), 8:1-33.
O'Leary MA et al., 'Experimental Images of Heterogeneous Turbid Media by Frequency-Domain Diffusing-Photon Tomography,' Opt Lett, Mar. 1, 1995 (Mar. 1, 1995), 20(5):426-8.
Ozmen B and Akkaya EU, 'Infrared Fluorescence Sensing of Submicromolar Calcium: Pushing the Limits of Photoinduced Electron Transfer,' Tetrahedron Lett, Nov. 18, 2000 (Nov. 18, 2000), 41(47):9185-8.
Pan C-P and Barkley MD, 'Conformational Effects on Tryptophan Fluorescence in Cyclic Hexapeptides,' Biophys J, Jun. 2004, 86(6):3828-35.
Pan D et al., 'Time-Resolved Resonance Raman Structural Studies of the pB' Intermediate in the Photocycle of Photoactive Yellow Protein,' Biophys J, Apr. 2004 (Apr. 2004), 86(4):2374-82.
Pham W et al., 'An Azulene Dimer as a Near-Infrared Quencher,' Angew Chem Int Ed Engl, Oct. 4, 2002 (Oct. 4, 2002), 41(19):3659-62.
Pottier RH et al., 'Non-Invasive Technique for Obtaining Fluorescence Excitation and Emission Spectra in vivo,' Photochem Photobiol, Nov. 1986 (Nov. 1986), 44(5):679-87.
Rajadhyaksha M et al., 'In vivo Confocal Scanning Laser Microscopy of Human Skin: Melanin Provides Strong Contrast,' J Invest Dermatol, Jun. 1995 (Jun. 1995), 104(6):946-52.
Rao J et al., 'Fluorescence Imaging in vivo: Recent Advances,' Curr Opin Biotechnol, Jan. 17, 2007 (Jan. 17, 2007)(ePub), 18(1):17-25.
Riedl CR et al., 'Fluorescence Detection of Bladder Tumors with 5-amino-levulinic Acid,' J Endourol, Dec. 1999 (Dec. 1999), 13(10):755-9.
Satchi-Fainaro R et al., 'Targeting Angiogenesis with a Conjugate of HPMA Copolymer and TNP-470,' Nat Med, Feb. 22, 2004 (Feb. 22, 2004)(ePub), 10(3):255-61.
Siegel A et al., 'Design and Evaluation of a Continuous-Wave Diffuse Optical Tomography System,' Opt Express, Apr. 12, 1999 (Apr. 12, 1999), 4(8):287-98.
Stepp H et al., 'Fluorescence Endoscopy of Gastrointestinal Diseases: Basic Principles, Techniques, and Clinical Experience,' Endoscopy, May 1998 (May 1998), 30(4):379-86.
Struck DK et al., 'Use of Resonance Energy Transfer to Monitor Membrane Fusion,' Biochemistry, Jul. 7, 1981 (Jul. 7, 1981), 20(14):4093-9.
Stryer L and Haugland RP, 'Energy Transfer: A Spectroscopic Ruler,' Proc Natl Acad Sci USA, Aug. 1967 (Aug. 1967), 58(2):719-26.
Tearney GJ et al., 'Images in Cardiovascular Medicine, Catheter-Based Optical Imaging of a Human Coronary Artery,' Circulation, Dec. 1, 1996 (Dec. 1, 1996), 94(11):3013.
Tearney GJ et al., 'In vivo Endoscopic Optical Biopsy with Optical Coherence Tomography,' Science, Jun. 27, 1997 (Jun. 27, 1997), 276(5321):2037-9.
Tromberg BJ et al., 'Non-Invasive Measurements of Breast Tissue Optical Properties Using Frequency-Domain Photon Migration,' Philos Trans R Soc Lond B Biol Sci, Jun. 29, 1997 (Jun. 29, 1997), 352(1354):661-8.
Tung CH et al., 'In vivo Imaging of Proteolytic Enzyme Activity Using a Novel Molecular Reporter,' Cancer Res, Sep. 1, 2000 (Sep. 1, 2000), 60(17):4953-8.
Tung CH et al., 'Preparation of Cathepsin D Sensitive Near-Infrared Fluorescence Probe for Imaging,' Bioconjug Chem, Sep.-Oct. 1999 (Sep.-Oct. 1999), 10(5):892-6.
Tyagi S and Kramer FR, 'Molecular Beacons: Probes that Fluoresce Upon Hybridization,' Nat Biotechnol, Mar. 1996 (Mar. 1996), 14(3):303-8.
Tyagi S et al., 'Multicolor Molecular Beacons for Allele Discrimination,' Nat Biotechnol, Jan. 1998 (Jan. 1998), 16(1):49-53.
Tyagi S et al., 'Wavelength-Shifting Molecular Beacons,' Nat Biotechnol, Nov. 2000 (Nov. 2000), 18(11):1191-6.
Veronese FM and Pasut G, 'PEGylation Successful Approach to Drug Delivery,' Drug Discov Today, Nov. 2005,10(21):1451-8.
Wagnieres GA et al., 'Photodetection of Early Cancer in the Upper Aerodigestive Tract and the Bronchi Using Photofrin II and Colorectal Adenocarcinoma with Fluoresceinated Monoclonal Antibodies,' SPIE Fut Trends Biomed Appl Lasers, Nov. 1, 1991 (Nov. 1, 1991), 1525:219-36.
Ward HA, 'New Laser Techniques for Diagnosis and Treatment of Deep-Seated Brain Lesions,' J Laser Appl, Oct. 1998 (Oct. 1998), 10(5):224-8.
Weissleder R et al., 'In vivo Imaging of Tumors with Protease-Activated Near-Infrared Fluorescent Probes,' Nat Biotechnol, Apr. 1999 (Apr. 1999), 17(4):375-8.
Weissleder R et al., 'In vivo Magnetic Resonance Imaging of Transgene Expression,' Nat Med, Mar. 2000 (Mar. 2000), 6(3):351-5.
Weissleder R, 'A Clearer Vision for in vivo Imaging,' Nat Biotechnol, Apr. 2001 (Apr. 2001), 19(4):316-7.
Weissleder R, 'Molecular Imaging: Exploring the Next Frontier,' Radiology, Sep. 1999 (Sep. 1999), 212(3):609-14.
Wouters FS and Bastiaens PI, 'Fluorescence Lifetime Imaging of Receptor Tyrosine Kinase Activity in Cells,' Curr Biol, Oct. 7, 1999 (Oct. 7, 1999), 9(19):1127-30.
Wu J et al., 'Fluorescence Tomographic Imaging in Turbid Media Using Early-Arriving Photons and Laplace Transforms,' Proc Natl Acad Sci USA, Aug. 5, 1997 (Aug. 5, 1997), 94(16):8783-8.
Wyatt JS, 'Cerebral Oxygenation and Haemodynamics in the Foetus and Newborn Infant,' Philos Trans R Soc Lond B Biol Sci, Jun. 29, 1997 (Jun. 29, 1997), 352(1354):697-700.
Yaron A et al., 'Intramolecularly Quenched Fluorogenic Substrates for Hydrolytic Enzymes,' Anal Biochem, May 1979 (May 1979), 95(1):228-35.
Extended European Search Report and Search Opinion for European Patent Application No. 17188506.4 dated Feb. 21, 2018 (8 pages).

\* cited by examiner

FIGURE 5
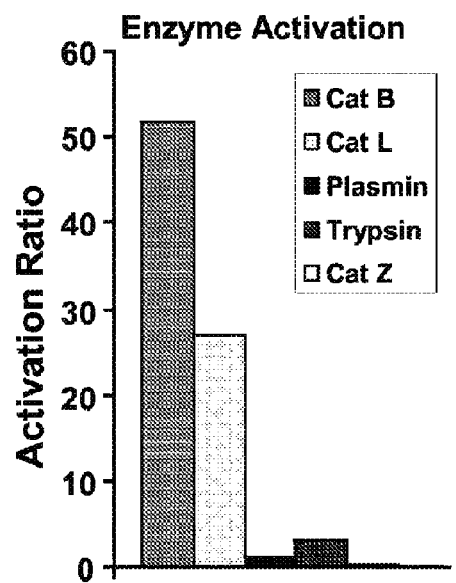
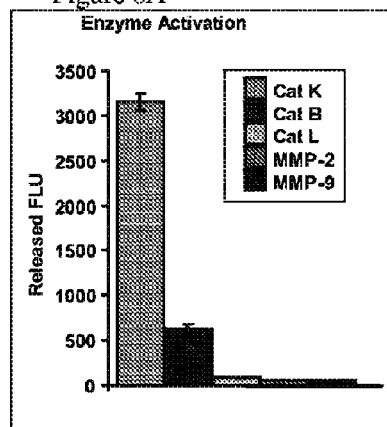
Figure 6A
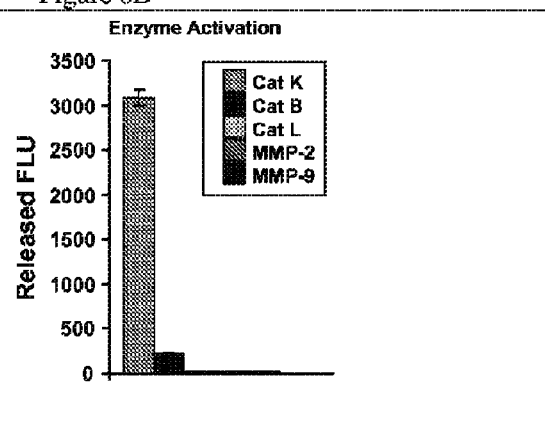
Figure 6B

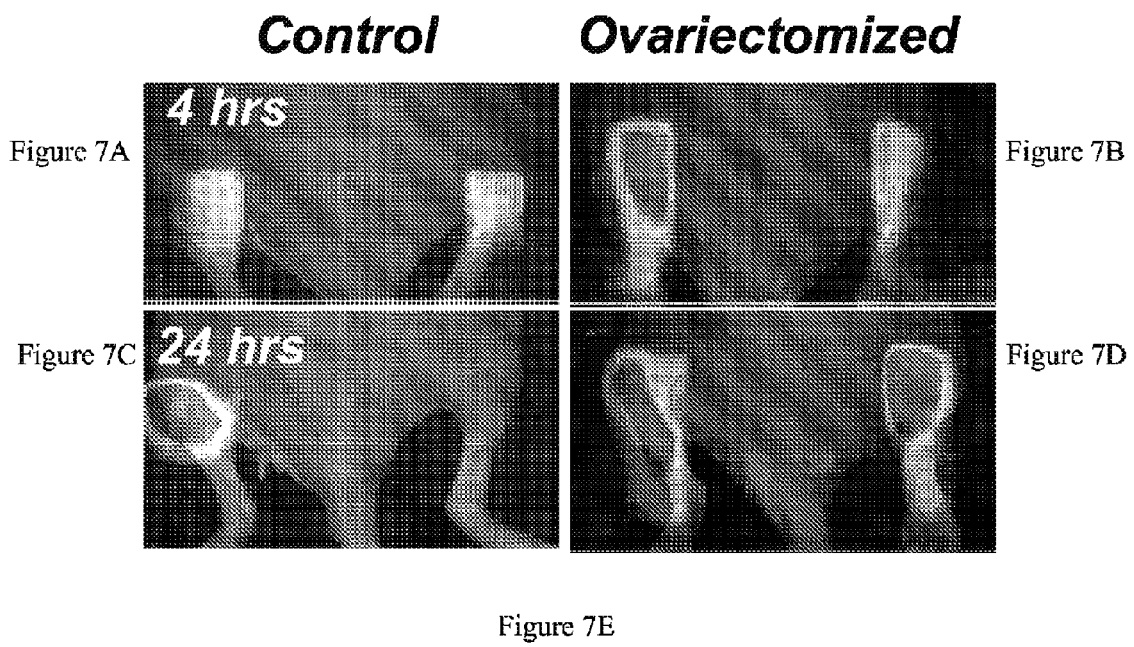
Figure 7A, Figure 7B, Figure 7C, Figure 7D
Figure 7E
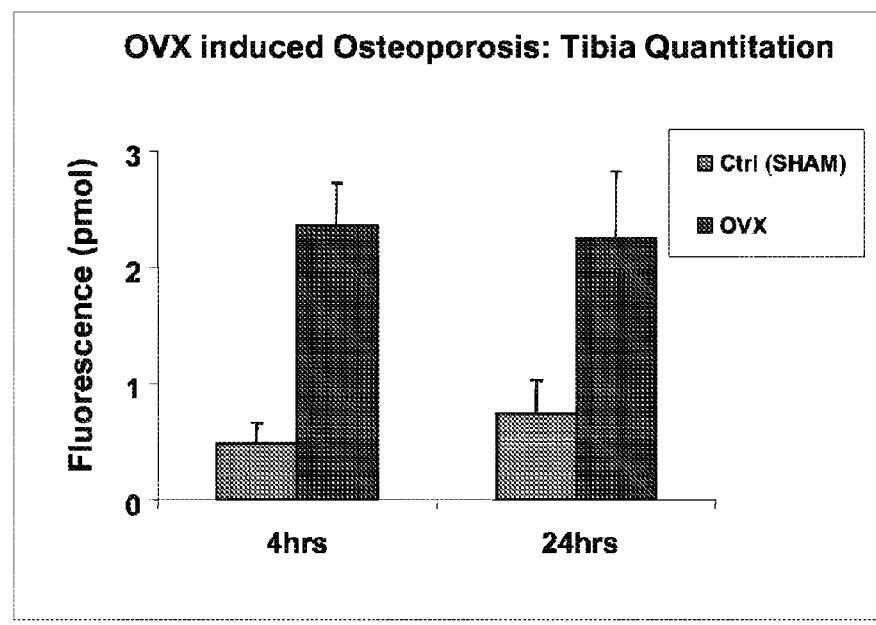

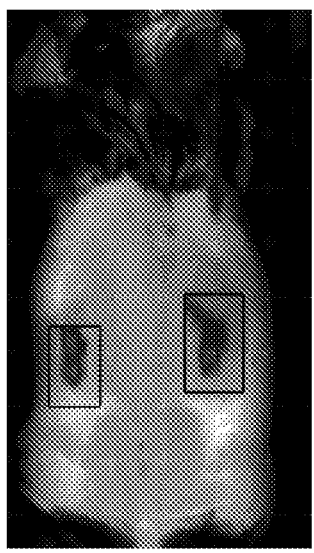 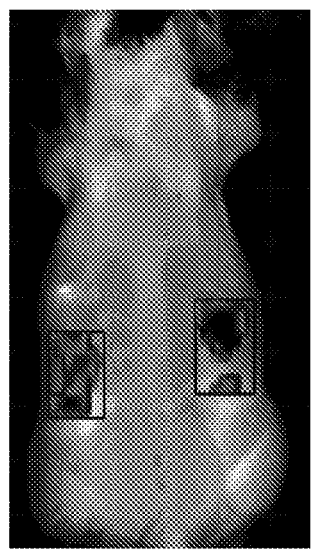 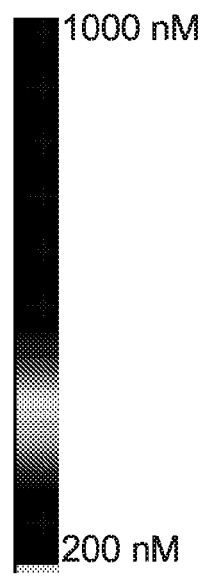
Figure 12A  Figure 12B
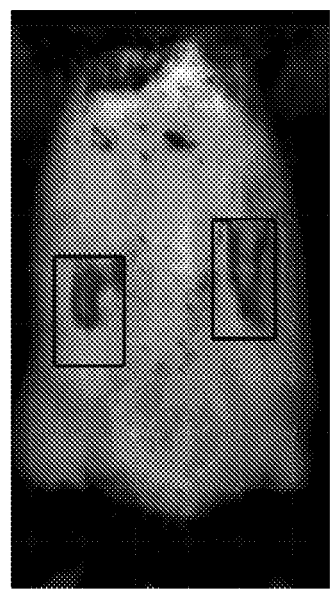 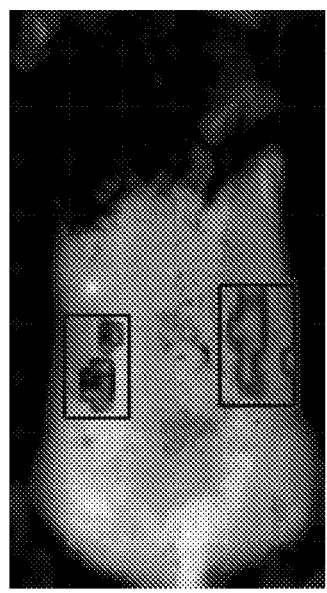 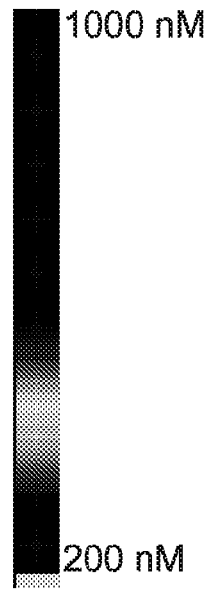
Figure 12C  Figure 12D Figure 14A  
Reflectance
Figure 14C  
Tomography
6 hrs
24 hrs
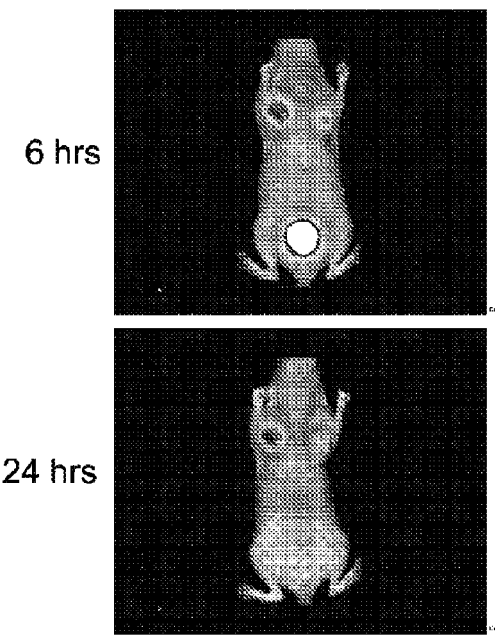
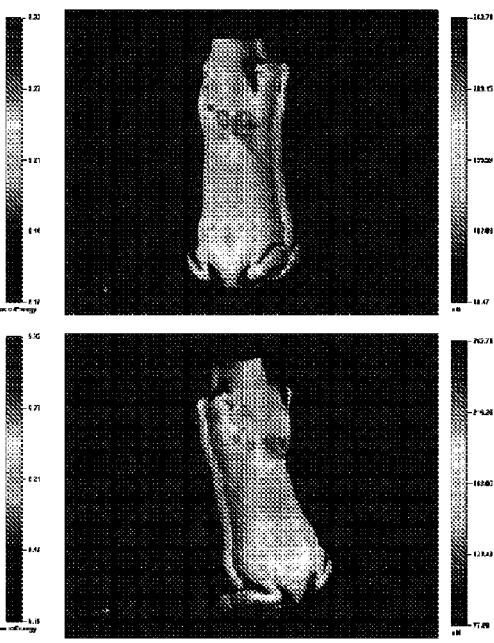
Figure 14B
Figure 14D
FIGURE 15
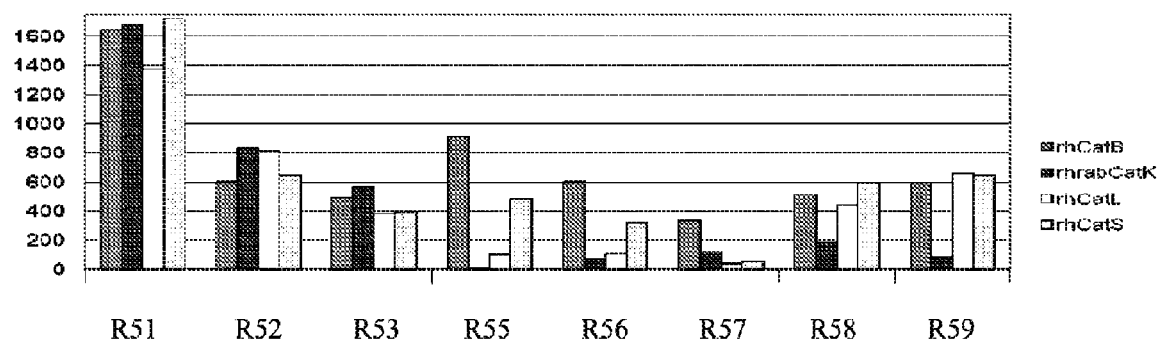

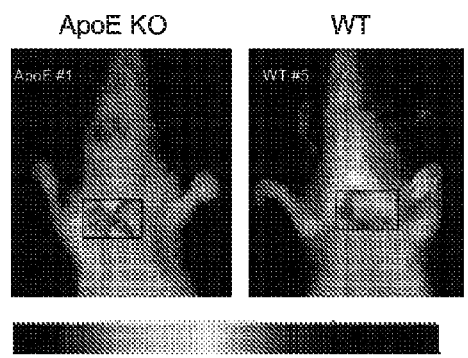
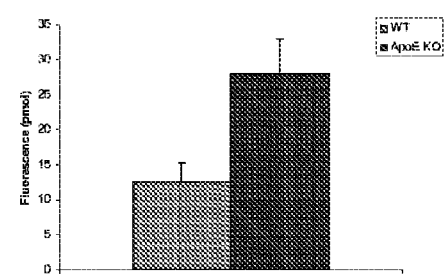
Figure 16A
Figure 16B
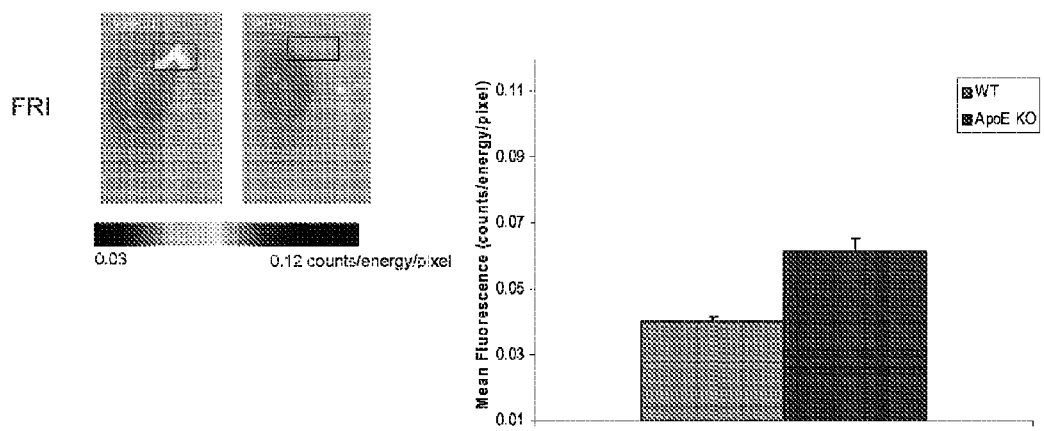
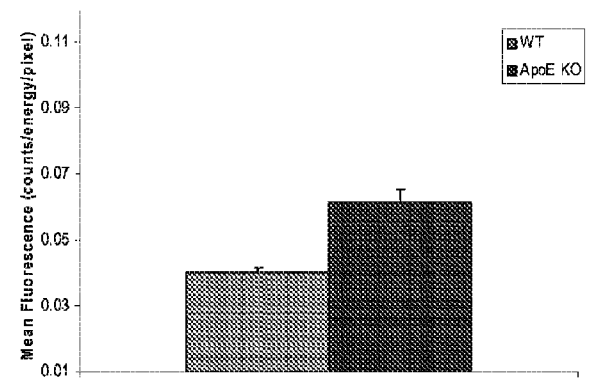
Figure 16C
Figure 16D

SEQUENCE LISTING

<160> NUMBER OF SEQ ID NOS: 472

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Ile Pro Leu Val Leu Pro Leu
1               5

<210> SEQ ID NO 2
<211> LENGTH: 7
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 2

Ser Pro Pro Thr Gly Ile Asn
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val His Pro Lys Gln His Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val His Pro Lys Gln His Arg
1               5

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Asp Ser Asp Ser Asp Ile Thr Trp Asp Gln Leu Trp Asp Asp Leu
1               5                   10                  15

Met Lys

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Arg Arg Gly Arg Arg Arg Arg
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Lys Lys Lys Gly
1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Lys Lys Gly
1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Lys Gly Lys Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (4)..(4)
<223> OTHER INFORMATION: Ornithine

<400> SEQUENCE: 10

Xaa Lys Lys Xaa Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (4)..(4)
<223> OTHER INFORMATION: Ornithine
<220> FEATURE:
<221> NAME/KEY: MOD_RES
<222> LOCATION: (5)..(5)
<223> OTHER INFORMATION: 6-aminohexanoic acid

<400> SEQUENCE: 11

Xaa Lys Lys Xaa Xaa
1               5

```
<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (4)..(4)
<223> OTHER INFORMATION: Ornithine
<220> FEATURE:
<221> NAME/KEY: MOD_RES
<222> LOCATION: (5)..(5)
<223> OTHER INFORMATION: 6-aminohexanoic acid

<400> SEQUENCE: 12

Xaa Lys Lys Xaa Xaa Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 6-aminohexanoic acid

<400> SEQUENCE: 13

Lys Lys Lys Lys Xaa
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Beta-Ala

<400> SEQUENCE: 14

Lys Lys Lys Ala
1

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Lys Lys Lys Gly Gly Gly Gly Gly
1               5

<210> SEQ ID NO 16
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Lys Lys Lys Lys Gly
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Lys Lys Lys Lys Lys Gly
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 6-aminohexanoic acid

<400> SEQUENCE: 18

Lys Lys Lys Lys Lys Lys Xaa
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Lys Lys Lys Lys Lys Gly Gly Gly Gly Gly
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Arg Lys Arg Lys Arg Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 21

Lys Arg Lys Arg Lys Arg Gly Cys
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Arg Arg Arg Lys Arg Gly
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Arg Lys Arg Lys Arg Lys Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Arg Arg Arg Arg Lys Arg Gly
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Phe Arg Lys Gly Gly Arg Lys
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Arg Lys Gly Gly Arg Arg Lys
1               5

<210> SEQ ID NO 27
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 6-aminohexanoic acid

<400> SEQUENCE: 27

Phe Arg Lys Gly Gly Arg Lys Xaa
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Arg Lys Gly Gly Arg Lys Gly Gly
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyclohexylalanine

<400> SEQUENCE: 29

Ala Arg Lys Gly Gly Arg Lys
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thienylalanine

<400> SEQUENCE: 30

Ala Arg Lys Gly Gly Arg Lys
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thienylalanine

<400> SEQUENCE: 31
```

```
Ala Arg Lys Gly Gly Arg Lys Gly
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Gly Lys Arg Arg Lys
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thienylalanine

<400> SEQUENCE: 33

Ala Gly Lys Arg Arg Lys
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyclohexylalanine

<400> SEQUENCE: 34

Ala Gly Lys Arg Arg Lys
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ornithine
<220> FEATURE:
<221> NAME/KEY: MOD_RES
<222> LOCATION: (6)..(6)
<223> OTHER INFORMATION: Diaminopropionic acid

<400> SEQUENCE: 35

Phe Gly Xaa Arg Arg Xaa
1               5

<210> SEQ ID NO 36
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ornithine
<220> FEATURE:
<221> NAME/KEY: MOD_RES
<222> LOCATION: (6)..(6)
<223> OTHER INFORMATION: Ornithine

<400> SEQUENCE: 36

Phe Gly Xaa Arg Arg Xaa
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Gly Lys Arg Arg Lys Gly Gly
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 6-aminohexanoic acid

<400> SEQUENCE: 38

Phe Gly Lys Arg Arg Lys Xaa
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 6-aminohexanoic acid

<400> SEQUENCE: 39

Phe Gly Lys Arg Arg Lys Arg Arg Arg Xaa
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (10)..(10)
<223> OTHER INFORMATION: 6-aminohexanoic acid

<400> SEQUENCE: 40

Phe Gly Lys Arg Arg Lys Glu Glu Glu Xaa
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 6-aminohexanoic acid

<400> SEQUENCE: 41

Phe Gly Lys Arg Arg Lys Arg Arg Arg Xaa Cys
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Beta-Ala

<400> SEQUENCE: 42

Lys Gly Phe Leu Gly Ala Lys
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: Ornithine

<400> SEQUENCE: 43

Xaa Gly Phe Leu Gly Ala Xaa
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<221> NAME/KEY: MOD_RES
<222> LOCATION: (6)..(6)
<223> OTHER INFORMATION: Beta-Ala

<400> SEQUENCE: 44

Lys Gly Phe Leu Gly Ala Lys Gly
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (8)..(8)
<223> OTHER INFORMATION: 6-aminohexanoic acid

<400> SEQUENCE: 45

Lys Gly Phe Leu Gly Ala Lys Xaa
1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Beta-Ala

<400> SEQUENCE: 46

Lys Gly Phe Leu Gly Ala Lys Gly Gly Gly
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Beta-Ala

<400> SEQUENCE: 47

Gly Gly Gly Lys Gly Phe Leu Gly Ala Lys
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid

```
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (9)..(9)
<223> OTHER INFORMATION: 6-aminohexanoic acid

<400> SEQUENCE: 48

Xaa Lys Gly Phe Leu Gly Ala Lys Xaa
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (8)..(8)
<223> OTHER INFORMATION: 6-aminohexanoic acid

<400> SEQUENCE: 49

Lys Gly Phe Leu Gly Ala Lys Xaa Cys
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Leu Gly Lys
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 6-aminohexanoic acid

<400> SEQUENCE: 51

Lys Phe Leu Gly Lys Xaa
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

Gly Phe Leu Gly Lys Gly Gly Gly
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 6-aminohexanoic acid

<400> SEQUENCE: 53

Gly Gly Phe Leu Gly Lys Xaa
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Phe Leu Gly Lys Cys
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 6-aminohexanoic acid

<400> SEQUENCE: 55

Gly Phe Leu Gly Lys Xaa Cys
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 6-aminohexanoic acid

<400> SEQUENCE: 56

Gly Gly Phe Leu Gly Lys Xaa Cys
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (5)..(5)
<223> OTHER INFORMATION: Ornithine

<400> SEQUENCE: 57

Gly Phe Leu Gly Xaa
1               5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Phe Leu Gly Lys Arg Arg Arg Arg Cys
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Beta-Ala

<400> SEQUENCE: 59

His Gly Pro Asn Lys His Gly Pro Asn Ala
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ornithine
<220> FEATURE:
<221> NAME/KEY: MOD_RES
<222> LOCATION: (10)..(10)
<223> OTHER INFORMATION: Beta-Ala

<400> SEQUENCE: 60

His Gly Pro Asn Xaa His Gly Pro Asn Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Beta-Ala

<400> SEQUENCE: 61
```

```
His Gly Pro Asn Lys His Gly Pro Asn Ala
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Beta-Ala

<400> SEQUENCE: 62

Lys His Gly Pro Asn Lys His Gly Pro Asn Ala
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (11)..(11)
<223> OTHER INFORMATION: Beta-Ala

<400> SEQUENCE: 63

Xaa His Gly Pro Asn Lys His Gly Pro Asn Ala
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (6)..(6)
<223> OTHER INFORMATION: Ornithine
<220> FEATURE:
<221> NAME/KEY: MOD_RES
<222> LOCATION: (11)..(11)
<223> OTHER INFORMATION: Beta-Ala

<400> SEQUENCE: 64

Xaa His Gly Pro Asn Xaa His Gly Pro Asn Ala
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

-continued

```
<222> LOCATION: (13)..(13)
<223> OTHER INFORMATION: 6-aminohexanoic acid

<400> SEQUENCE: 65

Phe Gly Gly His Gly Pro Asn Lys His Gly Pro Asn Xaa
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Beta-Ala

<400> SEQUENCE: 66

His Gly Pro Arg Lys His Gly Pro Arg Ala
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Beta-Ala

<400> SEQUENCE: 67

His Gly Pro Asn Lys His Gly Pro Arg Ala
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Beta-Ala

<400> SEQUENCE: 68

His Gly Pro Arg Lys His Gly Pro Asn Ala
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 6-aminohexanoic acid

<400> SEQUENCE: 69

His Gly Pro Asn Lys His Gly Pro Asn Xaa
1               5                   10
```

```
<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

His Gly Pro Arg Lys His Gly Pro Arg Gly Gly Gly Phe Gly
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ornithine
<220> FEATURE:
<221> NAME/KEY: MOD_RES
<222> LOCATION: (10)..(10)
<223> OTHER INFORMATION: Beta-Ala

<400> SEQUENCE: 71

His Gly Pro Arg Xaa His Gly Pro Arg Ala
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (10)..(10)
<223> OTHER INFORMATION: Beta-Ala

<400> SEQUENCE: 72

His Gly Pro Xaa Lys His Gly Pro Asn Ala
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: Beta-Ala

<400> SEQUENCE: 73

His Gly Pro Asn Lys His Gly Pro Xaa Ala
```

-continued

```
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ornithine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: Beta-Ala

<400> SEQUENCE: 74

His Gly Pro Asn Xaa His Gly Pro Xaa Ala
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

His Gly Pro Asn Lys
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ornithine

<400> SEQUENCE: 76

His Gly Pro Asn Xaa
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys His Gly Pro Asn Lys
1               5

<210> SEQ ID NO 78
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine

<400> SEQUENCE: 78

Xaa His Gly Pro Asn Lys
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

His Gly Pro Asn Lys Gly Gly Gly
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

His Gly Pro Asn Lys Gln Gly Gly
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ornithine
<220> FEATURE:
<221> NAME/KEY: MOD_RES
<222> LOCATION: (8)..(8)
<223> OTHER INFORMATION: 6-aminohexanoic acid

<400> SEQUENCE: 81

His Gly Pro Asn Xaa Gly Gly Xaa
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 6-aminohexanoic acid

<400> SEQUENCE: 82

His Gly Pro Asn Lys Arg Arg Arg Xaa
```

-continued

```
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Gly Pro Asn Lys Arg Gly Gly
1               5

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(6)
<223> OTHER INFORMATION: Ornithine

<400> SEQUENCE: 84

Gly Arg Arg Arg Xaa Xaa His Gly Pro Asn Lys Gly
1               5                   10

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

His Gly Pro Arg Lys
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ornithine

<400> SEQUENCE: 86

His Gly Pro Arg Xaa
1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 87

Lys His Gly Pro Arg Lys
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine

<400> SEQUENCE: 88

Xaa His Gly Pro Arg Lys
1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 6-aminohexanoic acid

<400> SEQUENCE: 89

His Gly Pro Arg Lys Xaa
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

His Gly Pro Arg Lys Gly Gly Gly
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ornithine
<220> FEATURE:
<221> NAME/KEY: MOD_RES
<222> LOCATION: (8)..(8)
<223> OTHER INFORMATION: 6-aminohexanoic acid

<400> SEQUENCE: 91

His Gly Pro Arg Xaa Gly Gly Xaa
1               5

<210> SEQ ID NO 92
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 6-aminohexanoic acid

<400> SEQUENCE: 92

His Gly Pro Arg Lys Arg Arg Arg Xaa
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

His Gly Pro Arg Lys Arg Gly Gly
1               5

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 6-aminohexanoic acid

<400> SEQUENCE: 94

Gly Arg Arg Arg Xaa Lys His Gly Pro Arg Lys Gly
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(6)
<223> OTHER INFORMATION: Ornithine
<220> FEATURE:
<221> NAME/KEY: MOD_RES
<222> LOCATION: (11)..(11)
<223> OTHER INFORMATION: Ornithine

<400> SEQUENCE: 95

Gly Lys Arg Arg Xaa Xaa His Gly Pro Asn Xaa Gly
1               5                   10

<210> SEQ ID NO 96
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(6)
<223> OTHER INFORMATION: Ornithine
<220> FEATURE:
<221> NAME/KEY: MOD_RES
<222> LOCATION: (11)..(11)
<223> OTHER INFORMATION: Ornithine

<400> SEQUENCE: 96

Gly Lys Lys Arg Xaa Xaa His Gly Pro Asn Xaa Gly
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 6-aminohexanoic acid

<400> SEQUENCE: 97

Gly Arg Arg Arg Lys Xaa His Gly Pro Asn Lys Gly
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Lys Pro Leu Gly Val Arg Lys
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Gly Pro Leu Gly Val Arg Lys
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid
```

```
<400> SEQUENCE: 100

Xaa Lys Pro Leu Gly Val Arg Lys
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 6-aminohexanoic acid

<400> SEQUENCE: 101

Lys Pro Leu Gly Val Arg Lys Xaa
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 6-aminohexanoic acid

<400> SEQUENCE: 102

Lys Pro Leu Gly Val Arg Lys Gln Xaa
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ornithine

<400> SEQUENCE: 103

Lys Pro Leu Gly Val Arg Xaa
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (7)..(7)
<223> OTHER INFORMATION: Ornithine

<400> SEQUENCE: 104
```

```
Xaa Pro Leu Gly Val Arg Xaa
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Lys Pro Leu Gly Val Arg Lys Cys
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Lys Gly Pro Leu Gly Val Arg Lys Cys
1               5

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Lys Pro Leu Gly Val Arg Lys Gly Gly Gly
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Lys Gly Pro Leu Gly Val Arg Lys Gly Gly Gly
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Lys Pro Leu Gly Val Arg Lys Arg Arg Arg
1               5                   10

<210> SEQ ID NO 110
<211> LENGTH: 11
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 110

Lys Gly Pro Leu Gly Val Arg Lys Arg Arg Arg
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Lys Val Arg Leu Gly Pro Lys
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Gly Val Arg Leu Gly Pro Lys
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid

<400> SEQUENCE: 113

Xaa Lys Val Arg Leu Gly Pro Lys
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 6-aminohexanoic acid

<400> SEQUENCE: 114

Lys Val Arg Leu Gly Pro Lys Xaa
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<221> NAME/KEY: MOD_RES
<222> LOCATION: (7)..(7)
<223> OTHER INFORMATION: Ornithine

<400> SEQUENCE: 115

Lys Val Arg Leu Gly Pro Xaa
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (7)..(7)
<223> OTHER INFORMATION: Ornithine

<400> SEQUENCE: 116

Xaa Val Arg Leu Gly Pro Xaa
1               5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Lys Val Arg Leu Gly Pro Lys Cys
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Lys Gly Val Arg Leu Gly Pro Lys Cys
1               5

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Lys Val Arg Leu Gly Pro Lys Gly Gly Gly
1               5                   10

<210> SEQ ID NO 120
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 120

Lys Gly Val Arg Leu Gly Pro Lys Gly Gly Gly
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Lys Val Arg Leu Gly Pro Lys Arg Arg Arg
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Lys Gly Val Arg Leu Gly Pro Lys Arg Arg Arg
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Lys Gly His Pro Gly Gly Pro Gln Gly Lys
1               5                   10

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

His Pro Gly Gly Pro Gln
1               5

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ornithine
<220> FEATURE:
```

```
<221> NAME/KEY: MOD_RES
<222> LOCATION: (11)..(11)
<223> OTHER INFORMATION: 6-aminohexanoic acid

<400> SEQUENCE: 125

Lys Gly His Pro Gly Gly Pro Gln Gly Xaa Xaa
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Lys Gly His Pro Gly Gly Pro Gln Lys
1               5                   10

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Lys His Pro Gly Gly Pro Gln Lys
1               5

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Lys Gly His Pro Gly Gly Pro Gln Gly Lys Cys
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Lys Gly His Pro Gly Gly Pro Gln Lys Gly Gly
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Lys Gly His Pro Gly Gly Pro Gln Lys Gly Gly Arg Arg
1               5                   10
```

```
<210> SEQ ID NO 131
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Gly His Pro Gly Gly Pro Gln Lys Gly Arg Arg Arg
1               5                   10

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 6-aminohexanoic acid

<400> SEQUENCE: 132

Lys Gly His Pro Gly Gly Pro Gln Lys Xaa Arg Arg Arg Cys Gly
1               5                   10                  15

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ile His Pro Phe His Leu Val Ile His
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Lys His Pro Phe His Leu Val Ile His
1               5

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Lys Ile His Pro Phe His Leu Val Ile His Lys
1               5                   10

<210> SEQ ID NO 136
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 136

Lys Lys His Pro Phe His Leu Val Ile His Lys
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ile His Pro Phe His Leu Val Ile His Lys
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys His Pro Phe His Leu Val Ile His Lys
1               5                   10

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Thr Pro Phe Ser Gly Gln
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Glu Pro Phe Trp Glu Asp Gln
1               5

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Leu Val Gly Gly Ala
1               5
```

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Tyr Pro Gly Gly Pro Gln
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Val Ala Asp Cys Ala Asp Gln
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Val Ala Asp Cys Ala Asp Arg Gln
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Val Ala Asp Cys Ala Asp Asp Gln
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Val Ala Asp Cys Arg Asp Gln
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 147

Ala Pro Glu Glu Ile Met Arg Arg Gln
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Pro Glu Glu Ile Met Asp Arg Gln
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Pro Glu Glu Ile Met Pro Arg Gln
1               5

<210> SEQ ID NO 150
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Phe Leu Gly
1

<210> SEQ ID NO 151
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Leu Phe Gly
1

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Glu Gly Phe Leu Gly
1               5

<210> SEQ ID NO 153
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 153

Glu Lys Gly Phe Leu Gly Lys
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Arg Glu Lys Gly Phe Leu Gly Lys
1               5

<210> SEQ ID NO 155
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Arg Gly Leu Gly Lys
1               5

<210> SEQ ID NO 156
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Gly Arg Arg
1

<210> SEQ ID NO 157
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cyclohexylalanine

<400> SEQUENCE: 157

Gly Phe Ala Gly
1

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 158

Arg Leu Val Gly Phe Asp
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Gly Phe Phe Leu
1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Gly Phe Phe Pro
1               5

<210> SEQ ID NO 161
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ala Phe Leu Gly
1

<210> SEQ ID NO 162
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Phe Pro Ala Met
1

<210> SEQ ID NO 163
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Glu Ala Ala Ala
1

<210> SEQ ID NO 164
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 164

Glu Lys Arg Arg Lys
1               5

<210> SEQ ID NO 165
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Succinyl-Glu

<400> SEQUENCE: 165

Glu Lys Arg Arg Lys
1               5

<210> SEQ ID NO 166
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Val Lys Lys Arg
1

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ala Ala Lys His Gly Pro Asn
1               5

<210> SEQ ID NO 168
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

His Gly Pro Arg
1

<210> SEQ ID NO 169
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 169

Gly Pro Arg Lys
1

<210> SEQ ID NO 170
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Pro Ala Gly Pro
1

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asn Gly Pro Asn Lys
1               5

<210> SEQ ID NO 172
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

His Gly Pro Ile
1

<210> SEQ ID NO 173
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline

<400> SEQUENCE: 173

His Gly Pro Asn
1

<210> SEQ ID NO 174
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline

<400> SEQUENCE: 174
```

```
His Gly Pro Xaa
1

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: hPro

<400> SEQUENCE: 175

His Gly Pro Asn Pro Leu Gly Val Arg
1               5

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Pro Leu Gly Val Arg
1               5

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Pro Leu Gly Val Arg Glu
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Pro Leu Gly Val Arg Asp
1               5

<210> SEQ ID NO 179
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Pro Leu Gly Met Arg
1               5
```

```
<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Pro Leu Gly Glu Arg Gly
1               5

<210> SEQ ID NO 181
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Pro Leu Gly Leu Ala Gly
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Val Arg Leu Gly Pro Lys
1               5

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Pro Gln Gly Ile Ala Gly Gln
1               5

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Val Pro Met Ser Met Arg Gly Gly
1               5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185
```

```
Ile Pro Val Ser Leu Arg Ser Gly
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Pro Phe Ser Met Ile Met Gly
1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Val Pro Leu Ser Leu Thr Met Gly
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Val Pro Leu Ser Leu Tyr Ser Gly
1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ile Pro Glu Ser Leu Arg Ala Gly
1               5

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(CO Me)

<400> SEQUENCE: 190

Lys His Pro Phe His Leu Val Ile His Lys
1               5                   10
```

```
<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(CO CF3)

<400> SEQUENCE: 191

Lys His Pro Phe His Leu Val Ile His Lys
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(CO Et)

<400> SEQUENCE: 192

Lys His Pro Phe His Leu Val Ile His Lys
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(CO mPEG20k)

<400> SEQUENCE: 193

Lys His Pro Phe His Leu Val Ile His Lys
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [Me CO] Lys

<400> SEQUENCE: 194

Lys His Pro Phe His Leu Val Ile His Lys
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: [carboxyethyl CO] Lys

<400> SEQUENCE: 195

Lys His Pro Phe His Leu Val Ile His Lys
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Lys His Pro Phe His Leu Leu Tyr His Lys
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ile His Pro Phe His Leu Leu Tyr His Lys
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Lys His Pro Phe His Leu Leu Tyr Tyr Lys
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ile His Pro Phe His Leu Leu Tyr Tyr Lys
1               5                   10

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Lys His Pro Phe His Leu Leu Val Tyr Lys
1               5                   10
```

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ile His Pro Phe His Leu Leu Val Tyr Lys
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr(Me)

<400> SEQUENCE: 202

Lys His Pro Tyr His Leu Val Ile His Lys
1               5                   10

<210> SEQ ID NO 203
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr(Et)

<400> SEQUENCE: 203

Lys His Pro Tyr His Leu Val Ile His Lys
1               5                   10

<210> SEQ ID NO 204
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr(Me)

<400> SEQUENCE: 204

Ile His Pro Tyr His Leu Val Ile His Lys
1               5                   10

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (4)..(4)
<223> OTHER INFORMATION: Tyr(Et)

<400> SEQUENCE: 205

Ile His Pro Tyr His Leu Val Ile His Lys
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine

<400> SEQUENCE: 206

Xaa His Pro Phe His Leu Val Ile His Lys
1               5                   10

<210> SEQ ID NO 207
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Diaminopropionic acid

<400> SEQUENCE: 207

Xaa His Pro Phe His Leu Val Ile His Lys
1               5                   10

<210> SEQ ID NO 208
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid

<400> SEQUENCE: 208

Xaa His Pro Phe His Leu Val Ile His Lys
1               5                   10

<210> SEQ ID NO 209
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Asp Arg Val Tyr Ile His Pro Phe His Leu Val Ile His Lys
1               5                   10

<210> SEQ ID NO 210
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Arg Val Tyr Ile His Pro Phe His Leu Val Ile His Lys
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Tyr Ile His Pro Phe His Leu Val Ile His Lys
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Tyr Ile His Pro Phe His Leu Val Ile His Lys
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Pro Leu Ala Gln Ala Val Arg Ser Ser Ser Arg Lys
1               5                   10

<210> SEQ ID NO 214
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Pro Leu Ala Gln Ala Val Lys Arg Ser Ser Ser Arg
1               5                   10

<210> SEQ ID NO 215
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ornithine
```

<400> SEQUENCE: 215

Ser Pro Leu Ala Gln Ala Val Arg Ser Ser Ser Arg Xaa
1               5                   10

<210> SEQ ID NO 216
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ornithine

<400> SEQUENCE: 216

Pro Leu Ala Gln Ala Val Xaa Arg Ser Ser Ser Arg
1               5                   10

<210> SEQ ID NO 217
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ser Pro Leu Ala Asn Ala Val Arg Ser Ser Ser Arg Lys
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Pro Leu Ala Asn Ala Val Lys Arg Ser Ser Ser Arg
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Pro Glu Glu Ile Met Asp Arg Gln Lys
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ala Pro Glu Glu Ile Met Arg Arg Gln Lys
1               5                   10

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ala Pro Glu Glu Ile Met Asp Gln Gln Lys
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ile Ser Leu Met Lys Arg Pro Pro Gly Phe
1               5                   10

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Lys Asp Glu Val Asp
1               5

<210> SEQ ID NO 224
<211> LENGTH: 5
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 224

Arg Gly Asp Phe Lys
1               5

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 225

Cys Arg Gly Asp Cys
1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 226

Lys Arg Arg Lys Arg Arg
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 227

Lys Arg Arg Arg Lys Arg Arg
1               5

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 228

Phe Lys Arg Arg Phe Lys Arg Arg
1               5

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 229

Cys Lys Arg Arg Cys Lys Arg Arg
1               5

<210> SEQ ID NO 230
<211> LENGTH: 11
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 230

Phe Lys Arg Arg Phe Lys Arg Arg Gly Gly Gly
1               5                   10

<210> SEQ ID NO 231
<211> LENGTH: 11
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 231

Lys His Gly Pro Asn Lys His Gly Pro Asn Gly
1               5                   10

<210> SEQ ID NO 232
<211> LENGTH: 7

```
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(1)
<223> OTHER INFORMATION: 6-aminohexanoic acid

<400> SEQUENCE: 232

Xaa Lys Arg Arg Lys Arg Arg
1               5

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 233

Lys Arg Arg Lys Lys Arg Arg Lys
1               5

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 234

Gly Lys Arg Arg Lys Lys Arg Arg Lys Gly
1               5                   10

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [Ac]-Lys(F5)
<220> FEATURE:
<221> NAME/KEY: MOD_RES
<222> LOCATION: (7)..(7)
<223> OTHER INFORMATION: Lys(F5)-[OH]

<400> SEQUENCE: 235

Lys Gly Phe Leu Gly Gly Lys
1               5

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [Ac]-Lys(F6)
<220> FEATURE:
<221> NAME/KEY: MOD_RES
```

```
<222> LOCATION: (7)..(7)
<223> OTHER INFORMATION: Lys(F6)-[OH]

<400> SEQUENCE: 236

Lys Gly Phe Leu Gly Gly Lys
1               5

<210> SEQ ID NO 237
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Gly
<220> FEATURE:
<221> NAME/KEY: MOD_RES
<222> LOCATION: (6)..(6)
<223> OTHER INFORMATION: Lys(F5)-[OH]

<400> SEQUENCE: 237

Gly Phe Leu Gly Gly Lys
1               5

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [Acetyl]-Lys(F5)
<220> FEATURE:
<221> NAME/KEY: MOD_RES
<222> LOCATION: (4)..(4)
<223> OTHER INFORMATION: Lys(F5)
<220> FEATURE:
<221> NAME/KEY: MOD_RES
<222> LOCATION: (7)..(7)
<223> OTHER INFORMATION: Gly-[OH]

<400> SEQUENCE: 238

Lys Lys Lys Lys Lys Lys Gly
1               5

<210> SEQ ID NO 239
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [Acetyl]-Lys(F5)
<220> FEATURE:
<221> NAME/KEY: MOD_RES
<222> LOCATION: (4)..(4)
<223> OTHER INFORMATION: Lys(F5)
<220> FEATURE:
<221> NAME/KEY: MOD_RES
<222> LOCATION: (5)..(5)
<223> OTHER INFORMATION: Gly-[OH]

<400> SEQUENCE: 239
```

```
Lys Lys Lys Lys Gly
1               5

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)-[OH]

<400> SEQUENCE: 240

His Gly Pro Asn Lys
1               5

<210> SEQ ID NO 241
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F6]-Gly
<220> FEATURE:
<221> NAME/KEY: MOD_RES
<222> LOCATION: (5)..(5)
<223> OTHER INFORMATION: Lys(F6)-[OH]

<400> SEQUENCE: 241

Gly Phe Leu Gly Lys
1               5

<210> SEQ ID NO 242
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)-[OH]

<400> SEQUENCE: 242

His Gly Pro Arg Lys
1               5

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)
<220> FEATURE:
<221> NAME/KEY: MOD_RES
<222> LOCATION: (10)..(10)
<223> OTHER INFORMATION: Beta-Ala-[OH]

<400> SEQUENCE: 243

His Gly Pro Asn Lys His Gly Pro Asn Ala
1               5                   10

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys(F5)
<220> FEATURE:
<221> NAME/KEY: MOD_RES
<222> LOCATION: (8)..(8)
<223> OTHER INFORMATION: Lys(F5)-[OH]

<400> SEQUENCE: 244

Lys His Pro Gly Gly Pro Gln Lys
1               5

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys(F5)
<220> FEATURE:
<221> NAME/KEY: MOD_RES
<222> LOCATION: (10)..(10)
<223> OTHER INFORMATION: Lys(F5)-[OH]

<400> SEQUENCE: 245

Lys Gly His Pro Gly Gly Pro Gln Gly Lys
1               5                   10

<210> SEQ ID NO 246
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys(F5)
<220> FEATURE:
<221> NAME/KEY: MOD_RES
<222> LOCATION: (7)..(7)
<223> OTHER INFORMATION: Lys(F5)-[OH]

<400> SEQUENCE: 246
```

Lys Val Arg Leu Gly Pro Lys
1               5

<210> SEQ ID NO 247
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys(F5)
<220> FEATURE:
<221> NAME/KEY: MOD_RES
<222> LOCATION: (7)..(7)
<223> OTHER INFORMATION: Lys(F5)-[OH]

<400> SEQUENCE: 247

Lys Pro Leu Gly Val Arg Lys
1               5

<210> SEQ ID NO 248
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (6)..(6)
<223> OTHER INFORMATION: Lys(F5)-[OH]

<400> SEQUENCE: 248

Phe Gly Lys Arg Arg Lys
1               5

<210> SEQ ID NO 249
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (7)..(7)
<223> OTHER INFORMATION: Lys(F5)-[OH]

<400> SEQUENCE: 249

Phe Arg Lys Gly Gly Arg Lys
1               5

<210> SEQ ID NO 250

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Gly
<220> FEATURE:
<221> NAME/KEY: MOD_RES
<222> LOCATION: (5)..(5)
<223> OTHER INFORMATION: Lys(F5)-[OH]

<400> SEQUENCE: 250

Gly Phe Leu Gly Lys
1               5

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (6)..(6)
<223> OTHER INFORMATION: Lys(F5)
<220> FEATURE:
<221> NAME/KEY: MOD_RES
<222> LOCATION: (7)..(7)
<223> OTHER INFORMATION: Gly-[OH]

<400> SEQUENCE: 251

Phe Gly Lys Arg Arg Lys Gly
1               5

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (7)..(7)
<223> OTHER INFORMATION: Lys(F5)-[OH]

<400> SEQUENCE: 252

Phe Arg Lys Gly Gly Arg Lys
1               5

<210> SEQ ID NO 253
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(1)
<223> OTHER INFORMATION: Lys(F5)
<220> FEATURE:
<221> NAME/KEY: MOD_RES
<222> LOCATION: (5)..(5)
<223> OTHER INFORMATION: Lys(F5)

<400> SEQUENCE: 253

Lys Arg Arg Arg Lys Arg Arg
1               5

<210> SEQ ID NO 254
<211> LENGTH: 11
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (2)..(2)
<223> OTHER INFORMATION: Lys(F6)
<220> FEATURE:
<221> NAME/KEY: MOD_RES
<222> LOCATION: (6)..(6)
<223> OTHER INFORMATION: Lys(F6)

<400> SEQUENCE: 254

Phe Lys Arg Arg Phe Lys Arg Arg Gly Gly Gly
1               5                   10

<210> SEQ ID NO 255
<211> LENGTH: 7
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(1)
<223> OTHER INFORMATION: 6-aminohexanoic acid
<220> FEATURE:
<221> NAME/KEY: MOD_RES
<222> LOCATION: (2)..(2)
<223> OTHER INFORMATION: Lys(F6)
<220> FEATURE:
<221> NAME/KEY: MOD_RES
<222> LOCATION: (5)..(5)
<223> OTHER INFORMATION: Lys(F6)

<400> SEQUENCE: 255

Xaa Lys Arg Arg Lys Arg Arg
1               5

<210> SEQ ID NO 256
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [Acetyl]-Lys(F5)
```

```
<220> FEATURE:
<221> NAME/KEY: MOD_RES
<222> LOCATION: (4)..(4)
<223> OTHER INFORMATION: Lys(F5)
<220> FEATURE:
<221> NAME/KEY: MOD_RES
<222> LOCATION: (7)..(7)
<223> OTHER INFORMATION: Gly-[mPEG20K]

<400> SEQUENCE: 256

Lys Lys Lys Lys Lys Lys Gly
1               5

<210> SEQ ID NO 257
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [Acetyl]-Lys(F5)
<220> FEATURE:
<221> NAME/KEY: MOD_RES
<222> LOCATION: (4)..(4)
<223> OTHER INFORMATION: Lys(F5)
<220> FEATURE:
<221> NAME/KEY: MOD_RES
<222> LOCATION: (5)..(5)
<223> OTHER INFORMATION: Gly-[mPEG20K]

<400> SEQUENCE: 257

Lys Lys Lys Lys Gly
1               5

<210> SEQ ID NO 258
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)-[mPEG20K]

<400> SEQUENCE: 258

His Gly Pro Asn Lys
1               5

<210> SEQ ID NO 259
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F6]-Gly
<220> FEATURE:
<221> NAME/KEY: MOD_RES
<222> LOCATION: (5)..(5)
<223> OTHER INFORMATION: Lys(F6)-[mPEG20K]
```

```
<400> SEQUENCE: 259

Gly Phe Leu Gly Lys
1               5

<210> SEQ ID NO 260
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)-[mPEG20K]

<400> SEQUENCE: 260

His Gly Pro Arg Lys
1               5

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)
<220> FEATURE:
<221> NAME/KEY: MOD_RES
<222> LOCATION: (10)..(10)
<223> OTHER INFORMATION: Beta-Ala-[mPEG20K]

<400> SEQUENCE: 261

His Gly Pro Asn Lys His Gly Pro Asn Ala
1               5                   10

<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)-[dPEG-1.1k]

<400> SEQUENCE: 262

His Gly Pro Asn Lys
1               5

<210> SEQ ID NO 263
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)-[mPEG-5k]

<400> SEQUENCE: 263

His Gly Pro Asn Lys
1               5

<210> SEQ ID NO 264
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)-[mPEG-10k]

<400> SEQUENCE: 264

His Gly Pro Asn Lys
1               5

<210> SEQ ID NO 265
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys(F5)
<220> FEATURE:
<221> NAME/KEY: MOD_RES
<222> LOCATION: (8)..(8)
<223> OTHER INFORMATION: Lys(F5)-[mPEG20K]

<400> SEQUENCE: 265

Lys His Pro Gly Gly Pro Gln Lys
1               5

<210> SEQ ID NO 266
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys(F5)
<220> FEATURE:
<221> NAME/KEY: MOD_RES
<222> LOCATION: (10)..(10)
<223> OTHER INFORMATION: Lys(F5)-[mPEG20K]
```

```
<400> SEQUENCE: 266

Lys Gly His Pro Gly Gly Pro Gln Gly Lys
1               5                   10

<210> SEQ ID NO 267
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys(F5)
<220> FEATURE:
<221> NAME/KEY: MOD_RES
<222> LOCATION: (7)..(7)
<223> OTHER INFORMATION: Lys(F5)-[mPEG20K]

<400> SEQUENCE: 267

Lys Val Arg Leu Gly Pro Lys
1               5

<210> SEQ ID NO 268
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys(F5)
<220> FEATURE:
<221> NAME/KEY: MOD_RES
<222> LOCATION: (7)..(7)
<223> OTHER INFORMATION: Lys(F5)-[mPEG20K]

<400> SEQUENCE: 268

Lys Pro Leu Gly Val Arg Lys
1               5

<210> SEQ ID NO 269
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (6)..(6)
<223> OTHER INFORMATION: Lys(F5)-[mPEG20K]

<400> SEQUENCE: 269

Phe Gly Lys Arg Arg Lys
1               5

<210> SEQ ID NO 270
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (7)..(7)
<223> OTHER INFORMATION: Lys(F5)-[mPEG20K]

<400> SEQUENCE: 270

Phe Arg Lys Gly Gly Arg Lys
1               5

<210> SEQ ID NO 271
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Gly
<220> FEATURE:
<221> NAME/KEY: MOD_RES
<222> LOCATION: (5)..(5)
<223> OTHER INFORMATION: Lys(F5)-OH

<400> SEQUENCE: 271

Gly Phe Leu Gly Lys
1               5

<210> SEQ ID NO 272
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys(F5)
<220> FEATURE:
<221> NAME/KEY: MOD_RES
<222> LOCATION: (6)..(6)
<223> OTHER INFORMATION: Lys(F5)-[NH2]

<400> SEQUENCE: 272

Lys Gly Phe Leu Gly Lys
1               5

<210> SEQ ID NO 273
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG-20k](F6)-Gly
<220> FEATURE:
```

```
<221> NAME/KEY: MOD_RES
<222> LOCATION: (5)..(5)
<223> OTHER INFORMATION: Lys(F6)-[NH2]

<400> SEQUENCE: 273

Gly Phe Leu Gly Lys
1               5

<210> SEQ ID NO 274
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG-40k]-(F5)-Gly
<220> FEATURE:
<221> NAME/KEY: MOD_RES
<222> LOCATION: (5)..(5)
<223> OTHER INFORMATION: Lys(F5)-[NH2]

<400> SEQUENCE: 274

Gly Phe Leu Gly Lys
1               5

<210> SEQ ID NO 275
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [diphenylpropylamine]-(F6)-Gly
<220> FEATURE:
<221> NAME/KEY: MOD_RES
<222> LOCATION: (5)..(5)
<223> OTHER INFORMATION: Lys(F6)-[NH2]

<400> SEQUENCE: 275

Gly Phe Leu Gly Lys
1               5

<210> SEQ ID NO 276
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [dPEG-1.1k]-(F6)-Gly
<220> FEATURE:
<221> NAME/KEY: MOD_RES
<222> LOCATION: (5)..(5)
<223> OTHER INFORMATION: Lys(F6)-[NH2]

<400> SEQUENCE: 276

Gly Phe Leu Gly Lys
1               5

<210> SEQ ID NO 277
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys(F6)
<220> FEATURE:
<221> NAME/KEY: MOD_RES
<222> LOCATION: (4)..(4)
<223> OTHER INFORMATION: Lys(F6)-[NH2]

<400> SEQUENCE: 277

Lys Arg Arg Lys
1

<210> SEQ ID NO 278
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG-20k-succinyl]-Lys(F6)
<220> FEATURE:
<221> NAME/KEY: MOD_RES
<222> LOCATION: (4)..(4)
<223> OTHER INFORMATION: Lys(F6)-[NH2]

<400> SEQUENCE: 278

Lys Arg Arg Lys
1

<210> SEQ ID NO 279
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [diphenylpropylamine-succinyl]-Lys(F6)
<220> FEATURE:
<221> NAME/KEY: MOD_RES
<222> LOCATION: (4)..(4)
<223> OTHER INFORMATION: Lys(F6)-[NH2]

<400> SEQUENCE: 279

Lys Arg Arg Lys
1

<210> SEQ ID NO 280
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [dPEG-1.1k-succinyl]-Lys(F6)
<220> FEATURE:
<221> NAME/KEY: MOD_RES
<222> LOCATION: (4)..(4)
<223> OTHER INFORMATION: Lys(F6)-[NH2]
```

```
<400> SEQUENCE: 280

Lys Arg Arg Lys
1

<210> SEQ ID NO 281
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys(F6)
<220> FEATURE:
<221> NAME/KEY: MOD_RES
<222> LOCATION: (5)..(5)
<223> OTHER INFORMATION: Lys(F6)-[NH2]

<400> SEQUENCE: 281

Lys Ala Arg Arg Lys
1               5

<210> SEQ ID NO 282
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG-20k]-Lys(F6)
<220> FEATURE:
<221> NAME/KEY: MOD_RES
<222> LOCATION: (5)..(5)
<223> OTHER INFORMATION: Lys(F6)-[NH2]

<400> SEQUENCE: 282

Lys Ala Arg Arg Lys
1               5

<210> SEQ ID NO 283
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys(F6)
<220> FEATURE:
<221> NAME/KEY: MOD_RES
<222> LOCATION: (5)..(5)
<223> OTHER INFORMATION: Lys(F6)-[NH2]

<400> SEQUENCE: 283

Lys Arg Arg Arg Lys
1               5

<210> SEQ ID NO 284
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: [mPEG-20k-succinyl]-Lys(F6)
<220> FEATURE:
<221> NAME/KEY: MOD_RES
<222> LOCATION: (5)..(5)
<223> OTHER INFORMATION: Lys(F6)-[NH2]

<400> SEQUENCE: 284

Lys Ala Arg Arg Lys
1               5

<210> SEQ ID NO 285
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys(F5)
<220> FEATURE:
<221> NAME/KEY: MOD_RES
<222> LOCATION: (4)..(4)
<223> OTHER INFORMATION: Lys(F5)-[NH2]

<400> SEQUENCE: 285

Lys Lys Lys Lys
1

<210> SEQ ID NO 286
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG-20k]-Lys(F5)
<220> FEATURE:
<221> NAME/KEY: MOD_RES
<222> LOCATION: (4)..(4)
<223> OTHER INFORMATION: Lys(F5)-[NH2]

<400> SEQUENCE: 286

Lys Lys Lys Lys
1

<210> SEQ ID NO 287
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [palmitoyl]-Lys(F5)
<220> FEATURE:
<221> NAME/KEY: MOD_RES
<222> LOCATION: (4)..(4)
<223> OTHER INFORMATION: Lys(F5)-[NH2]

<400> SEQUENCE: 287

Lys Phe Arg Lys
1
```

<210> SEQ ID NO 288
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [Ac]-Lys(F5)
<220> FEATURE:
<221> NAME/KEY: MOD_RES
<222> LOCATION: (4)..(4)
<223> OTHER INFORMATION: Lys(F5)
<220> FEATURE:
<221> NAME/KEY: MOD_RES
<222> LOCATION: (5)..(5)
<223> OTHER INFORMATION: Gly-[Iron Oxide Nanoparticle]

<400> SEQUENCE: 288

Lys Lys Lys Lys Gly
1               5

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F6]-Gly
<220> FEATURE:
<221> NAME/KEY: MOD_RES
<222> LOCATION: (7)..(7)
<223> OTHER INFORMATION: Lys(F6)-[mPEG-20k]

<400> SEQUENCE: 289

Gly Pro Leu Gly Val Arg Lys
1               5

<210> SEQ ID NO 290
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F6]-Gly
<220> FEATURE:
<221> NAME/KEY: MOD_RES
<222> LOCATION: (7)..(7)
<223> OTHER INFORMATION: Lys(F6)-[mPEG-40k]

<400> SEQUENCE: 290

Gly Pro Leu Gly Val Arg Lys
1               5

<210> SEQ ID NO 291
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: [F6]-Gly
<220> FEATURE:
<221> NAME/KEY: MOD_RES
<222> LOCATION: (7)..(7)
<223> OTHER INFORMATION: Lys(F6)-[Y-PEG-40k]

<400> SEQUENCE: 291

Gly Pro Leu Gly Val Arg Lys
1               5

<210> SEQ ID NO 292
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F6]-Gly
<220> FEATURE:
<221> NAME/KEY: MOD_RES
<222> LOCATION: (7)..(7)
<223> OTHER INFORMATION: Lys(F6)-[eda]

<400> SEQUENCE: 292

Gly Pro Leu Gly Val Arg Lys
1               5

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F6]-Gly
<220> FEATURE:
<221> NAME/KEY: MOD_RES
<222> LOCATION: (7)..(7)
<223> OTHER INFORMATION: Lys(F6)-[PVP-6k]

<400> SEQUENCE: 293

Gly Pro Leu Gly Val Arg Lys
1               5

<210> SEQ ID NO 294
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F6]-Gly
<220> FEATURE:
<221> NAME/KEY: MOD_RES
<222> LOCATION: (7)..(7)
<223> OTHER INFORMATION: Lys(F6)-[Dextran-10k]

<400> SEQUENCE: 294

Gly Pro Leu Gly Val Arg Lys
1               5
```

```
<210> SEQ ID NO 295
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F6]-Gly
<220> FEATURE:
<221> NAME/KEY: MOD_RES
<222> LOCATION: (7)..(7)
<223> OTHER INFORMATION: Lys(F6)
<220> FEATURE:
<221> NAME/KEY: MOD_RES
<222> LOCATION: (8)..(8)
<223> OTHER INFORMATION: Glu(mPEG-20k)-[mPEG-20k]

<400> SEQUENCE: 295

Gly Pro Leu Gly Val Arg Lys Glu
1               5

<210> SEQ ID NO 296
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (6)..(6)
<223> OTHER INFORMATION: Lys(F5)
<220> FEATURE:
<221> NAME/KEY: MOD_RES
<222> LOCATION: (7)..(7)
<223> OTHER INFORMATION: Gly-[mPEG20K]

<400> SEQUENCE: 296

Phe Gly Lys Arg Arg Lys Gly
1               5

<210> SEQ ID NO 297
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (7)..(7)
<223> OTHER INFORMATION: Lys(F5)-[mPEG20K]

<400> SEQUENCE: 297
```

Phe Arg Lys Gly Gly Arg Lys
1               5

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (10)..(10)
<223> OTHER INFORMATION: Lys(F5)-[OH]

<400> SEQUENCE: 298

Lys His Pro Phe His Leu Val Ile His Lys
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (10)..(10)
<223> OTHER INFORMATION: Lys(F5)-[NH H]

<400> SEQUENCE: 299

Lys His Pro Phe His Leu Val Ile His Lys
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (10)..(10)
<223> OTHER INFORMATION: Lys(F5)-[NH Me]

<400> SEQUENCE: 300

Lys His Pro Phe His Leu Val Ile His Lys
1               5                   10

<210> SEQ ID NO 301
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (10)..(10)
<223> OTHER INFORMATION: Lys(F5)-[NH Et]

<400> SEQUENCE: 301

Lys His Pro Phe His Leu Val Ile His Lys
1               5                   10

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (10)..(10)
<223> OTHER INFORMATION: Lys(F5)-[NH mPEG20k]

<400> SEQUENCE: 302

Lys His Pro Phe His Leu Val Ile His Lys
1               5                   10

<210> SEQ ID NO 303
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (10)..(10)
<223> OTHER INFORMATION: Lys(F5)-[NH mPEG10k]

<400> SEQUENCE: 303

Lys His Pro Phe His Leu Val Ile His Lys
1               5                   10

<210> SEQ ID NO 304
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (10)..(10)
<223> OTHER INFORMATION: Lys(F5)-[NH mPEG5k]

<400> SEQUENCE: 304

Lys His Pro Phe His Leu Val Ile His Lys
1               5                   10
```

```
<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (10)..(10)
<223> OTHER INFORMATION: Lys(F5)-[NH dPEG24]

<400> SEQUENCE: 305

Lys His Pro Phe His Leu Val Ile His Lys
1               5                  10

<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ile
<220> FEATURE:
<221> NAME/KEY: MOD_RES
<222> LOCATION: (10)..(10)
<223> OTHER INFORMATION: Lys(F5)-[OH]

<400> SEQUENCE: 306

Ile His Pro Phe His Leu Val Ile His Lys
1               5                  10

<210> SEQ ID NO 307
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ile
<220> FEATURE:
<221> NAME/KEY: MOD_RES
<222> LOCATION: (10)..(10)
<223> OTHER INFORMATION: Lys(F5)-[NH H]

<400> SEQUENCE: 307

Ile His Pro Phe His Leu Val Ile His Lys
1               5                  10

<210> SEQ ID NO 308
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ile
<220> FEATURE:
```

```
<221> NAME/KEY: MOD_RES
<222> LOCATION: (10)..(10)
<223> OTHER INFORMATION: Lys(F5)-[NH Me]

<400> SEQUENCE: 308

Ile His Pro Phe His Leu Val Ile His Lys
1               5                   10

<210> SEQ ID NO 309
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ile
<220> FEATURE:
<221> NAME/KEY: MOD_RES
<222> LOCATION: (10)..(10)
<223> OTHER INFORMATION: Lys(F5)-[NH Et]

<400> SEQUENCE: 309

Ile His Pro Phe His Leu Val Ile His Lys
1               5                   10

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ile
<220> FEATURE:
<221> NAME/KEY: MOD_RES
<222> LOCATION: (10)..(10)
<223> OTHER INFORMATION: Lys(F5)-[NH mPEG20k]

<400> SEQUENCE: 310

Ile His Pro Phe His Leu Val Ile His Lys
1               5                   10

<210> SEQ ID NO 311
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ile
<220> FEATURE:
<221> NAME/KEY: MOD_RES
<222> LOCATION: (10)..(10)
<223> OTHER INFORMATION: Lys(F5)-[NH mPEG10k]

<400> SEQUENCE: 311

Ile His Pro Phe His Leu Val Ile His Lys
1               5                   10

<210> SEQ ID NO 312
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ile
<220> FEATURE:
<221> NAME/KEY: MOD_RES
<222> LOCATION: (10)..(10)
<223> OTHER INFORMATION: Lys(F5)-[NH mPEG5k]

<400> SEQUENCE: 312

Ile His Pro Phe His Leu Val Ile His Lys
1               5                   10

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ile
<220> FEATURE:
<221> NAME/KEY: MOD_RES
<222> LOCATION: (10)..(10)
<223> OTHER INFORMATION: Lys(F5)-[NH dPEG24]

<400> SEQUENCE: 313

Ile His Pro Phe His Leu Val Ile His Lys
1               5                   10

<210> SEQ ID NO 314
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys (CO Me)
<220> FEATURE:
<221> NAME/KEY: MOD_RES
<222> LOCATION: (10)..(10)
<223> OTHER INFORMATION: Lys(F5)-[OH]

<400> SEQUENCE: 314

Lys His Pro Phe His Leu Val Ile His Lys
1               5                   10

<210> SEQ ID NO 315
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys (CO CF3)
<220> FEATURE:
<221> NAME/KEY: MOD_RES
<222> LOCATION: (10)..(10)
<223> OTHER INFORMATION: Lys(F5)-[OH]
```

```
<400> SEQUENCE: 315

Lys His Pro Phe His Leu Val Ile His Lys
1               5                   10

<210> SEQ ID NO 316
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys (COMe)
<220> FEATURE:
<221> NAME/KEY: MOD_RES
<222> LOCATION: (10)..(10)
<223> OTHER INFORMATION: Lys(F5)-[NH mPEG20k]

<400> SEQUENCE: 316

Lys His Pro Phe His Leu Val Ile His Lys
1               5                   10

<210> SEQ ID NO 317
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys (COCF3)
<220> FEATURE:
<221> NAME/KEY: MOD_RES
<222> LOCATION: (10)..(10)
<223> OTHER INFORMATION: Lys(F5)-[NH mPEG20k]

<400> SEQUENCE: 317

Lys His Pro Phe His Leu Val Ile His Lys
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [carboxyethyl CO]Lys (F5)
<220> FEATURE:
<221> NAME/KEY: MOD_RES
<222> LOCATION: (10)..(10)
<223> OTHER INFORMATION: Lys(F5)-[NH2]

<400> SEQUENCE: 318

Lys His Pro Phe His Leu Val Ile His Lys
1               5                   10

<210> SEQ ID NO 319
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: [carboxyethyl CO]Lys (F5)
<220> FEATURE:
<221> NAME/KEY: MOD_RES
<222> LOCATION: (11)..(11)
<223> OTHER INFORMATION: Lys(F5)-[NH2]

<400> SEQUENCE: 319

Lys Ile His Pro Phe His Leu Val Ile His Lys
1               5                   10

<210> SEQ ID NO 320
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [Me CO]Lys (F5)
<220> FEATURE:
<221> NAME/KEY: MOD_RES
<222> LOCATION: (10)..(10)
<223> OTHER INFORMATION: Lys(F5)-[NH2]

<400> SEQUENCE: 320

Lys His Pro Phe His Leu Val Ile His Lys
1               5                   10

<210> SEQ ID NO 321
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG5k CO]Lys (F5)
<220> FEATURE:
<221> NAME/KEY: MOD_RES
<222> LOCATION: (10)..(10)
<223> OTHER INFORMATION: Lys(F5)-[NH2]

<400> SEQUENCE: 321

Lys His Pro Phe His Leu Val Ile His Lys
1               5                   10

<210> SEQ ID NO 322
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG20k CO]Lys (F5)
<220> FEATURE:
<221> NAME/KEY: MOD_RES
<222> LOCATION: (10)..(10)
<223> OTHER INFORMATION: Lys(F5)-[NH2]

<400> SEQUENCE: 322

Lys His Pro Phe His Leu Val Ile His Lys
1               5                   10
```

```
<210> SEQ ID NO 323
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [Me CO]Lys (F5)
<220> FEATURE:
<221> NAME/KEY: MOD_RES
<222> LOCATION: (11)..(11)
<223> OTHER INFORMATION: Lys(F5)-[NH2]

<400> SEQUENCE: 323

Lys Ile His Pro Phe His Leu Val Ile His Lys
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG5k CO]Lys (F5)
<220> FEATURE:
<221> NAME/KEY: MOD_RES
<222> LOCATION: (11)..(11)
<223> OTHER INFORMATION: Lys(F5)-[NH2]

<400> SEQUENCE: 324

Lys Ile His Pro Phe His Leu Val Ile His Lys
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG20k CO]Lys (F5)
<220> FEATURE:
<221> NAME/KEY: MOD_RES
<222> LOCATION: (11)..(11)
<223> OTHER INFORMATION: Lys(F5)-[NH2]

<400> SEQUENCE: 325

Lys Ile His Pro Phe His Leu Val Ile His Lys
1               5                   10

<210> SEQ ID NO 326
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ornithine
```

```
<220> FEATURE:
<221> NAME/KEY: MOD_RES
<222> LOCATION: (10)..(10)
<223> OTHER INFORMATION: Lys(F5)[OH]

<400> SEQUENCE: 326

Xaa His Pro Phe His Leu Val Ile His Lys
1               5                   10

<210> SEQ ID NO 327
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine(F5)
<220> FEATURE:
<221> NAME/KEY: MOD_RES
<222> LOCATION: (10)..(10)
<223> OTHER INFORMATION: Lys(F5)[OH]

<400> SEQUENCE: 327

Xaa His Pro Phe His Leu Val Ile His Lys
1               5                   10

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ornithine
<220> FEATURE:
<221> NAME/KEY: MOD_RES
<222> LOCATION: (10)..(10)
<223> OTHER INFORMATION: Lys(F5)[NH H]

<400> SEQUENCE: 328

Xaa His Pro Phe His Leu Val Ile His Lys
1               5                   10

<210> SEQ ID NO 329
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ornithine
<220> FEATURE:
<221> NAME/KEY: MOD_RES
<222> LOCATION: (10)..(10)
<223> OTHER INFORMATION: Lys(F5)[NH Me]

<400> SEQUENCE: 329

Xaa His Pro Phe His Leu Val Ile His Lys
1               5                   10

<210> SEQ ID NO 330
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ornithine
<220> FEATURE:
<221> NAME/KEY: MOD_RES
<222> LOCATION: (10)..(10)
<223> OTHER INFORMATION: Lys(F5)[NH mPEG5k]

<400> SEQUENCE: 330

Xaa His Pro Phe His Leu Val Ile His Lys
1               5                   10

<210> SEQ ID NO 331
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ornithine
<220> FEATURE:
<221> NAME/KEY: MOD_RES
<222> LOCATION: (10)..(10)
<223> OTHER INFORMATION: Lys(F5)[NH mPEG20k]

<400> SEQUENCE: 331

Xaa His Pro Phe His Leu Val Ile His Lys
1               5                   10

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine(F5)
<220> FEATURE:
<221> NAME/KEY: MOD_RES
<222> LOCATION: (10)..(10)
<223> OTHER INFORMATION: Lys(F5)[NH H]

<400> SEQUENCE: 332

Xaa His Pro Phe His Leu Val Ile His Lys
1               5                   10

<210> SEQ ID NO 333
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine(F5)
<220> FEATURE:
<221> NAME/KEY: MOD_RES
<222> LOCATION: (10)..(10)
<223> OTHER INFORMATION: Lys(F5)[NH Me]
```

<400> SEQUENCE: 333

Xaa His Pro Phe His Leu Val Ile His Lys
1               5                   10

<210> SEQ ID NO 334
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine(F5)
<220> FEATURE:
<221> NAME/KEY: MOD_RES
<222> LOCATION: (10)..(10)
<223> OTHER INFORMATION: Lys(F5)[NH mPEG5k]

<400> SEQUENCE: 334

Xaa His Pro Phe His Leu Val Ile His Lys
1               5                   10

<210> SEQ ID NO 335
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine(F5)
<220> FEATURE:
<221> NAME/KEY: MOD_RES
<222> LOCATION: (10)..(10)
<223> OTHER INFORMATION: Lys(F5)[NH mPEG20k]

<400> SEQUENCE: 335

Xaa His Pro Phe His Leu Val Ile His Lys
1               5                   10

<210> SEQ ID NO 336
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Diaminopropionic acid
<220> FEATURE:
<221> NAME/KEY: MOD_RES
<222> LOCATION: (10)..(10)
<223> OTHER INFORMATION: Lys(F5)[OH]

<400> SEQUENCE: 336

Xaa His Pro Phe His Leu Val Ile His Lys
1               5                   10

<210> SEQ ID NO 337
<211> LENGTH: 10
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<221> NAME/KEY: MOD_RES
<222> LOCATION: (1)..(1)
<223> OTHER INFORMATION: Diaminopropionic acid(F5)
<220> FEATURE:
<221> NAME/KEY: MOD_RES
<222> LOCATION: (10)..(10)
<223> OTHER INFORMATION: Lys(F5)[OH]

<400> SEQUENCE: 337

Xaa His Pro Phe His Leu Val Ile His Lys
1               5                   10

<210> SEQ ID NO 338
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Diaminopropionic acid
<220> FEATURE:
<221> NAME/KEY: MOD_RES
<222> LOCATION: (10)..(10)
<223> OTHER INFORMATION: Lys(F5)[NH H]

<400> SEQUENCE: 338

Xaa His Pro Phe His Leu Val Ile His Lys
1               5                   10

<210> SEQ ID NO 339
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Diaminopropionic acid
<220> FEATURE:
<221> NAME/KEY: MOD_RES
<222> LOCATION: (10)..(10)
<223> OTHER INFORMATION: Lys(F5)[NH Me]

<400> SEQUENCE: 339

Xaa His Pro Phe His Leu Val Ile His Lys
1               5                   10

<210> SEQ ID NO 340
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Diaminopropionic acid
<220> FEATURE:
<221> NAME/KEY: MOD_RES
<222> LOCATION: (10)..(10)
<223> OTHER INFORMATION: Lys(F5)[NH mPEG5k]

<400> SEQUENCE: 340

Xaa His Pro Phe His Leu Val Ile His Lys
```

```
<210> SEQ ID NO 341
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Diaminopropionic acid
<220> FEATURE:
<221> NAME/KEY: MOD_RES
<222> LOCATION: (10)..(10)
<223> OTHER INFORMATION: Lys(F5)[NH mPEG20k]

<400> SEQUENCE: 341

Xaa His Pro Phe His Leu Val Ile His Lys
1               5                   10

<210> SEQ ID NO 342
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Diaminopropionic acid(F5)
<220> FEATURE:
<221> NAME/KEY: MOD_RES
<222> LOCATION: (10)..(10)
<223> OTHER INFORMATION: Lys(F5)[NH H]

<400> SEQUENCE: 342

Xaa His Pro Phe His Leu Val Ile His Lys
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Diaminopropionic acid(F5)
<220> FEATURE:
<221> NAME/KEY: MOD_RES
<222> LOCATION: (10)..(10)
<223> OTHER INFORMATION: Lys(F5)[NH Me]

<400> SEQUENCE: 343

Xaa His Pro Phe His Leu Val Ile His Lys
1               5                   10

<210> SEQ ID NO 344
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Diaminopropionic acid(F5)
<220> FEATURE:
<221> NAME/KEY: MOD_RES
<222> LOCATION: (10)..(10)
<223> OTHER INFORMATION: Lys(F5)[NH mPEG5k]

<400> SEQUENCE: 344

Xaa His Pro Phe His Leu Val Ile His Lys
1               5                   10

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Diaminopropionic acid(F5)
<220> FEATURE:
<221> NAME/KEY: MOD_RES
<222> LOCATION: (10)..(10)
<223> OTHER INFORMATION: Lys(F5)[NH mPEG20k]

<400> SEQUENCE: 345

Xaa His Pro Phe His Leu Val Ile His Lys
1               5                   10

<210> SEQ ID NO 346
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]6-aminohexanoic acid
<220> FEATURE:
<221> NAME/KEY: MOD_RES
<222> LOCATION: (10)..(10)
<223> OTHER INFORMATION: Lys(F5)[OH]

<400> SEQUENCE: 346

Xaa His Pro Phe His Leu Val Ile His Lys
1               5                   10

<210> SEQ ID NO 347
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid(F5)
<220> FEATURE:
<221> NAME/KEY: MOD_RES
<222> LOCATION: (10)..(10)
<223> OTHER INFORMATION: Lys(F5)[OH]

<400> SEQUENCE: 347

Xaa His Pro Phe His Leu Val Ile His Lys
1               5                   10

<210> SEQ ID NO 348
```

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]6-aminohexanoic acid
<220> FEATURE:
<221> NAME/KEY: MOD_RES
<222> LOCATION: (10)..(10)
<223> OTHER INFORMATION: Lys(F5)[NH H]

<400> SEQUENCE: 348

Xaa His Pro Phe His Leu Val Ile His Lys
1               5                   10

<210> SEQ ID NO 349
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]6-aminohexanoic acid
<220> FEATURE:
<221> NAME/KEY: MOD_RES
<222> LOCATION: (10)..(10)
<223> OTHER INFORMATION: Lys(F5)[NH Me]

<400> SEQUENCE: 349

Xaa His Pro Phe His Leu Val Ile His Lys
1               5                   10

<210> SEQ ID NO 350
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]6-aminohexanoic acid
<220> FEATURE:
<221> NAME/KEY: MOD_RES
<222> LOCATION: (10)..(10)
<223> OTHER INFORMATION: Lys(F5)[NH mPEG5k]

<400> SEQUENCE: 350

Xaa His Pro Phe His Leu Val Ile His Lys
1               5                   10

<210> SEQ ID NO 351
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]6-aminohexanoic acid
<220> FEATURE:
<221> NAME/KEY: MOD_RES
<222> LOCATION: (10)..(10)
```

<223> OTHER INFORMATION: Lys(F5)[NH mPEG20k]

<400> SEQUENCE: 351

Xaa His Pro Phe His Leu Val Ile His Lys
1               5                   10

<210> SEQ ID NO 352
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid(F5)
<220> FEATURE:
<221> NAME/KEY: MOD_RES
<222> LOCATION: (10)..(10)
<223> OTHER INFORMATION: Lys(F5)[NH H]

<400> SEQUENCE: 352

Xaa His Pro Phe His Leu Val Ile His Lys
1               5                   10

<210> SEQ ID NO 353
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid(F5)
<220> FEATURE:
<221> NAME/KEY: MOD_RES
<222> LOCATION: (10)..(10)
<223> OTHER INFORMATION: Lys(F5)[NH Me]

<400> SEQUENCE: 353

Xaa His Pro Phe His Leu Val Ile His Lys
1               5                   10

<210> SEQ ID NO 354
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid(F5)
<220> FEATURE:
<221> NAME/KEY: MOD_RES
<222> LOCATION: (10)..(10)
<223> OTHER INFORMATION: Lys(F5)[NH mPEG5k]

<400> SEQUENCE: 354

Xaa His Pro Phe His Leu Val Ile His Lys
1               5                   10

<210> SEQ ID NO 355
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid(F5)
<220> FEATURE:
<221> NAME/KEY: MOD_RES
<222> LOCATION: (10)..(10)
<223> OTHER INFORMATION: Lys(F5)[NH mPEG20k]

<400> SEQUENCE: 355

Xaa His Pro Phe His Leu Val Ile His Lys
1               5                   10

<210> SEQ ID NO 356
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Asp
<220> FEATURE:
<221> NAME/KEY: MOD_RES
<222> LOCATION: (14)..(14)
<223> OTHER INFORMATION: Lys(F5)[OH]

<400> SEQUENCE: 356

Asp Arg Val Tyr Ile His Pro Phe His Leu Val Ile His Lys
1               5                   10

<210> SEQ ID NO 357
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Asp
<220> FEATURE:
<221> NAME/KEY: MOD_RES
<222> LOCATION: (14)..(14)
<223> OTHER INFORMATION: Lys(F5)[NH H]

<400> SEQUENCE: 357

Asp Arg Val Tyr Ile His Pro Phe His Leu Val Ile His Lys
1               5                   10

<210> SEQ ID NO 358
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Asp
<220> FEATURE:
<221> NAME/KEY: MOD_RES
<222> LOCATION: (14)..(14)
<223> OTHER INFORMATION: Lys(F5)[NH Me]

<400> SEQUENCE: 358

Asp Arg Val Tyr Ile His Pro Phe His Leu Val Ile His Lys
1               5                   10

<210> SEQ ID NO 359
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Asp
<220> FEATURE:
<221> NAME/KEY: MOD_RES
<222> LOCATION: (14)..(14)
<223> OTHER INFORMATION: Lys(F5)[NH mPEG5k]

<400> SEQUENCE: 359

Asp Arg Val Tyr Ile His Pro Phe His Leu Val Ile His Lys
1               5                   10

<210> SEQ ID NO 360
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Asp
<220> FEATURE:
<221> NAME/KEY: MOD_RES
<222> LOCATION: (14)..(14)
<223> OTHER INFORMATION: Lys(F5)[NH mPEG20k]

<400> SEQUENCE: 360

Asp Arg Val Tyr Ile His Pro Phe His Leu Val Ile His Lys
1               5                   10

<210> SEQ ID NO 361
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Arg
<220> FEATURE:
<221> NAME/KEY: MOD_RES
<222> LOCATION: (13)..(13)
<223> OTHER INFORMATION: Lys(F5)[OH]

<400> SEQUENCE: 361

Arg Val Tyr Ile His Pro Phe His Leu Val Ile His Lys
1               5                   10

<210> SEQ ID NO 362
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(1)
<223> OTHER INFORMATION: [F5]Arg
<220> FEATURE:
<221> NAME/KEY: MOD_RES
<222> LOCATION: (13)..(13)
<223> OTHER INFORMATION: Lys(F5)[NH H]

<400> SEQUENCE: 362

Arg Val Tyr Ile His Pro Phe His Leu Val Ile His Lys
1               5                   10

<210> SEQ ID NO 363
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Arg
<220> FEATURE:
<221> NAME/KEY: MOD_RES
<222> LOCATION: (13)..(13)
<223> OTHER INFORMATION: Lys(F5)[NH Me]

<400> SEQUENCE: 363

Arg Val Tyr Ile His Pro Phe His Leu Val Ile His Lys
1               5                   10

<210> SEQ ID NO 364
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Arg
<220> FEATURE:
<221> NAME/KEY: MOD_RES
<222> LOCATION: (13)..(13)
<223> OTHER INFORMATION: Lys(F5)[NH mPEG5k]

<400> SEQUENCE: 364

Arg Val Tyr Ile His Pro Phe His Leu Val Ile His Lys
1               5                   10

<210> SEQ ID NO 365
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Arg
<220> FEATURE:
<221> NAME/KEY: MOD_RES
<222> LOCATION: (13)..(13)
<223> OTHER INFORMATION: Lys(F5)[NH mPEG20k]

<400> SEQUENCE: 365

Arg Val Tyr Ile His Pro Phe His Leu Val Ile His Lys
1               5                   10
```

```
<210> SEQ ID NO 366
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Val
<220> FEATURE:
<221> NAME/KEY: MOD_RES
<222> LOCATION: (12)..(12)
<223> OTHER INFORMATION: Lys(F5)[OH]

<400> SEQUENCE: 366

Val Tyr Ile His Pro Phe His Leu Val Ile His Lys
1               5                   10

<210> SEQ ID NO 367
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Val
<220> FEATURE:
<221> NAME/KEY: MOD_RES
<222> LOCATION: (12)..(12)
<223> OTHER INFORMATION: Lys(F5)[NH H]

<400> SEQUENCE: 367

Val Tyr Ile His Pro Phe His Leu Val Ile His Lys
1               5                   10

<210> SEQ ID NO 368
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Val
<220> FEATURE:
<221> NAME/KEY: MOD_RES
<222> LOCATION: (12)..(12)
<223> OTHER INFORMATION: Lys(F5)[NH Me]

<400> SEQUENCE: 368

Val Tyr Ile His Pro Phe His Leu Val Ile His Lys
1               5                   10

<210> SEQ ID NO 369
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Val
<220> FEATURE:
<221> NAME/KEY: MOD_RES
```

```
<222> LOCATION: (12)..(12)
<223> OTHER INFORMATION: Lys(F5)[NH mPEG5k]

<400> SEQUENCE: 369

Val Tyr Ile His Pro Phe His Leu Val Ile His Lys
1               5                   10

<210> SEQ ID NO 370
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Val
<220> FEATURE:
<221> NAME/KEY: MOD_RES
<222> LOCATION: (12)..(12)
<223> OTHER INFORMATION: Lys(F5)[NH mPEG20k]

<400> SEQUENCE: 370

Val Tyr Ile His Pro Phe His Leu Val Ile His Lys
1               5                   10

<210> SEQ ID NO 371
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Tyr
<220> FEATURE:
<221> NAME/KEY: MOD_RES
<222> LOCATION: (11)..(11)
<223> OTHER INFORMATION: Lys(F5)[OH]

<400> SEQUENCE: 371

Tyr Ile His Pro Phe His Leu Val Ile His Lys
1               5                   10

<210> SEQ ID NO 372
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Tyr
<220> FEATURE:
<221> NAME/KEY: MOD_RES
<222> LOCATION: (11)..(11)
<223> OTHER INFORMATION: Lys(F5)[NH H]

<400> SEQUENCE: 372

Tyr Ile His Pro Phe His Leu Val Ile His Lys
1               5                   10

<210> SEQ ID NO 373
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Tyr
<220> FEATURE:
<221> NAME/KEY: MOD_RES
<222> LOCATION: (11)..(11)
<223> OTHER INFORMATION: Lys(F5)[NH Me]

<400> SEQUENCE: 373

Tyr Ile His Pro Phe His Leu Val Ile His Lys
1               5                   10

<210> SEQ ID NO 374
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Tyr
<220> FEATURE:
<221> NAME/KEY: MOD_RES
<222> LOCATION: (11)..(11)
<223> OTHER INFORMATION: Lys(F5)[NH mPEG5k]

<400> SEQUENCE: 374

Tyr Ile His Pro Phe His Leu Val Ile His Lys
1               5                   10

<210> SEQ ID NO 375
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Tyr
<220> FEATURE:
<221> NAME/KEY: MOD_RES
<222> LOCATION: (11)..(11)
<223> OTHER INFORMATION: Lys(F5)[NH mPEG20k]

<400> SEQUENCE: 375

Tyr Ile His Pro Phe His Leu Val Ile His Lys
1               5                   10

<210> SEQ ID NO 376
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ser
<220> FEATURE:
<221> NAME/KEY: MOD_RES
<222> LOCATION: (13)..(13)
<223> OTHER INFORMATION: Lys(F5)

<400> SEQUENCE: 376
```

```
Ser Pro Leu Ala Gln Ala Val Arg Ser Ser Ser Arg Lys
1               5                   10
```

<210> SEQ ID NO 377
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Pro
<220> FEATURE:
<221> NAME/KEY: MOD_RES
<222> LOCATION: (7)..(7)
<223> OTHER INFORMATION: Lys(F5)

<400> SEQUENCE: 377

```
Pro Leu Ala Gln Ala Val Lys Arg Ser Ser Ser Arg
1               5                   10
```

<210> SEQ ID NO 378
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ser
<220> FEATURE:
<221> NAME/KEY: MOD_RES
<222> LOCATION: (13)..(13)
<223> OTHER INFORMATION: Ornithine(F5)

<400> SEQUENCE: 378

```
Ser Pro Leu Ala Gln Ala Val Arg Ser Ser Ser Arg Xaa
1               5                   10
```

<210> SEQ ID NO 379
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Pro
<220> FEATURE:
<221> NAME/KEY: MOD_RES
<222> LOCATION: (7)..(7)
<223> OTHER INFORMATION: Ornithine(F5)

<400> SEQUENCE: 379

```
Pro Leu Ala Gln Ala Val Xaa Arg Ser Ser Ser Arg
1               5                   10
```

<210> SEQ ID NO 380
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)..(1)
<223> OTHER INFORMATION: [F5]Ser
<220> FEATURE:
<221> NAME/KEY: MOD_RES
<222> LOCATION: (13)..(13)
<223> OTHER INFORMATION: Lys(F5)

<400> SEQUENCE: 380

Ser Pro Leu Ala Asn Ala Val Arg Ser Ser Arg Lys
1               5                   10

<210> SEQ ID NO 381
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Pro
<220> FEATURE:
<221> NAME/KEY: MOD_RES
<222> LOCATION: (7)..(7)
<223> OTHER INFORMATION: Lys(F5)

<400> SEQUENCE: 381

Pro Leu Ala Asn Ala Val Lys Arg Ser Ser Ser Arg
1               5                   10

<210> SEQ ID NO 382
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ala
<220> FEATURE:
<221> NAME/KEY: MOD_RES
<222> LOCATION: (10)..(10)
<223> OTHER INFORMATION: Lys(F5)

<400> SEQUENCE: 382

Ala Pro Glu Glu Ile Met Asp Arg Gln Lys
1               5                   10

<210> SEQ ID NO 383
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ala

<400> SEQUENCE: 383

Ala Pro Glu Glu Ile Met Arg Arg Gln Lys
1               5                   10

<210> SEQ ID NO 384
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ala

<400> SEQUENCE: 384

Ala Pro Glu Glu Ile Met Asp Gln Gln Lys
1               5                   10

<210> SEQ ID NO 385
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (7)..(7)
<223> OTHER INFORMATION: Lys(F5)-OH

<400> SEQUENCE: 385

Phe Arg Lys Gly Gly Arg Lys
1               5

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (6)..(6)
<223> OTHER INFORMATION: Lys(F5)
<220> FEATURE:
<221> NAME/KEY: MOD_RES
<222> LOCATION: (7)..(7)
<223> OTHER INFORMATION: Gly-OH

<400> SEQUENCE: 386

Phe Gly Lys Arg Arg Lys Gly
1               5

<210> SEQ ID NO 387
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: F5-Gly
<220> FEATURE:
<221> NAME/KEY: MOD_RES
<222> LOCATION: (5)..(5)
<223> OTHER INFORMATION: Lys(F5)-OH

<400> SEQUENCE: 387

Gly Phe Leu Gly Lys
1               5

<210> SEQ ID NO 388
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Phe
<220> FEATURE:
<221> NAME/KEY: MOD_RES
<222> LOCATION: (3)..(3)
<223> OTHER INFORMATION: Lys(F5)
<220> FEATURE:
<221> NAME/KEY: MOD_RES
<222> LOCATION: (7)..(7)
<223> OTHER INFORMATION: Lys(F5)-[OH]

<400> SEQUENCE: 388

Phe Arg Lys Gly Gly Arg Lys
1               5

<210> SEQ ID NO 389
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pentynoyl-Phe
<220> FEATURE:
<221> NAME/KEY: MOD_RES
<222> LOCATION: (3)..(3)
<223> OTHER INFORMATION: Lys-(F5)
<220> FEATURE:
<221> NAME/KEY: MOD_RES
<222> LOCATION: (7)..(7)
<223> OTHER INFORMATION: Lys(F5)-[OH]

<400> SEQUENCE: 389

Phe Arg Lys Gly Gly Arg Lys
1               5

<210> SEQ ID NO 390
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pentynoyl-Phe
<220> FEATURE:
<221> NAME/KEY: MOD_RES
```

```
<222> LOCATION: (3)..(3)
<223> OTHER INFORMATION: Lys(F5)
<220> FEATURE:
<221> NAME/KEY: MOD_RES
<222> LOCATION: (6)..(6)
<223> OTHER INFORMATION: Lys(F5)-[OH]

<400> SEQUENCE: 390

Phe Gly Lys Arg Arg Lys
1               5

<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pentynoyl-Lys(F5)
<220> FEATURE:
<221> NAME/KEY: MOD_RES
<222> LOCATION: (7)..(7)
<223> OTHER INFORMATION: Lys(F5)-[OH]

<400> SEQUENCE: 391

Lys Pro Leu Gly Val Arg Lys
1               5

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pentynoyl-Lys(F5)
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: Lys(F5)-[OH]

<400> SEQUENCE: 392

Lys Gly Phe Leu Gly Ala Lys
1               5

<210> SEQ ID NO 393
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pentynoyl-Lys(F5)
<220> FEATURE:
<221> NAME/KEY: MOD_RES
<222> LOCATION: (7)..(7)
<223> OTHER INFORMATION: Lys(F5)-[OH]

<400> SEQUENCE: 393
```

```
Lys Val Arg Leu Gly Pro Lys
1               5

<210> SEQ ID NO 394
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pentynoyl-Lys(F5)
<220> FEATURE:
<221> NAME/KEY: MOD_RES
<222> LOCATION: (10)..(10)
<223> OTHER INFORMATION: Lys(F5)-[OH]

<400> SEQUENCE: 394

Lys Gly His Pro Gly Gly Pro Gln Gly Lys
1               5                   10

<210> SEQ ID NO 395
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pentynoyl-Lys(F5)
<220> FEATURE:
<221> NAME/KEY: MOD_RES
<222> LOCATION: (8)..(8)
<223> OTHER INFORMATION: Lys(F5)-[OH]

<400> SEQUENCE: 395

Lys His Pro Gly Gly Pro Gln Lys
1               5

<210> SEQ ID NO 396
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Lys
<220> FEATURE:
<221> NAME/KEY: MOD_RES
<222> LOCATION: (10)..(10)
<223> OTHER INFORMATION: Lys(F5)-[NH2]

<400> SEQUENCE: 396

Lys His Pro Phe His Leu Val Ile His Lys
1               5                   10

<210> SEQ ID NO 397
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: [F5]-Ile
<220> FEATURE:
<221> NAME/KEY: MOD_RES
<222> LOCATION: (10)..(10)
<223> OTHER INFORMATION: Lys(F5)-[OH]

<400> SEQUENCE: 397

Ile His Pro Phe His Leu Leu Tyr His Lys
1               5                   10

<210> SEQ ID NO 398
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Ile
<220> FEATURE:
<221> NAME/KEY: MOD_RES
<222> LOCATION: (10)..(10)
<223> OTHER INFORMATION: Lys(F5)-[OH]

<400> SEQUENCE: 398

Ile His Pro Phe His Leu Leu Tyr Tyr Lys
1               5                   10

<210> SEQ ID NO 399
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Lys(F5)
<220> FEATURE:
<221> NAME/KEY: MOD_RES
<222> LOCATION: (4)..(4)
<223> OTHER INFORMATION: Lys(F5)
<220> FEATURE:
<221> NAME/KEY: MOD_RES
<222> LOCATION: (5)..(5)
<223> OTHER INFORMATION: Gly-[OH]

<400> SEQUENCE: 399

Lys Lys Lys Lys Gly
1               5

<210> SEQ ID NO 400
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Lys(F5)
<220> FEATURE:
<221> NAME/KEY: MOD_RES
<222> LOCATION: (4)..(4)
<223> OTHER INFORMATION: Lys(F5)
<220> FEATURE:
<221> NAME/KEY: MOD_RES
<222> LOCATION: (7)..(7)
```

```
<223> OTHER INFORMATION: Gly-[OH]

<400> SEQUENCE: 400

Lys Lys Lys Lys Lys Lys Gly
1               5

<210> SEQ ID NO 401
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Lys
<220> FEATURE:
<221> NAME/KEY: MOD_RES
<222> LOCATION: (10)..(10)
<223> OTHER INFORMATION: Lys(F5)-[OH]

<400> SEQUENCE: 401

Lys His Pro Phe His Leu Val Ile His Lys
1               5                   10

<210> SEQ ID NO 402
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Succinyl-Lys(F5)
<220> FEATURE:
<221> NAME/KEY: MOD_RES
<222> LOCATION: (6)..(6)
<223> OTHER INFORMATION: Lys(F5)-[NH2]

<400> SEQUENCE: 402

Lys Gly Phe Leu Gly Lys
1               5

<210> SEQ ID NO 403
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Succinyl-Lys(F6)
<220> FEATURE:
<221> NAME/KEY: MOD_RES
<222> LOCATION: (6)..(6)
<223> OTHER INFORMATION: Lys(F6)-[NH2]

<400> SEQUENCE: 403

Lys Gly Phe Leu Gly Lys
1               5

<210> SEQ ID NO 404
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Succinyl-Lys(F5)
<220> FEATURE:
<221> NAME/KEY: MOD_RES
<222> LOCATION: (4)..(4)
<223> OTHER INFORMATION: Lys(F5)-[NH2]

<400> SEQUENCE: 404

Lys Arg Arg Lys
1

<210> SEQ ID NO 405
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Succinyl-Lys(F6)
<220> FEATURE:
<221> NAME/KEY: MOD_RES
<222> LOCATION: (4)..(4)
<223> OTHER INFORMATION: Lys(F6)-[NH2]

<400> SEQUENCE: 405

Lys Arg Arg Lys
1

<210> SEQ ID NO 406
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Succinyl-Lys(F6)
<220> FEATURE:
<221> NAME/KEY: MOD_RES
<222> LOCATION: (5)..(5)
<223> OTHER INFORMATION: Lys(F6)-[NH2]

<400> SEQUENCE: 406

Lys Ala Arg Arg Lys
1               5

<210> SEQ ID NO 407
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Succinyl-Lys(F5)
<220> FEATURE:
<221> NAME/KEY: MOD_RES
<222> LOCATION: (4)..(4)
<223> OTHER INFORMATION: Lys(F5)-[NH2]

<400> SEQUENCE: 407
```

```
Lys Lys Lys Lys
1

<210> SEQ ID NO 408
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Succinyl-Lys(F6)
<220> FEATURE:
<221> NAME/KEY: MOD_RES
<222> LOCATION: (5)..(5)
<223> OTHER INFORMATION: Lys(F6)-[NH2]

<400> SEQUENCE: 408

Lys Arg Arg Arg Lys
1               5

<210> SEQ ID NO 409
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys-[OH]

<400> SEQUENCE: 409

His Gly Pro Ile Lys
1               5

<210> SEQ ID NO 410
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Asn
<220> FEATURE:
<221> NAME/KEY: MOD_RES
<222> LOCATION: (5)..(5)
<223> OTHER INFORMATION: Lys-[OH]

<400> SEQUENCE: 410

Asn Gly Pro Ile Lys
1               5

<210> SEQ ID NO 411
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: [F6]-Gly
<220> FEATURE:
<221> NAME/KEY: MOD_RES
<222> LOCATION: (7)..(7)
<223> OTHER INFORMATION: Lys(F6)-[OH]

<400> SEQUENCE: 411

Gly Pro Leu Gly Val Arg Lys
1               5

<210> SEQ ID NO 412
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Gly
<220> FEATURE:
<221> NAME/KEY: MOD_RES
<222> LOCATION: (7)..(7)
<223> OTHER INFORMATION: Lys(F5)-[OH]

<400> SEQUENCE: 412

Gly Val Arg Leu Gly Pro Lys
1               5

<210> SEQ ID NO 413
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Gly
<220> FEATURE:
<221> NAME/KEY: MOD_RES
<222> LOCATION: (7)..(7)
<223> OTHER INFORMATION: Lys(F5)-[OH]

<400> SEQUENCE: 413

Gly Pro Leu Gly Val Arg Lys
1               5

<210> SEQ ID NO 414
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F6]-His
<220> FEATURE:
<221> NAME/KEY: MOD_RES
<222> LOCATION: (5)..(5)
<223> OTHER INFORMATION: Lys(F6)-[OH]

<400> SEQUENCE: 414

His Gly Pro Asn Lys
1               5
```

```
<210> SEQ ID NO 415
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys-OH

<400> SEQUENCE: 415

Lys Pro Leu Gly Val Arg Lys
1               5

<210> SEQ ID NO 416
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Arg(Pbf)
<220> FEATURE:
<221> NAME/KEY: MOD_RES
<222> LOCATION: (3)..(3)
<223> OTHER INFORMATION: Lys(boc)
<220> FEATURE:
<221> NAME/KEY: MOD_RES
<222> LOCATION: (4)..(4)
<223> OTHER INFORMATION: Naphthylalanine
<220> FEATURE:
<221> NAME/KEY: MOD_RES
<222> LOCATION: (5)..(6)
<223> OTHER INFORMATION: Arg(Pbf)
<220> FEATURE:
<221> NAME/KEY: MOD_RES
<222> LOCATION: (7)..(7)
<223> OTHER INFORMATION: Lys(boc)
<220> FEATURE:
<221> NAME/KEY: MOD_RES
<222> LOCATION: (8)..(8)
<223> OTHER INFORMATION: Gly-OH

<400> SEQUENCE: 416

Arg Arg Lys Ala Arg Arg Lys Gly
1               5

<210> SEQ ID NO 417
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys(COCF3)
<220> FEATURE:
<221> NAME/KEY: MOD_RES
<222> LOCATION: (10)..(10)
<223> OTHER INFORMATION: Lys(F5)-[OH]

<400> SEQUENCE: 417

Lys His Pro Phe His Leu Val Ile His Lys
1               5                   10

<210> SEQ ID NO 418
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(COCF3)
<220> FEATURE:
<221> NAME/KEY: MOD_RES
<222> LOCATION: (10)..(10)
<223> OTHER INFORMATION: Lys-(OH)

<400> SEQUENCE: 418

Lys His Pro Phe His Leu Val Ile His Lys
1               5                   10

<210> SEQ ID NO 419
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (10)..(10)
<223> OTHER INFORMATION: Lys(F5)-[NHmPEG20k]

<400> SEQUENCE: 419

Lys His Pro Phe His Leu Val Ile His Lys
1               5                   10

<210> SEQ ID NO 420
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Ile
<220> FEATURE:
<221> NAME/KEY: MOD_RES
<222> LOCATION: (10)..(10)
<223> OTHER INFORMATION: Lys(F5)-[OH]

<400> SEQUENCE: 420

Ile His Pro Phe His Leu Leu Tyr Tyr Lys
1               5                   10

<210> SEQ ID NO 421
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Lys-[OH]

<400> SEQUENCE: 421
```

Ile His Pro Phe His Leu Leu Tyr Tyr Lys
1               5                   10

<210> SEQ ID NO 422
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentynoyl-Lys(F5)
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: Lys(F5)-PEG20kDa

<400> SEQUENCE: 422

Lys Gly Phe Leu Gly Ala Lys
1               5

<210> SEQ ID NO 423
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentynoyl-Lys(F6)
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: Lys(F6)-PEG20kDa

<400> SEQUENCE: 423

Lys Gly Phe Leu Gly Ala Lys
1               5

<210> SEQ ID NO 424
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentynoyl-Lys(F5)
<220> FEATURE:
<221> NAME/KEY: MOD_RES
<222> LOCATION: (7)..(7)
<223> OTHER INFORMATION: Lys(F5)-PEG20kDa

<400> SEQUENCE: 424

Lys Pro Leu Gly Val Arg Lys
1               5

<210> SEQ ID NO 425

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)-[PEG20kDa]

<400> SEQUENCE: 425

His Gly Pro Arg Lys
1               5

<210> SEQ ID NO 426
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)
<220> FEATURE:
<221> NAME/KEY: MOD_RES
<222> LOCATION: (10)..(10)
<223> OTHER INFORMATION: Beta-Ala-[PEG20kDa]

<400> SEQUENCE: 426

His Gly Pro Asn Lys His Gly Pro Asn Ala
1               5                   10

<210> SEQ ID NO 427
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-His
<220> FEATURE:
<221> NAME/KEY: MOD_RES
<222> LOCATION: (5)..(5)
<223> OTHER INFORMATION: Lys(F5)-[PEG20kDa]

<400> SEQUENCE: 427

His Gly Pro Asn Lys
1               5

<210> SEQ ID NO 428
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: [F5]-Lys
<220> FEATURE:
<221> NAME/KEY: MOD_RES
<222> LOCATION: (10)..(10)
<223> OTHER INFORMATION: Lys(F5)-[NHmPEG20k]

<400> SEQUENCE: 428

Lys His Pro Phe His Leu Val Ile His Lys
1               5                   10

<210> SEQ ID NO 429
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Lys(Ac)
<220> FEATURE:
<221> NAME/KEY: MOD_RES
<222> LOCATION: (10)..(10)
<223> OTHER INFORMATION: Lys(F5)-[OH]

<400> SEQUENCE: 429

Lys His Pro Phe His Leu Val Ile His Lys
1               5                   10

<210> SEQ ID NO 430
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Lys
<220> FEATURE:
<221> NAME/KEY: MOD_RES
<222> LOCATION: (6)..(6)
<223> OTHER INFORMATION: Cyclohexylalanine
<220> FEATURE:
<221> NAME/KEY: MOD_RES
<222> LOCATION: (10)..(10)
<223> OTHER INFORMATION: Lys(F5)-[OH]

<400> SEQUENCE: 430

Lys His Pro Phe His Ala Val Ile His Lys
1               5                   10

<210> SEQ ID NO 431

<400> SEQUENCE: 431

000

<210> SEQ ID NO 432

<400> SEQUENCE: 432

000

<210> SEQ ID NO 433
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]-Lys
<220> FEATURE:
<221> NAME/KEY: MOD_RES
<222> LOCATION: (10)..(10)
<223> OTHER INFORMATION: Lys(F5)-[NHmPEG5k]

<400> SEQUENCE: 433

Lys His Pro Phe His Leu Val Ile His Lys
1               5                   10

<210> SEQ ID NO 434
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F6]-Gly
<220> FEATURE:
<221> NAME/KEY: MOD_RES
<222> LOCATION: (7)..(7)
<223> OTHER INFORMATION: Lys(F6)-[YPEG 2x20kDa]

<400> SEQUENCE: 434

Gly Pro Leu Gly Val Arg Lys
1               5

<210> SEQ ID NO 435
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG-20kDa-succinyl]-Lys(F6)
<220> FEATURE:
<221> NAME/KEY: MOD_RES
<222> LOCATION: (6)..(6)
<223> OTHER INFORMATION: Lys(F6)-[NH2]

<400> SEQUENCE: 435

Lys Gly Phe Leu Gly Lys
1               5

<210> SEQ ID NO 436
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [dPEG-1kDa-succinyl]-Lys(F6)
<220> FEATURE:
<221> NAME/KEY: MOD_RES
<222> LOCATION: (6)..(6)
<223> OTHER INFORMATION: Lys(F6)-[NH2]

<400> SEQUENCE: 436
```

```
Lys Gly Phe Leu Gly Lys
1               5

<210> SEQ ID NO 437
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [dppa-succinyl]-Lys(F6)
<220> FEATURE:
<221> NAME/KEY: MOD_RES
<222> LOCATION: (6)..(6)
<223> OTHER INFORMATION: Lys(F6)-[NH2]

<400> SEQUENCE: 437

Lys Gly Phe Leu Gly Lys
1               5

<210> SEQ ID NO 438
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG-20kDa-succinyl]-Lys(F6)
<220> FEATURE:
<221> NAME/KEY: MOD_RES
<222> LOCATION: (4)..(4)
<223> OTHER INFORMATION: Lys(F6)-[NH2]

<400> SEQUENCE: 438

Lys Arg Arg Lys
1

<210> SEQ ID NO 439
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [dPEG-1kDa-succinyl]-Lys(F6)
<220> FEATURE:
<221> NAME/KEY: MOD_RES
<222> LOCATION: (4)..(4)
<223> OTHER INFORMATION: Lys(F6)-[NH2]

<400> SEQUENCE: 439

Lys Arg Arg Lys
1

<210> SEQ ID NO 440
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: [dppa-succinyl]-Lys(F6)
<220> FEATURE:
<221> NAME/KEY: MOD_RES
<222> LOCATION: (4)..(4)
<223> OTHER INFORMATION: Lys(F6)-[NH2]

<400> SEQUENCE: 440

Lys Arg Arg Lys
1

<210> SEQ ID NO 441
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG-20kDa-succinyl]-Lys(F6)
<220> FEATURE:
<221> NAME/KEY: MOD_RES
<222> LOCATION: (5)..(5)
<223> OTHER INFORMATION: Lys(F6)-[NH2]

<400> SEQUENCE: 441

Lys Ala Arg Arg Lys
1               5

<210> SEQ ID NO 442
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [mPEG-20kDa-succinyl]-Lys(F6)
<220> FEATURE:
<221> NAME/KEY: MOD_RES
<222> LOCATION: (5)..(5)
<223> OTHER INFORMATION: Lys(F6)-[NH2]

<400> SEQUENCE: 442

Lys Arg Arg Arg Lys
1               5

<210> SEQ ID NO 443
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 443

Xaa Gly Phe Leu Gly Xaa Gly Phe Leu Gly
1               5                   10
```

-continued

```
<210> SEQ ID NO 444
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 444

Xaa Gly Arg Arg Gly Xaa Gly Phe Leu Gly
1               5                   10

<210> SEQ ID NO 445
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 445

Xaa Arg Arg Arg Xaa Xaa Gly Phe Leu Gly
1               5                   10

<210> SEQ ID NO 446
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 446

Xaa Xaa Arg Arg Xaa Xaa Gly Phe Leu Gly
1               5                   10

<210> SEQ ID NO 447
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
```

<222> LOCATION: (6)..(6)
<223> OTHER INFORMATION: Any amino acid

<400> SEQUENCE: 447

Xaa Xaa Arg Arg Arg Xaa Gly Phe Leu Gly
1               5                   10

<210> SEQ ID NO 448
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Naphthylalanine
<220> FEATURE:
<221> NAME/KEY: MOD_RES
<222> LOCATION: (5)..(5)
<223> OTHER INFORMATION: Naphthylalanine
<220> FEATURE:
<221> NAME/KEY: MOD_RES
<222> LOCATION: (6)..(6)
<223> OTHER INFORMATION: Any amino acid

<400> SEQUENCE: 448

Xaa Ala Lys Lys Ala Xaa Gly Phe Leu Gly
1               5                   10

<210> SEQ ID NO 449
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (5)..(5)
<223> OTHER INFORMATION: Naphthylalanine
<220> FEATURE:
<221> NAME/KEY: MOD_RES
<222> LOCATION: (6)..(6)
<223> OTHER INFORMATION: Any amino acid

<400> SEQUENCE: 449

Xaa Xaa Lys Lys Ala Xaa Gly Phe Leu Gly
1               5                   10

<210> SEQ ID NO 450
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (5)..(5)

<223> OTHER INFORMATION: Naphthylalanine
<220> FEATURE:
<221> NAME/KEY: MOD_RES
<222> LOCATION: (6)..(6)
<223> OTHER INFORMATION: Any amino acid

<400> SEQUENCE: 450

Xaa Xaa Arg Arg Ala Xaa Gly Arg Arg Arg
1               5                   10

<210> SEQ ID NO 451
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cyclohexylalanine

<400> SEQUENCE: 451

Lys His Pro Phe His Ala Val Ile His Lys
1               5                   10

<210> SEQ ID NO 452
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(CO Me) or Lys(CO CF3)
<220> FEATURE:
<221> NAME/KEY: MOD_RES
<222> LOCATION: (6)..(6)
<223> OTHER INFORMATION: Cyclohexylalanine

<400> SEQUENCE: 452

Lys His Pro Phe His Ala Val Ile His Lys
1               5                   10

<210> SEQ ID NO 453
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (6)..(6)
<223> OTHER INFORMATION: Cyclohexylalanine
<220> FEATURE:
<221> NAME/KEY: MOD_RES
<222> LOCATION: (10)..(10)
<223> OTHER INFORMATION: Lys(F5)[OH]

<400> SEQUENCE: 453

Lys His Pro Phe His Ala Val Ile His Lys
1               5                   10

<210> SEQ ID NO 454

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (6)..(6)
<223> OTHER INFORMATION: Cyclohexylalanine
<220> FEATURE:
<221> NAME/KEY: MOD_RES
<222> LOCATION: (10)..(10)
<223> OTHER INFORMATION: Lys(F5)[NH mPEG5k]

<400> SEQUENCE: 454

Lys His Pro Phe His Ala Val Ile His Lys
1               5                   10

<210> SEQ ID NO 455
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys
<220> FEATURE:
<221> NAME/KEY: MOD_RES
<222> LOCATION: (6)..(6)
<223> OTHER INFORMATION: Cyclohexylalanine
<220> FEATURE:
<221> NAME/KEY: MOD_RES
<222> LOCATION: (10)..(10)
<223> OTHER INFORMATION: Lys(F5)[NH mPEG20k]

<400> SEQUENCE: 455

Lys His Pro Phe His Ala Val Ile His Lys
1               5                   10

<210> SEQ ID NO 456
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys(CO Me)
<220> FEATURE:
<221> NAME/KEY: MOD_RES
<222> LOCATION: (6)..(6)
<223> OTHER INFORMATION: Cyclohexylalanine
<220> FEATURE:
<221> NAME/KEY: MOD_RES
<222> LOCATION: (10)..(10)
<223> OTHER INFORMATION: Lys(F5)[OH]

<400> SEQUENCE: 456

Lys His Pro Phe His Ala Val Ile His Lys
1               5                   10

<210> SEQ ID NO 457
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys(CO CF3)
<220> FEATURE:
<221> NAME/KEY: MOD_RES
<222> LOCATION: (6)..(6)
<223> OTHER INFORMATION: Cyclohexylalanine
<220> FEATURE:
<221> NAME/KEY: MOD_RES
<222> LOCATION: (10)..(10)
<223> OTHER INFORMATION: Lys(F5)[OH]

<400> SEQUENCE: 457

Lys His Pro Phe His Ala Val Ile His Lys
1               5                   10

<210> SEQ ID NO 458
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [F5]Lys(CO CF3)
<220> FEATURE:
<221> NAME/KEY: MOD_RES
<222> LOCATION: (6)..(6)
<223> OTHER INFORMATION: Cyclohexylalanine
<220> FEATURE:
<221> NAME/KEY: MOD_RES
<222> LOCATION: (10)..(10)
<223> OTHER INFORMATION: Lys(F5)-[OH]

<400> SEQUENCE: 458

Lys His Pro Phe His Ala Val Ile His Lys
1               5                   10

<210> SEQ ID NO 459
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: Lys-[OH]

<400> SEQUENCE: 459

Lys Gly Phe Leu Gly Ala Lys
1               5

<210> SEQ ID NO 460
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: Lys-[OH]

<400> SEQUENCE: 460

Lys Gly Phe Leu Gly Ala Lys
1               5

<210> SEQ ID NO 461
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [pentynoyl]-Lys

<400> SEQUENCE: 461

Lys Pro Leu Gly Val Arg Lys
1               5

<210> SEQ ID NO 462
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [H]-His
<220> FEATURE:
<221> NAME/KEY: MOD_RES
<222> LOCATION: (9)..(9)
<223> OTHER INFORMATION: Asn-[OH]

<400> SEQUENCE: 462

His Gly Pro Asn Lys His Gly Pro Asn
1               5

<210> SEQ ID NO 463
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [H]-Gly
<220> FEATURE:
<221> NAME/KEY: MOD_RES
<222> LOCATION: (7)..(7)
<223> OTHER INFORMATION: Lys-[OH]
```

```
<400> SEQUENCE: 463

Gly Pro Leu Gly Val Arg Lys
1               5

<210> SEQ ID NO 464
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys
<220> FEATURE:
<221> NAME/KEY: MOD_RES
<222> LOCATION: (6)..(6)
<223> OTHER INFORMATION: Lys-[NH2]

<400> SEQUENCE: 464

Lys Gly Phe Leu Gly Lys
1               5

<210> SEQ ID NO 465
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys
<220> FEATURE:
<221> NAME/KEY: MOD_RES
<222> LOCATION: (6)..(6)
<223> OTHER INFORMATION: Lys-[NH2]

<400> SEQUENCE: 465

Lys Gly Phe Leu Gly Lys
1               5

<210> SEQ ID NO 466
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys
<220> FEATURE:
<221> NAME/KEY: MOD_RES
<222> LOCATION: (6)..(6)
<223> OTHER INFORMATION: Lys-[NH2]

<400> SEQUENCE: 466

Lys Gly Phe Leu Gly Lys
1               5

<210> SEQ ID NO 467
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: [succinyl]-Lys
<220> FEATURE:
<221> NAME/KEY: MOD_RES
<222> LOCATION: (4)..(4)
<223> OTHER INFORMATION: Lys-[NH2]

<400> SEQUENCE: 467

Lys Arg Arg Lys
1

<210> SEQ ID NO 468
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys
<220> FEATURE:
<221> NAME/KEY: MOD_RES
<222> LOCATION: (4)..(4)
<223> OTHER INFORMATION: Lys-[NH2]

<400> SEQUENCE: 468

Lys Arg Arg Lys
1

<210> SEQ ID NO 469
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys
<220> FEATURE:
<221> NAME/KEY: MOD_RES
<222> LOCATION: (4)..(4)
<223> OTHER INFORMATION: Lys-[NH2]

<400> SEQUENCE: 469

Lys Arg Arg Lys
1

<210> SEQ ID NO 470
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys
<220> FEATURE:
<221> NAME/KEY: MOD_RES
<222> LOCATION: (5)..(5)
<223> OTHER INFORMATION: Lys-[NH2]

<400> SEQUENCE: 470

Lys Ala Arg Arg Lys
1               5
```

```
<210> SEQ ID NO 471
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [succinyl]-Lys
<220> FEATURE:
<221> NAME/KEY: MOD_RES
<222> LOCATION: (5)..(5)
<223> OTHER INFORMATION: Lys-[NH2]

<400> SEQUENCE: 471

Lys Ala Arg Arg Lys
1               5

<210> SEQ ID NO 472
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(COCF3)
<220> FEATURE:
<221> NAME/KEY: MOD_RES
<222> LOCATION: (6)..(6)
<223> OTHER INFORMATION: Cyclohexylalanine
<220> FEATURE:
<221> NAME/KEY: MOD_RES
<222> LOCATION: (10)..(10)
<223> OTHER INFORMATION: Lys-(OH)

<400> SEQUENCE: 472

Lys His Pro Phe His Ala Val Ile His Lys
1               5                   10
```

FLUORESCENT IMAGING AGENTS

CROSS-REFERENCE TO RELATED APPLICATION

This application is a divisional of U.S. patent application Ser. No. 14/457,064, filed Aug. 11, 2014, which is a divisional of U.S. patent application Ser. No. 12/355,777, filed Jan. 17, 2009, issued as U.S. Pat. No. 8,815,214, which claims the benefit of and priority to U.S. Provisional Patent Application No. 61/022,014, filed Jan. 18, 2008, the entire contents of each of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jan. 12, 2017, is named VIS-029D2_SL.txt and is 143,360 bytes in size.

BACKGROUND

Current approaches for assessing of molecular endpoints in disease usually require tissue and blood sampling, surgery, and in the case of experimental animals, sacrifice at different time points. Despite improvements in noninvasive imaging, more sensitive and specific imaging agents and methods are urgently needed. Imaging techniques capable of visualizing specific molecular targets and/or entire pathways would significantly enhance the ability to diagnose and assess treatment efficacy of therapeutic interventions for many different disease states. Most current imaging techniques report primarily on anatomical or physiological information (e.g., magnetic resonance imaging (MRI), computed tomography (CT), and ultrasound). Newer modalities, such as, optical imaging and new molecular imaging probes have the potential to revolutionize the way disease is detected, treated, and monitored.

Molecular imaging is a developing field in the imaging sciences that transcends the traditional boundaries of imaging structure or physiology, and has the potential to revolutionize current research and clinical practices towards real molecular medicine. The one paradigm for molecular imaging involves the use of a "molecular" probe or agent that selectively targets a particular gene, protein, receptor or a cellular function, with the absence, presence, amount or concentration of the specific target being indicative of a particular disease state.

In particular, optical imaging offers several strong performance attributes that make it a truly powerful molecular imaging approach, both in the research and clinical settings. Specifically, optical imaging is fast, safe, cost effective and highly sensitive. Scan times typically are on the order of seconds to minutes, there is no ionizing radiation, and the imaging systems are relatively simple to use. In addition, optical probes can be designed as dynamic molecular imaging agents that can alter their reporting profiles in vivo to provide molecular and functional information in real time. In order to achieve maximum penetration and sensitivity in vivo, the choice for most optical imaging in biological systems is within the red and near-infrared (NIR) spectral region, although other wavelengths in the visible region can also be used. In the NIR wavelength range, absorption by physiologically abundant absorbers such as hemoglobin or water is minimized.

Although different types of optical imaging probes have been developed including (1) probes that become activated after target contact (e.g., binding or interaction), (2) wavelength shifting beacons, (3) multicolor fluorescence probes, (4) probes that have high binding affinity to targets, i.e., that remain within a target region while non-specific probes are cleared from the body (Achilefu et al., Invest. Radiol., 35:479-485, 2000; Becker et al., Nature Biotech. 19:327-331, 2001; Bujai et al., J. Biomed. Opt. 6:122-133, 2001; Ballou et al. Biotechnol. Prog. 13:649-658, 1997; and Neri et al., Nature Biotech. 15:1271-1275, 1997), and (5) fluorescent semiconductor based probes, there is still an ongoing need for imaging probes that, for example, are capable of providing high quality images and molecular information.

SUMMARY OF THE INVENTION

The present invention provides fluorescent imaging agents that have significantly enhanced fluorescent properties upon activation and can be used for in vivo and in vitro imaging applications. The imaging agents have a fluorescence reporter system, which in certain embodiments, contains two fluorophores or a fluorophore and a quencher, where one fluorophore quenches the other fluorophore or the quencher quenches the fluorophore. Although the imaging agents may have no more than two fluorophores they still have an extinction coefficient sufficient for in vivo imaging applications. Furthermore, their size permits the agents to become quickly distributed through the tissues or body fluid of a subject, which allows the agent to travel to tissues or cells for activation by proteases, binding to cell surface receptors or internalization within cells.

The imaging agents have enhanced fluorescent properties upon activation and under certain circumstances can have magnetic properties, for example, paramagnetic or superparamagnetic properties, so that the imaging agents can be used as MRI or multi-modality imaging agents (for example, optical imaging and magnetic resonance imaging). In addition, the imaging agents optionally can include diagnostic and or therapeutic moieties, for example, radioactive metals, so that the resulting imaging agents can be used like radiopharmaceuticals, nuclear imaging agents or multi-modality imaging agents (for example, in an optical imaging and nuclear imaging environment).

In one aspect, the invention provides an intramolecularly-quenched imaging agent. The agent comprises (a) an enzymatically cleavable oligopeptide comprising from about 2 to about 30 amino acid residues; (b) an optional biological modifier chemically linked to the enzymatically cleavable oligopeptide; and (c) either two fluorophores or one fluorophore and one quencher, each covalently linked, directly or indirectly, to the oligopeptide or to the optional biological modifier, wherein one fluorophore quenches the other fluorophore or the quencher quenches the fluorophore and upon enzymatic cleavage of the oligopeptide, at least one fluorophore becomes unquenched and is capable of producing a greater fluorescent signal when excited by electromagnetic radiation than before enzymatic cleavage of the oligopeptide.

The oligopeptide can comprise from about 2 to about 25 amino acid residues, from about 2 to about 14 amino acid residues, from about 4 to about 10 amino acid residues, or from about 5 to about 8 amino acid residues.

In certain embodiments, the imaging agent can be represented by Formula I:

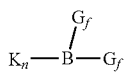

(I)

wherein:
B is [$M_m$-ECO-$M_m$];
ECO is an enzymatically cleavable oligopeptide;
G is L-F;
F is a fluorophore or quencher,
M is a biological modifier.
K is N-L;
N is a non-fluorescent reporter;
L, independently, for each occurrence, is a linker moiety or a bond;
n is an integer from 0 to 3;
m, independently, for each occurrence, is 0 or 1, and optionally at least one m is 1; and
f, independently, for each occurrence, is an integer from 0 to 2, wherein the total number of fluorophores F in the agent is no greater than 2.

Each F can be chemically linked, directly or through the linker moiety L, to a separate amino acid of the oligopeptide. Alternatively, at least one F is chemically linked, directly or through the linker moiety L, to M. In certain embodiments, ECO is a cyclic oligopeptide.

In addition, in certain embodiments, the imaging agent is represented by Formula II:

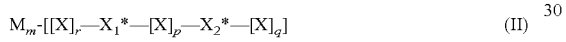

(II)

wherein:
X, independently, for each occurrence, is an amino acid residue;
$X_1^*$ and $X_2^*$ are each independently X-L-F;
L, independently, for each occurrence, is a linker moiety or a bond;
F is a fluorophore;
M is a biological modifier;
m is 0, 1 or 2;
r is an integer from 0 to 28;
p is an integer from 1 to 28;
q is an integer from 0 to 28; wherein the sum of r, p and q is no greater than 28.

Depending upon the circumstances, amino acid residue $X_1^*$ is a lysine and/or amino acid residue $X_2^*$ is a lysine.

In another aspect, the invention provides an intramolecularly-quenched imaging agent represented by Formula III:

[[ECO-$G_g$]$_p$-M]-$K_n$ (III)

wherein:
ECO is an enzymatically cleavable oligopeptide;
G is L-F;
F, independently, is selected from a fluorophore or quencher, wherein at least one F is a fluorophore;
L, independently for each occurrence, is selected from a linker moiety or a bond;
M is a biological modifier;
K is L-N;
N is a non-fluorescent reporter;
p is an integer from 1 to 4;
n is an integer from 0 to 3; and
g, independently, for each occurrence, is an integer from 1 to 2, wherein the sum of each occurrence of g is no greater than 2.

The oligopeptide can comprise from about 2 to about 25 amino acid residues, from about 2 to about 14 amino acid residues, from about 4 to about 10 amino acid residues, or from about 5 to about 8 amino acid residues. In certain embodiments, at least one F is chemically linked, directly or indirectly, to a lysine residue.

In another aspect the invention provides cyclic intramolecularly quenched imaging agent comprising (a) a first fluorophore chemically linked, directly or indirectly, to the C-terminus of a first cleavable oligopeptide and chemically linked, directly or indirectly, to the N-terminus of a second, optionally cleavable, oligopeptide; (b) a second fluorophore chemically linked, directly or indirectly, to the N-terminus of the first cleavable oligopeptide and chemically linked directly or indirectly, to the C-terminus of the second, optionally cleavable oligopeptide; and (c) optionally, at least one biological modifier chemically linked to the first or second oligopeptide or fluorophore.

In one embodiment, the imaging agent can be represented by Formula IV:

(IV)

Wherein,
ECO, independently, for each occurrence, is an enzymatically cleavable oligopeptide;
G is L-F-L;
F, independently, for each occurrence, is a fluorophore;
L, independently, for each occurrence, is a linker moiety or a bond;
M is a biological modifier;
K is L-N;
N is a non-fluorescent reporter;
n is an integer from 0 to 3; and
m is an integer from 0 to 3.

In another aspect, the invention provides an intramolecularly-quenched imaging agent comprising (a) an enzymatically cleavable oligopeptide comprising from 2 to 14 amino acid residues; (b) at least one biological modifier with a molecular weight of from about 5 kDa to about 35 kDa covalently linked to the enzymatically cleavable oligopeptide; and (c) two fluorophores, each covalently linked, directly or indirectly, to the oligopeptide at locations so that the fluorophores quench one another, and wherein, upon enzymatic cleavage of the oligopeptide, at least one fluorophore becomes unquenched and is capable of emitting a fluorescent signal when excited by electromagnetic radiation.

In another aspect, the invention provides an intramolecularly-quenched imaging agent represented by Formula V:

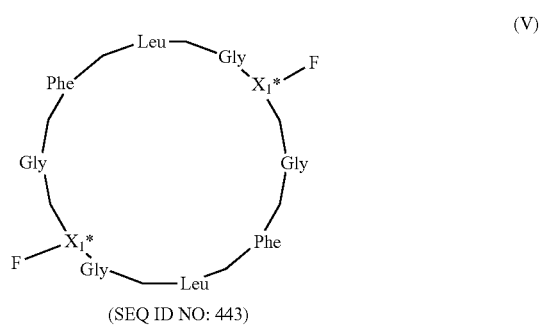

(V)

(SEQ ID NO: 443)

wherein
  $X_1^*$ independently, at each occurrence, is X-L-;
  X is an amino acid residue;
  L is a linker moiety or a bond; and
  F, independently, at each occurrence, is a fluorophore.

In another aspect, the invention provides an intramolecularly-quenched imaging agent represented by Formula VI:

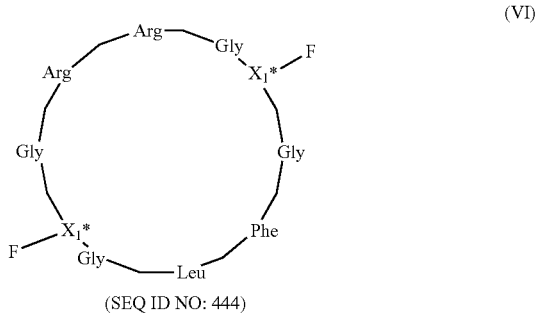

(VI)

(SEQ ID NO: 444)

wherein
  $X_1^*$, independently, at each occurrence, is X-L-;
  X is an amino acid residue;
  L is a linker moiety or a bond;
  F, independently, at each occurrence, is a fluorophore.

In any of the foregoing imaging agents, the fluorophore preferably is a far-red or a near-infrared fluorophore. Exemplary fluorophores include carbocyanine fluorophore and indocyanine fluorophore. It is understood that when the agent comprises two fluorophores, they can be the same or different. Other useful fluorophores and quenchers, as well as useful linkers, biological modifiers, and non-fluorescent reporters are described in more detail below.

In certain embodiments, the enzymatically cleavable oligopeptide is cleavable by at least one enzyme selected from the group consisting of a cathepsin, a matrix metalloprotease, a peptidase, a carboxypeptidase, a glycosidase, a lipase, a phospholipase, a phosphatase, a phosphodiesterase, a sulfatase, a reducatese, and a bacterial enzyme.

In addition, the invention provides methods of imaging in-vivo or in-vitro. In one aspect, the invention provides a method for performing in vivo optical imaging in a subject, for example, a mammal, for example, an animal or a human. The method comprises the steps of (a) administering to a subject one of more of the foregoing imaging agents, (b) allowing the agent or agents to distribute within the subject; (c) exposing the subject to light of a wavelength absorbable by at least one fluorophore in the agent; and (d) detecting a signal emitted by the fluorophore. The emitted signal can be used to construct an image, for example, a tomographic image. Furthermore, steps (c)-(d) can be repeated at predetermined intervals thereby to permit evaluation of the emitted signals of the agent in the subject over time. Similarly, steps (a)-(d) can be repeated at predetermined time intervals thereby to permit evaluation of the emitted signals of the agent in the subject over time. The presence, absence, or level of emitted signal can be indicative of a disease state and or can be used to detect and/or monitor a disease.

In another aspect, the invention provides an in vitro imaging method. The method comprises (a) contacting a sample, for example, a biological sample, with any one ore more of the foregoing imaging agents, (b) allowing the agent to bind to or associate with a biological target; optionally, removing unbound agents; and (d) detecting a signal emitted from the fluorophore thereby to determine whether the agent has been activated by or bound to the biological target.

The imaging agents can also be incorporated into a kit, for example, a kit with optional instructions for using the agents during in vivo or in vitro imaging. The kit optionally comprises components that aid in the use of the imaging agents for the disclosed methods, such as buffers, and other formulating agents. Alternatively, the kit can comprise medical devices that aid in the administration and/or detection of the agents to subjects.

The imaging agents and methods disclosed herein provide various advantages and have broad applications in both research and clinical settings. For example, the imaging agents and methods permit the acquisition of molecular images and optionally, high resolution anatomical images. The imaging agents and methods may provide insights into specific molecular abnormalities that form the basis of many diseases, and can be used to assess efficacy of established therapies at the molecular level. This, in turn, is expected to have an impact in drug development, drug testing, disease diagnosis, and choosing appropriate therapies and therapy changes in a given subject.

Other features and advantages of the invention will be apparent from the following figures, detailed description, and the claims.

BRIEF DESCRIPTION OF THE DRAWINGS

FIG. 5 depicts the enzymatic activation profile of the imaging agent Q65.

FIGS. 6A and 6B depict the enzymatic activation profiles of the exemplary imaging agents, referred to as Q92 (FIG. 6A) and Q93 (FIG. 6B).

FIGS. 7A-7D depict fluorescent images of control (FIGS. 7A and 7C) and ovariectomy induced osteoporosis (FIGS. 7B and 7D) in mice taken 4 hours (FIGS. 7A and 7B) and 24 hours (FIGS. 7C and 7D) after administering an exemplary imaging agent referred to as Q94. FIG. 7E is a bar chart showing quantitation of tibial fluorescence of induced osteoporosis 4 hours and 24 hours after administration of imaging agent Q94.

FIGS. 12A-D show images of mice on a control or low sodium diet using two exemplary imaging agents, wherein FIG. 12A represents a mouse on a control diet having received the imaging agent R20, FIG. 12B represents a mouse on a low sodium diet having received the imaging agent R20, FIG. 12C represents a mouse on a control diet having received the imaging agent R21, and FIG. 12D represents a mouse on a low sodium diet having received the imaging agent R21.

FIGS. 14A-14D show images created by fluorescent reflectance imaging after 6 hours (FIG. 14A) and after 24 hours (FIG. 14B) and by tomographic imaging after 6 hours (FIG. 14C) and after 24 hours (FIG. 14D) using the exemplary imaging agent R22.

FIG. 15 is a bar chart showing enzyme activation profiles of exemplary imaging agents referred to as R51, R52, R53, R55, R56, R57, R58, and R59.

FIGS. 16A-D depict images and quantification of the images in ApoE −/− and control mice using the exemplary imaging agent R51. FIG. 16A shows images taken by fluorescent tomography, and FIG. 16B is a bar chart showing quantification of the resulting images. FIG. 16C is a reflectance image, and FIG. 16D is a bar chart showing quantification of the resulting images.

FIG. 17A shows images taken by fluorescence tomography, and FIG. 17B is a bar chart showing quantification of the resulting images.

DETAILED DESCRIPTION

Figure 1:
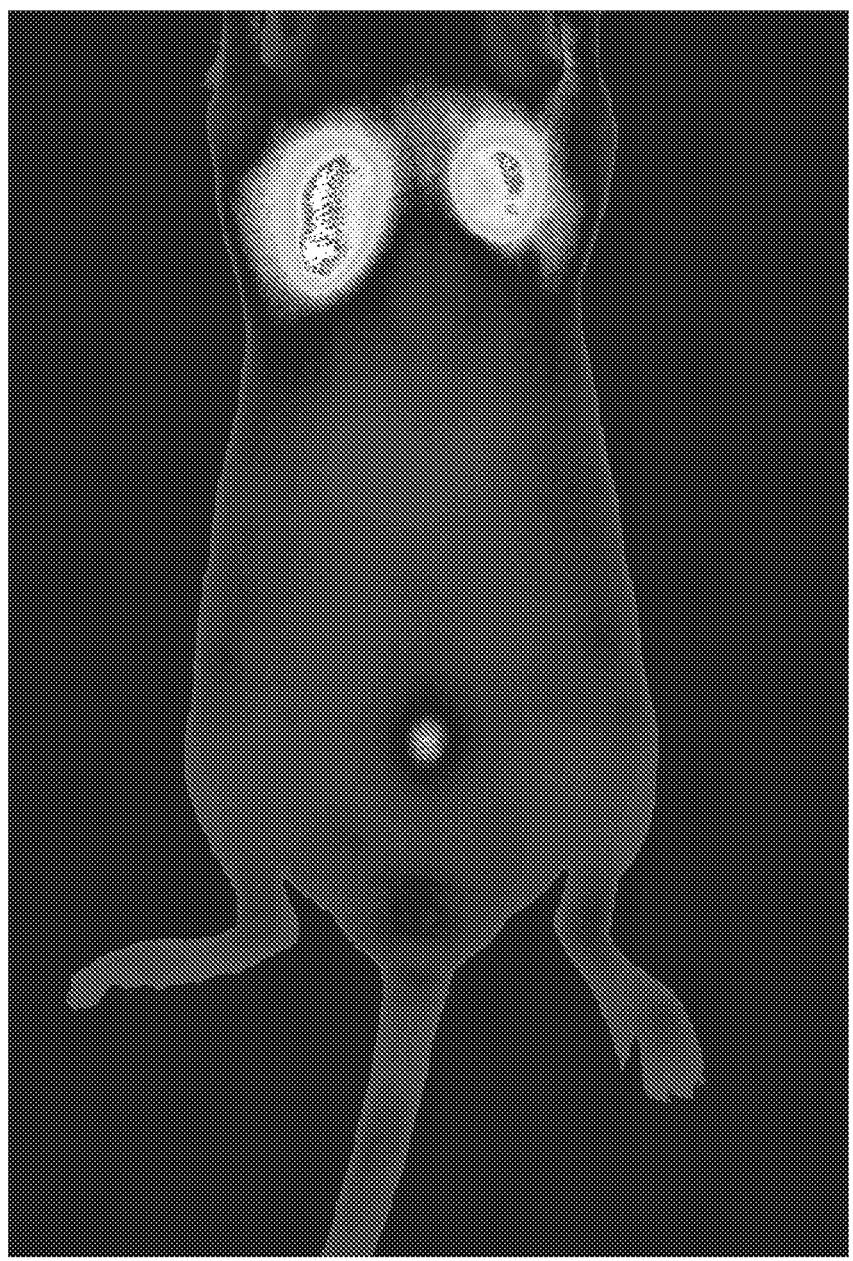
FIG. 1 depicts a planar image of bilateral tumors at 6 hours after administration of an exemplary imaging agent referred to as Q65.

This invention provides imaging agents that include one or more fluorescently labeled peptides. The fluorescence of the imaging agents is enhanced upon activation, e.g. an increase of fluorescence occurs, due to a cleavage of a peptide sequence by a protease after, before or during binding of the agent or following internalization of the imaging agent.

For example, the imaging agents of the present invention includes at least one oligopeptide comprising a proteolytic cleavage site, and two fluorophores or a single fluorophore and a quencher) covalently linked (directly or indirectly) to the oligopeptide or an optional biological modifier such that the fluorescence of at least one fluorophore is significantly quenched. Cleavage of the peptide by, for example, enzymatic cleavage, the agent emits a fluorescent signal when excited by electromagnetic radiation of appropriate wavelength and frequency. In certain embodiments, the imaging agents contain no more than two fluorophores. For example, the imaging agents may contain a fluorescent reporter system consisting of, or consisting essentially of, (i) two fluorophores, (ii) two fluorophores and two quenchers, (iii) two fluorophores and one quencher, or (iv) one fluorophore and one quencher.

As used herein, the term "quench" is understood to mean the process of partial or complete reduction of the fluorescent signal from a fluorophore. For example, a fluorescent signal can be reduced inter-molecularly or intra-molecularly through the placement of another fluorophore (either the same or a different fluorophore) in fluorescent quenching proximity to the first fluorophore or the placement of a non-fluorogenic quenching chromophore molecule (quencher) in fluorescent quenching proximity to the first fluorophore. The agent is de-quenched (or activated), for example, through the enzymatic cleavage of a peptide sequence.

The peptide of the imaging agents optionally can be chemically linked to a biological modifier. Furthermore the imaging agents optionally can be chemically linked to another non-fluorescent reporter. As used herein, the term "chemically linked" is understood to mean connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions.

In one aspect of the invention, the agents of the present invention are intramolecularly-quenched agents that include (a) an enzymatically cleavable oligopeptide comprising from about 2 to about 30 amino acid residues; (b) an optional biological modifier chemically linked to the enzymatically cleavable oligopeptide; and (c) either two fluorophores or one fluorophore and one quencher, each covalently linked, directly or indirectly, to the oligopeptide or to the biological modifier, wherein one fluorophore quenches the other fluorophore or the quencher quenches the fluorophore and upon enzymatic cleavage of the oligopeptide, at least one fluorophore becomes unquenched and is capable of producing a greater fluorescent signal when excited by electromagnetic radiation than before enzymatic cleavage of the oligopeptide.

For example, the imaging agent can comprise one or more oligopeptides from about 2 to about 25 amino acid residues in length, from about 2 to about 14 amino acid residues in length, from about 5 to about 8 amino acid residues in length, or from about 4 to about 10 amino acid residues in length. In certain embodiments, the oligopeptide comprises 2, 3, 4, 5, 6, 7, 8, 9, 10, 11, 12, 13, 14, 15, 16, 17, 18, 19, 20, 21, 22, 23, 24, or 25 amino acids.

The biological modifier, before being chemically linked to the enzymatically cleavable oligopeptide, can have a molecular weight less than about 35 kDa, for example, from about 10 kDa to about 35 kDa, from about 5 kDa to about 30 kDa, or from about 15 kDa to about 25 kDa. The biological modifier preferably is linked to the oligopeptide at a position that does not interfere with fluorescent quenching. For example, the biological modifier may be chemically linked to a moiety of the oligopeptide that is not positioned between two fluorophores that quench one another or between a fluorophore and a quencher.

In some embodiments, the imaging agents disclosed herein comprise two fluorophores, which may be the same or different. Imaging agents of the invention can further comprise a non-fluorescent reporter chemically linked to the enzymatically cleavable oligopeptide or the biological modifier.

In one embodiment, the imaging agent is represented by Formula I:

(I)

wherein:

B is [$M_m$-ECO-$M_m$];

ECO is the enzymatically cleavable oligopeptide;

G is L-F;

F is a fluorophore or quencher;

M is a biological modifier;

K is N-L;

N is a non-fluorescent reporter;

L, independently, for each occurrence, is a linker moiety or a bond;

n is an integer from 0 to 3 (for example, 0, 1, 2, or 3);

m, independently, for each occurrence, is 0 or 1, and optionally at least one m is 1; and f, independently, for each occurrence, is an integer from 0 to 2, wherein the total number of fluorophores F in the agent is no greater than 2.

In one embodiment, f is 2 and at least one F is a fluorophore.

Each F may be covalently linked, directly or indirectly (for example, through a linker moiety L), to a different amino acid residue (for example, a lysine) of the oligopeptide. In another embodiment, at least one F is covalently linked, directly or indirectly (for example, through a linker moiety L), to the biological modifier M. It is understood that ECO can be a linear oligopeptide, or can be a cyclic oligopeptide.

In another aspect, the imaging agent is represented by formula II:

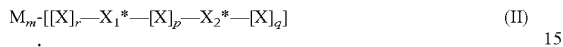

$$M_m\text{-}[[X]_r\text{—}X_1^*\text{—}[X]_p\text{—}X_2^*\text{—}[X]_q] \quad (II)$$

wherein:
X, independently, for each occurrence, is an amino acid residue;
$X_1^*$ and $X_2^*$ are each independently X-L-F;
L, independently, for each occurrence, is a linker moiety or a bond;
F is a fluorophore;
M is a biological modifier;
m is 0, 1 or 2;
r is an integer from 0 to 28;
p is an integer from 1 to 28;
q is an integer from 0 to 28; wherein the sum of r, p and q is no greater than 28.

In certain embodiments, the sum of r, p and q is 3, 4, 5, 6, 7, 8, 9 or 10. The amino acid residue $X_2^*$ and/or $X_1^*$ can be, for example, a lysine.

In another aspect, the imaging agent is represented by Formula III:

$$[[ECO\text{-}G_g]_p\text{-}M]\text{-}K_n \quad (III)$$

wherein:
ECO is an enzymatically cleavable oligopeptide;
G is L-F;
F, independently, is selected from a fluorophore or quencher, wherein at least one F is a fluorophore;
L, independently, for each occurrence, is selected from a linker moiety or a bond;
M is a biological modifier;
K is L-N;
N is a non-fluorescent reporter;
p is an integer from 1 to 4;
n is an integer from 0 to 3; and
g, independently, for each occurrence, is an integer from 1 to 2, wherein the sum of each occurrence of g is no greater than 2.

For example, ECO can be about 5 to about 8 amino acid residues in length. The integer n can be 0, 1, 2 or 3; g of formula III can be, independently for each occurrence, 1, 2, 3, 4 5 or 6. In certain embodiments, at least one F is chemically linked, directly or indirectly, to a lysine residue of the oligopeptide ECO. For example, F, for each occurrence, is covalently bound to the oligopeptide ECO.

In another aspect, the imaging agent is a cyclic intramolecularly quenched imaging agent comprising: a) a first fluorophore chemically linked, directly or indirectly, to the C-terminus of a first cleavable oligopeptide and chemically linked, directly or indirectly, to the N-terminus of a second, optionally cleavable oligopeptide; b) a second fluorophore chemically linked, directly or indirectly, to the N-terminus of the first cleavable oligopeptide and chemically linked directly or indirectly, to the C-terminus of the second, optionally cleavable oligopeptide; and c) optionally, at least one biological modifier chemically linked to the first or second oligopeptide or fluorophore.

In one embodiment, the cyclic agents can be represented by Formula IV:

wherein
ECO, independently for each occurrence, is an enzymatically cleavable oligopeptide;
G is L-F-L;
F, independently, for each occurrence, is a fluorophore;
L, independently, for each occurrence, is a linker moiety or a bond;
M is a biological modifier;
K is L-N;
N is a non-fluorescent reporter;
n is an integer from 0 to 3 (for example 0, 1, 2 or 3); and
m is an integer from 0 to 3 (for example 0, 1, 2 or 3).

Also contemplated herein are stereoisomeric forms, mixtures of stereoisomeric forms, and pharmaceutically acceptable salt forms of the disclosed imaging agents.

I. Fluorophores

As used herein, the term "fluorophore" is understood to mean a fluorochrome, a dye molecule, a organic or inorganic fluorophore, or metal chelate. A fluorophore can include a far-red or a near-infrared fluorophore. In certain embodiments, imaging agents disclosed herein include a fluorophore selected from the group consisting of a carbocyanine fluorophore or an indocyanine fluorophore. Exemplary fluorophores include sulfonated fluorophores. It is understood that fluorophores can also be nanoparticles having fluorescent or luminescent properties.

In certain embodiments, the fluorophores are near infrared fluorophores (NIRFs) with absorption and emission maximum between about 600 nm and about 900 nm. It is appreciated that the use of fluorophores with excitation and emission wavelengths in other spectrums can also be employed in the compositions and methods of the present invention.

For example, certain exemplary NIRFs have an extinction coefficient of at least 30,000 $M^{-1}$ $cm^{-1}$ per fluorophore molecule in aqueous medium, or at least 50,000 $M^{-1}$ $cm^{-1}$ per fluorophore molecule in aqueous medium. NIRFs preferably also have (1) high quantum yield (i.e., quantum yield greater than 5% in aqueous medium), (2) narrow excitation/emission spectrum, spectrally separated absorption and excitation spectra (i.e., excitation and emission maxima separated by at least 15 nm), (3) high chemical and photostability, (4) little or no nontoxicity, (5) good biocompatibility, biodegradability and excretability, and (6) commercial viability and scalable production for large quantities (i.e., gram and kilogram quantities) required for in vivo and human use.

An extinction coefficient of the agents that include a fluorophore can be calculated as the ratio of the absorbance of fluorophore at its absorption maxima (for example at ~750 nm for VivoTag-S-750, VisEn Medical) in a 1 cm path length cell to the concentration of particles, ($\varepsilon$=A/c1, where A is absorbance, c is molar concentration and 1 is path length in cm).

In particular, certain carbocyanine or polymethine fluorescent fluorophores can be used to produce the imaging agents of the invention, for example, those described in U.S. Pat. No. 6,747,159; U.S. Pat. No. 6,448,008; U.S. Pat. No. 6,136,612; U.S. Pat. Nos. 4,981,977; 5,268,486; U.S. Pat. No. 5,569,587; U.S. Pat. No. 5,569,766; U.S. Pat. No. 5,486,616; U.S. Pat. No. 5,627,027; U.S. Pat. No. 5,808,044; U.S. Pat. No. 5,877,310; U.S. Pat. No. 6,002,003; U.S. Pat. No. 6,004,536; U.S. Pat. No. 6,008,373; U.S. Pat. No. 6,043,025; U.S. Pat. No. 6,127,134; U.S. Pat. No. 6,130,094; U.S. Pat. No. 6,133,445; also WO 97/40104, WO 99/51702, WO 01/21624, and EP 1 065 250 A1; and Tetrahedron Letters 41, 9185-88 (2000).

Various useful, exemplary fluorophores are commercially available and include, for example: Cy5.5, Cy5 and Cy7 (GE Healthcare); AlexaFlour660, AlexaFluor680, AlexaFluor750, and AlexaFluor790 (Invitrogen); VivoTag680, VivoTag-S680, and VivoTag-S750 (VisEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye800CW, IRDye 800RS, and IRDye 700DX (Li-Cor); and ADS780WS, ADS830WS, and ADS832WS (American Dye Source).

Table 1 lists a number of exemplary fluorophores useful in the practice of the invention together with their spectral properties.

TABLE 1

| Fluorophore | $\varepsilon_{max}$ M$^{-1}$cm$^{-1}$ | Absorbance max (nm) |
|---|---|---|
| Cy5 | 250,000 | 649 |
| Cy5.5 | 250,000 | 675 |
| Cy7 | 250,000 | 743 |
| AlexaFlour660 | 132,000 | 663 |
| AlexaFlour680 | 184,000 | 679 |
| AlexaFlour750 | 280,000 | 749 |
| VivoTag-S680 | 220,000 | 674 |
| VivoTag-S750 | 100,000 | 750 |
| Dy677 | 180,000 | 673 |
| Dy682 | 140,000 | 690 |
| Dy752 | 270,000 | 748 |
| Dy780 | 170,000 | 782 |
| DyLight547 | 150,000 | 557 |
| DyLight647 | 250,000 | 653 |

For example, certain useful fluorophores are represented by the following general Formula VII:

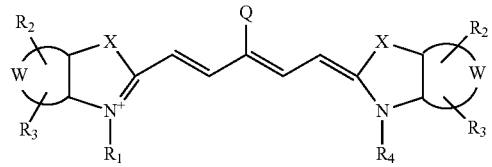

(VII)

or a salt thereof, wherein:

X is independently selected from the group consisting of $C(CH_2Y_1)(CH_2Y_2)$, O, S, and Se;

$Y_1$ and $Y_2$ are independently selected from the group consisting of H, $C_1$-$C_{20}$ aliphatic group and a $C_1$-$C_{20}$ aliphatic group substituted with —OR*, N(R*)$_2$ or —SR*;

W represents a benzo-condensed, a naphtho-condensed or a pyrido-condensed ring;

$R_1$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;

$R_2$ and $R_3$ independently are selected, for each occurrence, from the group consisting of H, carboxylate, carboxylic acid, carboxylic ester, amine, amide, sulfonamide, hydroxyl, alkoxyl, a sulphonic acid moiety and a sulphonate moiety;

$R_4$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6; and Q is selected from a group consisting of a heteroaryl ring substituted with a carboxyl group or 6-membered heteroaryl ring substituted with a carbonyl group.

In certain embodiments, Q can be selected from the group consisting of (i) a carboxyl functionalized heterocyclic ring, (ii) a carboxyl functionalized nitrogen containing heterocyclic ring, (iii) a carboxyl functionalized nitrogen containing 6-membered heterocyclic ring, such as pyridine, pyrimidone, pyrazine, and pyridazine, (iv) a carboxyl functionalized nitrogen containing 6-membered heterocyclic ring, such as pyridine, (v) a carbonyl functionalized nitrogen containing 6-membered heterocyclic ring, such as pyridine, (vi) an isonicotinic acid, nicotinic acid and picolinic acid, and a group selected from:

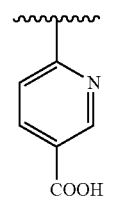 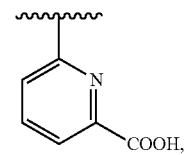

wherein the carboxyl group may also be in the form of an ester, an activated ester or carbonyl halide that is capable of reacting with nucleophiles, and can be, for example, a CO—O-benzotriazolyl, CO—ON-hydroxysuccinimidyl, CO—O-tetrafluorophenyl, CO—O-pentafluorophenyl, CO—O-imidazole, and CO—O-p-nitrophenyl.

Other useful, exemplary fluorophores are represented by the general Formula VII:

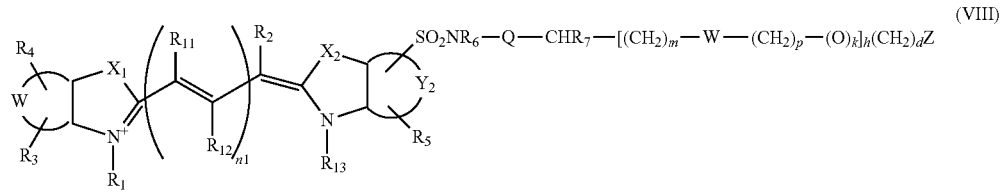

(VIII)

or a salt thereof, wherein:
  $X_1$ and $X_2$ are independently selected from the group consisting of $C(CH_2K_1)(CH_2K_2)$, O, S and Se;
  $K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*;
  or $K_1$ and $K_2$ together are part of a substituted or unsubstituted carbocyclic, or heterocyclic ring;
  $Y_1$ and $Y_2$ are each independently a benzo-condensed ring, a naphtha-condensed ring or a pyrido-condensed ring;
  $n_1$ is 1, 2, or 3;
  $R_2$, $R_{11}$ and $R_{12}$ are independently H, F, Br, Cl, $C_1$-$C_6$ alkyl, $C_1$-$C_6$ alkoxy, aryloxy, a nitrogen-containing heterocyclic ring, a nitrogen-containing heteroaromatic ring, a sulfonate, an iminium ion, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;
  $R_1$ and $R_{13}$ are $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;
  $R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;
  Q is absent, or is selected from a carbonyl moiety or a substituted or unsubstituted $C_1$-$C_6$ alkyl group, wherein 0-2 of the methylene groups of the alkyl group can optionally be replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms;
  $R_6$ is selected from the group consisting of H, a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or SR*, when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or
  $R_6$ is H, when Q is a carbonyl; and
  $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*; or
  $R_6$ and $R_7$, taken together form a 4-, 5-, 6- or 7-membered heterocyclic or non-aromatic heterocyclic ring optionally substituted with halogen, OR*, N(R*)$_2$ or SR*; or
  $NR_6$, Q and $CHR_7$ together form a substituted or unsubstituted or heterocyclic or non-aromatic heterocyclic ring system wherein the rings contain 1 or 2 heteroatoms, wherein rings are optionally substituted with —OR*, N(R*)$_2$ or —SR*; and
  W is absent or is a group selected from the group consisting of —SO$_2$NR$_6$-Q-CHR$_7$—, —O—, —COO—, and —CONH—;
  h=0-70; k=0 or 1; d=0-12; m=0-12; p=0-12; and
  Z is, or contains a N, O or S nucleophile functionality or is, or contains a functionality capable of reacting with N, O or S nucleophiles; and
  each R* is independently H or $C_{1\text{-}20}$ alkyl.

The imaging agents disclosed herein can include various fluorophore derivatives and other forms of fluorophores, such as N-hydroxysuccinimide forms of fluorophores. The fluorophores may be chemically linked to enzymatically cleavable oligopeptides using chemistries known in the art.

Exemplary fluorophores that can be used in the synthesis of the imaging agents of the invention include, for example, those listed in Table 2.

TABLE 2

| No. | Fluorophore |
|---|---|
| 1 | |

TABLE 2-continued
| No. | Fluorophore |
|---|---|
| 2 | 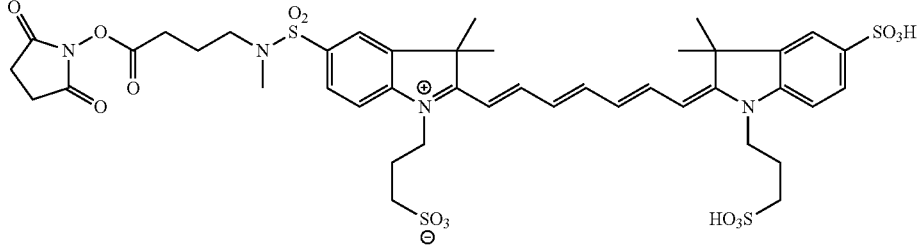 |
| 3 | 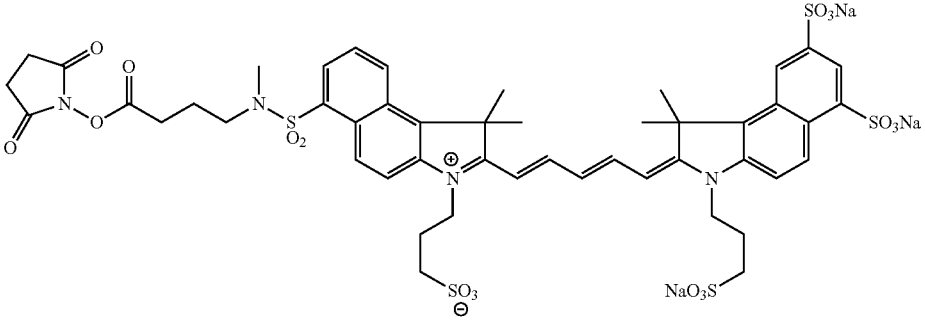 |
| 4 | 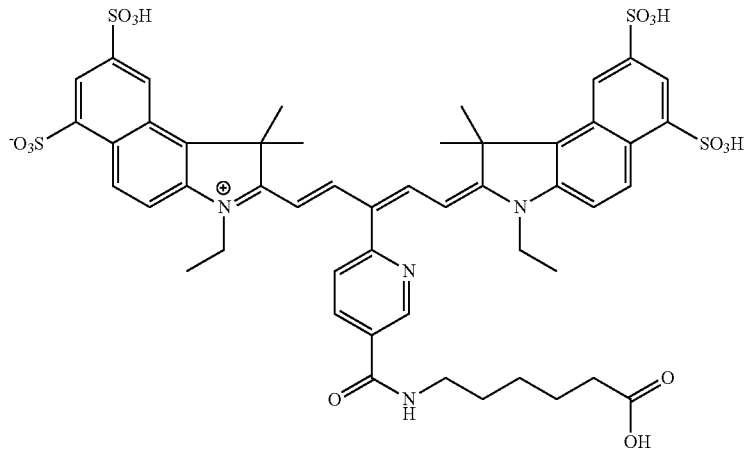 |
| 5 | 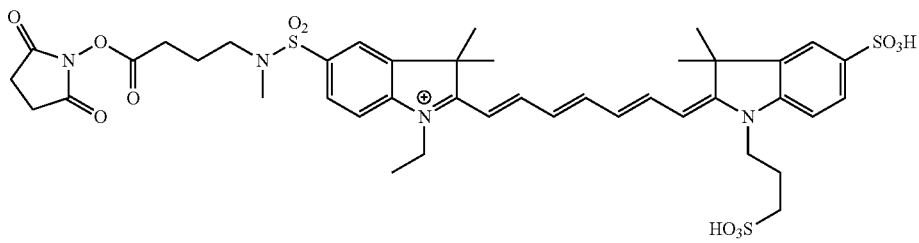 |
| 6 | 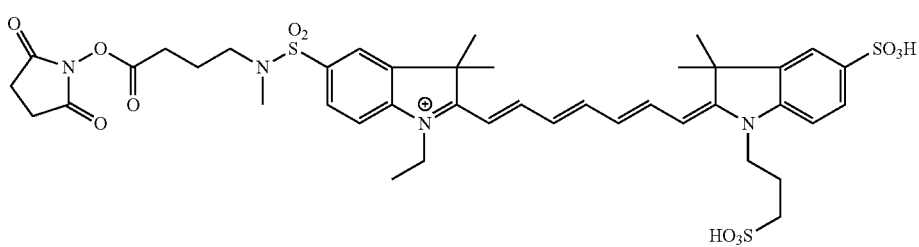 [SMILES: CC[N+]1=C(/C=C/C=C/C=C/C=C2/N(CCCS(=O)(=O)O)c3ccc(S(=O)(=O)O)cc3C2(C)C)C(C)(C)c2cc(S(=O)(=O)N(C)CCCC(=O)ON3C(=O)CCC3=O)ccc21] |

TABLE 2-continued

| No. | Fluorophore |
|---|---|
| 7 | |
| 8 | |
| 9 | |
| 10 | |
| 11 | |

TABLE 2-continued
| No. | Fluorophore |
|---|---|
| 12 | 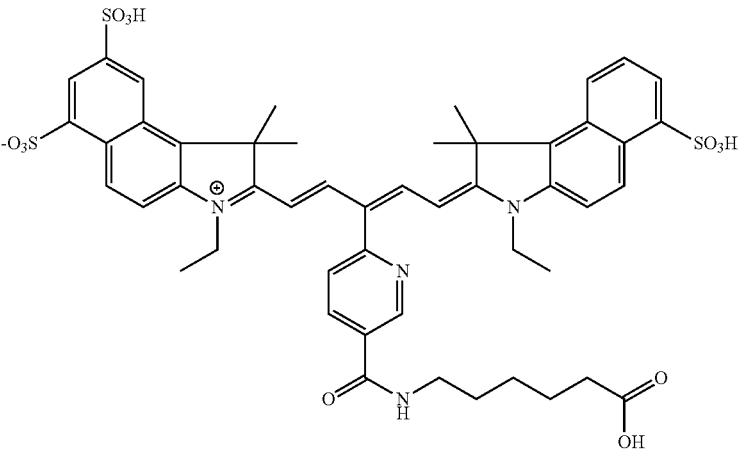 |
| 13 | 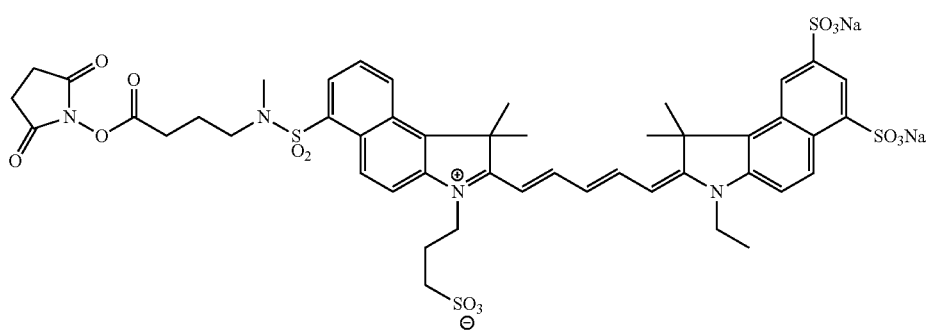 |
| 14 | 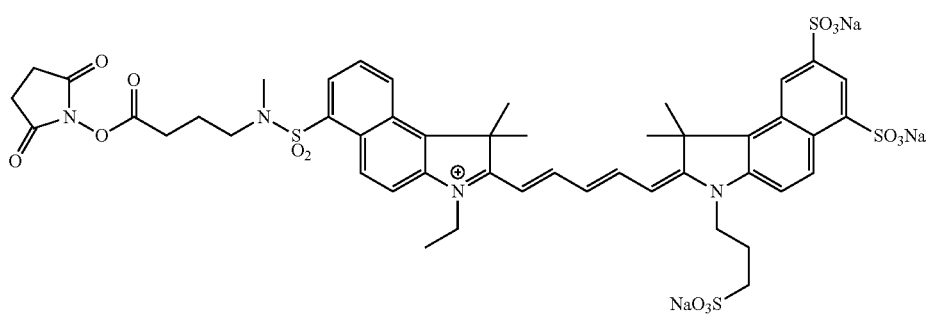 |
| 15 | 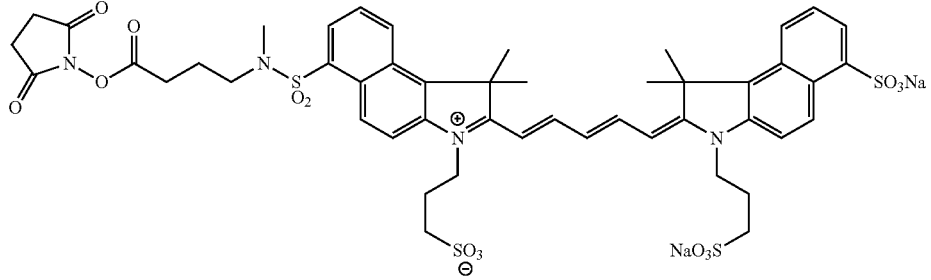 |

In another embodiment, the fluorophore is a nanoparticle having fluorescent or luminescent properties. For example, an enzymatically cleavable oligopeptide can be grafted onto nanoparticles comprising silicon in a form that has fluorescent or luminescent properties or fluorescent nanoparticles. Aggregates of crystalline silicon (as multiple or single crystals of silicon), porous silicon, or amorphous silicon, or a combination of these forms, can form the nanoparticle. Preferred fluorescent silicon nanoparticles have a diameter from about 0.5 nm to about 25 nm, more preferably from about 2 nm and about 10 nm. The size of nanoparticles can be determined by laser light scattering or by atomic force microscopy or other suitable techniques.

Fluorescent silicon nanoparticles can have excitation and emission spectra 200 nm to 2000 nm, however, preferred fluorescent silicon nanoparticles have excitation and emission maximum from about 400 nm to about 1200 nm (and preferably 500 nm-900 nm, for example, 500 nm-600 nm, 600 nm-700 nm, 700 nm-800 nm, or 800 nm-900 nm). Preferred fluorescent silicon nanoparticles also have extinction coefficients of at least 50,000 $M^{-1}$ $cm^{-1}$ in aqueous medium. Although fluorescent silicon nanoparticles with excitation and emission maximum between 400 nm and 1200 nm are preferred, it will be appreciated that the use of fluorescent silicon nanoparticles with excitation and emission wavelengths in other spectrums can also be employed in the compositions and methods of the present invention. For example, in certain embodiments, the particles can have excitation approximately about 300-350 nm, and emission approximately about 400-450 nm.

Fluorescent silicon nanoparticles also have the following properties: (1) high quantum yield (i.e., quantum yield greater than 5% in aqueous medium), (2) narrow emission spectrum (i.e., less than 75 nm; more preferably less than 50 nm), (3) spectrally separated absorption and emission spectra (i.e., separated by more than 20 nm; more preferably by more than 50 nm), (3) have high chemical stability and photostability (i.e., retain luminescent properties after exposure to light), (4) are biocompatible (as discussed below) or can be made more biocompatible; (5) are non toxic or minimally toxic to cells or subjects at doses used for imaging protocols, (as measured for example, by $LD_{50}$ or irritation studies, or other similar methods known in the art) and/or (6) have commercial viability and scalable production for large quantities (i.e., gram and kilogram quantities) required for in vivo use, for example use in humans.

Fluorescent quantum dots are also contemplated, for example, enzymatically cleavable oligopeptide can be grafted onto a fluorescent quantum dot such as amine T2 MP EviTags (Evident Technologies) or Qdot Nanocrystals (Invitrogen). In general, fluorescent quantum dots are nanocrystals containing several atoms of a semiconductor material (including but not limited to those containing cadmium and selenium, sulfide, or tellurium; zinc sulfide, indium-antimony, lead selenide, gallium arsenide, and silica or ormosil, which have been coated with zinc sulfide to improve the properties of these fluorescent agents.

Fluorophores can include metal oxide nanoparticles that are fluorescent and can be used in a variety of in vitro and in vivo applications. In an embodiment, an enzymatically cleavable oligopeptide is conjugated to at least one fluorescent metal oxide nanoparticle with one or more of the following features: (1) a polymer coating suitable for attaching a plurality of fluorophores thereby achieving large extinction coefficients (in excess of 1,000,000 $M^{-1}$ $cm^{-1}$), (2) a non-crosslinked polymer coating suitable for attaching from about 10 to about 300 fluorophores per particle, (3) a polymer coating suitable for attaching a plurality of fluorophores in a manner that does not significantly compromise the quantum yield of the fluorophores (e.g., the nanoparticles retain at least 50% of the fluorescent signal that is created by substantially the same number of free fluorophores when tested under the same conditions), and (4) a polymer coating that is amenable to efficient chemical linking of biomolecules with retention of their biological properties to yield molecular imaging agents. The fluorescent metal oxide nanoparticles can be highly stable molecular imaging agents in vitro, both before and after chemical linking of fluorophores and agents, but yet are labile and/or degradable in vivo.

In certain embodiments, one or more different fluorophore molecules can be covalently linked to the oligopeptide, or alternatively, two substantially similar fluorophores can be covalently linked to the oligopeptide, at fluorescene-quenching permissive locations to produce the imaging agents of the present invention.

In certain embodiments, a quencher is used to quench the fluorescent signal from the fluorophore covalently linked to the oligopeptide. For example, an agent can be designed such that the quencher quenches the fluorescence of the fluorophore of the imaging agent when the agent is in an unactivated state, so that the imaging agent exhibits little or no signal until it is activated. It is understood that the quencher can be a non-fluorescent agent, which when suitably located relative to a fluorophore (i.e., at a fluorescence-quenching permissive location) is capable of quenching the emission signal from the fluorophore. As discussed above, it is understood that certain of the foregoing fluorophores can act to quench the fluorescent signal of another spaced apart fluorophore, when the two fluorophores are positioned at fluorescence-quenching interaction permissive locations.

A number of quenchers are available and known to those skilled in the art including, but not limited to 4-{[4-(dimethylamino)-phenyl]-azo}-benzoic acid (DABCYL), QSY®-7 (9-[2-[(4-carboxy-1-piperidinyl)sulfonyl]phenyl]-3,6-bis(methylphenylamino)-xanthylium chloride) (Molecular Probes, Inc., OR), QSY®-33 (Molecular Probes, Inc., OR). ATTO612Q, ATTO580Q (ATTO-TEC, Germany); Black Hole Quenchers® (Bioresearch Technologies, Novato, Calif.), QXL™680 Acid (AnaSpec, San Jose Calif.), and fluorescence fluorophores such as Cy5 and Cy5.5 (e.g., 2-[5-[3-[6-[(2,5-dioxo-1-pyrrolidinyl)oxy]-6-oxohexyl]-1,3-dihydro-1,1-dimethyl-6,8-disulfo-2H-benz[e]indol-2-ylidene]-1,3-pentadienyl]-3-ethyl-1,1-dimethyl-6,8-disulfo-1H-benz[e]indolium, inner salt) (Schobel, *Bioconjugate* 10:1107, 1999). Other quenching strategies can be used, for example, using various solvents to quench fluorescence of the agents.

Exemplary fluorophores that can quench the emission of other fluorophores are represented in Table 3.

TABLE 3

| No. | Quencher |
|---|---|
| 1 | (structure) |
| 2 | (structure) |

As with all the imaging agents discussed herein, the two fluorophores or the fluorophore and the quencher are located within the intact imaging agent at fluorescent-quenching interaction permissive positions. In other words, a first fluorophore is located close enough in the intact imaging agent to a second fluorophore (or quencher) to permit them to interact photochemically with one another so that the second fluorophore (or quencher) quenches the signal from the first fluorophore. In the case of the imaging agents with two fluorophores, one fluorophore preferably quenches the other fluorophore. For principles of quenching, see U.S. Pat. No. 6,592,847.

II. Non-Fluorescent Reporters

The term "non-fluorescent reporter" as used herein, refers to a chemical moiety that is not fluorescent but which can be used to provide the contrast or signal in imaging and is detectable by a non-fluorescent imaging technique. In certain embodiments, other non-fluorescent reporters can be chemically linked with the imaging agents, or can be administered to a subject simultaneously or sequentially with the imaging agents of the invention. Such reporters can include photoluminescent nanoparticles, radioisotopes, superparamagnetic agents, X-ray contrast agents, and ultrasound agents. A reporter may also comprise therapeutic reporters such as porphyrins, Photofrin®, Lutrin®, Antrin®, aminolevulinic acid, hypericin, benzoporphryrin derivatives used in photodynamic therapy, and radionuclides used for radiotherapy.

(A) Radioactive Reporters

The imaging agents can include one or more radioactive labels. Radioisotopic forms of metals such as copper, gallium, indium, technetium, yttrium, and lutetium can be chemically linked to the metallic imaging agents and can be used for nuclear imaging or therapeutic applications. Exemplary radioactive labels include, without limitation, $^{99m}$Tc, $^{111}$In, $^{64}$Cu, $^{67}$Ga, $^{186}$Re, $^{198}$Re, $^{153}$Sm, $^{177}$Lu, and $^{67}$Cu.

Other exemplary labels include, for example, $^{123}$I, $^{124}$I, $^{125}$I, $^{11}$C, $^{13}$N, $^{15}$O, and $^{18}$F. Other exemplary labels can be therapeutic radiopharmaceuticals including for example, $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir.

Chelators or bonding moieties for diagnostic and therapeutic radiopharmaceuticals are also contemplated and can be chemically associated with the imaging agents. Exemplary chelators can be selected to form stable complexes with radioisotopes that have imagable gamma ray or positron emissions, such as $^{99m}$Tc, $^{111}$In, $^{64}$Cu, and $^{67}$Ga. Exemplary chelators include diaminedithiols, monoamine-monoamidedithiols, triamide-monothiols, monoamine-diamide-monothiols, diaminedioximes, and hydrazines. Chelators generally are tetradentate with donor atoms selected from nitrogen, oxygen and sulfur, and may include for example, cyclic and acyclic polyaminocarboxylates such as diethylenetriaminepentaacetic acid (DTPA), 1,4,7,10-tetraazacyclododecane-1,4,7,10-tetraacetic acid (DOTA), (DO3A), 2-benzyl-DOTA, alpha-(2-phenethyl) 1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

Chelators or bonding moieties for therapeutic radiopharmaceuticals can be selected to form stable complexes with the radioisotopes that have alpha particle, beta particle, Auger or Coster-Kronig electron emissions, such as $^{186}$Re, $^{188}$Re, $^{153}$Sm, $^{177}$Lu, and $^{67}$Cu. Chelators can be selected from diaminedithiols, monoamine-monoamidedithiols, triamide-monothiols, monoamine-diamide-monothiols, diaminedioximes, and hydrazines, cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N', N"-tetra(carboxymethyl)aminomethyl)-4'-(3-amino-4-methoxyphenyl)-2,2':6',2"-terpyridine.

(B) Magnetic Reporters

Other exemplary reporters can include a chelating agent for magnetic resonance agents. Such chelators can include for example, polyamine-polycarboxylate chelators or iminoacetic acid chelators that can be chemically linked to the agents.

Chelators for magnetic resonance imaging agents can be selected to form stable complexes with paramagnetic metal ions, such as Gd(III), Dy(III), Fe(III), and Mn(II), are selected from cyclic and acyclic polyaminocarboxylates such as DTPA, DOTA, DO3A, 2-benzyl-DOTA, alpha-(2-phenethyl) 1,4,7,10-tetraazacyclododecane-1-acetic-4,7,10-tris(met hylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

In one embodiment, the imaging agents are chemically linked to superparamagnetic metal oxide nanoparticles that are either (a) non-fluorescent or (b) are fluorescent and can be used in a variety of in vitro and in vivo applications. Fluorescent metal oxide nanoparticles that also have magnetic properties can be used for MRI, thus providing a multi-modality imaging agent.

In certain embodiments, the imaging agents can include a fluorescent and/or non-fluorescent superparamagenetic metal oxide nanoparticle with one or more of the following features: (1) a polymer coating suitable for attaching a plurality of agents (2) a non-crosslinked polymer coating suitable for attaching from about 10 to about 300 agents per particle, and (3) a polymer coating that is amenable to efficient chemical linking of the agents with retention of their biological properties to yield molecular imaging agents. The agent modified metal oxide nanoparticle can be a highly stable molecular imaging agent in vitro, both before and after chemical linking of the agents, but yet are labile and/or degradable in vivo.

(C) Ultrasound Reporters

A non-fluorescent reporter can include gas-filled bubbles such as Levovist, Albunex, or Echovist, or particles or metal chelates where the metal ions have atomic numbers 21-29, 42, 44 or 57-83, for example to facilitate ultrasound imaging. Examples of such compounds are described in Tyler et al., *Ultrasonic Imaging*, 3, pp. 323-29 (1981) and D. P. Swanson, "Enhancement Agents for Ultrasound: Fundamentals," *Pharmaceuticals in Medical Imaging*, pp. 682-87 (1990).

(D) X-Ray Reporters

Exemplary reporters can comprise of iodinated organic molecules or chelates of heavy metal ions of atomic numbers 57 to 83, for example, for X-ray imaging. Examples of such compounds are described in M. Sovak, ed., "Radiocontrast Agents," Springer-Verlag, pp. 23-125 (1984) and U.S. Pat. No. 4,647,447.

III. Linkers

Linker or spacer moieties can be used to covalently link one or more fluorophores, quenchers, biological modifiers and non-fluorescent reporters to an enzymatically cleavable oligopeptide or to an optional biological modifier to produce agents of the present invention. It is understood that there is no particular structural, size or content limitation of a linker, if present. Linkers can include, for example, a variety of functional groups such as maleimide, dithiopyridyl, thiol, azide, alkene, or alkyne that permit the assembly of molecules of diverse architecture.

Linkers can be homofunctional linkers or heterofunctional linkers. For example, amine (NH$_2$)-functionalized moieties can be reacted with bifunctional cross-linkers designed to react with amino groups. Particularly useful conjugation reagents that can facilitate formation of a linker or facilitate covalent linkage between, for example, a fluorophore, and an enzymatically cleavable oligopeptide can include a N-hydroxysuccinimide (NHS) ester and/or a maleimide. The NHS ester can react with the amine group of, for example, a peptide or fluorophore. The maleimide can react with the sulfhydryl group of another molecule. Other particularly useful linker moieties are bifunctional cross-linkers such as N-succinimidyl 3-(2-pyridyldithio)propionate (SPDP), long chain-SPDP, maleimidobenzoic acid-N-hydroxysuccinimide ester (MBS), succinimidyl trans-4-(maleimidylmethyl)cyclohexane-1-carboxylate (SMCC), succinimidyl iodoacetate (SIA).

In certain embodiments a linker, if present, may be a derivative of a diamine. A diamine moiety or derivative can provide a linker arm of varying lengths and chemistries for chemically linking molecules by derivatizing, optionally, with carboxylic acids. Non-limiting examples of diamines include ethylenediamine (EDA), propylenediamine, spermidine, spermine, hexanediamine, and diamine-amino acids, such as homolysine, lysine, omithine, diaminobutyric acid and diaminopropionic acid. In other embodiments, moieties of an imaging agent can be chemically linked to a dicarboxylic acid, for example, succinic acid, glutaric acid, suberic acid, or adipic acid. In one embodiment, the linker is aminoethylmaleimide.

In certain embodiments, a linker can be formed from an azide moiety that can react with substituted alkynes in an azide-acetylene Huisgen [3+2] cycloaddition. In certain embodiments the azide or alkyne linker can link a polyethyleneglycol (PEG) moiety to, for example, an enzymatically cleavable oligopeptide. Other contemplated linkers include propargylglycine, pentanoyl, pentynoic acid, propargylic acid, and/or propargylamine moieties.

In certain embodiments, fluorophores, quenchers, or other reporters are directly linked to the imaging agent using reactive NHS ester groups on the fluorophores, quenchers, or reporters which react with an amine group on the enzymatically cleavable oligopeptide. In certain other embodiments, carboxylic acid groups on the fluorophores, quenchers, or other reporters can be activated in situ by activating agents known in the art, such as 2-(1H-benzotriazole-1-yl)-

1,1,3,3,-tetramethyluronium hexafluorophosphate (HBTU), 1-ethyl-3-(3'-dimethylaminopropyl)-carbodiimide hydrochloride (EDC), N,N'-dicyclohexylcarbodiimide (DCC), N,N'-disuccinimidyl carbonate (DSC). In other embodiments, reporters including a sulfhydryl or thiol group, can be chemically linked to the agent via a bifunctional cross-linker that has a second moiety that can react with a sulfhydryl (thiol) group. Such crosslinking agents include, for example and as described above, SPDP, long chain-SPDP, SIA, MBS, SMCC, and others that are well known in the art.

Useful linker moieties include both natural and non-natural amino acids, oligopeptides, for example, linear or cyclic oligopeptides, and nucleic acids.

The linker can be a peptide or peptide moiety which optionally includes a proteolytic or non-proteolytic cleavage site, such as anester linkage, that can be cleaved due to pH changes at the site of interest.

IV Biological Modifiers

As used herein, the term "biological modifier" is understood to mean any moiety that can be used to alter the biological properties of the imaging agent, such as, without limitations, making the imaging agent more water soluble or more dispersible in media for administration, increasing binding specificity, decreasing immunogenicity or toxicity, or modifying pharmacokinetic profile compared to the non-biological modifier modified agents.

In an embodiment, one or more biological modifiers can be chemically linked to the enzymatically cleavable oligopeptide or fluorophore. In one embodiment, the biological modifier is covalently linked to the enzymatically cleavable peptide at a position that is not between two amino acids covalently linked to a fluorophore or a quencher.

Exemplary biological modifiers include polyethylene glycol (PEG) and derivatives thereof (for example, alkoxy polyethylene glycol (for example, methoxypolyethylene glycol, ethoxypolyethylene glycol and the like), branched polypropylene glycol, polypropylene glycol, a graft copolymer of poly-lysine and methoxypolyethyleneglycol, amino acids, peptides, lipids, fatty acids, palmitate, phospholipids, phospholipid-PEG conjugates, carbohydrates (such as dextran, amino-dextran, carboxymethyl-dextran), iron oxide nanoparticles, sulfonates, polysulfonates, cysteic acid, naphthylalanine, phenylalanine, and 3,3-diphenylpropylamine.

In general, the biological modifier may have a molecular weight of from about 2 kDa to less than 50 kDa, such as from about 5 kDa to about 40 kDa, such as from about 10 kDa to about 35 kDa, further such as from about 15 kDa to 30 kDa. In another embodiment, the biological modifier may have a molecular weight of from about 5 kDa to about 45 kDa, such as from about 5 kDa to about 40 kDa, such as from about 5 kDa to about 35 kDa, such as from about 5 kDa to about 30 kDa, such as from about 5 kDa to about 25 kDa, such as from about 5 kDa to about 20 kDa, such as from about 5 kDa to about 15 kDa, further such as from about 5 kDa to 10 kDa. In another embodiment, the biological modifier may have a molecular weight of from about 2 kDa to less than 50 kDa, such as from about 2 kDa to about 45 kDa, such as from about 2 kDa to about 40 kDa, such as from about 2 kDa to about 35 kDa, such as from about 2 kDa to about 30 kDa, such as from about 2 kDa to about 25 kDa, such as from about 2 kDa to about 10 kDa, further such as from about 2 kDa to 5 kDa.

In certain embodiments, as discussed above, the biological modifier may be a PEG moiety that has a molecular weight, for example, from about 0.5 kDa to about 50 kDa, about 5 kDa to about 35 kDa, or about 10 kDa to about 30 kDa. Alternatively, the PEG may be dPEG, functionalized at a discrete molecular weight, for example, of about 1100 daltons.

In certain embodiments, the PEG is methoxyPEG$_{(5000)}$-succinimidylpropionate (mPEG-SPA), methoxyPEG$_{(5000)}$-succinimidylsuccinate (mPEG-SS). Such PEGS are commercially available from Nektar Therapeutics or SunBiowest or LaysanBio or NOF.

In one embodiment, a PEG moiety may be conjugated to reactive amines on the enzymatically cleavable oligopeptide or fluorophore via a carboxyl functionality. Alternatively, the PEG modifier can be conjugated to the enzymatically cleavable oligopeptide or fluorophore by using a thiol reactive cross linker and then reacting with a thiol group on the PEG.

In one embodiment, the PEG may be branched, or Y-shaped, as available from JenKem USA or NOF, or comb-shaped, or synthesized by coupling two or more PEGs to a small molecule such as glutamic acid.

The omega position of PEG may include a hydroxyl group or a methoxy group and the PEG may also contain an amino group in the omega position. Such an amino group can in turn be coupled to a variety of agents. In another embodiment of the present invention, the biological modifier can be a pegylated poly-L-lysine or a pegylated poly-D-lysine.

In other embodiments, the biological modifier can be polyvinylpyrrolidone (PVP)-type polymers. The biological modifier can be a functionalized polyvinylpyrrolidone, for example, carboxy or amine functionalized on one (or both) ends of the polymer (as available from Polymersource) or within the polymer chain.

Alternatively, the biological modifier can include Poly N-(2-hydroxypropyl)methacrylamide (HPMA), or functionalized HPMA (amine, carboxy, etc.), Poly(N-isopropyl acrylamide) or functionalized poly(N-isopropylacrylamide).

Biological modifiers can include straight or branched chain acyl groups, such as pentynoyl; acidic groups, such as succinyl; lower alkyl groups, such as methyl, ethyl, propyl, etc.; carboxyalkyl groups, such as carboxyethyl; haloalkyl groups, such as trifluoromethyl; and the like.

In other embodiments, the biological modifier can include, but is not limited to, proteins, peptides, antibodies and antigen binding fragments thereof (for example, Fab, Fab', (Fab')$_2$ fragments), single chain antibodies or sFvs, oligonucleotides, aptamers, glycoproteins, ligands for cell receptors, polysaccharides, cell receptors, enzyme substrates, enzyme cofactors, biotin, hormones, neurohormones, neurotransmitters, growth factors, cytokines, lymphokines, lectins, selectins, toxins, nucleic acids, oligonucleotides and derivatives thereof. Other biomolecules can also be used, such as folate-mediated targeting molecules (Leamon & Low, *Drug Discovery Today*, 6:44-51, 2001), transferrin, vitamins, carbohydrates and ligands that target internalizing receptors, including, but not limited to, asialoglycoprotein receptor, somatostatin, nerve growth factor, oxytocin, bombesin, calcitonin, arginine vasopressin, angiotensin II, atrial natriuretic peptide, insulin, glucagons, prolactin, gonadotropin, various opioids and urokinase-type plasminogen activator. Biomolecules such as integrin targeting agents are contemplated, such as $\alpha_v\beta_3$ and $GP\alpha_{IIb}\beta_3$, bombesin, CD4 and VCAM-1. Also contemplated are peptides for Hepsin, SPARC, PAR1, colon cancer, Factor 13.

Exemplary peptides for use as biological modifiers include: (Hepsin) Ile-Pro-Leu-Val-Leu-Pro-Leu (SEQ ID NO:1); (SPARC) Ser-Pro-Pro-Thr-Gly-Ile-Asn (SEQ ID NO:2); (VCAM1) Val-His-Pro-Lys-Gln-His-Arg (SEQ ID NO:3); (Cathepsin K) Val-His-Pro-Lys-Gln-His-Arg (SEQ ID NO:4); (E-selection binding peptide) Cys-Asp-Ser-Asp-Ser-Asp-Ile-Thr-Trp-Asp-Gln-Leu-Trp-Asp-Asp-Leu-Met-Lys (SEQ ID NO:5); and (Tat) Arg-Arg-Arg-Arg-Gly-Arg-Arg-Arg-Arg (SEQ ID NO:6).

Other contemplated biological modifiers include membrane, transmembrane, and nuclear translocation signal compounds and sequences, which can be derived from a number of sources including, without limitation, viruses and bacteria. Non-limiting examples include HIV-tat derived peptides, protamine, and polyArg and Arg-rich peptides.

Biological modifiers can also include synthetic compounds including, but not limited to, small molecule drugs, phototherapeutic molecules and derivatives thereof. Other contemplated biological modifiers include antibiotics such as vancomycin, clindamycin, chemotherapeutics such as doxorubicin, molecules such as glycine, derivatives of AMG706, Zactima™, MP-412, erlotinib, sorafenib, dasatinib, lestaurtinib, lapatinib, XL647, XL999, MLN518, PKC412, STI571, AMN107, AEE788, OSI-930, OSI-817, sunitinib, AG-013736; molecules that target/inhibit VEGF receptors, PDGF receptor, HER2, SSKI, EphB4, EGFR, FGFR. VEGFR-2, VEGFR-3, serine/threonine and receptor kinases, FLT-3, type III RTKs, c-KIT, Bcr-Abl, CSF-1R, CCR-2, RET, VDGF-2 and photodynamic reagents including but not limited to Chlorin e6, Photofrin®, Lutrin®, Antrin®, aminolevulinic acid, hypericin, porphyrins, and porphyrin derivatives, for example, benzoporphyrin derivative.

The biological modifiers may, under certain circumstances, render the imaging agents more useful for biological imaging. For example, the biological modifier may render agents more water soluble, and/or more dispersible in media for administration and/or may have an increased binding specificity, and/or may be less immunogenic and/or less toxic, and/or have a reduced non-specific binding and/or altered biodistribution and/or pharmacokinetic profile as compared to a non-biologically modified agents. For example, incorporation of methoxypolyethylene glycol (mPEG) or polypeptides may function to modify the pharmacodynamics and blood clearance rates of the agents in vivo. Other biological modifiers may be chosen to accelerate the clearance of the agents from background tissue, such as muscle or liver, and/or from the blood, thereby reducing the background interference and improving image quality. Additionally, the biological modifiers may also be used to favor a particular route of excretion, e.g., via the kidneys rather than via the liver. The biological modifiers may also aid in formulating agents in pharmaceutical compositions or may be used to alter or preserve the signal reporting properties of the agents. In one embodiment of the present invention, the biological modifier can be a polyamino acid or a peptide, including cyclic peptides. In particular, chemical linking of polyethylene glycol (PEG) or a derivative thereof to agents can result in longer blood residence time (longer circulation) and decreasing immunogenicity.

V. Enzymatically Cleavable Oligopeptides

As used herein, the term "enzymatically cleavable oligopeptide" is understood to mean a peptide comprising two or more amino acids (as defined herein) that are linked by means of a enzymatically cleavable peptide bond. Also included are moieties that include a pseudopeptide or peptidomimetic. Examples of cleavable peptide substrates can be found in U.S. Pat. No. 7,439,319.

The term "amino acid" as used herein is understood to mean an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Natural amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Other amino acids include, but are not limited to, arginosuccinic acid, citrulline, cysteine sulfinic acid, 3,4-dihydroxyphenylalanine, homocysteine, homoserine, ornithine, carnitine, selenocysteine, selenomethionine, 3-monoiodotyrosine, 3,5-diiodotryosine, 3,5,5'-triiodothyronine, and 3,3',5,5'-tetraiodothyronine.

Modified or unusual amino acids which can be used to practice the invention include, but are not limited to, D-amino acids, hydroxylysine, dehydroalanine, pyrrolysine, 2-aminoisobutyric acid, gamma aminobutyric acid, 5-hydroxytryptophan, S-adenosyl methionine, S-adenosyl homocysteine, 4-hydroxyproline, an N-Cbz-protected amino acid, 2,4-diaminobutyric acid, homoarginine, norleucine, N-methylaminobutyric acid, naphthylalanine, phenylglycine, .beta.-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used herein, a "pseudopeptide" or "peptidomimetic" is a compound which mimics the structure of an amino acid residue or a peptide, for example, by using linking groups other than via amide linkages (pseudopeptide bonds) and/or by using non-amino acid substituents and/or a modified amino acid residue. A "pseudopeptide residue" means that portion of a pseudopeptide or peptidomimetic that is present in a peptide. The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation. The following conventional three-letter amino acid abbreviations are used herein: Ala=alanine; Aca=aminocaproic acid, Ahx=6-aminohexanoic acid, Arg=arginine; Asn=asparagines; Asp=aspartic acid; Cha=cyclohexylalanine; Cit=citrulline; Cys=cysteine; Dap=diaminopropionic acid; Gln=glutamine; Glu=glutamic acid; Gly=glycine; His=histidine; Ile=isoleucine; Leu=leucine; Lys=lysine; Met=methionine; Nal=naphthylalanine; Nle=norleucine; Orn=ornithine; Phe=phenylalanine; Phg=phenylglycine; Pro=praline; Sart=sarcosine; Ser=serine; Thi=Thienylalanine; Thr=threonine; Trp=tryptophan; Tyr=tyrosine; and Val=valine. Use of the prefix D-indicates the D-isomer of that amino acid; for example D-lysine is represented as D-Lys.

The peptides can be synthesized using either solution phase chemistry or solid phase chemistry or a combination of both (Albericio, Curr. Opinion. Cell Biol., 8, 211-221 (2004), M. Bodansky, Peptide Chemistry: A Practical Textbook, Springer-Verlag; N. L. Benoiton, Chemistry of Peptide Synthesis, 2005, CRC Press).

Selective or orthogonal amine protecting groups may be required to prepare the agents of the invention. As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Synthesis, Biology, Vol. 3, Academic Press, New York (1981). Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. Also included in the term "amine protecting group" are acyl groups such as azidobenzoyl, p-benzoylbenzoyl, o-benzylbenzoyl, p-acetylbenzoyl, dansyl, glycyl-p-benzoylbenzoyl, phenylbenzoyl, m-benzoylbenzoyl, benzoylbenzoyl.

In certain embodiments the enzymatically cleavable oligopeptide can include oligo-L-arginine, oligo-L-lysine, oligo-L-aspartic acid or oligo-L-glutamic acid.

In certain embodiments the enzymatically cleavable oligopeptide includes lysine and arginine. In certain embodiments of the present invention, the enzymatically cleavable oligopeptide can include lysine, arginine and phenylalanine, or may include lysine, phenylalanine and glycine. In another embodiment, the enzymatically cleavable oligopeptide can include lysine, phenylalanine, leucine, and glycine, or can include ornithine, phenylalanine, leucine, and glycine. In one embodiment, the enzymatically cleavable oligopeptide may include diaminopropionic acid, ornithine, phenylalanine, leucine, and glycine.

Exemplary enzymatically cleavable oligopeptides are set forth in Table 4.

TABLE 4

| Oligopeptide | SEQ ID NO. |
|---|---|
| Lys-Lys-Lys-Lys-Gly | 7 |
| Lys-Lys-Lys-Gly | 8 |
| Lys-Lys-Gly-Lys-Lys | 9 |
| Orn-Lys-Lys-Orn-Gly | 10 |
| Orn-Lys-Lys-Orn-Ahx | 11 |
| Orn-Lys-Lys-Orn-Ahx-Gly-Gly | 12 |
| Lys-Lys-Lys-Lys-Ahx | 13 |
| Lys-Lys-Lys-βAla | 14 |
| Lys-Lys-Lys-Lys-Gly-Gly-Gly-Gly-Gly | 15 |
| Gly-Gly-Lys-Lys-Lys-Lys-Gly | 16 |
| Lys-Lys-Lys-Lys-Lys-Lys-Gly<br>D-Lys-Lys-Lys-Lys-D-Lys-Lys-Gly | 17 |
| Lys-Lys-Lys-Lys-Lys-Lys-Ahx | 18 |
| Lys-Lys-Lys-Lys-Lys-Lys-Gly-Gly-Gly-Gly-Gly<br>Lys-Lys-Lys-Lys-Lys-D-Lys-Gly-Gly-Gly-Gly-Gly | 19 |
| Lys-Arg-Lys-Arg-Lys-Arg-Gly | 20 |
| Lys-Arg-Lys-Arg-Lys-Arg-Gly-Cys | 21 |
| Lys-Arg-Arg-Arg-Lys-Arg-Gly | 22 |
| Lys-Arg-Lys-Arg-Lys-Arg-Lys-Gly | 23 |
| Lys-Arg-Arg-Arg-Arg-Lys-Arg-Gly | 24 |
| Phe-Arg-Lys-Gly-Gly-Arg-Lys<br>Phe-Arg-Lys-Gly-Gly-Arg-D-Lys | 25 |
| Phe-Arg-Lys-Gly-Gly-Arg-Arg-Lys | 26 |
| Phe-Arg-Lys-Gly-Gly-Arg-Lys-Ahx | 27 |
| Phe-Arg-Lys-Gly-Gly-Arg-Lys-Gly-Gly | 28 |
| Cha-Arg-Lys-Gly-Gly-Arg-Lys | 29 |
| Thi-Arg-Lys-Gly-Gly-Arg-Lys | 30 |
| Thi-Arg-Lys-Gly-Gly-Arg-Lys-Gly | 31 |

TABLE 4-continued

| Oligopeptide | SEQ ID NO. |
|---|---|
| Phe-Gly-Lys-Arg-Arg-Lys<br>D-Phe-Gly-Lys-Arg-Arg-Lys | 32 |
| Thi-Gly-Lys-Arg-Arg-Lys | 33 |
| Cha-Gly-Lys-Arg-Arg-Lys | 34 |
| Phe-Gly-Orn-Arg-Arg-Dap | 35 |
| Phe-Gly-Orn-Arg-Arg-Orn | 36 |
| Phe-Gly-Lys-Arg-Arg-Lys-Gly-Gly | 37 |
| Phe-Gly-Lys-Arg-Arg-Lys-Ahx | 38 |
| Phe-Gly-Lys-Arg-Arg-Lys-Arg-Arg-Arg-Ahx<br>Phe-Gly-Lys-Arg-Arg-Lys-Arg-Arg-Arg-D-Arg-Ahx | 39 |
| Phe-Gly-Lys-Arg-Arg-Lys-Glu-Glu-Glu-Ahx | 40 |
| Phe-Gly-Lys-Arg-Arg-Lys-Arg-Arg-Arg-Ahx-Cys | 41 |
| Lys-Gly-Phe-Leu-Gly-βAla-Lys<br>D-Lys-Gly-Phe-Leu-Gly-βAla-Lys | 42 |
| Orn-Gly-Phe-Leu-Gly-βAla-Orn | 43 |
| Lys-Gly-Phe-Leu-Gly-βAla-Lys-Gly | 44 |
| Lys-Gly-Phe-Leu-Gly-βAla-Lys-Ahx | 45 |
| Lys-Gly-Phe-Leu-Gly-βAla-Lys-Gly-Gly-Gly | 46 |
| Gly-Gly-Gly-Lys-Gly-Phe-Leu-Gly-βAla-Lys | 47 |
| Ahx-Lys-Gly-Phe-Leu-Gly-βAla-Lys-Ahx | 48 |
| Lys-Gly-Phe-Leu-Gly-βAla-Lys-Ahx-Cys | 49 |
| Gly-Phe-Leu-Gly-Lys | 50 |
| Lys-Phe-Leu-Gly-Lys-Ahx | 51 |
| Gly-Phe-Leu-Gly-Lys-Gly-Gly-Gly | 52 |
| Gly-Gly-Phe-Leu-Gly-Lys-Ahx | 53 |
| Gly-Phe-Leu-Gly-Lys-Cys | 54 |
| Gly-Phe-Leu-Gly-Lys-Ahx-Cys | 55 |
| Gly-Gly-Phe-Leu-Gly-Lys-Ahx-Cys | 56 |
| Gly-Phe-Leu-Gly-Orn | 57 |
| Gly-Phe-Leu-Gly-Lys-Arg-Arg-Arg-Arg-Cys | 58 |
| His-Gly-Pro-Asn-Lys-His-Gly-Pro-Asn-βAla | 59 |
| His-Gly-Pro-Asn-Orn-His-Gly-Pro-Asn-βAla | 60 |
| His-Gly-Pro-Asn-Lys-His-Gly-Pro-Asn-βAla | 61 |
| Lys-His-Gly-Pro-Asn-Lys-His-Gly-Pro-Asn-βAla | 62 |
| Orn-His-Gly-Pro-Asn-Lys-His-Gly-Pro-Asn-βAla | 63 |
| Orn-His-Gly-Pro-Asn-Orn-His-Gly-Pro-Asn-βAla | 64 |
| Phe-Gly-Gly-His-Gly-Pro-Asn-Lys-His-Gly-Pro-Asn-Ahx | 65 |
| His-Gly-Pro-Arg-Lys-His-Gly-Pro-Arg-βAla | 66 |
| His-Gly-Pro-Asn-Lys-His-Gly-Pro-Arg-βAla | 67 |

TABLE 4-continued

| Oligopeptide | SEQ ID NO. |
|---|---|
| His-Gly-Pro-Arg-Lys-His-Gly-Pro-Asn-βAla | 68 |
| His-Gly-Pro-Asn-Lys-His-Gly-Pro-Asn-Ahx | 69 |
| His-Gly-Pro-Arg-Lys-His-Gly-Pro-Arg-Gly-Gly-Gly-Phe-Gly | 70 |
| His-Gly-Pro-Arg-Orn-His-Gly-Pro-Arg-βAla | 71 |
| His-Gly-Pro-Cit-Lys-His-Gly-Pro-Asn-βAla | 72 |
| His-Gly-Pro-Asn-Lys-His-Gly-Pro-Cit-βAla | 73 |
| His-Gly-Pro-Asn-Orn-His-Gly-Pro-Cit-βAla | 74 |
| His-Gly-Pro-Asn-Lys | 75 |
| His-Gly-Pro-Asn-Orn | 76 |
| Lys-His-Gly-Pro-Asn-Lys | 77 |
| Orn-His-Gly-Pro-Asn-Lys | 78 |
| His-Gly-Pro-Asn-Lys-Gly-Gly-Gly | 79 |
| His-Gly-Pro-Asn-Lys-Gln-Gly-Gly | 80 |
| His-Gly-Pro-Asn-Orn-Gly-Gly-Ahx | 81 |
| His-Gly-Pro-Asn-Lys-Arg-Arg-Arg-Ahx | 82 |
| His-Gly-Pro-Asn-Lys-Arg-Gly-Gly | 83 |
| Gly-Arg-Arg-Arg-Ahx-Orn-His-Gly-Pro-Asn-Lys-Gly<br>Gly-Arg-Arg-Arg-Ahx-D-Lys-His-Gly-Pro-Asn-Lys-Gly | 84 |
| His-Gly-Pro-Arg-Lys | 85 |
| His-Gly-Pro-Arg-Orn | 86 |
| Lys-His-Gly-Pro-Arg-Lys | 87 |
| Orn-His-Gly-Pro-Arg-Lys | 88 |
| His-Gly-Pro-Arg-Lys-Ahx | 89 |
| His-Gly-Pro-Arg-Lys-Gly-Gly-Gly | 90 |
| His-Gly-Pro-Arg-Orn-Gly-Gly-Ahx | 91 |
| His-Gly-Pro-Arg-Lys-Arg-Arg-Arg-Ahx | 92 |
| His-Gly-Pro-Arg-Lys-Arg-Gly-Gly | 93 |
| Gly-Arg-Arg-Arg-Ahx-Lys-His-Gly-Pro-Arg-Lys-Gly | 94 |
| Gly-Lys-Arg-Arg-Ahx-Orn-His-Gly-Pro-Asn-Orn-Gly | 95 |
| Gly-Lys-Lys-Arg-Ahx-Orn-His-Gly-Pro-Asn-Orn-Gly | 96 |
| Gly-Arg-Arg-Arg-Lys-Ahx-His-Gly-Pro-Asn-Lys-Gly | 97 |
| Lys-Pro-Leu-Gly-Val-Arg-Lys | 98 |
| Lys-Gly-Pro-Leu-Gly-Val-Arg-Lys | 99 |
| Ahx-Lys-Pro-Leu-Gly-Val-Arg-Lys | 100 |
| Lys-Pro-Leu-Gly-Val-Arg-Lys-Ahx | 101 |
| Lys-Pro-Leu-Gly-Val-Arg-Lys-Gln-Ahx | 102 |
| Lys-Pro-Leu-Gly-Val-Arg-Orn<br>Lys-Pro-Leu-Gly-Val-Arg-Gly-D-Lys | 103 |
| Orn-Pro-Leu-Gly-Val-Arg-Orn | 104 |
| Lys-Pro-Leu-Gly-Val-Arg-Lys-Cys | 105 |

TABLE 4-continued

| Oligopeptide | SEQ ID NO. |
|---|---|
| Lys-Gly-Pro-Leu-Gly-Val-Arg-Lys-Cys | 106 |
| Lys-Pro-Leu-Gly-Val-Arg-Lys-Gly-Gly-Gly | 107 |
| Lys-Gly-Pro-Leu-Gly-Val-Arg-Lys-Gly-Gly-Gly | 108 |
| Lys-Pro-Leu-Gly-Val-Arg-Lys-Arg-Arg-Arg | 109 |
| Lys-Gly-Pro-Leu-Gly-Val-Arg-Lys-Arg-Arg-Arg | 110 |
| Lys-Val-Arg-Leu-Gly-Pro-Lys | 111 |
| Lys-Gly-Val-Arg-Leu-Gly-Pro-Lys | 112 |
| Ahx-Lys-Val-Arg-Leu-Gly-Pro-Lys<br>Ahx-D-Lys-Val-Arg-Leu-Gly-Pro-D-Lys | 113 |
| Lys-Val-Arg-Leu-Gly-Pro-Lys-Ahx | 114 |
| Lys-Val-Arg-Leu-Gly-Pro-Orn | 115 |
| Orn-Val-Arg-Leu-Gly-Pro-Orn | 116 |
| Lys-Val-Arg-Leu-Gly-Pro-Lys-Cys | 117 |
| Lys-Gly-Val-Arg-Leu-Gly-Pro-Lys-Cys | 118 |
| Lys-Val-Arg-Leu-Gly-Pro-Lys-Gly-Gly-Gly | 119 |
| Lys-Gly-Val-Arg-Leu-Gly-Pro-Lys-Gly-Gly-Gly | 120 |
| Lys-Val-Arg-Leu-Gly-Pro-Lys-Arg-Arg-Arg<br>Lys-Val-Arg-Leu-Gly-Pro-Lys-Arg-Arg-Arg-D-Arg | 121 |
| Lys-Gly-Val-Arg-Leu-Gly-Pro-Lys-Arg-Arg-Arg | 122 |
| Lys-Gly-His-Pro-Gly-Gly-Pro-Gln-Gly-Lys | 123 |
| His-Pro-Gly-Gly-Pro-Gln | 124 |
| Lys-Gly-His-Pro-Gly-Gly-Pro-Gln-Gly-Orn-Ahx | 125 |
| Gly-Lys-Gly-His-Pro-Gly-Gly-Pro-Gln-Lys | 126 |
| Lys-His-Pro-Gly-Gly-Pro-Gln-Lys | 127 |
| Lys-Gly-His-Pro-Gly-Gly-Pro-Gln-Gly-Lys-Cys | 128 |
| Lys-Gly-His-Pro-Gly-Gly-Pro-Gln-Lys-Gly-Gly | 129 |
| Lys-Gly-His-Pro-Gly-Gly-Pro-Gln-Lys-Gly-Gly-Arg-Arg | 130 |
| Lys-Gly-His-Pro-Gly-Gly-Pro-Gln-Lys-Gly-Arg-Arg-Arg | 131 |
| Lys-Gly-His-Pro-Gly-Gly-Pro-Gln-Lys-Ahx-Arg-Arg-Arg-Cys-Gly | 132 |
| Ile-His-Pro-Phe-His-Leu-Val-Ile-His | 133 |
| Lys-His-Pro-Phe-His-Leu-Val-Ile-His | 134 |
| Lys-Ile-His-Pro-Phe-His-Leu-Val-Ile-His-Lys | 135 |
| Lys-Lys-His-Pro-Phe-His-Leu-Val-Ile-His-Lys | 136 |
| Ile-His-Pro-Phe-His-Leu-Val-Ile-His-Lys | 137 |
| Lys-His-Pro-Phe-His-Leu-Val-Ile-His-Lys | 138 |
| Thr-Pro-Phe-Ser-Gly-Gln | 139 |
| Glu-Pro-Phe-Trp-Glu-Asp-Gln | 140 |
| Leu-Val-Gly-Gly-Ala | 141 |
| Tyr-Pro-Gly-Gly-Pro-Gln | 142 |
| Val-Ala-Asp-Cys-Ala-Asp-Gln | 143 |

TABLE 4-continued

| Oligopeptide | SEQ ID NO. |
|---|---|
| Val-Ala-Asp-Cys-Ala-Asp-Arg-Gln | 144 |
| Val-Ala-Asp-Cys-Ala-Asp-Asp-Gln | 145 |
| Val-Ala-Asp-Cys-Arg-Asp-Gln | 146 |
| Ala-Pro-Glu-Glu-Ile-Met-Arg-Arg-Gln | 147 |
| Ala-Pro-Glu-Glu-Ile-Met-Asp-Arg-Gln | 148 |
| Ala-Pro-Glu-Glu-Ile-Met-Pro-Arg-Gln | 149 |
| Gly-Phe-Leu-Gly | 150 |
| Gly-Leu-Phe-Gly | 151 |
| Glu-Gly-Phe-Leu-Gly | 152 |
| Glu-Lys-Gly-Phe-Leu-Gly-Lys | 153 |
| Arg-Arg-Glu-Lys-Gly-Phe-Leu-Gly-Lys | 154 |
| Arg-Gly-Leu-Gly-Lys | 155 |
| Gly-Gly-Arg-Arg<br>Gly-Gly | 156 |
| Gly-Phe-Cha-Gly | 157 |
| Arg-Leu-Val-Gly-Phe-Asp | 158 |
| Arg-Gly-Phe-Phe-Leu | 159 |
| Arg-Gly-Phe-Phe-Pro | 160 |
| Ala-Phe-Leu-Gly | 161 |
| Phe-Pro-Ala-Met | 162 |
| Glu-Ala-Ala-Ala<br>Gly-Gly-Arg<br>Gly-Arg<br>Phe-Arg | 163 |
| Glu-Lys-Arg-Arg-Lys | 164 |
| Succinyl-Glu-Lys-Arg-Arg-Lys | 165 |
| Val-Lys-Lys-Arg<br>Ala-Pro | 166 |
| Ala-Ala-Lys His-Gly-Pro-Asn | 167 |
| His-Gly-Pro-Arg<br>Gly-Pro-Arg | 168 |
| Gly-Pro-Arg-Lys<br>Gly-Pro-Asn | 169 |
| Pro-Ala-Gly-Pro | 170 |
| Asn-Gly-Pro-Asn-Lys | 171 |
| His-Gly-Pro-Ile | 172 |
| His-Gly-Hyp-Asn | 173 |
| His-Gly-Pro-Cit | 174 |
| His-Gly-hPro-Asn Pro-Leu-Gly-Val-Arg | 175 |
| Gly-Pro-Leu-Gly-Val-Arg | 176 |
| Gly-Pro-Leu-Gly-Val-Arg-Glu | 177 |
| Gly-Pro-Leu-Gly-Val-Arg-Asp | 178 |

TABLE 4-continued

| Oligopeptide | SEQ ID NO. |
|---|---|
| Gly-Pro-Leu-Gly-Met-Arg | 179 |
| Pro-Leu-Gly-Glu-Arg-Gly | 180 |
| Pro-Leu-Gly-Leu-Ala-Gly | 181 |
| Gly-Val-Arg-Leu-Gly-Pro-Lys | 182 |
| Gly-Pro-Gln-Gly-Ile-Ala-Gly-Gln | 183 |
| Val-Pro-Met-Ser-Met-Arg-Gly-Gly | 184 |
| Ile-Pro-Val-Ser-Leu-Arg-Ser-Gly | 185 |
| Arg-Pro-Phe-Ser-Met-Ile-Met-Gly | 186 |
| Val-Pro-Leu-Ser-Leu-Thr-Met-Gly | 187 |
| Val-Pro-Leu-Ser-Leu-Tyr-Ser-Gly | 188 |
| Ile-Pro-Glu-Ser-Leu-Arg-Ala-Gly<br>Lys-His-Pro-Phe-His-Leu-Val-Ile-His-D-Lys | 189 |
| Lys(COR)-His-Pro-Phe-His-Leu-Val-Ile-His-Lys; R = Me | 190 |
| Lys(COR)-His-Pro-Phe-His-Leu-Val-Ile-His-Lys; R = CF3 | 191 |
| Lys(COR)-His-Pro-Phe-His-Leu-Val-Ile-His-Lys; R = Et | 192 |
| Lys(COR)-His-Pro-Phe-His-Leu-Val-Ile-His-Lys; R = mPEG20k | 193 |
| [R'CO] Lys-His-Pro-Phe-His-Leu-Val-Ile-His-Lys; R' = Me | 194 |
| [R'CO] Lys-His-Pro-Phe-His-Leu-Val-Ile-His-Lys; R' = carboxyethyl | 195 |
| Lys-His-Pro-Phe-His-Leu-Leu-Tyr-His-Lys | 196 |
| Ile-His-Pro-Phe-His-Leu-Leu-Tyr-His-Lys | 197 |
| Lys-His-Pro-Phe-His-Leu-Leu-Tyr-Tyr-Lys | 198 |
| Ile-His-Pro-Phe-His-Leu-Leu-Tyr-Tyr-Lys | 199 |
| Lys-His-Pro-Phe-His-Leu-Leu-Val-Tyr-Lys | 200 |
| Ile-His-Pro-Phe-His-Leu-Leu-Val-Tyr-Lys | 201 |
| Lys-His-Pro-Tyr(R)-His-Leu-Val-Ile-His-Lys; R = Me | 202 |
| Lys-His-Pro-Tyr(R)-His-Leu-Val-Ile-His-Lys; R = Et | 203 |
| Ile-His-Pro-Tyr(R)-His-Leu-Val-Ile-His-Lys; R = Me | 204 |
| Ile-His-Pro-Tyr(R)-His-Leu-Val-Ile-His-Lys; R = Et | 205 |
| Orn-His-Pro-Phe-His-Leu-Val-Ile-His-Lys | 206 |
| Dap-His-Pro-Phe-His-Leu-Val-Ile-His-Lys | 207 |
| Ahx-His-Pro-Phe-His-Leu-Val-Ile-His-Lys | 208 |
| Asp-Arg-Val-Tyr-Ile-His-Pro-Phe-His-Leu-Val-Ile-His-Lys | 209 |
| Arg-Val-Tyr-Ile-His-Pro-Phe-His-Leu-Val-Ile-His-Lys | 210 |
| Val-Tyr-Ile-His-Pro-Phe-His-Leu-Val-Ile-His-Lys | 211 |
| Tyr-Ile-His-Pro-Phe-His-Leu-Val-Ile-His-Lys | 212 |
| Ser-Pro-Leu-Ala-Gln-Ala-Val-Arg-Ser-Ser-Ser-Arg-Lys | 213 |
| Pro-Leu-Ala-Gln-Ala-Val-Lys-Arg-Ser-Ser-Ser-Arg | 214 |

TABLE 4-continued

| Oligopeptide | SEQ ID NO. |
|---|---|
| Ser-Pro-Leu-Ala-Gln-Ala-Val-Arg-Ser-Ser-Ser-Arg-Orn | 215 |
| Pro-Leu-Ala-Gln-Ala-Val-Orn-Arg-Ser-Ser-Ser-Arg | 216 |
| Ser-Pro-Leu-Ala-Asn-Ala-Val-Arg-Ser-Ser-Ser-Arg-Lys | 217 |
| Pro-Leu-Ala-Asn-Ala-Val-Lys-Arg-Ser-Ser-Ser-Arg | 218 |
| Ala-Pro-Glu-Glu-Ile-Met-Asp-Arg-Gln-Lys | 219 |
| Ala-Pro-Glu-Glu-Ile-Met-Arg-Arg-Gln-Lys | 220 |
| Ala-Pro-Glu-Glu-Ile-Met-Asp-Gln-Gln-Lys | 221 |
| Ile-Ser-Leu-Met-Lys-Arg-Pro-Pro-Gly-Phe | 222 |
| Gly-Lys-Asp-Glu-Val-Asp | 223 |
| Lys-His-Pro-Phe-His-Cha-Val-Ile-His-Lys | 451 |
| Lys(COR)-His-Pro-Phe-His-Cha-Val-Ile-His-Lys; R = Me, CF3 | 452 |

Other exemplary enzymatically cleavable oligopeptides include a Cys-S-S-Cys moiety.

In one embodiment of the present invention, the enzymatically cleavable oligopeptide can be a enzymatically cleavable cyclic peptide, which may for example, include about 4 to about 30 amino acids. In one embodiment of the present invention, the agent can include 2-5 cyclic peptides. In another embodiment of the present invention, the cyclic peptide may include an acyclic component.

Cyclic peptides can be prepared by methods known in the art, for example, by the linking the N-terminus of a linear peptide with the C-terminus of the linear peptide: head-to-tail cyclization. Such linkages can be via a bond, for example, an amide bond or through a linker. In one embodiment, cyclic peptides can be prepared by the linking the N-terminus of a linear peptide with the side chain carboxylic acid of a linear peptide, by the linking the side chain amine of a linear peptide with the C-terminus carboxylic acid of a linear peptide, or by the linking the side chain amine of a linear peptide with the side chain carboxylic acid of a linear peptide. For example, cyclic peptides can be prepared by the linking the side chain thiol group of a linear peptide with the side chain thiol group of a linear peptide; for example by forming a Cys-Cys disulfide bond. Cyclic peptides can be made in solution phase or on solid phase and that cyclization of linear peptides can be achieved in solution phase or on solid phase.

Cyclic peptides are described using conventional nomenclature. For example a head to tail cyclic peptide containing Arg, Gly, Asp, Phe, Lys can be written as cyclo(Arg-Gly-Asp-Phe-Lys) (SEQ ID NO:224); a cyclic peptide containing Cys, Arg, Gly, Asp, Cys can be shown as follows: head to tail: cyclo(Cys-Arg-Gly-Asp-Cys) (SEQ ID NO:225); disulphide:

(SEQ ID NO: 225)
Cys-Arg-Gly-Asp-Cys.

In certain embodiments, the enzymatically cleavable cyclic oligopeptide can include oligo-L-arginine, oligo-L-lysine, oligo-L-aspartic acid or oligo-L-glutamic acid. In certain embodiments the enzymatically cleavable cyclic oligopeptide includes lysine and arginine. In another embodiment of the present invention, the enzymatically cleavable cyclic oligopeptide includes lysine, arginine and phenylalanine. In one embodiment, an enzymatically cleavable cyclic oligopeptide includes lysine, phenylalanine and glycine, or includes lysine, phenylalanine, leucine, and glycine, or includes ornithine, phenylalanine, leucine, and glycine. In another embodiment, the enzymatically cleavable cyclic oligopeptide comprises diaminopropionic acid, ornithine, phenylalanine, leucine, and glycine.

In one embodiment of the present invention, the enzymatically cleavable cyclic oligopeptide may include one or more enzymatically cleavable oligopeptide units.

Exemplary enzymatically cleavable cyclic oligopeptides include those shown in Table 5.

TABLE 5

| Cyclic Oligopeptide | SEQ ID NO. |
|---|---|
| cyclo(Lys-Arg-Arg-Lys-Arg-Arg)<br>cyclo(D-Lys-Arg-Arg-Lys-Arg-Arg) | 226 |
| cyclo(Lys-Arg-Arg-Arg-Lys-Arg-Arg)<br>cyclo(D-Phe-Lys-Arg-Arg-Lys-Arg-Arg-Gly) | 277 |
| cyclo(Phe-Lys-Arg-Arg-Phe-Lys-Arg-Arg)<br>cyclo(D-Phe-Lys-Arg-Arg-D-PheLys-Arg-Arg) | 228 |
| cyclo(Cys-Lys-Arg-Arg-Cys-Lys-Arg-Arg)<br>cyclo(Phe-Lys-Arg-Arg-Phe-Lys-Arg-Arg-D-Lys) | 229 |
| cyclo(Phe-Lys-Arg-Arg-Phe-Lys-Arg-Arg-Gly-Gly-Gly) | 230 |
| cyclo(Lys-His-Gly-Pro-Asn-Lys-His-Gly-Pro-Asn-Gly)<br>cyclo(D-Lys-His-Gly-Pro-Asn-D-Lys-His-Gly-Pro-Asn-Gly) | 231 |
| cyclo(Ahx-Lys-Arg-Arg-Lys-Arg-Arg) | 232 |
| cyclo(Lys-Arg-Arg-Lys-Lys-Arg-Arg-Lys) | 233 |
| cyclo(Gly-Lys-Arg-Arg-Lys-Lys-Arg-Arg-Lys-Gly)<br>cyclo(Gly-D-Lys-Arg-Arg-Lys-D-Lys-Arg-Arg-Lys-Gly) | 234 |

Such cyclopeptides may include peptide structures wherein one or two proteolytic events may be required for activation of the agent.

The enzymatically cleavable oligopeptide is cleavable by at least one enzyme chosen from hydrolases, elastases, cathepsins, matrix metalloproteases, peptidases, exopeptidases, endopeptidases, carboxypeptidases, glycosidases, lipases, nucleases, lyases, amylases, phospholipases, phosphatases, phosphodiesterases, sulfatases, serine proteases, subtilisin, chymotrypsin, trypsin, threonine proteases, cysteine proteases, calpains, papains, caspases, aspartic acid proteases, pepsins, chymosins, glutamic acid proteases, renin, reductases, and parasitic, viral and bacterial enzymes.

VI. Exemplary Imaging Agents

Useful imaging agents can be created using one or more of the enzymatically cleavable oligopeptides, fluorophores, quenchers (if appropriate), biological modifiers and non-fluorescent reporters described hereinabove and coupled together using standard chemistries known in the art. The imaging agents can be water soluble or water dispersible (i.e., sufficiently soluble or suspendable in aqueous or physiological media solutions). The in vivo half-life of the agent can be designed to be at least about 10 minutes, but more preferably 30 minutes to several hours. The in vivo half-life of the agent preferably is a time (for example, at least about 30 minutes) sufficient to achieve good tissue exposure, target binding, and imaging signal. In a preferred embodiment, the agent imaging probe is water soluble or dispersible in aqueous media, and is biocompatible i.e., non-toxic having, for example, an $LD_{50}$ of greater than about 50 mg/kg body weight. The imaging agents also preferably do not have any undesired phototoxic properties and/or display low serum protein binding affinity.

In certain embodiments, the disclosed agents include peptide or linker moieties capable of releasing one, two or more fluorophores from the oligopeptide and/or biological modifier upon contact with an enzyme. Such imaging agents can include a biological modifier that can be released from a cleavable oligopeptide by an enzyme that is different from the one that cleaves the peptide.

Certain preferred imaging agents are disclosed in the sections that follow.

One exemplary imaging agent represented by Formula Q77 includes [Ac]-Lys(F5)-Gly-Phe-Leu-Gly-Gly-Lys(F5)-[OH] (SEQ ID NO:235), wherein Ac is an acetyl group and F5 is represented by:

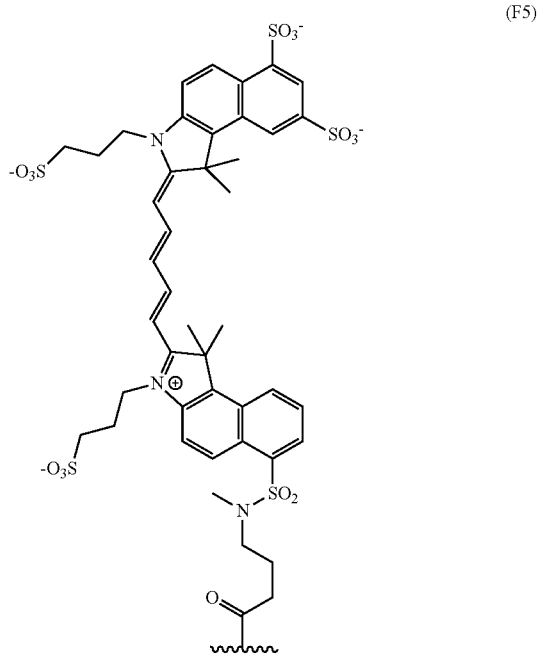

(F5)

One exemplary imaging agent represented by Formula Q77 includes

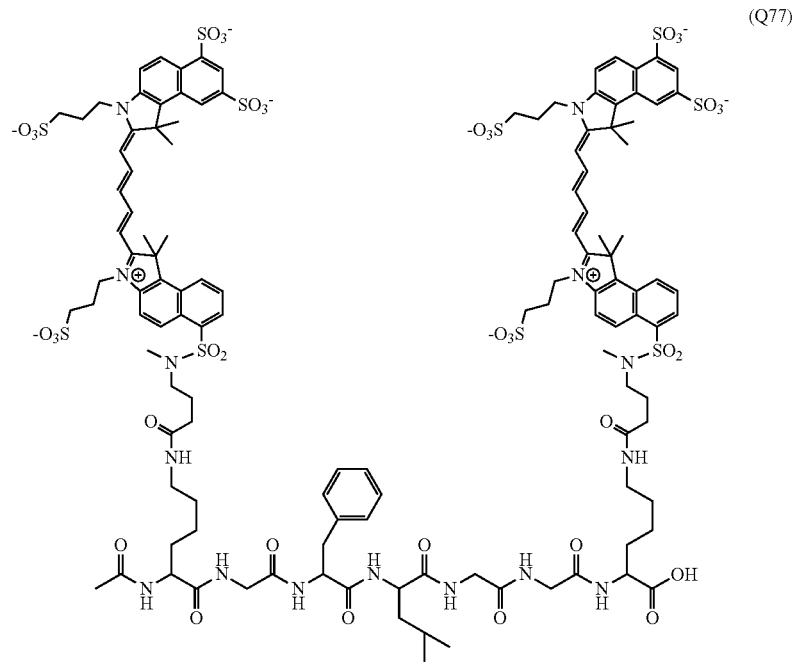

(Q77)

One exemplary imaging agent represented by Formula Q88 includes [Ac]-Lys(F6)-Gly-Phe-Leu-Gly-Gly-Lys(F6)-[OH] (SEQ ID NO:236), wherein Ac is an acetyl group and F6 is An exemplary imaging agent represented by Q90 includes [F5]-Gly-Phe-Leu-Gly-Gly-Lys(F5)-[OH] (SEQ ID NO:237), wherein F5 is

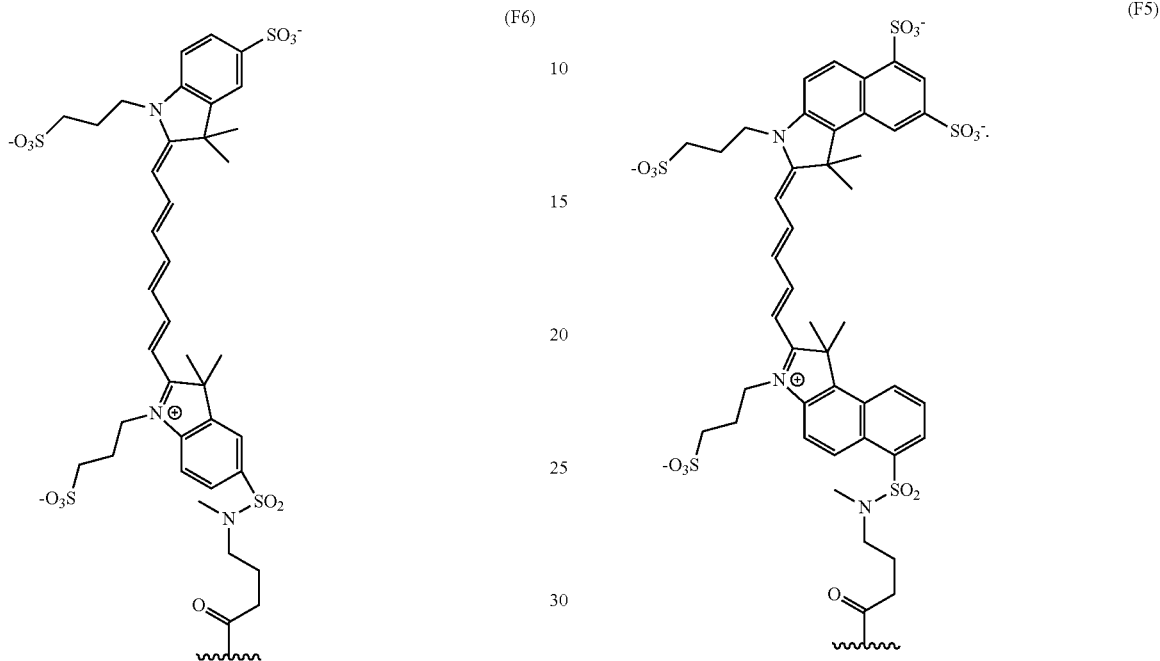

One exemplary imaging agent represented by Formula Q88 includes

An exemplary imaging agent represented by the Formula Q90 can be depicted as:

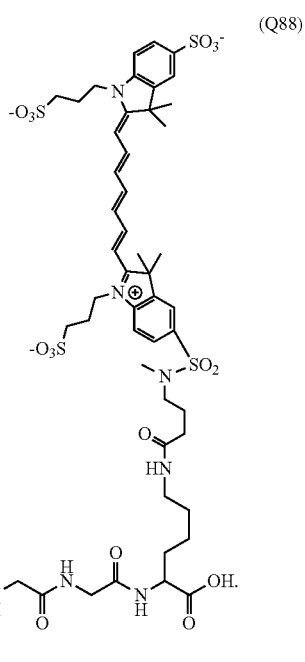

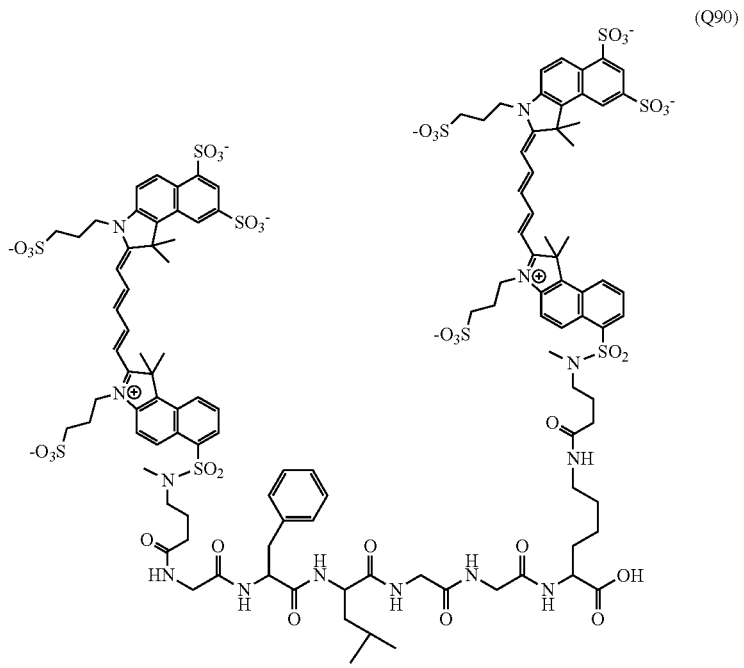

(Q90)

Other exemplary imaging agents can include moieties set forth in Table 6.

TABLE 6

| Imaging Agent | SEQ ID NO. |
|---|---|
| [Acetyl]-Lys(F5)-Lys-Lys-Lys(F5)-Lys-Lys-Gly-[OH] | 238 |
| [Acetyl]-Lys(F5)-Lys-Lys-Lys(F5)-Gly-[OH] | 239 |
| [F5]-His-Gly-Pro-Asn-Lys(F5)-[OH] | 240 |
| [F6]-Gly-Phe-Leu-Gly-Lys(F6)-[OH] | 241 |
| [F5]-His-Gly-Pro-Arg-Lys(F5)-[OH] | 242 |
| [F5]His-Gly-Pro-Asn-Lys(F5)-His-Gly-Pro-Asn-βA-[OH] | 243 |
| [pentynoyl]-Lys(F5)-His-Pro-Gly-Gly-Pro-Gln-Lys(F5)-[OH] | 244 |
| [pentynoyl]-Lys(F5)-Gly-His-Pro-Gly-Gly-Pro-Gln-Gly-Lys(F5)-[OH] | 245 |
| [pentynoyl]-Lys(F5)-Val-Arg-Leu-Gly-Pro-Lys(F5)-[OH] | 246 |
| [pentynoyl]-Lys(F5)-Pro-Leu-Gly-Val-Arg-Lys(F5)-[OH] | 247 |
| [pentynoyl]-Phe-Gly-Lys(F5)-Arg-Arg-Lys(F5)-[OH] | 248 |
| [pentynoyl]-Phe-Arg-Lys(F5)-Gly-Gly-Arg-Lys(F5)-[OH] | 249 |
| [F5]-Gly-Phe-Leu-Gly-Lys(F5)-[OH] | 250 |
| Acetyl-Phe-Gly-Lys(F5)-Arg-Arg-Lys(F5)-Gly-[OH] | 251 |
| Acetyl-Phe-Arg-Lys(F5)-Gly-Gly-Arg-Lys(F5)-[OH] | 252 |
| cyclo(Lys(F5)-Arg-Arg-Arg-Lys(F5)-Arg-Arg) | 253 |

TABLE 6-continued

| Imaging Agent | SEQ ID NO. |
|---|---|
| cyclo(Phe-Lys(F6)-Arg-Arg-Phe-Lys(F6)-Arg-Arg-Gly-Gly-Gly) | 254 |
| cyclo(Ahx-Lys(F6)-Arg-Arg-Lys(F6)-Arg-Arg) | 255 |
| [Acetyl]-Lys(F5)-Lys-Lys-Lys(F5)-Lys-Lys-Gly-[mPEG20K] | 256 |
| [Acetyl]-Lys(F5)-Lys-Lys-Lys(F5)-Gly-[mPEG20K] | 257 |
| [F5]-His-Gly-Pro-Asn-Lys(F5)-[mPEG20K] | 258 |
| [F6]-Gly-Phe-Leu-Gly-Lys(F6)-[mPEG20K] | 259 |
| [F5]-His-Gly-Pro-Arg-Lys(F5)-[mPEG20K] | 260 |
| [F5]-His-Gly-Pro-Asn-Lys(F5)-His-Gly-Pto-Asn-βA-[mPEG20K] | 261 |
| [F5]-His-Gly-Pro-Asn-Lys(F5)-[dPEG-1.1k] | 262 |
| [F5]-His-Gly-Pro-Asn-Lys(F5)-[mPEG-5k] | 263 |
| [F5]-His-Gly-Pro-Asn-Lys(F5)-[mPEG-10k] | 264 |
| [pentynoyl]-Lys(F5)-His-Pro-Gly-Gly-Pro-Gln-Lys(F5)-[mPEG20K] | 265 |
| [pentynoyl]-Lys(F5)-Gly-His-Pro-Gly-Gly-Pro-Gln-Gly-Lys(F5)-[mPEG20K] | 266 |
| [pentynoyl]-Lys(F5)-Val-Arg-Leu-Gly-Pro-Lys(F5)-[mPEG20K] | 267 |
| [pentynoyl]-Lys(F5)-Pro-Leu-Gly-Val-Arg-Lys(F5)-[mPEG20K] | 268 |
| [pentynoyl]-Phe-Gly-Lys(F5)-Arg-Arg-Lys(F5)-[mPEG20K] | 269 |
| [pentynoyl]-Phe-Arg-Lys-(F5)-Gly-Gly-Arg-Lys(F5)-[mPEG20K] | 270 |
| [F5]-Gly-Phe-Leu-Gly-Lys(F5)-OH | 271 |
| [succinyl]-Lys(F5)-Gly-Phe-Leu-Gly-Lys(F5)-[NH$_2$] | 272 |
| [mPEG-20k] (F6)-Gly-Phe-Leu-Gly-Lys(F6)-[NH$_2$] | 273 |
| [mPEG-40k]-(F5)-Gly-Phe-Leu-Gly-Lys(F5)-[NH$_2$] | 274 |
| [diphenylpropylamine]-(F6)-Gly-Phe-Leu-Gly-Lys(F6)-[NH$_2$] | 275 |
| [dPEG-1.1k]-(F6)-Gly-Phe-Leu-Gly-Lys(F6)-[NH$_2$] | 276 |
| [succinyl]-Lys(F6)-Arg-Arg-Lys(F6)-[NH$_2$] | 277 |
| [mPEG-20k-succinyl]-Lys(F6)-Arg-Arg-Lys(F6)-[NH$_2$] | 278 |
| [diphenylpropylamine-succinyl]-Lys(F6)-Arg-Arg-Lys(F6)-[NH$_2$] | 279 |
| [dPEG-1.1k-succinyl]-Lys(F6)-Arg-Arg-Lys(F6)-[NH$_2$] | 280 |
| [succinyl]-Lys(F6)-Ala-Arg-Arg-Lys(F6)-[NH$_2$] | 281 |
| [mPEG-20k]-Lys(F6)-Ala-Arg-Arg-Lys(F6)-[NH$_2$] | 282 |
| [succinyl]-Lys(F6)-Arg-Arg-Arg-Lys(F6)-[NH$_2$] | 283 |
| [mPEG-20k-succinyl]-Lys(F6)-Ala-Arg-Arg-Lys(F6)-[NH$_2$] | 284 |
| [succinyl]-Lys(F5)-Lys-Lys-Lys(F5)-[NH$_2$] | 285 |
| [mPEG-20k]-Lys(F5)-Lys-Lys-Lys(F5)-[NH$_2$] | 286 |
| [palmitoyl]-Lys(F5)-Phe-Arg-Lys(F5)-[NH$_2$] | 287 |
| [Ac]-Lys(F5)-Lys-Lys-Lys(F5)-Gly[Iron Oxide Nanoparticle] | 288 |

TABLE 6-continued

| Imaging Agent | SEQ ID NO. |
|---|---|
| [F6]-Gly-Pro-Leu-Gly-Val-Arg-Lys(F6)-[mPEG-20k] | 289 |
| [F6]-Gly-Pro-Leu-Gly-Val-Arg-Lys(F6)-[mPEG-40k] | 290 |
| [F6]-Gly-Pro-Leu-Gly-Val-Arg-Lys(F6)-[Y-PEG-40k] | 291 |
| [F6]-Gly-Pro-Leu-Gly-Val-Arg-Lys(F6)-[eda] | 292 |
| [F6]-Gly-Pro-Leu-Gly-Val-Arg-Lys(F6)-[PVP-6k] | 293 |
| [F6]-Gly-Pro-Leu-Gly-Val-Arg-Lys(F6)-[Dextran-10k] | 294 |
| [F6]-Gly-Pro-Leu-Gly-Val-Arg-Lys(F6)-Glu(mPEG-20k)-[mPEG-20k] | 295 |
| Ac-Phe-Gly-Lys(F5)-Arg-Arg-Lys(F5)-Gly-[mPEG20K] | 296 |
| Ac-Phe-Arg-Lys(F5)-Gly-Gly-Arg-Lys(F5)-[mPEG20K] | 297 |
| [F5]Lys-His-Pro-Phe-His-Leu-Val-Ile-His-Lys(F5)-[OH] | 298 |
| [F5]Lys-His-Pro-Phe-His-Leu-Val-Ile-His-Lys(F5)-[NHR]; R = H | 299 |
| [F5]Lys-His-Pro-Phe-His-Leu-Val-Ile-His-Lys(F5)-[NHR]; R = Me | 300 |
| [F5]Lys-His-Pro-Phe-His-Leu-Val-Ile-His-Lys(F5)-[NHR]; R = Et | 301 |
| [F5]Lys-His-Pro-Phe-His-Leu-Val-Ile-His-Lys(F5)-[NHR]; R = mPEG20k | 302 |
| [F5]Lys-His-Pro-Phe-His-Leu-Val-Ile-His-Lys(F5)-[NHR]; R = mPEG10k | 303 |
| [F5]Lys-His-Pro-Phe-His-Leu-Val-Ile-His-Lys(F5)-[NHR]; R = mPEG5k | 304 |
| [F5]Lys-His-Pro-Phe-His-Leu-Val-Ile-His-Lys(F5)-[NHR]; R = dPEG24 | 305 |
| [F5]Ile-His-Pro-Phe-His-Leu-Val-Ile-His-Lys(F5)-[OH] | 306 |
| [F5]Ile-His-Pro-Phe-His-Leu-Val-Ile-His-Lys(F5)-[NHR]; R = H | 307 |
| [F5]Ile-His-Pro-Phe-His-Leu-Val-Ile-His-Lys(F5)-[NHR]; R = Me | 308 |
| [F5]Ile-His-Pro-Phe-His-Leu-Val-Ile-His-Lys(F5)-[NHR]; R = Et | 309 |
| [F5]Ile-His-Pro-Phe-His-Leu-Val-Ile-His-Lys(F5)-[NHR]; R = mPEG20k | 310 |
| [F5]Ile-His-Pro-Phe-His-Leu-Val-Ile-His-Lys(F5)-[NHR]; R = mPEG10k | 311 |
| [F5]Ile-His-Pro-Phe-His-Leu-Val-Ile-His-Lys(F5)-[NHR]; R = mPEG5k | 312 |
| [F5]Ile-His-Pro-Phe-His-Leu-Val-Ile-His-Lys(F5)-[NHR]; R = dPEG24 | 313 |
| [F5]Lys (COR)-His-Pro-Phe-His-Leu-Val-Ile-His-Lys(F5)-[OH]; R = Me | 314 |
| [F5]Lys (COR)-His-Pro-Phe-His-Leu-Val-Ile-His-Lys(F5)-[OH]; R = CF3 | 315 |
| [F5]Lys (COMe)-His-Pro-Phe-His-Leu-Val-Ile-His-Lys(F5)-[NHR]; R = mPEG20k | 316 |
| [F5]Lys (COCF3)-His-Pro-Phe-His-Leu-Val-Ile-His-Lys(F5)-[NHR]; R = mPEG20k | 317 |
| [RCO]Lys (F5)-His-Pro-Phe-His-Leu-Val-Ile-His-Lys(F5)-NH2]; R = carboxyethyl | 318 |
| [RCO]Lys (F5)-Ile-His-Pro-Phe-His-Leu-Val-Ile-His-Lys(F5)-[NH2]; R = carboxyethyl | 319 |
| [RCO]Lys (F5)-His-Pro-Phe-His-Leu-Val-Ile-His-Lys(F5)-[NH2]; R = Me | 320 |
| [RCO]Lys (F5)-His-Pro-Phe-His-Leu-Val-Ile-His-Lys(F5)-[NH2]; R = mPEG5k | 321 |

TABLE 6-continued

| Imaging Agent | SEQ ID NO. |
|---|---|
| [RCO]Lys(F5)-His-Pro-Phe-His-Leu-Val-Ile-His-Lys(F5)-[NH2]; R = mPEG20k | 322 |
| [RCO]Lys(F5)-Ile-His-Pro-Phe-His-Leu-Val-Ile-His-Lys(F5)-[NH2]; R = Me | 323 |
| [RCO]Lys(F5)-Ile-His-Pro-Phe-His-Leu-Val-Ile-His-Lys(F5)-[NH2]; R = mPEG5k | 324 |
| [RCO]Lys(F5)-Ile-His-Pro-Phe-His-Leu-Val-Ile-His-Lys(F5)-[NH2]; R = mPEG20k | 325 |
| [F5]Orn-His-Pro-Phe-His-Leu-Val-Ile-His-Lys(F5)[OH] | 326 |
| Orn(F5)-His-Pro-Phe-His-Leu-Val-Ile-His-Lys(F5)[OH] | 327 |
| [F5]Orn-His-Pro-Phe-His-Leu-Val-Ile-His-Lys(F5)[NHR]; R = H | 328 |
| [F5]Orn-His-Pro-Phe-His-Leu-Val-Ile-His-Lys(F5)[NHR]; R = Me | 329 |
| [F5]Orn-His-Pro-Phe-His-Leu-Val-Ile-His-Lys(F5)[NHR]; R = mPEG5k | 330 |
| [F5]Orn-His-Pro-Phe-His-Leu-Val-Ile-His-Lys(F5)[NHR]; R = mPEG20k | 331 |
| Orn(F5)-His-Pro-Phe-His-Leu-Val-Ile-His-Lys(F5)[NHR] R = H | 332 |
| Orn(F5)-His-Pro-Phe-His-Leu-Val-Ile-His-Lys(F5)[NHR] R = Me | 333 |
| Orn(F5)-His-Pro-Phe-His-Leu-Val-Ile-His-Lys(F5)[NHR] R = mPEG5k | 334 |
| Orn(F5)-His-Pro-Phe-His-Leu-Val-Ile-His-Lys(F5)[NHR] R = mPEG20k | 335 |
| [F5]Dap-His-Pro-Phe-His-Leu-Val-Ile-His-Lys(F5)[OH] | 336 |
| Dap(F5)-His-Pro-Phe-His-Leu-Val-Ile-His-Lys(F5)[OH] | 337 |
| [F5]Dap-His-Pro-Phe-His-Leu-Val-Ile-His-Lys(F5)]NHR; R = H | 338 |
| [F5]Dap-His-Pro-Phe-His-Leu-Val-Ile-His-Lys(F5)[NHR]; R = Me | 339 |
| [F5]Dap-His-Pro-Phe-His-Leu-Val-Ile-His-Lys(F5)[NHR]; R = mPEG5k | 340 |
| [F5]Dap-His-Pro-Phe-His-Leu-Val-Ile-His-Lys(F5)[NHR]; R = mPEG20k | 341 |
| Dap(F5)-His-Pro-Phe-His-Leu-Val-Ile-His-Lys(F5)[NHR] R = H | 342 |
| Dap(F5)-His-Pro-Phe-His-Leu-Val-Ile-His-Lys(F5)[NHR] R = Me | 343 |
| Dap(F5)-His-Pro-Phe-His-Leu-Val-Ile-His-Lys(F5)[NHR] R = mPEG5k | 344 |
| Dap(F5)-His-Pro-Phe-His-Leu-Val-Ile-His-Lys(F5)[NHR] R = mPEG20k | 345 |
| [F5]Ahx-His-Pro-Phe-His-Leu-Val-Ile-His-Lys(F5)[OH] | 346 |
| Ahx(F5)-His-Pro-Phe-His-Leu-Val-Ile-His-Lys(F5)[OH] | 347 |
| [F5]Ahx-His-Pro-Phe-His-Leu-Val-Ile-His-Lys(F5)[NHR]; R = H | 348 |
| [F5]Ahx-His-Pro-Phe-His-Leu-Val-Ile-His-Lys(F5)[NHR]; R = Me | 349 |
| [F5]Ahx-His-Pro-Phe-His-Leu-Val-Ile-His-Lys(F5)[NHR]; R = mPEG5k | 350 |
| [F5]Ahx-His-Pro-Phe-His-Leu-Val-Ile-His-Lys(F5)[NHR]; R = mPEG20k | 351 |
| Ahx(F5)-His-Pro-Phe-His-Leu-Val-Ile-His-Lys(F5)[NHR]; R = H | 352 |
| Ahx(F5)-His-Pro-Phe-His-Leu-Val-Ile-His-Lys(F5)[NHR]; R = Me | 353 |
| Ahx(F5)-His-Pro-Phe-His-Leu-Val-Ile-His-Lys(F5)[NHR]; R = mPEG5k | 354 |
| Ahx(F5)-His-Pro-Phe-His-Leu-Val-Ile-His-Lys(F5)[NHR]; R = mPEG20k | 355 |
| [F5]Asp-Arg-Val-Tyr-Ile-His-Pro-Phe-His-Leu-Val-Ile-His-Lys(F5)[OH] | 356 |

TABLE 6-continued

| Imaging Agent | SEQ ID NO. |
|---|---|
| [F5]Asp-Arg-Val-Tyr-Ile-His-Pro-Phe-His-Leu-Val-Ile-His-Lys(F5)[NHR]; R = H | 357 |
| [F5]Asp-Arg-Val-Tyr-Ile-His-Pro-Phe-His-Leu-Val-Ile-His-Lys(F5)[NHR]; R = Me | 358 |
| [F5]Asp-Arg-Val-Tyr-Ile-His-Pro-Phe-His-Leu-Val-Ile-His-Lys(F5)[NHR]; R = mPEG5k | 359 |
| [F5]Asp-Arg-Val-Tyr-Ile-His-Pro-Phe-His-Leu-Val-Ile-His-Lys(F5)[NHR]; R = mPEG20k | 360 |
| [F5]Arg-Val-Tyr-Ile-His-Pro-Phe-His-Leu-Val-Ile-His-Lys(F5)[OH] | 361 |
| [F5]Arg-Val-Tyr-Ile-His-Pro-Phe-His-Leu-Val-Ile-His-Lys(F5)[NHR]; R = H | 362 |
| [F5]Arg-Val-Tyr-Ile-His-Pro-Phe-His-Leu-Val-Ile-His-Lys(F5)[NHR]; R = Me | 363 |
| [F5]Arg-Val-Tyr-Ile-His-Pro-Phe-His-Leu-Val-Ile-His-Lys(F5)[NHR]; R = mPEG5k | 364 |
| [F5]Arg-Val-Tyr-Ile-His-Pro-Phe-His-Leu-Val-Ile-His-Lys(F5)[NHR]; R = mPEG20k | 365 |
| [F5]Val-Tyr-Ile-His-Pro-Phe-His-Leu-Val-Ile-His-Lys(F5)[OH] | 366 |
| [F5]Val-Tyr-Ile-His-Pro-Phe-His-Leu-Val-Ile-His-Lys(F5)[NHR]; R = H | 367 |
| [F5]Val-Tyr-Ile-His-Pro-Phe-His-Leu-Val-Ile-His-Lys(F5)[NHR]; R = Me | 368 |
| [F5]Val-Tyr-Ile-His-Pro-Phe-His-Leu-Val-Ile-His-Lys(F5)[NHR]; R = mPEG5k | 369 |
| [F5]Val-Tyr-Ile-His-Pro-Phe-His-Leu-Val-Ile-His-Lys(F5)[NHR]; R = MPEG20k | 370 |
| [F5]Tyr-Ile-His-Pro-Phe-His-Leu-Val-Ile-His-Lys(F5)[OH] | 371 |
| [F5]Tyr-Ile-His-Pro-Phe-His-Leu-Val-Ile-His-Lys(F5)[NHR]; R = H | 372 |
| [F5]Tyr-Ile-His-Pro-Phe-His-Leu-Val-Ile-His-Lys(F5)[NHR]; R = Me | 373 |
| [F5]Tyr-Ile-His-Pro-Phe-His-Leu-Val-Ile-His-Lys(F5)[NHR]; R = mPEG5k | 374 |
| [F5]Tyr-Ile-His-Pro-Phe-His-Leu-Val-Ile-His-Lys(F5)[NHR]; R = mPEG20k | 375 |
| [F5]Ser-Pro-Leu-Ala-Gln-Ala-Val-Arg-Ser-Ser-Ser-Arg-Lys(F5) | 376 |
| [F5]Pro-Leu-Ala-Gln-Ala-Val-Lys(F5)-Arg-Ser-Ser-Ser-Arg | 377 |
| [F5]Ser-Pro-Leu-Ala-Gln-Ala-Val-Arg-Ser-Ser-Ser-Arg-Orn(F5) | 378 |
| [F5]Pro-Leu-Ala-Gln-Ala-Val-Orn(F5)-Arg-Ser-Ser-Ser-Arg | 379 |
| [F5]Ser-Pro-Leu-Ala-Asn-Ala-Val-Arg-Ser-Ser-Ser-Arg-Lys(F5) | 380 |
| [F5]Pro-Leu-Ala-Asn-Ala-Val-Lys(F5)-Arg-Ser-Ser-Ser-Arg | 381 |
| [F5]Ala-Pro-Glu-Glu-Ile-Met-Asp-Arg-Gln-Lys(F5) | 382 |
| [F5]Ala-Pro-Glu-Glu-Ile-Met-Arg-Arg-Gln-Lys | 383 |
| [F5]Ala-Pro-Glu-Glu-Ile-Met-Asp-Gln-Gln-Lys | 384 |
| [F5]Lys-His-Pro-Phe-His-Cha-Val-Ile-His-Lys(F5)[OH] | 453 |
| [F5]Lys-His-Pro-Phe-His-Cha-Val-Ile-His-Lys(F5)[NHR]; R = mPEG5k | 454 |
| [F5]Lys-His-Pro-Phe-His-Cha-Val-Ile-His-Lys(F5)[NHR]; R = mPEG20k | 455 |
| [F5]Lys(COR)-His-Pro-Phe-His-Cha-Val-Ile-His-Lys(F5)[OH]; R = Me | 456 |
| [F5]Lys(COR)-His-Pro-Phe-His-Cha-Val-Ile-His-Lys(F5)[OH]; R = CF3 | 457 |

As used in Table 6, F5 is the fluorochrome as depicted above in agent Q77, F6 is the fluorochrome as depicted above in agent Q88, MPEG is methoxypolyethylene glycol of a specified molecular weight (for example, mPEG20K is a 20 kDa methoxypolyethylene glycol). Ahx is aminohexanoic acid, Orn is ornithine, and DAP is 2,3-diaminopropionic acid.

Figure 10:
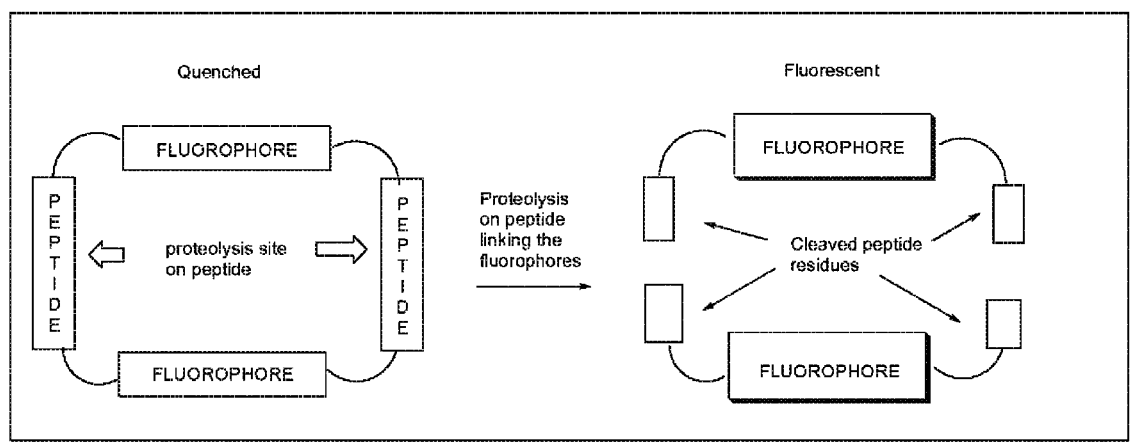
FIG. 10 is a schematic representation of an exemplary cyclic imaging agent that comprises two fluorophores separated by two peptides. Each peptide contains a proteolytic cleavage site where, when intact, the imaging agent is quenched and when the peptides are cleaved by exposure to one or more proteases, at least one fluorophore is no longer quenched by the other.

FIG. 10 is a schematic representation of an exemplary cyclic imaging agent. The cyclic imaging agent comprises two peptides connected at each end to a fluorophore. A first peptide has a first fluorophore attached in the vicinity of its N-terminus and a second fluorophore attached in the vicinity of its C-terminus, and a second oligopeptide has the first fluorophore attached in the vicinity of its C-terminus and the second fluorophore attached in the vicinity of its N-terminus. When intact, the fluorophore quenches the other fluorophore, and more preferably each fluorophore quenches the other fluorophore. It is understood, however, that one of the fluorophores could be replaced with a suitable non fluorescent quencher. Although both peptides, as shown, contain a proteolytic cleavage site, it is understood that, under certain circumstances, only one of the two peptides may have a proteolytic cleavage site. Upon cleavage of the proteolytic cleavage site(s), the fluorophores are no longer constrained in fluorescent quenching proximity to one another and the fluorophores can now fluorescence upon excitation following exposure to light of an appropriate wavelength.

Exemplary cyclic imaging agents can include an enzymatically cleavable cyclic oligopeptide, for example, an agent represented by Formula IX, wherein, for each occurrence, X is an amino acid residue, M is a biological modifier, F is a fluorophore or quencher, $X_1^*$ is X-L, $X_2^*$ is X-L, and L is a linker moiety or a bond:

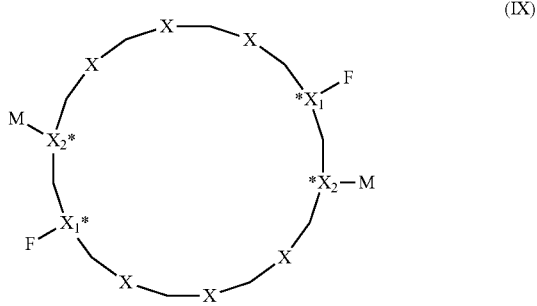

(IX)

Another exemplary enzymatically cleavable cyclic oligopeptide is represented by Formula X, wherein each X, M, F, $X_1^*$ and $X_2^*$ is as defined for Formula IX:

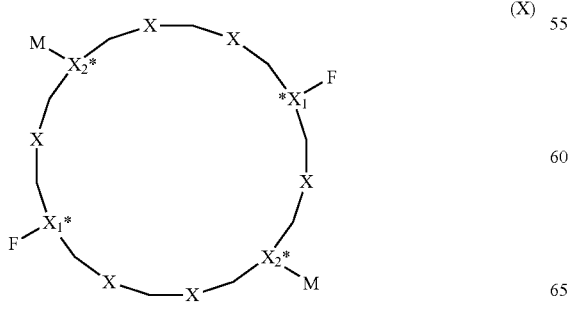

(X)

In another embodiment, an enzymatically cleavable cyclic oligopeptide is represented by Formula XI, wherein each X, M, F, $X_1^*$ and $X_2^*$ is as defined in Formula II, above:

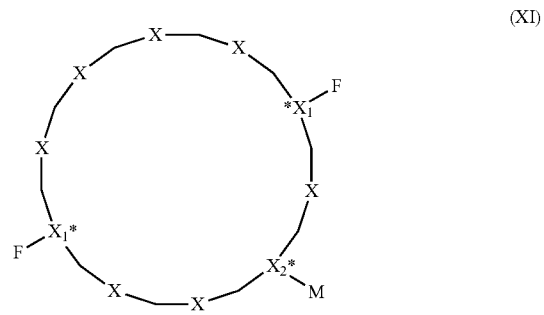

(XI)

Other exemplary enzymatically cleavable cyclic oligopeptides are represented by Formulas V, VI, and XII-XVII wherein, each F, M, $X_1^*$, and $X_2^*$ is as defined in Formula IX:

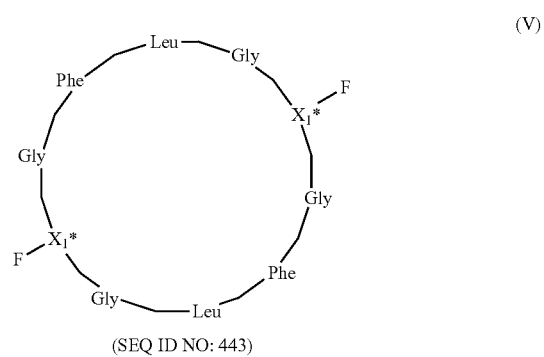

(V)

(SEQ ID NO: 443)

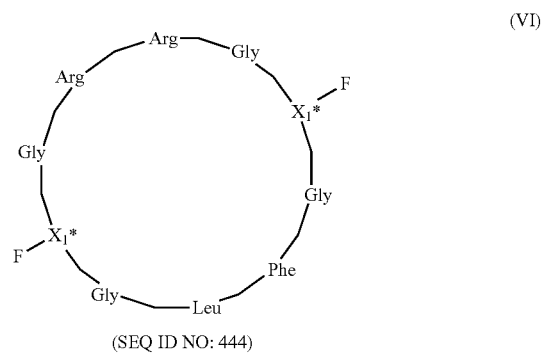

(VI)

(SEQ ID NO: 444)

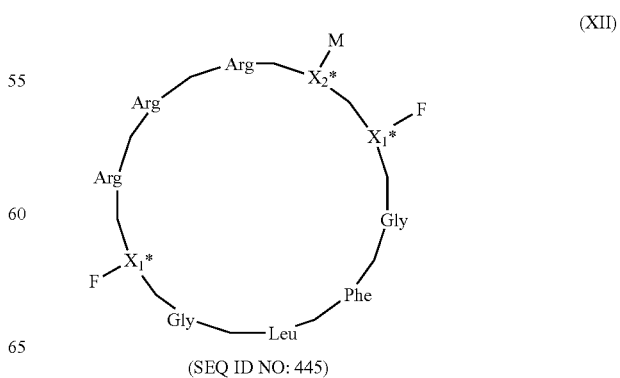

(XII)

(SEQ ID NO: 445)

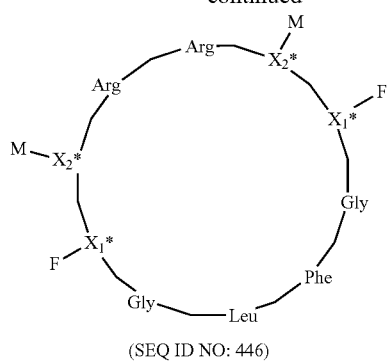
(SEQ ID NO: 446)
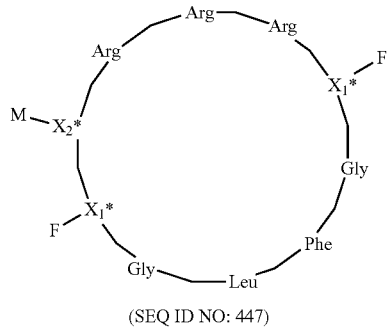
(SEQ ID NO: 447)
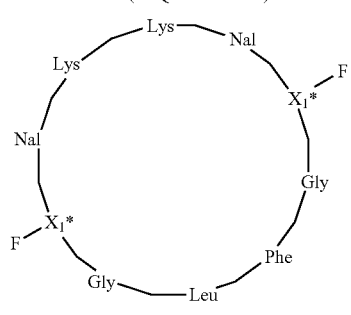
(SEQ ID NO: 448)
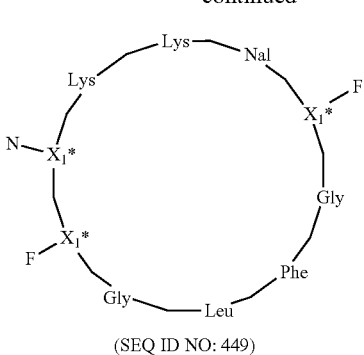
(SEQ ID NO: 449)
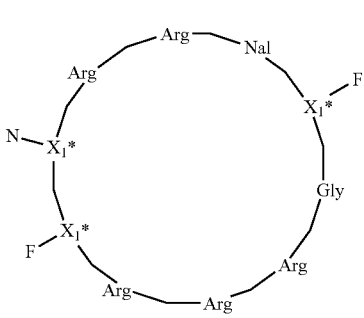
(SEQ ID NO: 450)
An enzymatically cleavable cyclic oligopeptide is represented by Formula XIII, wherein the fluorophore and modifiers are as discussed hereinabove:
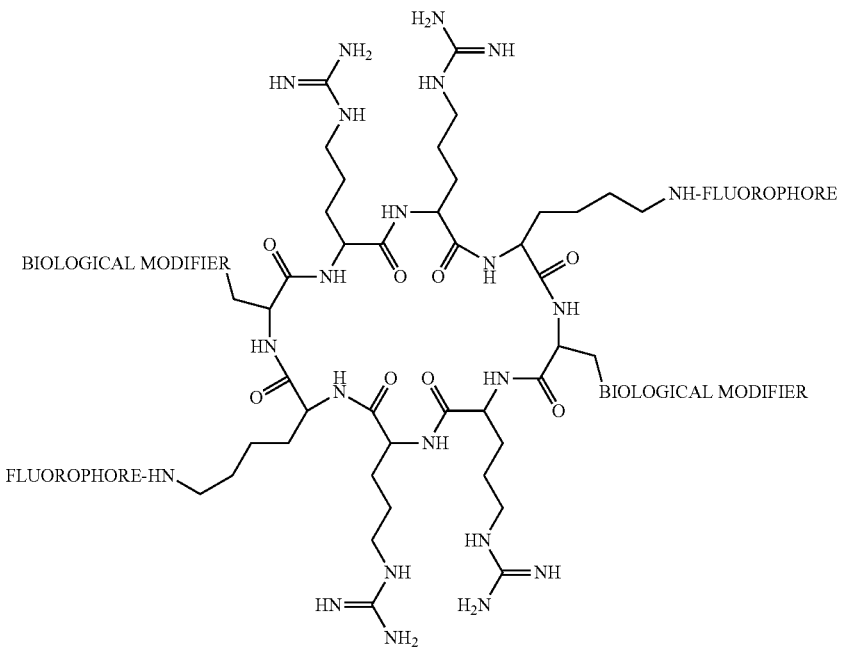

In an exemplary embodiment, an enzymatically cleavable cyclic oligopeptide imaging agent can also be represented as Formula XIX wherein the biological modifiers are as described hereinabove:

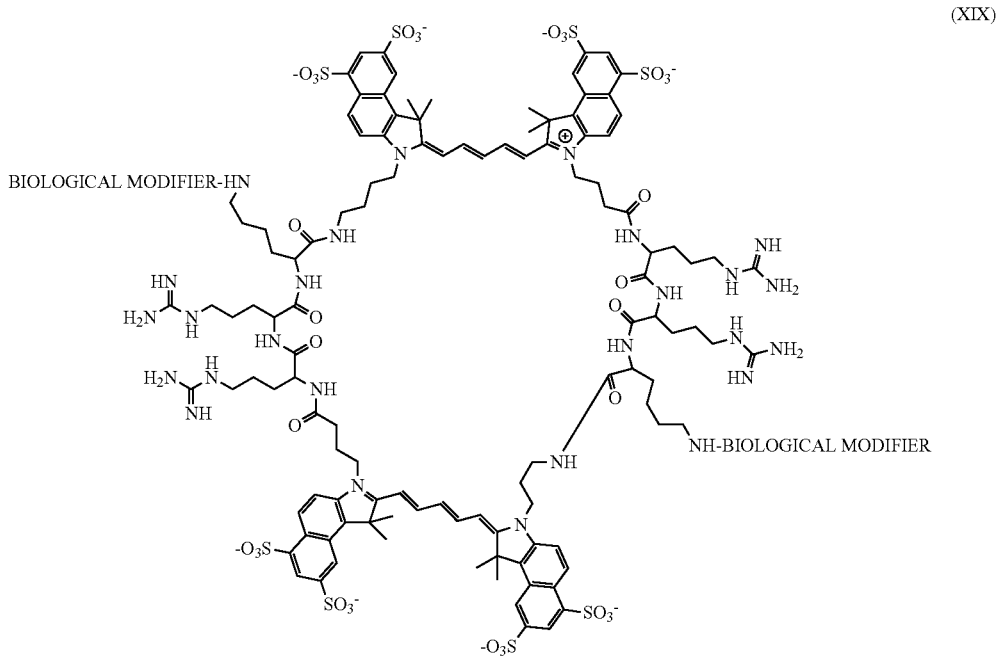

(XIX)

The resulting imaging agents preferably have a molecular weight from about 2 kDa to about 60 kDa, such as from about 5 kDa to about 50 kDa, such as from about 10 kDa to about 40 kDa, or from about 20 kDa to about 30 kDa. In certain embodiments, the imaging agent may have a molecular weight of from about 2 kDa to about 50 kDa, such as from about 2 kDa to about 45 kDa, such as from about 2 kDa to about 40 kDa, such as from about 2 kDa to about 35 kDa, such as from about 2 kDa to about 30 kDa, such as from about 2 kDa to about 25 kDa, such as from about 2 kDa to about 10 kDa, or such as from about 2 kDa to 5 kDa. In certain other embodiments, the intact imaging agent may have a molecular weight of from about 5 kDa to about 50 kDa, such as from about 5 kDa to about 45 kDa, such as from about 5 kDa to about 40 kDa, such as from about 5 kDa to about 35 kDa, such as from about 5 kDa to about 30 kDa, such as from about 5 kDa to about 25 kDa, such as from about 5 kDa to about 20 kDa, such as from about 5 kDa to about 15 kDa, or such as from about 5 kDa to about 10 kDa.

VII. Formulations

The imaging agents disclosed herein can be formulated into a pharmaceutical composition suitable for administration to a subject, for example, an animal and/or a human. The pharmaceutical composition can include one or more imaging agents and one or more excipients, for example, a stabilizer in a physiologically relevant carrier.

For in vivo use, the compositions of the present invention can be provided in a formulation suitable for administration to a subject, for example, an animal or a human. Accordingly, the formulations include the agents together with a physiologically relevant carrier suitable for the desired form and/or dose of administration. The term, "physiologically relevant carrier" is understood to mean a carrier in which the agents are dispersed, dissolved, suspended, admixed and physiologically tolerable, i.e., can be administered to, in, or on the subject's body without undue discomfort, or irritation, or toxicity. The preferred carrier is a fluid, preferably a liquid, more preferably an aqueous solution; however, carriers for solid formulations, topical formulations, inhaled formulations, ophthalmic formulations, and transdermal formulations are also contemplated as within the scope of the invention.

It is contemplated that the agents can be administered orally or parenterally. For parenteral administration, the agents can be administered intravenously, intramuscularly, cutaneously, percutaneously, subcutaneously, rectally, nasally, vaginally, and ocularly. Thus, the composition may be in the form of, e.g., solid tablets, capsules, pills, powders including lyophilized powders, colloidal suspensions, microspheres, liposomes granulates, suspensions, emulsions, solutions, gels, including hydrogels, pastes, ointments, creams, plasters, irrigation solutions, drenches, osmotic delivery devices, suppositories, enemas, injectables, implants, sprays, or aerosols. The pharmaceutical compositions can be formulated according to conventional pharmaceutical practice (see, e.g., Remington: The Science and Practice of Pharmacy, 20th edition, 2000, ed. A. R. Germaro, Lippincott Williams & Wilkins, Philadelphia, and Encyclopedia of Pharmaceutical Technology, eds. J. Swarbrick and J. C. Boylan, 1988-1999, Marcel Dekker, New York).

It is understood that the formulation of the agents, the choice of mode of administration, the dosages of agents administered to the subject, and the timing between administration of the agents and imaging is within the level of skill in the art.

VIII. Imaging Methods

The present invention provides methods for in vitro and in vivo imaging using the imaging agents disclosed herein. For a review of optical imaging techniques, see, e.g., Alfano et al., *Ann. NY Acad. Sci.* 820:248-270 (1997); Weissleder, *Nature Biotechnology* 19, 316-317 (2001); Ntziachristos et al., *Eur. Radiol.* 13:195-208 (2003); Graves et al., *Curr. Mol.*

Med. 4:419-430 (2004); Citrin et al., *Expert Rev. Anticancer Ther.* 4:857-864 (2004); Ntziachristos, Ann. Rev. Biomed. Eng. 8:1-33 (2006); Koo et al., *Cell Oncol.* 28:127-139 (2006); and Rao et al., *Curr. Opin. Biotechnol.* 18:17-25 (2007).

Optical imaging includes all methods from direct visualization without use of any device and use of devices such as various scopes, catheters and optical imaging equipment, for example computer based hardware for tomographic presentations. The imaging agents are useful with optical imaging modalities and measurement techniques including, but not limited to: endoscopy; fluorescence endoscopy; luminescence imaging; time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

An imaging system useful in the practice of the invention typically includes three basic components: (1) an appropriate light source for inducing excitation of the imaging agent, (2) a system for separating or distinguishing emissions from light used for fluorophore excitation, and (3) a detection system. The detection system can be hand-held or incorporated into other useful imaging devices, such as intraoperative microscopes. Exemplary detection systems include an endoscope, catheter, tomographic system, hand-held imaging system, or a intraoperative microscope.

Preferably, the light source provides monochromatic (or substantially monochromatic) light. The light source can be a suitably filtered white light, i.e., bandpass light from a broadband source. For example, light from a 150-watt halogen lamp can be passed through a suitable bandpass filter commercially available from Omega Optical (Brattleboro, Vt.). Depending upon the system, the light source can be a laser. See, e.g., Boas et al., *Proc. Natl. Acad. Sci. USA* 91:4887-4891, 1994; Ntziachristos et al., *Proc. Natl. Acad. Sci. USA* 97:2767-2772, 2000; and Alexander, *J. Clin. Laser Med. Surg.* 9:416-418, 1991. Information on lasers for imaging can be found, for example, at Imaging Diagnostic Systems, Inc., Plantation, Fla. and various other sources. A high pass or bandpass filter can be used to separate optical emissions from excitation light. A suitable high pass or bandpass filter is commercially available from Omega Optical, Burlington, Vt.

In general, the light detection system can be viewed as including a light gathering/image forming component and a light/signal detection/image recording component. Although the light detection system can be a single integrated device that incorporates both components, the light gathering/image forming component and light detection/image recording component are discussed separately.

A particularly useful light gathering/image forming component is an endoscope. Endoscopic devices and techniques which have been used for in vivo optical imaging of numerous tissues and organs, including peritoneum (Gahlen et al., *J. Pholochem. Photobiol. B* 52:131-135, 1999), ovarian cancer (Major et al., *Gynecol. Oncol.* 66:122-132, 1997), colon and rectum (Mycek et al., *Gastrointest. Endosc.* 48:390-394, 1998; and Stepp et al., *Endoscopy* 30:379-386, 1998), bile ducts (Izuishi et al., *Hepatogastroenterology* 46:804-807, 1999), stomach (Abe et al., *Endoscopy* 32:281-286, 2000), bladder (Kriegmair et al., *Urol. Int.* 63:27-31, 1999; and Riedl et al., *J. Endourol.* 13:755-759, 1999), lung (Hirsch et al., *Clin Cancer Res* 7:5-220, 2001), brain (Ward, *J. Laser Appl.* 10:224-228, 1998), esophagus, and head and neck regions can be employed in the practice of the present invention.

Other types of light gathering components are catheter-based devices, including fiber optics devices. Such devices are particularly suitable for intravascular imaging. See, e.g., Tearney et al., Science 276:2037-2039, 1997; and Circulation 94:3013, 1996.

Still other imaging technologies, including phased array technology (Boas et al., *Proc. Natl. Acad. Sci. USA* 91:4887-4891, 1994; Chance, *Ann. NY Acad. Sci.* 838:29-45, 1998), optical tomography (Cheng et al., *Optics Express* 3:118-123, 1998; and Siegel et al., *Optics Express* 4:287-298, 1999), intravital microscopy (Dellian et al., *Br. J. Cancer* 82:1513-1518, 2000; Monsky et al., *Cancer Res.* 59:4129-4135, 1999; and Fukumura et al., *Cell* 94:715-725, 1998), confocal imaging (Korlach et al., *Proc. Natl. Acad. Sci. USA* 96:8461-8466, 1999; Rajadhyaksha et al., *J. Invest. Dermatol.* 104:946-952, 1995; and Gonzalez et al., *J. Med.* 30:337-356, 1999) and fluorescence molecular tomography (FMT) (Nziachristos et al., *Nature Medicine* 8:757-760, 2002; U.S. Pat. No. 6,615,063, PCT WO 03/102558, and PCT WO 03/079015) can be used with the imaging agents of the invention. Similarly, the imaging agents can be used in a variety of imaging systems, for example, (1) the IVIS® Imaging Systems: 100 Series, 200 Series (Xenogen, Alameda, Calif.), (2) SPECTRUM and LUMINA (Xenogen, Alameda, Calif.), (3) the SoftScan® or the eXplore Optix™ (GE Healthcare. United Kingdom), (4) Maestro™ and Nuance™-2 Systems (CRi, Woburn, Mass.), (5) Image Station In-Vivo FX from Carestream Molecular Imaging, Rochester, N.Y. (formerly Kodak Molecular Imaging Systems), (6) OV100, IV100 (Olympus Corporation, Japan), (7) Cellvizio Mauna Kea Technologies, France), (8)] Nano-SPECT/CT or HiSPECT (Bioscan, Washington, D.C.), (9) CTLM® or LILA™ (Imaging Diagnostic Systems, Plantation, Fla.), (10) DYNOT™ (NIRx Medical Technologies, Glen Head, N.Y.), and (11) NightOWL Imaging Systems by Berthold Technologies, Germany.

A variety of light detection/image recording components, e.g., charge coupled device (CCD) systems or photographic film, can be used in such systems. The choice of light detection/image recording depends on factors including the type of light gathering/image forming component being used. It is understood, however, that the selection of suitable components, assembling them into an optical imaging system, and operating the system is within ordinary skill in the art.

For agents that have magnetic properties, MRI imaging well known in the art can also be applied in the practice of the invention. For a review of MRI techniques see Westbrook, Handbook of MRI Technique, $2^{nd}$ Edition, 1999, Blackwell Science. It is possible that images obtained, for example, by optical imaging and by magnetic resonance imaging can be co-registered or fused with one another to provide additional information about the item being imaged. Furthermore, multi-modality imaging systems (i.e., combined optical and MR imaging systems) can be used to create combined optical MR images.

In addition, the compositions and methods of the present invention can be used for other imaging compositions and methods. For example, the agents of the present invention can be imaged by other imaging modalities, such as, X-ray, computed tomography (CT), MR imaging, ultrasound, positron emission tomography (PET), and single photon computerized tomography (SPECT).

In addition, the compositions and methods of the present invention can be used in combination with other imaging compositions and methods. For example, the agents of the present invention can be imaged by optical imaging protocols either alone or in combination with other traditional imaging modalities, such as, X-ray, computed tomography (CT), MR imaging, ultrasound, positron emission tomography (PET), and single photon computerized tomography (SPECT). For instance, the compositions and methods of the present invention can be used in combination with CT or MRI to obtain both anatomical and molecular information simultaneously, for example, by co-registration of with an image generated by another imaging modality. The compositions and methods of the present invention can also be used in combination with X-ray, CT, PET, ultrasound, SPECT and other optical and MR contrast agents or alternatively, the agents of the present invention may also include imaging agents, such as iodine, gadolinium atoms and radioactive isotopes, which can be detected using CT, PET, SPECT, and MR imaging modalities in combination with optical imaging. The imaging agents can be linked to or incorporated in the agents.

(A) In Vivo Imaging

With respect to optical in vivo imaging, such a method comprises (a) administering to a subject one or more imaging agents; (b) allowing the agent(s) to distribute within the subject; (c) exposing the subject to light of a wavelength absorbable by at least one fluorophore in the imaging agent; and (d) detecting an optical signal emitted by the fluorophore. The emitted optical signal can be used to construct an image. The image can be a tomographic image. Furthermore, it is understood that steps (a)-(d) or steps (c)-(d) can be repeated at predetermined intervals thereby to permit evaluation of the subject over time.

The illuminating and/or detecting steps (steps (c) and (d), respectively) can be performed using an endoscope, catheter, tomographic system, planar system, hand-held imaging system, goggles, or an intraoperative imaging system or microscope.

Before or during these steps, a detection system can be positioned around or in the vicinity of a subject (for example, an animal or a human) to detect signals emitted from the subject. The emitted signals can be processed to construct an image, for example, a tomographic image. In addition, the processed signals can be displayed as images either alone or as fused (combined) images.

In addition, it is possible to practice an in vivo imaging method that selectively detects and images one or more molecular imaging probes, including the imaging agents simultaneously. In such an approach, for example, in step (a) noted above, two or more imaging probes whose signal properties are distinguishable from one another are administered to the subject, either at the same time or sequentially, wherein at least one of the molecular imaging probes is a agent. The use of multiple probes permits the recording of multiple biological processes, functions or targets.

The subject may be a vertebrate, for example, a mammal, for example, a human. The subject may also be a non-vertebrate (for example, C. elegans, drosophila, or another model research organism, etc.) used in laboratory research.

Information provided by such in vivo imaging approaches, for example, the presence, absence, or level of emitted signal can be used to detect and/or monitor a disease in the subject. Exemplary diseases include, without limitation, autoimmune disease, bone disease, cancer, cardiovascular disease, environmental disease, dermatological disease, immunologic disease, inherited disease, infectious disease, metabolic disease, neurodegenerative disease, ophthalmic disease, and respiratory disease. In addition, in vivo imaging can be used to assess the effect of a compound or therapy by using the imaging agents, wherein the subject is imaged prior to and after treatment with the compound or therapy, and the corresponding signal/images are compared.

The invention also features an in vivo imaging method where labeled cells are administered to the recipient. The cells can be labeled with the imaging agents ex vivo. The cells can be derived directly from a subject or from another source (e.g., from another subject, cell culture, etc.). The imaging agents can be mixed with the cells to effectively label the cells and the resulting labeled cells administered to the subject into a subject in step (a). Steps (b)-(d) then are followed as described above. This method can be used for monitoring trafficking and localization of certain cell types, including T-cells, tumor cells, immune cells and stem cells, and other cell types. In particular, this method may be used to monitor cell-based therapies.

The methods of the invention can be used to determine a number of indicia, including tracking the localization of the agent in the subject over time or assessing changes or alterations in the metabolism and/or excretion of the agent in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The methods and compositions described herein can be used to help a physician or surgeon to identify and characterize areas of disease, such as arthritis, cancers and specifically colon polyps, or vulnerable or unstable plaque, atherosclerosis, to distinguish diseased and normal tissue, such as detecting tumor margins that are difficult to detect using an ordinary operating microscope, e.g., in brain surgery, to help dictate a therapeutic or surgical intervention, e.g., by determining whether a lesion is cancerous and should be removed or non-cancerous and left alone, or in surgically staging a disease, e.g., intraoperative lymph node staging, sentinel lymph node mapping, or assessing intraoperative bleeding.

The methods and compositions described herein can also be used in the detection, characterization and/or determination of the localization of a disease, especially early disease, the severity of a disease or a disease-associated condition, the staging of a disease, and/or monitoring a disease. The presence, absence, or level of an emitted signal can be indicative of a disease state.

The methods and compositions disclosed herein can also be used to monitor and/or guide various therapeutic interventions, such as surgical procedures, and monitoring drug therapy, including cell based therapies. The methods can also be used in prognosis of a disease or disease condition.

With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone), cardiovascular disease (for example, atherosclerosis and inflammatory conditions of blood vessels, ischemia, hypertension, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, Malaria, Chagas Disease, Schistosomiasis), immunologic disease (for example, an autoimmune disorder, lymphoma, multiple sclerosis, rheumatoid arthritis, diabetes mellitus, lupus erythematosis, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants).

The methods and compositions described herein, therefore, can be used, for example, to determine the presence and/or localization of tumor cells, the presence and/or localization of inflammation, including the presence of activated macrophages, for instance in atherosclerosis or arthritis, the presence and in localization of vascular disease including areas at risk for acute occlusion (i.e., vulnerable plaques) in coronary and peripheral arteries, regions of expanding aneurysms, unstable plaque in carotid arteries, and ischemic areas. The methods and compositions of the invention can also be used in identification and evaluation of cell death, injury, apoptosis, necrosis, hypoxia and angiogenesis. The methods and compositions can also be used for drug delivery and to monitor drug delivery, especially when drugs or drug-like molecules are chemically attached to the imaging agents.

(B) In Vitro Methods

With respect to in vitro imaging, the imaging agents can be used in a variety of in vitro assays. For example, an exemplary in vitro imaging method comprises: (a) contacting a sample, for example, a biological sample, with one or more imaging agents of the invention; (b) allowing the agent(s) to interact with a biological target in the sample; (c) optionally, removing unbound agents; (d) in the case of fluorescent agents, illuminating the sample with light of a wavelength absorbable by a fluorophore of the agents; and (e) detecting a signal emitted from fluorophore thereby to determine whether the agent has been activated by or bound to the biological target.

After an agent has been designed, synthesized, and optionally formulated, it can be tested in vitro by one skilled in the art to assess its biological and performance characteristics. For instance, different types of cells grown in culture can be used to assess the biological and performance characteristics of the agent. Cellular uptake, binding or cellular localization of the agent can be assessed using techniques known in the art, including, for example, fluorescent microscopy, FACS analysis, immunohistochemistry, immunoprecipitation, in situ hybridization and Forster resonance energy transfer (FRET) or fluorescence resonance energy transfer. By way of example, the agents can be contacted with a sample for a period of time and then washed to remove any free agents. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the agents. Other detection methods including, but not limited to flow cytometry, immunoassays, hybridization assays, and microarray analysis can also be used.

The invention will now be illustrated by the following examples, which are given for the purpose of illustration only and without any intention of limiting the scope of the present invention.

EXAMPLES

Representative materials and methods that may be used in preparing the materials of the invention are described below. All chemicals and solvents (reagent grade) were used as commercially obtained without further purification. HPLC Analysis: Analytical RP HPLC was performed on a Waters 2695 system using either a Phenomenex Phenyl-hexyl column (3μ, 100×4.6 mm) or C18 column (5μ, 50×4.6 mm) with a flow rate of 1 to 2 mL/min. Chromatograms were monitored at 254 nm and 675 nm. Preparative HPLC was performed on a Varian system using either a Phenomenex Phenyl-hexyl column or a Phenomenex C18 column (250× 10 mm) at 4.7 mL/min using similar gradient as the analytical run.

Example 1: Synthesis of the Succinimidyl Ester Form of Fluorophore Conjugated Peptides The imaging agents set forth in Table 7 were made in accordance with the principles discussed in this Example.

TABLE 7

| Imaging Agent | SEQ ID NO. |
|---|---|
| Acetyl-Phe-Arg-Lys(F5)-Gly-Gly-Arg-Lys(F5)-OH | 385 |
| Acetyl-Phe-Gly-Lys(F5)-Arg-Arg-Lys(F5)-Gly-OH | 386 |
| F5-Gly-Phe-Leu-Gly-Lys(F5)-OH | 387 |
| Acetyl-Phe-Arg-Lys(F5)-Gly-G-Arg-Lys(F5)-[OH] | 388 |
| pentynoyl-Phe-Arg-Lys-(F5)-Gly-Gly-Arg-Lys(F5)-[OH] | 389 |
| pentynoyl-Phe-Gly-Lys(F5)-Arg-Arg-Lys(F5)-[OH] | 390 |
| pentynoyl-Lys(F5)-Pro-Leu-Gly-Val-Arg-Lys(F5)-[OH] | 391 |
| pentynoyl-Lys(F5)-Gly-Phe-Leu-Gly-βA-Lys(F5)-[OH] | 392 |
| pentynoyl-Lys(F5)-Val-Arg-Leu-Gly-Pro-Lys(F5)-[OH] | 393 |
| pentynoyl-Lys(F5)-Gly-His-Pro-Gly-Gly-Pro-Gln-Gly-Lys(F5)-[OH] | 394 |
| pentynoyl-Lys(F5)-His-Pro-Gly-Gly-Pro-Gln-Lys(F5)-[OH] | 395 |
| [F5]-His-Gly-Pro-Arg-Lys(F5)-[OH] | 242 |

TABLE 7-continued

| Imaging Agent | SEQ ID NO. |
|---|---|
| [F5]-Lys-His-Pro-Phe-His-Leu-Val-Ile-His-Lys(F5)-[NH2] | 396 |
| [F5]-His-Gly-Pro-Asn-Lys(F5)-[OH] | 240 |
| [F5]-His-Gly-Pro-Asn-Lys(F5)-His-Gly-Pro-Asn-βA-[OH] | 243 |
| [F5]-Ile-His-Pro-Phe-His-Leu-Leu-Tyr-His-Lys(F5)-[OH] | 397 |
| [F5]-Ile-His-Pro-Phe-His-Leu-Leu-Tyr-Tyr-Lys(F5)-[OH] | 398 |
| Acetyl-Lys(F5)-Lys-Lys-Lys(F5)Gly-[OH] | 399 |
| Acetyl-Lys(F5)-Lys-Lys-Lys(F5)-Lys-Lys-Gly-[OH] | 400 |
| [F5]-Lys-His-Pro-Phe-His-Leu-Val-Ile-His-Lys(F5)-[OH] | 401 |
| succinyl-Lys(F5)-Gly-Phe-Leu-Gly-Lys(F5)-[NH$_2$] | 402 |
| succinyl-Lys(F6)-Gly-Phe-Leu-Gly-Lys(F6)-[NH$_2$] | 403 |
| succinyl-Lys(F5)-Arg-Arg-Lys(F5)-[NH$_2$] | 404 |
| succinyl-Lys(F6)-Arg-Arg-Lys(F6)-[NH$_2$] | 405 |
| succinyl-Lys(F6)-Ala-Arg-Arg-Lys(F6)-[NH$_2$] | 406 |
| succinyl-Lys(F5)-Lys-Lys-Lys(F5)-[NH$_2$] | 407 |
| succinyl-Lys(F6)-Arg-Arg-Arg-Lys(F6)-[NH$_2$] | 408 |
| [F5]-His-Gly-Pro-Ile-Lys-[OH] | 409 |
| [F5]-Asn-Gly-Pro-Ile-Lys-[OH] | 410 |
| [F6]-Gly-Pro-Leu-Gly-Val-Arg-Lys(F6)-[OH] | 411 |
| [F5]-Gly-Val-Arg-Leu-Gly-Pro-Lys(F5) = [OH] | 412 |
| [F5]-Gly-Pro-Leu-Gly-Val-Arg-Lys(F5)-[OH] | 413 |
| [F6]-His-Gly-Pro-Asn-Lys-[OH] | 414 | wherein F5 was the fluorophore described in the imaging agent of Formula Q77, and F6 was the fluorophore described in the imaging agent of Formula Q88.

Part A. Preparation of Fluorophore Conjugated Peptide

Individual peptide (as set forth in Table 7; 0.45 μmol) and fluorophore No. 3 from Table 2 (1.0 μmol) were combined in 100 μL of N,N-dimethylformamide (DMF) with 1 μL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 μL of 0.1 M sodium bicarbonate and purified by HPLC using a 10% to 35% gradient of acetonitrile in 25 mM triethylammonium acetate, pH 7, on a 10 mm×250 mm 300 Å C18 column. The purified peptide was characterized by LC-MS.

Part B. Preparation of the Succinimidyl Ester of the Labeled Peptide at the C-Terminus The fluorophore labeled peptide (0.25 μmol) was dissolved in 50 μL DMF containing 0.5 mg of disuccinimidyl carbonate (DSC) and 0.5 μL NMM. The solution was placed on rotator shielded from light and rotated at room temperature for 4 h. The peptide succinimidyl ester was precipitated by addition of 1.5 mL of MTBE, isolated by centrifugation and decanting of the supernatant and dried briefly under vacuum.

Example 2: Synthesis of mPEG-5kDa Conjugated Peptide

Methoxypolyethylene glycol amine (mPEG-NH$_2$, Laysan Bio, molecular weight 5 kDa, 2.5 mg, 0.50 μmol) was dissolved in 100 μL DMF and 1 μL NMM. The solution was added to 0.25 μmol of the labeled peptide succinimidyl ester (from Example 1) and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 μL water and purified by HPLC on a 10 mm×250 mm 300 Å C18 column. The pegylated peptide was characterized by RP-18 HPLC and SEC HPLC.

Example 3: Synthesis of mPEG-20kDa Conjugated Peptide

Methoxypolyethylene glycol amine (mPEG-NH$_2$, Laysan Bio, molecular weight 20 kDa, 10 mg, 0.50 μmol) was dissolved in 100 μL DMF and 1 μL NMM. The solution was added to 0.25 μmol of the labeled peptide succinimidyl ester (from Example 1) and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 μL water and purified by HPLC on a 10 mm×250 mm 300 Å C18 column. The pegylated peptide was characterized by RP-18 HPLC and SEC HPLC.

Example 4: Synthesis of mPEG-30kDa Conjugated Peptide

Methoxypolyethylene glycol amine (mPEG-NH$_2$, Laysan Bio, molecular weight 30 kDa, 15 mg, 0.50 μmol) was dissolved in 100 μL DMF and 1 μL NMM. The solution was added to 0.25 μmol of the labeled peptide succinimidyl ester (from Example 1) and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 μL water and purified by HPLC on a 10 mm×250 mm 300 Å C18 column. The pegylated peptide was characterized by RP-18 HPLC and SEC HPLC.

Example 5: Synthesis of Pegylated Poly-L-Lysine Conjugated Peptide

The peptide succinimidyl ester (0.25 μmol) from Example 1, was dissolved in 50 μL DMSO and added to a solution containing approximately 400,000-500,000 Da pegylated poly-L-lysine (0.17 μmol) in 1.5 mL HEPES buffer, pH 7. The solution was rotated at room temperature for 4 hours, then 20 μL of acetic anhydride and 1.0 mL of carbonate/ bicarbonate buffer, pH 9 was added and rotation continued for 2 hours. The polymer conjugated peptide was purified from unreacted peptide by gel filtration using P-100 gel (BioRad) and elution with 1×PBS. Purity of the product was assessed by RP-18 HPLC and SEC HPLC.

Example 6: Synthesis of Pegylated Poly-D-Lysine Conjugated Peptide

The peptide succinimidyl ester (0.25 µmol) from Example 1, is dissolved in 50 µL DMSO and added to a solution containing approximately 300,000-500,000 Da pegylated poly-L-lysine (0.17 µmol) in 1.5 mL HEPES buffer, pH 7. The solution is rotated at room temperature for 4 hours, then 20 µL of acetic anhydride and 1.0 mL of carbonate/bicarbonate buffer, pH 9 added and rotation continued for 2 hours. The polymer conjugated peptide is purified from unreacted peptide by gel filtration using P-100 gel (BioRad) and eluted with 1×PBS. Purity of the product is assessed by RP-18 HPLC and SEC HPLC.

Example 7: Synthesis of a Branched PEG Peptide Conjugate

Methoxypolyethylene glycol amine (mPEG-NH$_2$, Laysan Bio, molecular weight 20 kDa, 100 mg, 5.0 µmol) was dissolved in 1000 µL DMF. The solution was added to 175 µL of DMF containing N-fmoc glutamic acid (0.9 mg, 2.5 µmol) and 2-(1H-7-Azabenzotriazol-1-yl)-1,1,3,3-tetramethyl uronium hexafluorophosphate (HATU, 1.9 mg, 5 µmol) followed by addition of 2.1 µL (12 µmol) of diisopropylethylamine. The solution was stirred at room temperature for 2 hours, and the resulting product was precipitated by addition of 10 mL of methyl tertiary-butyl ether. The solvent was decanted and the branched PEG was purified by by HPLC on a 21 mm×250 mm 300 Å C18 column.

The fmoc group of the purified product was deprotected with 20% v/v diethylamine in DMF for 30 minutes, followed by precipitation with methyl tertiary-butyl ether to yield amine-functionalized branched PEG. The amine-functionalized branched PEG (15 mg, 0.50 µmol) was dissolved in 100 µL DMF and 1 µL NMM. The solution was added to 0.25 µmol of the labeled peptide (from Example 1) along with 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) and the solution was placed on rotator shielded from light and rotated at room temperature for 16 h. The pegylated peptide was precipitated by addition of 1.5 mL of MTBE, isolated by centrifugation and decanting of the supernatant. The pegylated peptide was dried briefly under vacuum, dissolved in 350 µL water and purified by HPLC using a 10% to 85% gradient of acetonitrile in 25 mM triethylammonium bicarbonate, pH 8.5, on a 21 mm×250 mm 300 Å C18 column. The branched PEG conjugated peptide was further purified by strong anion exchange chromatography. The branched PEG conjugated peptide was characterized by RP-18 HPLC and SEC HPLC.

Example 8: Synthesis of a Polyvinylpyrrolidone Peptide Conjugate

Carboxy functionalized polyvinylpyrrolidone (6 kDa, Polymersource, 20 mg, 3.3 µmol) was dissolved in 200 µL DMF with disuccinimidyl carbonate (5 mg, 20 µmol) and DMAP (0.5 mg, 5 µmol) and rotated at room temperature for 4 hours. The succinimidyl ester functionalized polyvinylpyrrolidone was precipitated with 1.5 mL of ethyl acetate.

The labeled peptide from Example 1A above (0.75 µmol) along with 1-ethyl-3-(3-dimethylaminopropyl) carbodiimide hydrochloride (EDC, 2.5 mg, 13 µmol) and hydroxybenzotriazole (HOBT, 2.5 mg, 19 µmol) were dissolved in 750 µL of 0.1 M MES buffer, pH 6. To the solution was added 200 µL of 1 M ethylene diamine dihydrochloride in 1 M HEPES buffer, pH 7 and the solution was placed on rotator shielded from light and rotated at room temperature for 16 hours. The amine functionalized peptide was purified by HPLC.

The amine functionalized peptide (0.5 µmol) described in the paragraph above, was dissolved in 200 µL DMF containing 20 mg of the succinimidyl ester functionalized polyvinylpyrrolidone described above along with DMAP (0.5 mg, 5 µmol). The solution was rotated at RT for 24 hours. The polyvinylpyrrolidone conjugated peptide was precipitated by addition of 1.5 mL of MTBE and isolated by centrifugation and decanting of the supernatant. The pegylated peptide was dried briefly under vacuum, dissolved in 350 µL water and purified by HPLC. The polyvinylpyrrolidone conjugated peptide was further purified by strong anion exchange chromatography. The polyvinylpyrrolidone conjugated peptide was characterized by RP-18 HPLC and SEC HPLC.

Example 9: Synthesis of an Aminodextran Peptide Conjugate

Aminodextran (Invitrogen, molecular weight 10 kDa, 19 mg, 1.9 µmol) was dissolved in 150 µL 0.1 mM MES pH 6. The solution was added to 0.75 µmol of the labeled peptide (from Example 1) along with 1-ethyl-3-(3-dimethylaminopropyl) carbodiimide hydrochloride (EDC, 2 mg, 10 µmol) and hydroxybenzotriazole (HOBT, 2 mg, 15 µmol) and the solution was placed on rotator shielded from light and rotated at room temperature for 16 hours. The aminodextran conjugated peptide was purified by HPLC. The aminodextran conjugated peptide was further purified by gel filtration chromatography using Biogel P10 (Biorad) and eluting with 1×PBS. The aminodextran conjugated peptide was characterized by RP-18 HPLC and SEC HPLC.

Example 10: Synthesis of an Iron Oxide Nanoparticle Peptide Conjugate

A solution of amine-functionalized iron oxide nanoparticles (16 mg total iron) in 8 mL 0.1 mM MES pH 6 was combined with 0.5 µmol of the labeled peptide (from Example 1A above) along with 1-ethyl-3-(3-dimethylaminopropyl) carbodiimide hydrochloride (EDC, 5 mg, 25 µmol) and hydroxybenzotriazole (HOBT, 5 mg, 38 µmol) and the solution was placed on rotator shielded from light and rotated at room temperature for 16 hours. The iron oxide nanoparticle conjugated peptide was purified by gel filtration chromatography using Biogel P100 (Biorad) and eluting with 1×PBS. The aminodextran conjugated peptide was characterized by SEC HPLC.

Example 11: Synthesis of Exemplary Imaging Agent

This example describes the synthesis of an exemplary imaging agent denoted by Formula XXII.

(XXII)

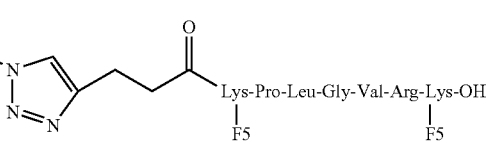
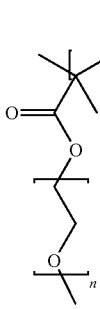

The fluorophore labeled, alkyne-modified peptide Lys-Pro-Leu-Gly-Val-Arg-Lys (SEQ ID NO:415) (400 μmol) was combined with the azide 11-azido-3,6,9-trioxaundecan-1-amine (azido-PEG-amine, n=3) in 200 μL of 65 mM triethylammonium chloride, 25 mM sodium phosphate, pH 5 to which 0.2 mg of nano-sized copper powder was added. The mixture was rotated at room temperature for 1 hour, filtered, and purified by HPLC on a 10 mm×250 mm 300 Å C18 column. The purified peptide was characterized by MALDI MS (calculated 3135.05, found 3135.13).

The resulting amine functionalized peptide (0.16 μmol) was dissolved in 200 μL DMSO with 0.35 μmol PolyPEG NHS ester (Warwick Effect Polymers) and 0.2 μL diisopropylethylamine. The solution was rotated at RT for 24 hours. The pegylated peptide was precipitated by addition of 1.5 mL of MTBE, isolated by centrifugation and decanting of the supernatant. The pegylated peptide was dried briefly under vacuum, dissolved in 350 μL water and purified by HPLC on a 10 mm×250 mm 300 Å C18 column. The pegylated peptide was characterized by RP-18 HPLC and SEC HPLC.

Example 12: Cyclic Peptide Imaging Agent

This example describes the synthesis of the cyclic imaging agent represented by Formula XXIII.

(XXIII)

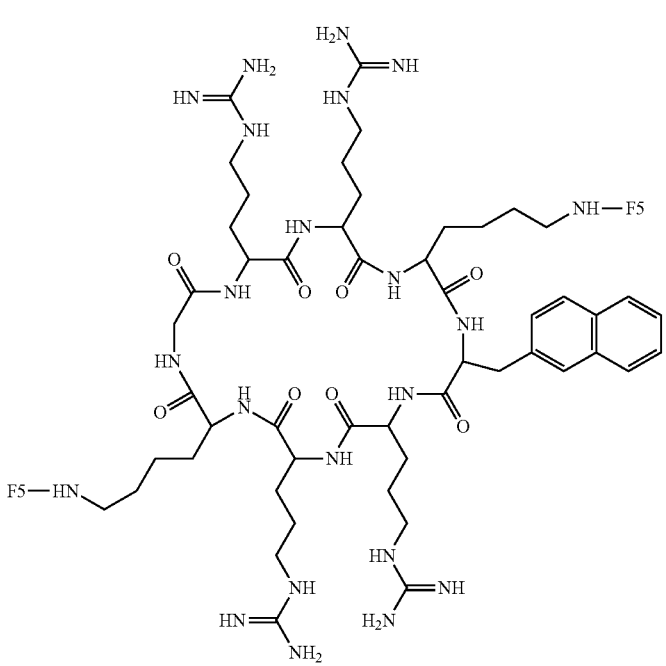

The peptide Arg(Pbf)-Arg(Pbf)-Lys(boc)-Nal-Arg(Pbf)-Arg(Pbf)-Lys(boc)-Gly-OH (SEQ ID NO:416) is prepared using solid phase synthesis as known in the art of solid phase peptide synthesis using the Fmoc protection/deprotection strategy. The resin used is Fmoc-Gly-HMPB-MBHA resin that is commercially available. The peptide is cleaved off the resin using 1% TFA in methylene chloride to retain acid labile side chain protecting groups. Head-tail cyclization is effected by heating a solution of the peptide in DMF in the presence of Hunig's base and HBTU. After cyclization is achieved, the side chain protecting groups are removed under acidic conditions such as 95% TFA-5% water or other similar deprotection cocktails known in the art. Fluorophore 3 from Table 2 is coupled to the two lysine side chain amines and the product is isolated and purified by reversed phase HPLC.

Example 13: Synthesis of Exemplary Imaging Agent

This Example describes the synthesis of the exemplary imaging agent [F5]Lys(COCF$_3$)-His-Pro-Phe-His-Leu-Val-Ile-His-Lys(F5)-[OH] (SEQ ID NO:417).

Starting material peptide Lys(COCF3)-His-Pro-Phe-His-Leu-Val-Ile-His-Lys-(OH) (SEQ ID NO:418) (6 µmol) and fluorophore No. 3 from Table 2 (20 µmol) were combined in 2 mL of N,N-dimethylformamide (DMF) with 6 µL of N-methylmorpholine (NMM). The solution was shielded from light and magnetically stirred at room temperature for 16 hOURS. The labeled peptide was precipitated by addition of 2 mL of methyl-t-butyl ether (MTBE) followed by centrifugation and decanting of the supernatant. The solid peptide was dried briefly under vacuum, dissolved in 1.2 mL of 0.1 M sodium bicarbonate and stirred at room temperature for 4 hrs. The mixture then was purified by HPLC on a 10 mm×250 mm phenyl hexyl column. The purified peptide was characterized by LC-MS (ESI+, (M+3)/3: 1,131.02).

Example 14: Synthesis of Exemplary Imaging Agent

This Example describes the synthesis of the exemplary imaging agent [F5]Lys-His-Pro-Phe-His-Leu-Val-Ile-His-Lys(F5)-[OH] (SEQ ID NO:298) (agent R20).

Product agent from Example 13 (2 µmol) was dissolved in 0.9 mL of water and 0.3 mL of concentrated ammonium hydroxide. The solution was shielded from light and magnetically stirred at room temperature for 16 hours. The mixture then was purified by HPLC on a 10 mm×250 mm phenyl hexyl column. The purified peptide was characterized by LC-MS (ESI+, (M+3)/3: 1,099.03)

Example 15: Synthesis of Exemplary Imaging Agent

This Example describes the synthesis of the imaging agent [F5]Lys-His-Pro-Phe-His-Leu-Val-Ile-His-Lys(F5)-[NHmPEG20k (SEQ ID NO:419) (agent R21).

A mixture of product agent from Example 13 (9 µmol), methoxypolyethylene glycol amine (mPEG-NH$_2$, Laysan Bio, molecular weight 20 kDa, 220 mg, 11 µmol) was dissolved, EDC (52 µmol), HOBt (74 µmol), NMM (40 µL) in 6 mL of DMF was shielded from light and magnetically stirred at room temperature for 3 days. The pegylated peptide was precipitated by addition of 20 mL of MTBE, isolated by centrifugation and decanting of the supernatant. The pegylated peptide was dissolved in 3 mL of 0.1 M aqueous sodium bicarbonate and stirred at room temperature for 4 hrs. Concentrated ammonium hydroxide (1.2 mL) was added and the resulting mixture was stirred at room temperature for 16 hours. The mixture was purified by HPLC. The pegylated peptide was further purified by anion exchange chromatography and characterized by RP-HPLC.

Example 16: Synthesis of Exemplary Imaging Agent

This Example describes the synthesis of the imaging agent [F5]Ile-His-Pro-Phe-His-Leu-Leu-Tyr-Tyr-Lys(F5)-[OH] (SEQ ID NO:420).

Starting material peptide, Ile-His-Pro-Phe-His-Leu-Leu-Tyr-Tyr-Lys-(OH] (SEQ ID NO:421) (1.9 µmol) and fluorophore No. 3 from Table 2 (9 µmol) were combined in 900 µL of N,N-dimethylformamide (DMF) with 5 µL of N-methylmorpholine (NMM). The solution was placed on rotator shielded from light and rotated at room temperature for 16 hours. The labeled peptide was precipitated by addition of 5 mL of methyl-t-butyl ether (MTBE) followed by centrifugation and decanting of the supernatant. The solid peptide was dried briefly under vacuum, dissolved in 0.9 mL of 0.1 M hydroxylamine and stirred at room temperature for 2 hrs. To this solution was added 0.3 mL of 0.1 M aqueous sodium bicarbonate and the mixture was stirred at room temperature for 3 days. The mixture was purified by HPLC. The purified peptide was characterized by LC-MS (ESI+, (M+3)/3: 1,124.03).

Example 17: Synthesis of Exemplary Imaging Agent

This Example describes the synthesis of the imaging agent [F5]Lys-His-Pro-Phe-His-Leu-Val-Ile-His-Lys(F5)-[NHmPEG5k] (SEQ ID NO:304) (Agent R27)

A mixture of product from Example 13 (2.5 µmol), methoxypolyethylene glycol amine (mPEG-NH$_2$, Laysan Bio, molecular weight 5 kDa, 30 mg, 6 µmol), EDC (78 µmol), HOBt (111 µmol), NMM (15 µL) in 2 mL of DMF was shielded from light and magnetically stirred at room temperature for 16 hours. The pegylated peptide was precipitated by addition of 10 mL of MTBE, isolated by centrifugation and decanting of the supernatant. The pegylated peptide was dissolved in 0.8 mL of 0.1 M aqueous sodium bicarbonate and stirred at room temperature for 5 hours. Concentrated ammonium hydroxide (0.6 mL) was added and the resulting mixture was stirred at room temperature for 16 hours. The mixture was purified by HPLC using a 10% to 85% gradient of acetonitrile in 25 mM triethylammonium bicarbonate, pH 8.5, on a 10 mm×250 mm 300 Å C18 column. The pegylated peptide was characterized by RP-HPLC.

Example 18: Synthesis of Exemplary Imaging Agent

This Example describes the synthesis of the imaging agent [F5]Lys-His-Pro-Phe-His-Leu-Val-Ile-His-Lys(F5)-[NHdPEG$_{24}$] (SEQ ID NO:305) (Agent R26)

A mixture of product agent from Example 13 (1.0 µmol), methyl-PEG$_{24}$-Amine (MA(PEG)24 Thermo Scientific, 5.5 µmol), EDC (15 µmol), HOBt (17 µmol), NMM (20 µL) in 1 mL of DMF was shielded from light and magnetically stirred at room temperature for 16 hours. The pegylated peptide was precipitated by addition of 10 mL of MTBE, isolated by centrifugation and decanting of the supernatant. The pegylated peptide was dissolved in 0.7 mL of 0.1 M aqueous sodium bicarbonate and stirred at room temperature for 2 hours. The main component of the mixture was isolated by preparative HPLC using a 10% to 85% gradient of acetonitrile in 25 mM triethylammonium bicarbonate, pH 8.5, on a C18 column. The combined fractions were treated with concentrated ammonium hydroxide (1.0 mL) and the resulting mixture was stirred at room temperature for 5 days. The mixture was purified by HPLC using a 10% to 35% gradient of acetonitrile in 25 mM triethylammonium bicarbonate, pH 8.5 on C18 column. The pegylated peptide was characterized by RP-HPLC.

Example 19: Synthesis of Exemplary Imaging Agent

This Example describes the synthesis of the imaging agent [F5]Lys(Ac)-His-Pro-Phe-His-Leu-Val-Ile-His-Lys(F5)-[OH] (SEQ ID NO:314) (Agent R23)

To a solution of product agent from Example 14 (1.0 µmol) in DMF (1 mL) was added N-methylmorpholine (30 µL) and a solution of succinimidyl acetate (2.8 µmol) in acetic acid (4 µL). The solution was placed on rotator shielded from light and rotated at room temperature for 17 hours. The peptide was precipitated by addition of ether followed by centrifugation and decanting of the supernatant. The crude product was dissolved in 1 mL of 0.1 M aqueous sodium bicarbonate and stirred at room temperature overnight. The mixture then was purified by HPLC using a 20% to 35% gradient of acetonitrile in 25 mM triethylammonium bicarbonate, pH 8.5 on phenyl hexyl column. The purified peptide was characterized by LC-MS (ESI+, (M+3)/3: 1,113.03).

Example 20: Synthesis of Exemplary Imaging Agent

This Example describes the synthesis of the exemplary imaging agent [F5]Lys(COCF3)-His-Pro-Phe-His-Cha-Val-Ile-His-Lys(F5)-[OH] (SEQ ID NO:458).

Starting material peptide Lys(COCF3)-His-Pro-Phe-His-Cha-Val-Ile-His-Lys-(OH) (7.8 µmol) and a fluorophore No. 3 of Table 2 (20 µmol) were combined in 2 mL of N,N-dimethylformamide (DMF) with 100 µL of N-methylmorpholine (NMM). The solution was shielded from light and magnetically stirred at room temperature for 16 hours. The labeled peptide was precipitated by addition of 20 mL of ether followed by centrifugation and decanting of the supernatant. The solid peptide was dried briefly under vacuum, dissolved in 1.2 mL of 0.1 M sodium bicarbonate and stirred at room temperature for 6 hours. The mixture then was purified by HPLC using a 10% to 40% gradient of acetonitrile in 25 mM triethylammonium bicarbonate, pH 8.5 on a phenyl hexyl column. The purified peptide was characterized by LC-MS (ESI+, (M+3)/3: 1,144.37).

Example 21: Synthesis of Exemplary Imaging Agent

This Example describes the synthesis of the exemplary imaging agent [F5]Lys-His-Pro-Phe-His-Cha-Val-Ile-His-Lys(F5)-[OH] (SEQ ID NO:430) (Agent R24).

Combined pure fractions of product from Example 20 (1 µmol, in 4 mL of HPLC solvent) were combined with 0.4 mL of concentrated ammonium hydroxide. The solution was shielded from light and stirred at room temperature for 16 hours. The mixture was concentrated in vacuo and then was purified by HPLC using a 10% to 40% gradient of acetonitrile in 25 mM triethylammonium bicarbonate, pH 8.5 on a phenyl hexyl column. The purified peptide was characterized by LC-MS (ESI+, (M+3)/3: 1,112.37).

Example 22: Synthesis of Exemplary Imaging Agents

This Example describes the synthesis of the exemplary imaging agents denoted as Q65, Q66, Q91, Q92, Q93, Q94, R22, R51, R52, R53, R55, R56, R57, R58 and R59.

(Agent Q65)
(SEQ ID NO: 422)
Pentynoyl-Lys(F5)-Gly-Phe-Leu-Gly-βAla-Lys(F5)-

PEG20kDa

The peptide [pentynoyl]-Lys-Gly-Phe-Leu-Gly-βAla-Lys-[OH] (SEQ ID NO:459) (Tufts University Core Facility, 0.45 µmol) and fluorophore No. 3 from Table 2 (1.0 µmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 µL of 0.1 M sodium bicarbonate and purified by HPLC. The purified peptide was characterized by LC-MS.

The labeled peptide (25 µmol) then was combined with methoxy polyethylene glycol amine (mPEG-NH2, Laysan Bio, 10 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 µL water and purified by HPLC. The mPEG conjugated peptide was characterized by RP-18 HPLC and SEC HPLC.

(Agent Q66)
(SEQ ID NO: 423)
Pentynoyl-Lys(F6)-Gly-Phe-Leu-Gly-βAla-Lys(F6)-

PEG20kDa

The peptide [pentynoyl]-Lys-Gly-Phe-Leu-Gly-βAla-Lys-[OH] (SEQ ID NO:460) (Tufts University Core Facility, 0.45 µmol) and fluorophore No. 2 (Table 2, 1.0 µmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 µL of 0.1 M sodium bicarbonate and purified by HPLC. The purified peptide was characterized by LC-MS.

The labeled peptide (25 µmol) was then combined with methoxy polyethylene glycol amine (mPEG-NH2, Laysan Bio, 10 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 µL water and purified by HPLC. The mPEG conjugated peptide was characterized by RP-18 HPLC and SEC HPLC.

(Agent 91)
(SEQ ID NO: 424)
Pentynoyl-Lys(F5)-Pro-Leu-Gly-Val-Arg-Lys(F5)-

PEG20kDa

The peptide [pentynoyl]-Lys-Pro-Leu-Gly-Val-Arg-Lys (SEQ ID NO:461) (Tufts University Core Facility, 0.45

µmol) and fluorophore No. 3 from Table 2) (1.0 µmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 µL of 0.1 M sodium bicarbonate and purified by HPLC. The purified peptide was characterized by LC-MS.

The labeled peptide (25 µmol) was then combined with methoxy polyethylene glycol amine (mPEG-NH2, Laysan Bio, 10 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 µL water and purified by HPLC. The mPEG conjugated peptide was characterized by RP-18 HPLC and SEC HPLC.

```
(Agent Q92)
                                    (SEQ ID NO: 425)
[F5]-His-Gly-Pro-Arg-Lys(F5)-[PEG20kDa]
```

The peptide [H]-His-Gly-Pro-Arg-Lys-[OH] (SEQ ID NO:85) (Tufts University Core Facility, 0.45 µmol) and fluorophore 3 (Table 2, 1.0 µmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 µL of 0.1 M sodium bicarbonate and purified by HPLC on a 10 mm×250 mm 300 Å C18 column. The purified peptide was characterized by LC-MS.

The labeled peptide (25 µmol) was then combined with methoxy polyethylene glycol amine (mPEG-NH2, Laysan Bio, 10 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 h. The pegylated peptide was precipitated by addition of 1.5 mL of MTBE, isolated by centrifugation and decanting of the supernatant. The pegylated peptide was dried briefly under vacuum, dissolved in 350 µL water and purified by HPLC on a 21 mm×250 mm 300 Å C18 column. The mPEG conjugated peptide was characterized by RP-18 HPLC and SEC HPLC.

```
(Agent Q93)
                                    (SEQ ID NO: 426)
[F5]-His-Gly-Pro-Asn-Lys(F5)-His-Gly-Pro-Asn-βA-
[PEG20kDa]
```

The peptide [H]-His-Gly-Pro-Asn-Lys-His-Gly-Pro-Asn-[OH] (SEQ ID NO:462) (Tufts University Core Facility, 0.45 µmol) and fluorophore No. 3 from Table 2 (1.0 µmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 µL of 0.1 M sodium bicarbonate and purified by HPLC. The purified peptide was characterized by LC-MS.

The labeled peptide (25 µmol) was then combined with methoxy polyethylene glycol amine (mPEG-NH2, Laysan Bio, 10 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 h. The pegylated peptide was precipitated by addition of 1.5 mL of MTBE, isolated by centrifugation and decanting of the supernatant. The pegylated peptide was dried briefly under vacuum, dissolved in 350 µL water and purified by HPLC. The mPEG conjugated peptide was characterized by RP-18 HPLC and SEC HPLC.

```
(Agent Q94)
                                    (SEQ ID NO: 427)
[F5]-His-Gly-Pro-Asn-Lys(F5)-[PEG20kDa]
```

The peptide [H]-His-Gly-Pro-Asn-Lys-[OH] (SEQ ID NO:75) (Tufts University Core Facility, 0.45 µmol) and fluorophore No. 3 from Table 2 (1.0 µmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 µL of 0.1 M sodium bicarbonate and purified by HPLC. The purified peptide was characterized by LC-MS.

The labeled peptide (25 µmol) was then combined with methoxy polyethylene glycol amine (mPEG-NH2. Laysan Bio, 10 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 µL water and purified by HPLC. The mPEG conjugated peptide was characterized by RP-18 HPLC and SEC HPLC.

```
(Agent R22)
                                    (SEQ ID NO: 434)
[F6]-Gly-Pro-Leu-Gly-Val-Arg-Lys(F6)-[YPEG 2 x 20
kDa]
```

The peptide [H]-Gly-Pro-Leu-Gly-Val-Arg-Lys-[OH] (SEQ ID NO:463) (Tufts University Core Facility, 0.45 µmol) and fluorophore No. 2 of Table 2 (1.0 µmol) were combined in 100 μL of N,N-dimethylformamide (DMF) with 1 μL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 μL of 0.1 M sodium bicarbonate and purified by HPLC. The purified peptide was characterized by LC-MS.

The labeled peptide (25 μmol) was then combined Y-PEG-amine 2×20 k (Y-shape PEG Amine, MW 40000, JenKem USA, 40 mg, 0.50 μmol) and dissolved in 100 μL DMF with 1 μL NMM. 1-ethyl-3-(3-dimethylaminopropyl) carbodiimide hydrochloride (EDC, 0.25 mg, 1.3 μmol) and hydroxybenzotriazole (HOBT, 0.2 mg, 1.5 μmol) were added and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 μL water and purified by HPLC. The Y-PEG conjugated peptide was further purified by strong anion exchange chromatography. The Y-PEG conjugated peptide was characterized by RP-18 HPLC and SEC HPLC.

(Agent R51)

(SEQ ID NO: 435)
[mPEG-20kDa-Suc]-Lys(F6)-Gly-Phe-Leu-Gly-Lys(F6)-[NH₂]

The peptide [succinyl]-Lys-Gly-Phe-Leu-Gly-Lys-[NH₂] (SEQ ID NO:464) (Tufts University Core Facility, 0.45 μmol) and fluorophore No. 2 of Table 2 (1.0 μmol) were combined in 100 μL of N,N-dimethylformamide (DMF) with 1 μL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 μL of 0.1 M sodium bicarbonate and purified by HPLC. The purified peptide was characterized by LC-MS.

The labeled peptide (25 μmol) was then combined with methoxy polyethylene glycol amine (mPEG-NH2. Laysan Bio, 10 mg, 0.50 μmol) and dissolved in 100 μL DMF with 1 μL NMM. 1-ethyl-3-(3-dimethylaminopropyl) carbodiimide hydrochloride (EDC, 0.25 mg, 1.3 μmol) and hydroxybenzotriazole (HOBT, 0.2 mg, 1.5 μmol) were added and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 μL water and purified by HPLC. The mPEG conjugated peptide was characterized by RP-18 HPLC and SEC HPLC.

(Agent R52)

(SEQ ID NO: 436)
[dPEG-1kDa-Suc]-Lys(F6)-Gly-Phe-Leu-Gly-Lys(F6)-[NH₂]

The peptide [succinyl]-Lys-Gly-Phe-Leu-Gly-Lys-[NH₂] (SEQ ID NO:465) (Tufts University Core Facility, 0.45 μmol) and fluorophore No. 2 of Table 2 (1.0 μmol) were combined in 100 μL of N,N-dimethylformamide (DMF) with 1 μL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 μL of 0.1 M sodium bicarbonate and purified by HPLC. The purified peptide was characterized by LC-MS.

The labeled peptide (25 μmol) was then combined with Methyl-PEG₂₄-Amine (MA(PEG)24 Thermo Scientific, 0.54 mg, 0.50 μmol) and dissolved in 100 μL DMF with 1 μL NMM. 1-ethyl-3-(3-dimethylaminopropyl) carbodiimide hydrochloride (EDC, 0.25 mg, 1.3 μmol) and hydroxybenzotriazole (HOBT, 0.2 mg, 1.5 μmol) were added and the solution was placed on rotator shielded from light and rotated at room temperature for 16 hours. The discrete-pegylated peptide was precipitated by addition of 1.5 mL of MTBE, isolated by centrifugation and decanting of the supernatant. The discrete-pegylated peptide was dried briefly under vacuum, dissolved in 350 μL water and purified by HPLC. The dPEG conjugated peptide was characterized by RP-18 HPLC and LC-MS (Agent R53)

(SEQ ID NO: 437)
[dppa-Suc]-Lys(F6)-Gly-Phe-Leu-Gly-Lys(F6)-[NH₂]

The peptide [succinyl]-Lys-Gly-Phe-Leu-Gly-Lys-[NH₂] (SEQ ID NO:466) (Tufts University Core Facility, 0.45 μmol) and fluorophore 2 (Table 2, 1.0 μmol) were combined in 100 μL of N,N-dimethylformamide (DMF) with 1 μL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 μL of 0.1 M sodium bicarbonate and purified by HPLC on a 10 mm×250 mm 300 Å C18 column. The purified peptide was characterized by LC-MS.

The labeled peptide (25 μmol) was then combined with 3,3-diphenylpropylamine (dppa, 0.11 mg, 0.50 μmol) and dissolved in 100 μL DMF with 1 μL NMM. 1-ethyl-3-(3-dimethylaminopropyl) carbodiimide hydrochloride (EDC, 0.25 mg, 1.3 μmol) and hydroxybenzotriazole (HOBT, 0.2 mg, 1.5 μmol) were added and the solution was placed on rotator shielded from light and rotated at room temperature for 16 h. The dppa conjugated peptide was precipitated by addition of 1.5 mL of MTBE, isolated by centrifugation and decanting of the supernatant. The dppa conjugated peptide was dried briefly under vacuum, dissolved in 350 μL water and purified by HPLC. The dppa conjugated peptide was characterized by RP-18 HPLC and LC-MS.

(Agent R55)

(SEQ ID NO: 438)
[mPEG-20kDa-Suc]-Lys(F6)-Arg-Arg-Lys(F6)-[NH₂]

The peptide [succinyl]-Lys-Arg-Arg-Lys-[NH₂] (SEQ ID NO:467) (Tufts University Core Facility, 0.45 μmol) and fluorophore No. 2 of Table 2 (1.0 μmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 µL of 0.1 M sodium bicarbonate and purified by HPLC. The purified peptide was characterized by LC-MS.

The labeled peptide (25 µmol) was then combined with methoxy polyethylene glycol amine (mPEG-NH$_2$, Laysan Bio, 10 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 µL water and purified by HPLC. The mPEG conjugated peptide was characterized by RP-18 HPLC and SEC HPLC.

(Agent R56)

(SEQ ID NO: 439)

[dPEG-1kDa-Suc]-Lys(F6)-Arg-Arg-Lys(F6)-[NH$_2$]

The peptide [succinyl]-Lys-Arg-Arg-Lys-[NH$_2$] (SEQ ID NO:468) (Tufts University Core Facility, 0.45 µmol) and fluorophore No. 2 of Table 2 (1.0 µmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 µL of 0.1 M sodium bicarbonate and purified by HPLC. The purified peptide was characterized by LC-MS.

The labeled peptide (25 µmol) was then combined with Methyl-PEG$_{24}$-Amine (MA(PEG)24 Thermo Scientific, 0.54 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 hours. The discrete-pegylated peptide was precipitated by addition of 1.5 mL of MTBE, isolated by centrifugation and decanting of the supernatant. The discrete-pegylated peptide was dried briefly under vacuum, dissolved in 350 µL water and purified by HPLC. The dPEG conjugated peptide was characterized by RP-18 HPLC and LC-MS (Agent R57)

(SEQ ID NO: 440)

[dppa-Suc]-Lys(F6)-Arg-Arg-Lys(F6)-[NH$_2$]

The peptide [succinyl]-Lys-Arg-Arg-Lys-[NH$_2$] (SEQ ID NO:469) (Tufts University Core Facility, 0.45 µmol) and fluorophore No. 2 of Table 2 (1.0 µmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 µL of 0.1 M sodium bicarbonate and purified by HPLC. The purified peptide was characterized by LC-MS.

The labeled peptide (25 µmol) was then combined with 3,3-diphenylpropylamine (dppa, 0.11 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 hours. The dppa conjugated peptide was precipitated by addition of 1.5 mL of MTBE, isolated by centrifugation and decanting of the supernatant. The dppa conjugated peptide was dried briefly under vacuum, dissolved in 350 µL water and purified by HPLC. The dppa conjugated peptide was characterized by RP-18 HPLC and LC-MS.

(Agent 1458)

(SEQ ID NO: 441)

[mPEG-20kDa-Suc]-Lys(F6)-Ala-Arg-Arg-Lys(F6)-[NH$_2$]

The peptide [succinyl]-Lys-Ala-Arg-Arg-Lys-[NH$_2$] (SEQ ID NO:470) (Tufts University Core Facility, 0.45 µmol) and fluorophore No. 2 of Table 2 (1.0 µmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant. The solid peptide was dried briefly under vacuum, dissolved in 200 µL of 0.1 M sodium bicarbonate and purified by HPLC. The purified peptide was characterized by LC-MS.

The labeled peptide (25 µmol) was then combined with methoxy polyethylene glycol amine (mPEG-NH2, Laysan Bio, 10 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 µL water and purified by HPLC. The mPEG conjugated peptide was characterized by RP-18 HPLC and SEC HPLC.

(Agent R59)

(SEQ ID NO: 442)

[mPEG-20kDa-Suc]-Lys(F6)-Arg-Arg-Arg-Lys(F6)-[NH$_2$]

The peptide [succinyl]-Lys-Ala-Arg-Arg-Lys-[NH$_2$] (SEQ ID NO:471) (Tufts University Core Facility, 0.45 µmol) and fluorophore No. 2 of Table 2 (1.0 µmol) were combined in 100 µL of N,N-dimethylformamide (DMF) with 1 µL of N-methylmorpholine (NMM) and 0.25 mg of N,N-dimethylaminopyridine (DMAP). The solution was placed on a rotator shielded from light and rotated at room temperature for 16 hours. The labeled peptide was precipitated by addition of 1.5 mL of methyl-t-butyl ether (MTBE) followed by centrifugation and decanting of the supernatant.

The solid peptide was dried briefly under vacuum, dissolved in 200 µL of 0.1 M sodium bicarbonate and purified by HPLC. The purified peptide was characterized by LC-MS.

The labeled peptide (25 µmol) was then combined with methoxy polyethylene glycol amine (mPEG-NH2, Laysan Bio, 10 mg, 0.50 µmol) and dissolved in 100 µL DMF with 1 µL NMM. 1-ethyl-3-(3-dimethylaminopropyl) carbodiimide hydrochloride (EDC, 0.25 mg, 1.3 µmol) and hydroxybenzotriazole (HOBT, 0.2 mg, 1.5 µmol) were added and the solution was placed on rotator shielded from light and rotated at room temperature for 16 hours. The pegylated peptide was precipitated by addition of 1.5 mL of MTBE, isolated by centrifugation and decanting of the supernatant. The pegylated peptide was dried briefly under vacuum, dissolved in 350 µL water and purified by HPLC. The mPEG conjugated peptide was characterized by RP-18 HPLC and SEC HPLC.

Example 23: Tumor Imaging

NU/NU mice 6-8 weeks old (Charles River Laboratory. Wilmington, Mass.) were injected SC with 2×106 4T-1 or HT-29 cells bilaterally in each mammary fat pad. When tumors reached an approximate size of 3×3 mm (around 7 days after cell injection), mice were injected intravenously with 2-4 nmoles of each imaging agent (5 mice/probe and 2 mice/no probe as control) in 100 µL volume via tail vein. Imaging was conducted at 24 hours using a Fluorescence Molecular Tomography system (VisEn Medical, Woburn Mass.).

Figure 2:
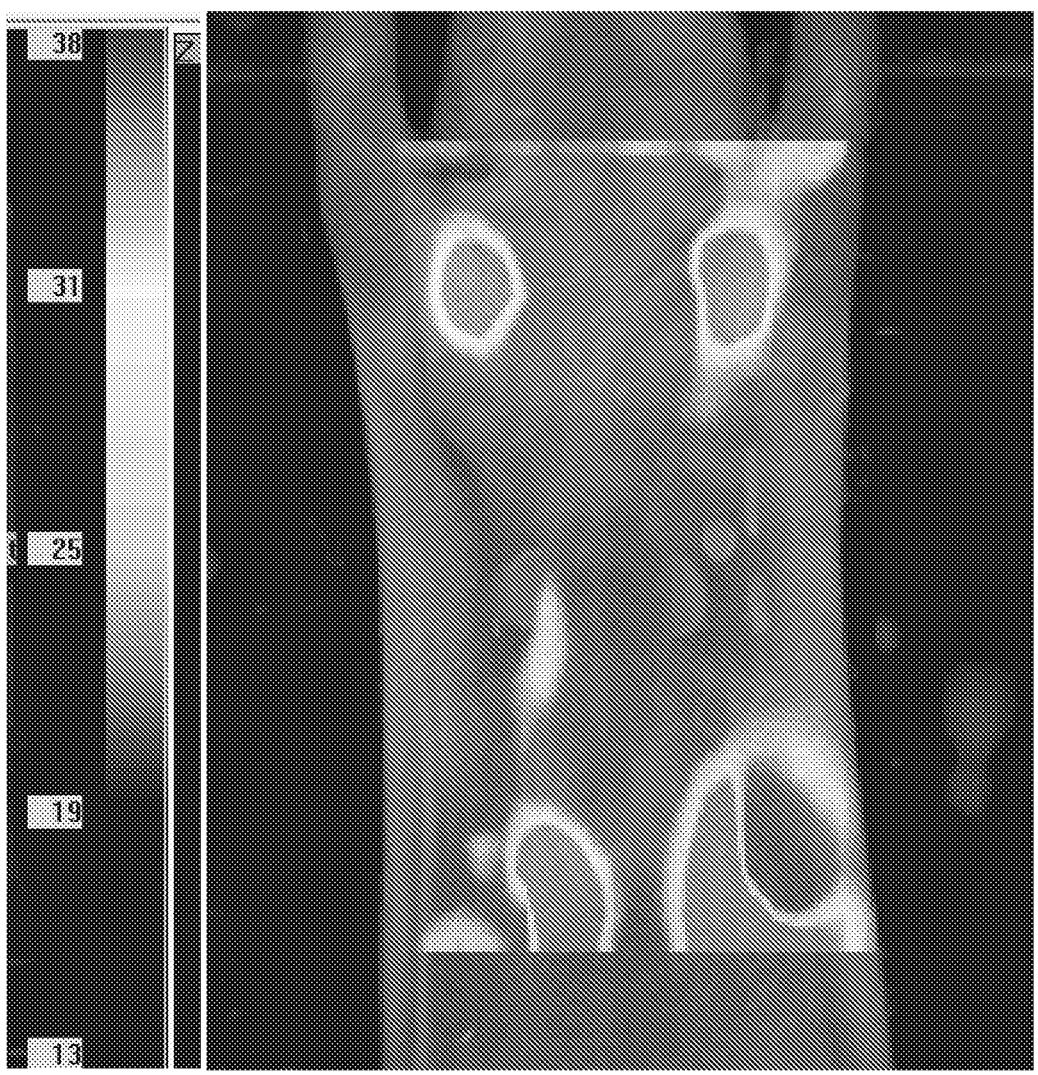
FIG. 2 depicts fluorescence tomography bilateral images of tumors at 6 hours after administration of the exemplary imaging agent Q65.

Pentynoyl-Lys(F5)-Gly-Phe-Leu-Gly-βAla-Lys(F5)-PEG20kDa (SEQ ID NO:422) (Agent Q65) was used to image tumors in vivo. FIG. 1 shows the planar image of bilateral 4T1 tumors 6 hours after administration of the agent. FIG. 2 shows a fluorescence molecular tomography bilateral image of 4T1 tumors 6 hours after administration of agent Q65.

Figure 3:
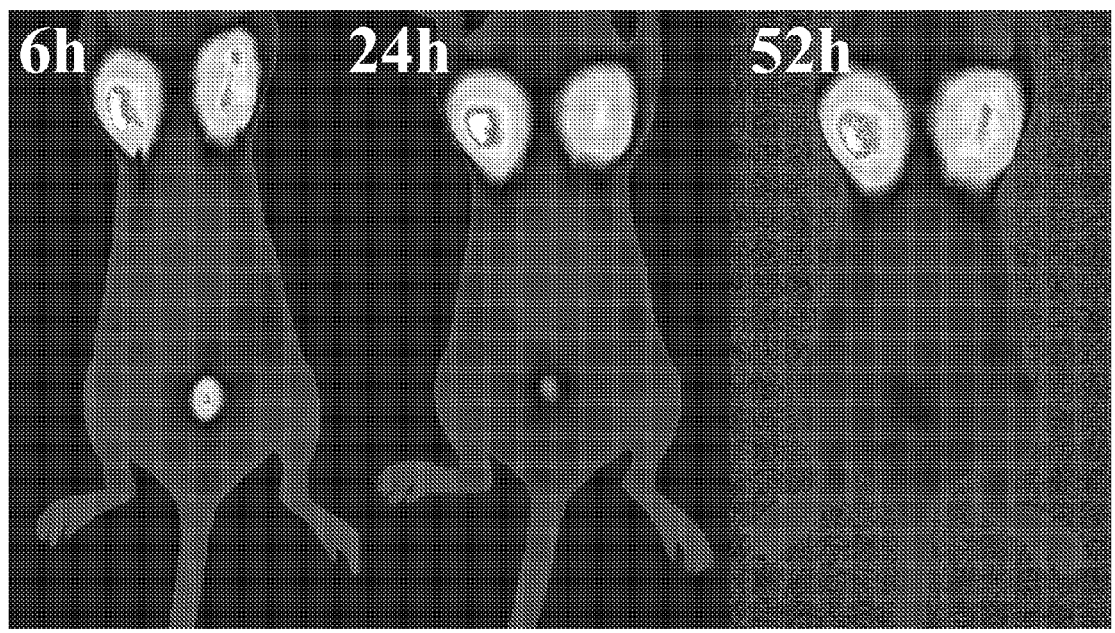
FIG. 3 depicts planar fluorescence reflectance images of 4T1 Xenograft tumors using an exemplary agent referred to as Q66.

Pentynoyl-Lys(F6)-Gly-Phe-Leu-Gly-βAla-Lys(F6)-PEG20kDa (SEQ ID NO:423) (Agent Q66) was also used to image tumors in vivo. FIG. 3 shows the image of the 4T1 tumors at 5, 24 and 52 hours after administration of agent Q66.

Figure 4:
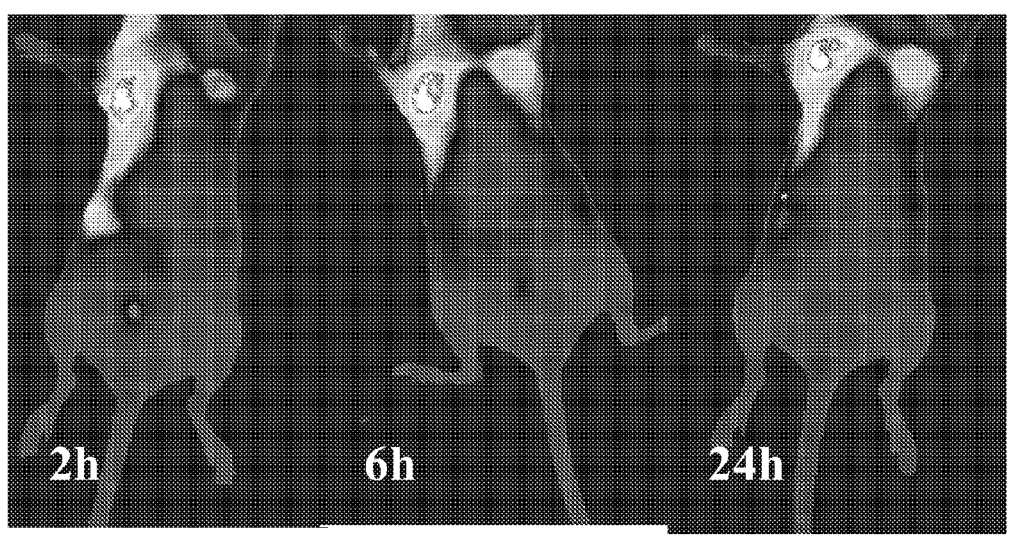
FIG. 4 depicts a planar fluorescence reflectance image of HT-29 Xenograft tumors using an exemplary agent referred to as Q91.

Pentynoyl-Lys(F5)-Pro-Leu-Gly-Val-Arg-Lys(F5)-PEG20kDa (SEQ ID NO:424) (Agent Q91) was also used to image tumors in vivo. FIG. 4 shows planar fluorescence reflectance images of HT-29 xenograft tumors at 2, 6 and 24 hour after administration of Agent Q91.

Example 24: Enzyme Activation Profile of Imaging Agent Q65

In this Example, the enzyme activation profile of imaging agent pentynoyl-Lys(F5)-Gly-Phe-Leu-Gly-βAla-Lys(F5)-PEG20kDa (SEQ ID NO:422) (Agent Q65) was characterized.

The reactions were performed with appropriate buffer at room temperature in a 96-well plate with a final assay volume of 250 µL and probe and enzyme concentrations of 0.5 µM and 0.05 µM, respectively. The buffer for Cathepsin B was 25 mM MES (pH 5.0), 1 mM DTT. Recombinant human Cathepsin B (R&D Systems) was activated in buffer of 25 mM MES (pH 5.0) and 5 mM DTT for 15 minutes at room temperature. Recombinant human Cathepsin L (R&D Systems) was activated in buffer of 50 mM MES (pH 6.0), 5 mM DTT, for 15 minutes on ice. Recombinant mouse Cathepsin Z (R&D Systems) was activated in buffer of 25 mM NaOAc (pH 3.0), 5 mM DTT for 5 minutes at room temperature. The buffer for plasmin (CalBiochem) and trypsin (Sigma) was PBS at pH 7.4.

The plate was incubated at room temperature and the activity monitored at 0, 1, 3, 5, and 24 hours with a Gemini (Molecular Devices) plate reader at excitation wavelength 663 nm, emission 690 nm, and cut off 665 nm. The activity was calculated as the fold of activation by comparing the fluorescence of the enzyme with probe to the fluorescence of probe alone.

The results are shown in FIG. 5, which show that the imaging agent Q65 is activated by Cathepsin B but not by plasmin, trypsin and Cathepsin Z.

Example 25: Enzyme Activation Profile of Imaging Agents Q92 and Q93

In this Example, the enzyme activation profile of imaging agents [F5]-His-Gly-Pro-Arg-Lys(F5)-[PEG20kDa] (SEQ ID NO:425) (Agent Q92) and [F5]-His-Gly-Pro-Asn-Lys(F5)-His-Gly-Pro-Asn-βA-[PEG20kDa] (SEQ ID NO:426) (Agent Q93) were characterized.

The reactions were performed with appropriate buffer at room temperature in a 96-well plate with a final assay volume of 250 µL and probe and enzyme concentrations of 0.5 µM and 0.05 µM respectively. The buffer for activated humanized rabbit Cathepsin K (Merck) was 50 mM MES (pH 5.0), 2.5 mM EDTA, 2.5 mM DTT. The buffer for Cathepsin B was 25 mM MES (pH 5.0), 1 mM DTT. The recombinant human Cathepsin B (R&D Systems) was activated in buffer of 25 mM MES (pH 5.0) and 5 mM DTT for 15 minutes at room temperature. The recombinant human Cathepsin L (R&D Systems) was activated in buffer of 50 mM MES (pH 6.0), 5 mM DTT, for 15 minutes on ice. The buffer for MMP-2 (BIOMOL) and MMP-9 (BIOMOL) was 50 mM Tris (pH 7.5), 10 mM CaCl2, 150 mM NaCl, and 0.05% Brij-35 detergent. The plate was incubated at room temperature and the activity was monitored at 0, 1, 3, 5, and 24 hours with a Gemini (Molecular Devices) plate reader at excitation wavelength 663 nm, emission 690 nm, and cut off 665 nm. The released fluorescent unit was determined by subtracting the fluorescence of the probe alone from the total fluorescence.

The results for Q92 are presented in FIG. 6A, and the results for Q93 are shown in FIG. 6B, which show that both Q92 and Q93 are activated primarily by Cathepsin K.

Example 26: Bone Imaging

BALB/c female mice 7 weeks old (Charles River Laboratory, Wilmington, Mass.) were subjected to ovariectomy or sham surgery to induce osteoporosis. After one to two weeks after surgery, the mice were injected intravenously with imaging agent [F5]-His-Gly-Pro-Asn-Lys(F5)-[PEG20kDa] (SEQ ID NO:427) (Agent Q94). Imaging was conducted at various time points using a Fluorescence Molecular Tomography system (VisEn Medical, Bedford, Mass.). The results are shown in FIG. 7.

FIG. 7A shows images of an ovariectomized mouse (OVX) compared to a control (sham) mouse at 4 and 24 hours post-injection. The quantitation of absolute fluorescence of osteoporosis for the sham and ovariectomized mice is shown in FIG. 7B. The increased probe signal detected in the tibia region appears to be due to increased Cathepsin K levels in bone loss induced by the ovariectomy procedure.

Example 27: Cardiovascular Disease Imaging

This Example show the imaging of cardiovascular disease using the imaging agent Pentynoyl-Lys(F5)-Gly-Phe-Leu-Gly-βAla-Lys(F5)-PEG20kDa) (SEQ ID NO:422) (Agent Q65).

Figure 8:
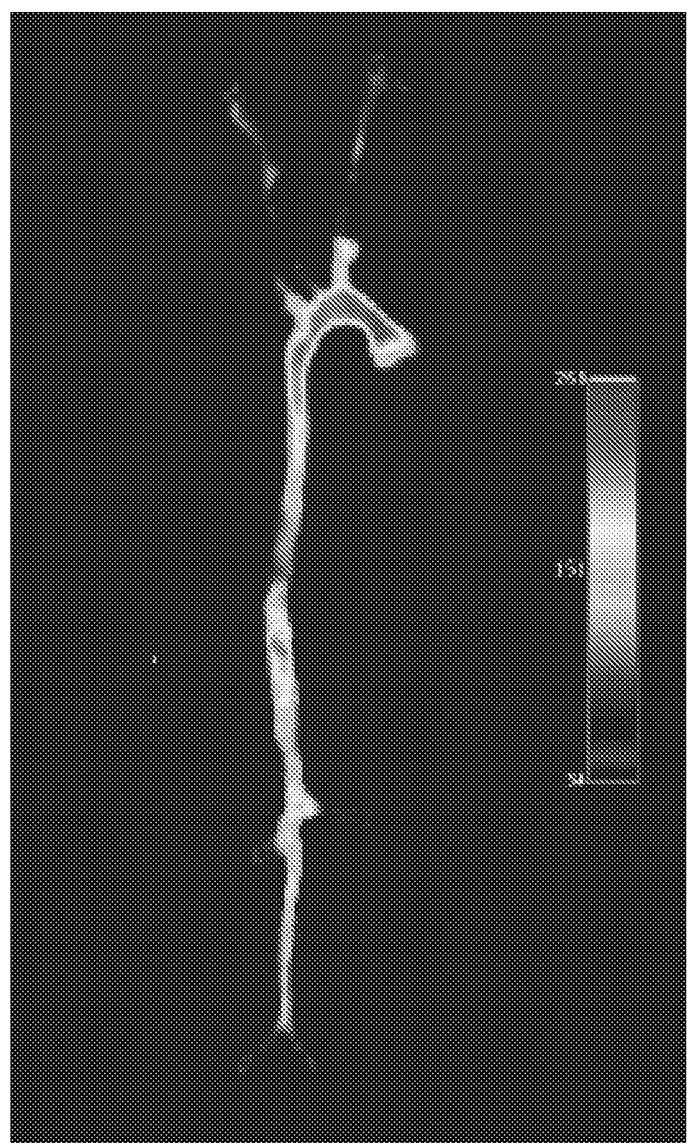
FIG. 8 depicts an image produced by fluorescence reflectance imaging of cardiovascular disease using the exemplary imaging agent Q65.

High cholesterol fed apoE−/− mice were injected with 2 nmol of imaging agent and in vivo imaging was performed with ex vivo fluorescence reflectance imaging. FIG. 8 shows fluorescence reflectance imaging of cardiovascular disease in inflamed atherosclerotic plaques of mice 24 hours post-injection of agent Q65. Fluorescence was detected in plaque-laden vascular sections in the aortic root, the arch and carotid arteries.

Example 28: Inflammation Imaging (Carrageenan Induced Paw Edema)

Figure 9:
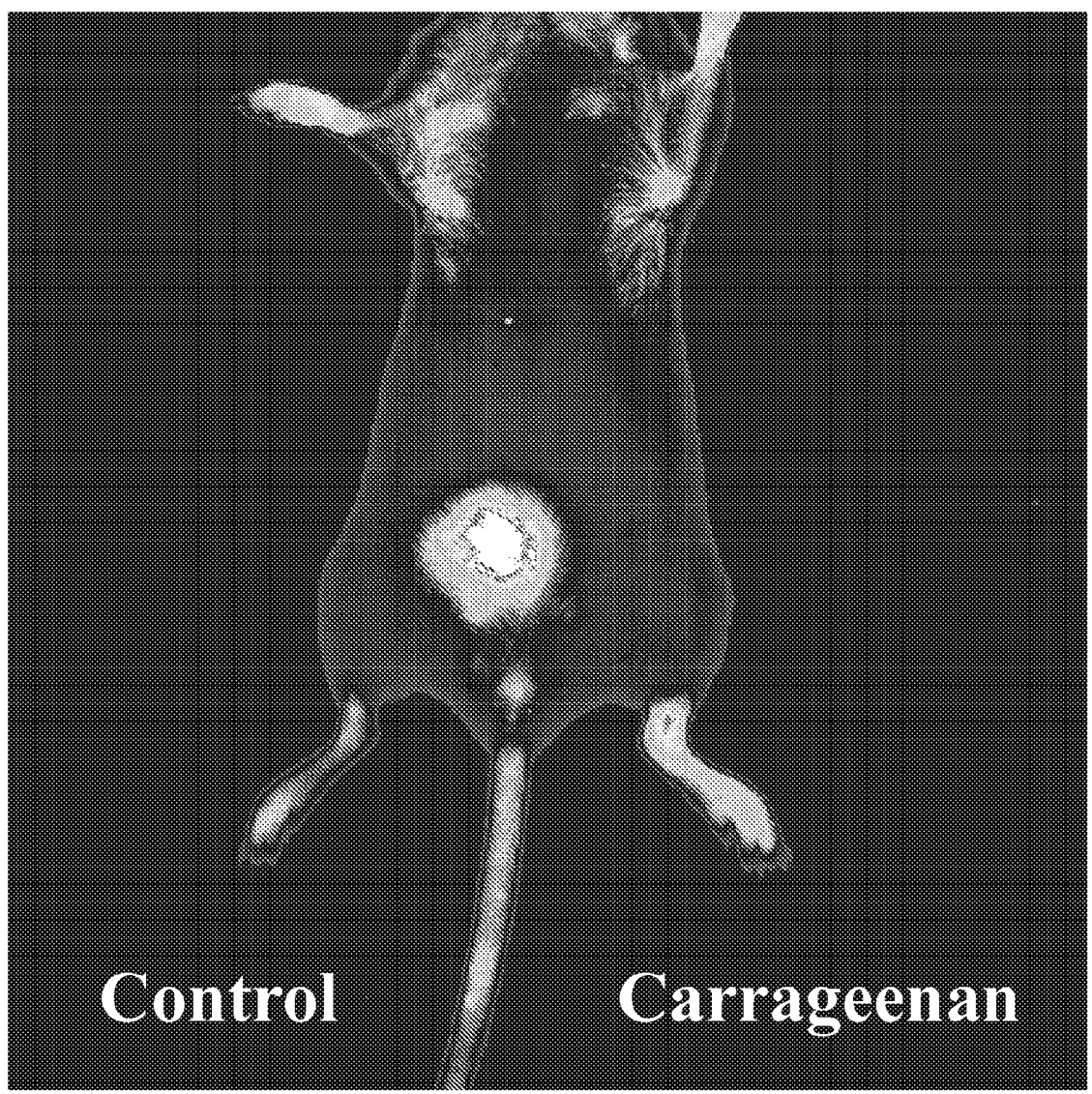
FIG. 9 depicts an image of a mouse following carrageenan induced paw edema using the exemplary imaging agent Q91.

This Example shows the imaging of inflammation in a mouse model. Briefly, BALB/c female mice 6-8 weeks old (Charles River Laboratory, Wilmington, Mass.) were injected subcutaneously with a 1% solution of carrageenan in PBS. After 1 minute post-injection, mice were injected the imaging agent Q91. Imaging was conducted at various time points using a Fluorescence Molecular Tomography system (VisEn Medical, Woburn Mass.). An image is shown in FIG. 9, which shows that significantly more fluorescence is observed in the mouse paw injected with carrageenan compared to the control paw (no injection).

Example 29: Enzyme Activation Profiles of Agents R20, R21, R23, R24, and R27

In this Example, the enzyme activity profiles of the agents ([F5]-Lys-His-Pro-Phe-His-Leu-Val-Ile-His-Lys(F5)-[OH]) (SEQ ID NO:401) (R20), ([F5]-Lys-His-Pro-Phe-His-Leu-Val-Ile-His-Lys(F5)-[NHmPEG20k]) (SEQ ID NO:428) (R21), ([F5]-Lys(Ac)-His-Pro-Phe-His-Leu-Val-Ile-His-Lys(F5)-[OH]) (SEQ ID NO:429) (R23), ([F5]-Lys-His-Pro-Phe-His-Cha-Val-Ile-His-Lys(F5)-[OH]) (SEQ ID NO:430) (R24), and ([F5]-Lys-His-Pro-Phe-His-Leu-Val-Ile-His-Lys(F5)-[NHmPEG5k]) (SEQ ID NO:433) (R27) were characterized.

The reactions were performed with appropriate buffer in a 96-well plate with a final assay volume of 250 µL and probe and enzyme concentrations of 1 µM and 100 nM, respectively. The reactions were incubated at 37 C for Renin and room temperature for the other proteases. The buffer for human neutrophil Cathepsin G (BIOMOL) was 100 mM Tris (pH 7.5), 1.6 M NaCl. The buffer for Cathepsin D (BIOMOL) was 100 mM Formic Acid (pH 3.3). The buffer for recombinant human neutrophil elastase (Innovative Research) was 100 mM Tris (pH 7.5). The buffer for plasmin (CalBiochem) and trypsin (Sigma) was 1× phosphate buffered saline (PBS) (pH 7.4). The buffer for recombinant human Renin (rhRenin) (Proteos) and recombinant rat Renin (rrRenin) (Proteos) was 50 mM MOPS (pH 7.4), 100 mM NaCl, with freshly prepared 0.002% tween-20. The plate was incubated at the appropriate temperature and the activity was monitored at 24 hours with a Gemini (Molecular Devices) plate reader at excitation wavelength 663 nm, emission 690 nm, and cut off 665 nm. The released fluorescent unit was determined by subtracting the fluorescence of the probe alone from the total fluorescence.

Figure 11A:
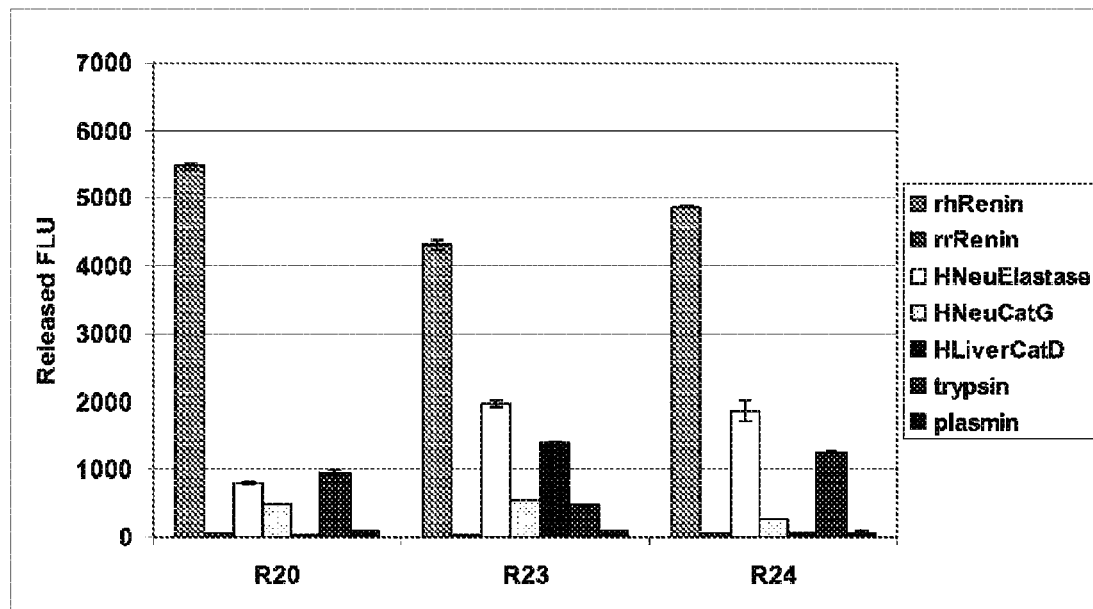
FIGS. 11A and 11B are bar charts showing the enzyme activation profile for exemplary imaging agents referred to as R20, R21, R23, R24, R26, and R27.
Figure 11B:
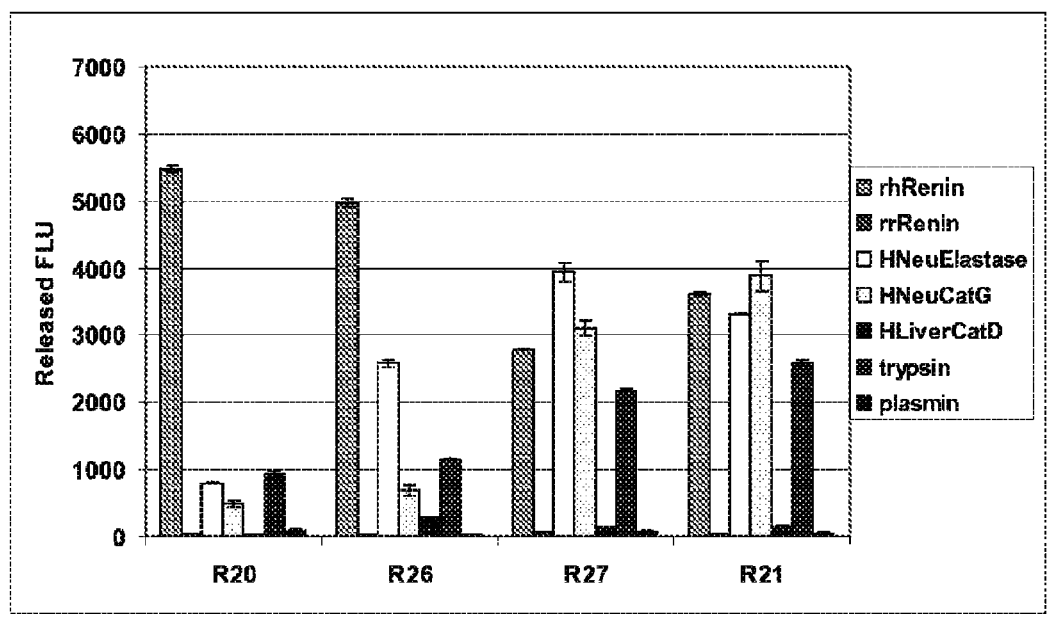

The results are shown in FIG. 11, which show that agents R20, R23, and R24 were activated primarily by recombinant human Renin. Agents R21 and R27 were activated by recombinant human rennin, human neutrophil elastase, human neutrophil cathepsin, and trypsin.

Example 30: Renal Imaging

This example shows the in vivo imaging of kidneys in mice on a control diet versus a low sodium diet.

C57BL6 mice (Jackson Laboratories) were fed a sodium deficient diet (0.02% Na) and water was replaced with a solution of amiloride (0.1 mg/5 mL or 5 mg/kg/day) for 2 days. Control C57BL6 mice were fed regular chow diet and water. Imaging agents [F5]-Lys-His-Pro-Phe-His-Leu-Val-Ile-His-Lys(F5)-[OH] (SEQ ID NO:401) (R20) and ([F5]-Lys-His-Pro-Phe-His-Leu-Val-Ile-His-Lys(F5)-[NHmPEG20k] (SEQ ID NO:428) (R21) were injected intravenously at different concentrations (0.2, 0.7, 2 and 4 nmol/mouse) following 2 days on a low salt diet. Imaging was conducted at 24 hrs using a Fluorescence Molecular Tomography system (VisEn Medical, Woburn Mass.).

The results are shown in FIG. 12, which demonstrate that for both imaging agents, the kidneys in the mice on the low sodium diet (FIGS. 12B and 12D) gave an increased signal relative to the kidneys in the mice on the control diet (FIGS. 12A and 12C).

Example 31: Enzyme Activation of Imaging Agent R22

In this Example, the enzyme activation profile of the imaging agent [F6]-Gly-Pro-Leu-Gly-Val-Arg-Lys(F6)-[YPEG 2×20 kDa] (SEQ ID NO:434) (R22) was characterized.

Activation by recombinant enzymes was carried out in 250 µL volumes set up in 96 well plates. MMPs were activated prior to the reaction according to manufacturers' protocols. Reactions contained 0.5 µM of R22 and 0.05 µM of activated enzyme in the appropriate activation buffer for each enzyme and incubated at room temperature for 24 hours. The plates were read at 24 hours with excitation/emission wavelength 740/770 nm. Fluorescence readings were performed using a Gemini (Molecular Devices) Fluorescence Plate Reader. Wells in which no enzyme was added were used as controls. Fold activation was obtained by dividing the enzyme-activated read-out (in relative fluorescence units) by its corresponding control well.

Figure 13:
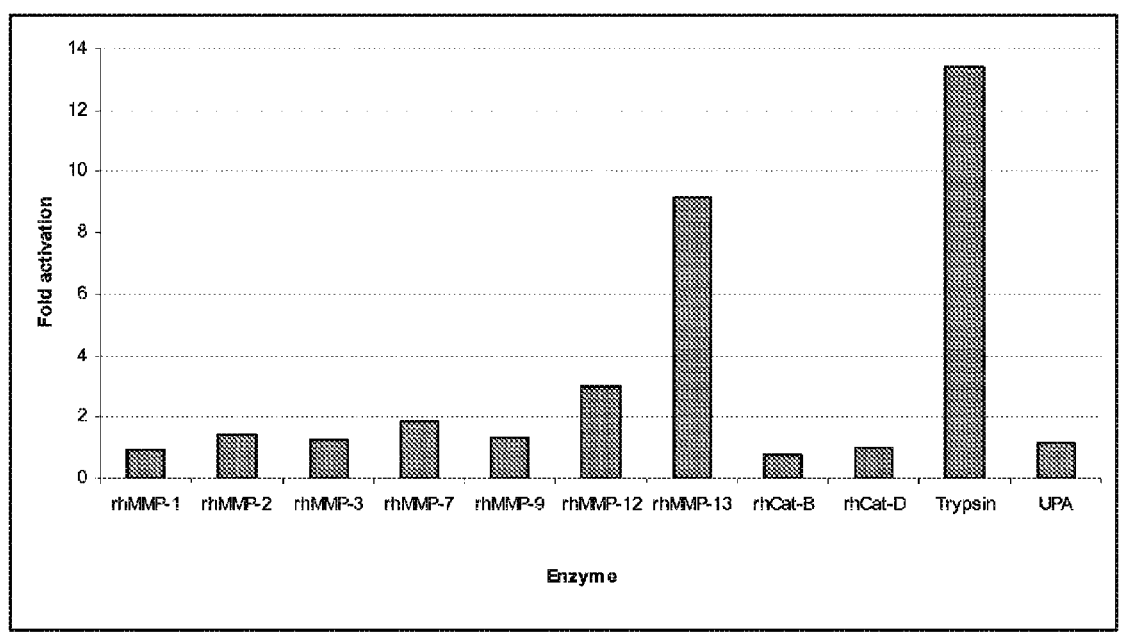
FIG. 13 is a bar chart showing an enzyme activation panel for an exemplary imaging agent referred to as R22.

An example of the activation of the R22 by MMPs and other proteases is shown in FIG. 13, which shows that R22 is activated primarily by recombinant human MMP-13 and trypsin.

Example 32: Tumor Imaging with Agent R22

This Example describes the imaging of tumors in vivo using imaging agent R22.

Male and female NU/NU Mice (Charles River Laboratories, Wilmington, Mass.), 6-8 weeks of age, were injected with tumor cells bilaterally in the first or second mammary fat pads (human colorectal cancer cell line HT-29: $3 \times 10^6$ cells/site). Once the tumors reached the desired volume, as measured with calipers (100 mm³) mice were injected intravenously with 2 nmoles of compound R22. Imaging was performed at 6 and 24 hours later using the Fluorescence Tomography System (FMT2500) (VisEn Medical, Bedford, Mass.). For in vivo imaging, mice were anesthetized by gas anesthesia (isoflurane/oxygen mixture), placed in the FMT2500 system imaging chamber one at a time and imaged using the reflectance and tomographic modes. Examples of imaging with the agent in the HT-29 tumor model are shown in FIG. 14.

The images taken by reflectance imaging after 6 hours are shown in FIG. 14A and after 24 hours in FIG. 14B. Tomographic images taken after 6 hours are shown in FIG. 14C and after 24 hours in FIG. 14D.

Example 33: Enzyme Activation Profiles of Agents R51, R52, R55, R56, R57, R58, and R59

This Example shows the enzymatic activation profiles for compounds ([mPEG-20kDa-Suc]-Lys(F6)-Gly-Phe-Leu-Gly-Lys(F6)-[NH$_2$]) (SEQ ID NO:435) (R51), ([dPEG-1kDa-Suc]-Lys(F6)-Gly-Phe-Leu-Gly-Lys(F6)-[NH$_2$]) (SEQ ID NO:436) (R52), ([dppa-Suc]-Lys(F6)-Gly-Phe-Leu-Gly-Lys(F6)-[NH$_2$]) (SEQ ID NO:437) (R53), ([mPEG-20kDa-Suc]-Lys(F6)-Arg-Arg-Lys(F6)-[NH$_2$]) (SEQ ID NO:438) (R55), ([dPEG-1kDa-Suc]-Lys(F6)-Arg-Arg-Lys(F6)-[NH$_2$]) (SEQ ID NO:439) (R56), ([dppa-Suc]-Lys(F6)-Arg-Arg-Lys(F6)-[NH$_2$]) (SEQ ID NO:440) (R57), ([mPEG-20kDa-Suc]-Lys(F6)-Ala-Arg-Arg-Lys(F6)-[NH$_2$]) (SEQ ID NO:441) (R58), and ([mPEG-20kDa-Suc]-Lys(F6)-Arg-Arg-Arg-Lys(F6)-[NH$_2$]) (SEQ ID NO:442) (R59).

Compounds at a concentration of 0.5 uM were incubated with Cathepsin B, Cathepsin K, Cathepsin L, or Cathepsin S at a concentration of 0.05 uM. The reaction buffers used were as follows: Cathepsin K—50 mM MES, pH 5.0, 2.5 mM EDTA, 2.5 mM DTT; Cathepsin B—25 mM MES, pH 5.0, 1 mM DTT; Cathepsin S—50 mM NaOAc, pH 4.5, 5 mM DTT, 0.25M NaCl; Cathepsin L—50 mM MES, pH 6, 5 mM DTT. The activity was monitored for 24 hours with a Gemini (Molecular Devices) fluorescence plate reader at excitation 663 nm and emission 690 nm with a cut off of 690 nm. FIG. 15 indicates that activation of imaging agent R51 by various Cathepsin proteases is greater than that of the other imaging agents.

Example 34: Imaging of Macrophage Activity in Atherosclerotic Plaque

Age-matched C57BL6 wild type female mice (Charles river Laboratories) were fed a normal diet and ApoE −/− knockout female mice (Jackson Laboratories) were fed a high cholesterol diet for 10-20 weeks. The mice were injected intravenously with compounds of formula R51 ([mPEG-20kDa-Suc]-Lys(F6)-Gly-Phe-Leu-Gly-Lys(F6)-[NH2]) (SEQ ID NO:435) and R55 ([mPEG-20kDa-Suc]-Lys(F6)-Arg-Arg-Lys(F6)-[NH2]) (SEQ ID NO:438). The mice were then imaged at 6 and 24 hours by fluorescence molecular tomography or fluorescence reflectance using an FMT2500 (VisEn Medical, Bedford, Mass.).

FIG. 16 shows an example of fluorescence imaging using compound R51. FIG. 16A shows fluorescence imaging of the aortic arch in ApoE −/− and wild type mice at 6 hours post-injection. FIG. 16B compares the quantified fluorescence of wild type versus ApoE −/− knockout mice at 6 hours post-injection with compound R51. FIG. 16C displays the reflectance imaging of the same mice with compound R51 at 6 hours. FIG. 16D compares the quantified fluorescence of wild type versus ApoE −/− knockout mice at 6 hours post-injection with compound R51. Imaging agent R51 produced a greater fluorescent signal in the ApoE knockout mice over controls demonstrating the use of R51 in imaging cardiovascular disease models.

Figure 17:
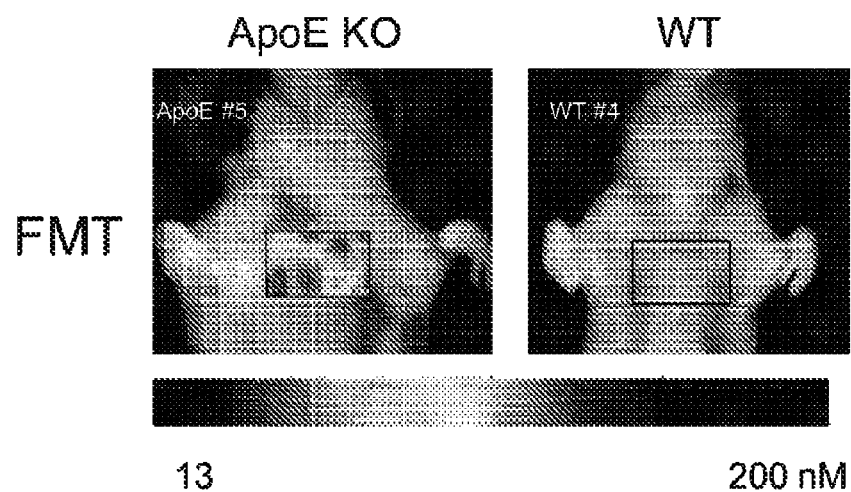
FIGS. 17A-B depict images and quantification of the images in ApoE −/− and control mice using the exemplary imaging agent R55.
Figure 17B:
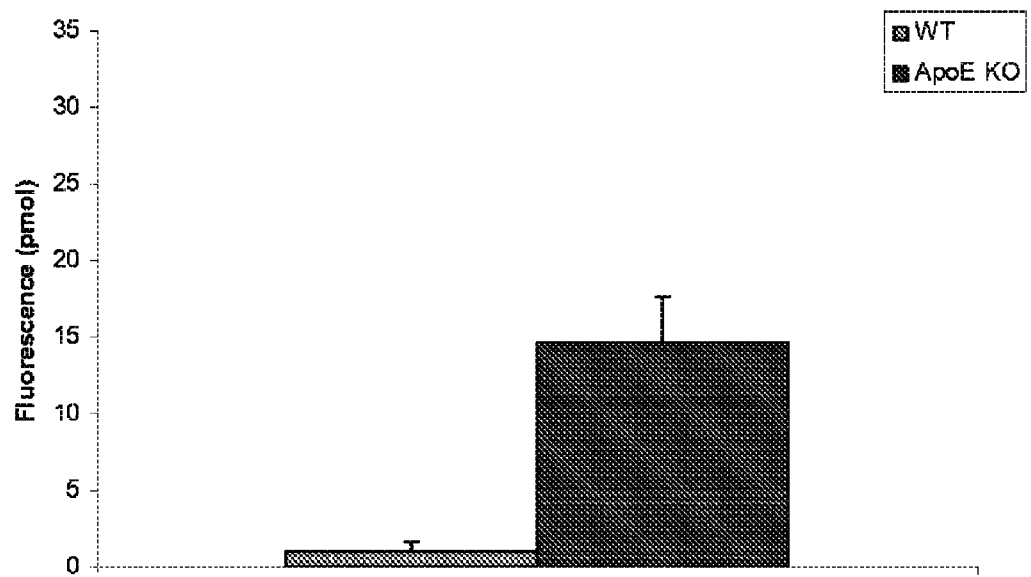

FIG. 17A shows an example of fluorescence molecular tomographic imaging of mice at 6 hours post-injection with R55. FIG. 17B compares the quantified fluorescence of wild type versus ApoE knockout mice at 6 hours post-injection with compound R55. Imaging agent R51 produced a greater fluorescent signal in the ApoE knockout mice over controls, demonstrating the use of R51 in imaging cardiovascular disease models.

INCORPORATION BY REFERENCE

All publications, patents, and patent applications cited herein are hereby expressly incorporated by reference in their entirety and for all purposes to the same extent as if each was so individually denoted.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. An intramolecularly-quenched imaging agent represented by Formula III:

$$[[ECO-G^g]_p-M]-K_n \quad (III)$$

wherein:

ECO is an enzymatically cleavable oligopeptide;

G is L-F;

F, independently, is selected from a fluorophore or quencher, wherein at least one F is a fluorophore;

L, independently for each occurrence, is selected from a linker moiety or a bond;

M is a biological modifier;

K is L-N;

N is a non-fluorescent reporter;

p is an integer from 1 to 4;

n is an integer from 0 to 3; and g, independently, for each occurrence, is an integer from 1 to 2, wherein the sum of each occurrence of g is no greater than 2; and wherein the fluorophore is represented by the following general Formula VII:

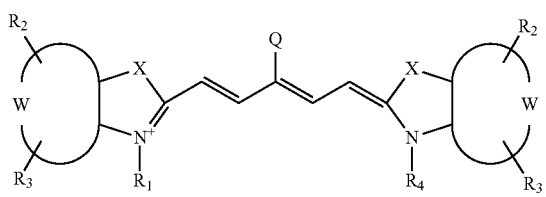

or a salt thereof, wherein:

X is independently, for each occurrence, selected from the group consisting of $C(CH_2Y_1)(CH_2Y_2)$, O, S, and Se;

$Y_1$ and $Y_2$ are independently selected from the group consisting of H and a $C_1$-$C_{20}$ aliphatic group optionally substituted with —OR*, $N(R*)_2$ or —SR*, wherein R* is H or alkyl;

W represents a benzo-condensed, a naphtho-condensed or a pyrido-condensed ring;

$R_1$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;

$R_2$ and $R_3$ independently are selected, for each occurrence, from the group consisting of H, carboxylate, carboxylic acid, carboxylic ester, amine, amide, sulfonamide, hydroxyl, alkoxyl, a sulphonic acid moiety and a sulphonate moiety;

$R_4$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6; and Q is selected from a group consisting of a heteroaryl ring substituted with a carboxyl group or 6-membered heteroaryl ring substituted with a carbonyl group.

2. An intramolecularly-quenched imaging agent represented by Formula III:

$$[[ECO-G^g]_p-M]-K_n \quad (III)$$

wherein:

ECO is an enzymatically cleavable oligopeptide;

G is L-F;

F, independently, is selected from a fluorophore or quencher, wherein at least one F is a fluorophore;

L, independently for each occurrence, is selected from a linker moiety or a bond;

M is a biological modifier;

K is L-N;

N is a non-fluorescent reporter;

p is an integer from 1 to 4;

n is an integer from 0 to 3; and g, independently, for each occurrence, is an integer from 1 to 2, wherein the sum of each occurrence of g is no greater than 2; and wherein the fluorophore is represented by the general Formula VIII:

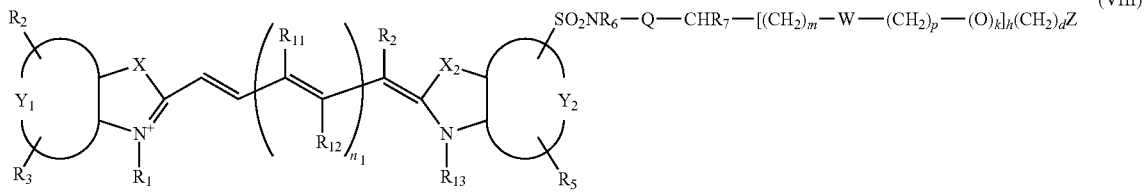

or a salt thereof, wherein:

$X_1$ and $X_2$ are independently selected, for each occurrence from the group consisting of $C(CH_2K_1)(CH_2K_2)$, O, S and Se;

$K_1$ and $K_2$ are independently selected from the group consisting of H, a $C_1$-$C_{20}$ aliphatic group optionally substituted with —OR*, N(R*)$_2$ or —SR*; or $K_1$ and $K_2$ together form part of a substituted or unsubstituted carbocyclic, or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently selected from the group consisting of H, F, Br, Cl, $C_1$-$C_6$ alkyl, $C_1$-$C_6$ alkoxy, aryloxy, a nitrogen-containing heterocyclic ring, a nitrogen-containing heteroaromatic ring, a sulfonate, an iminium ion, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;

$R_1$ and $R_{13}$ are $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is absent, or is selected from a carbonyl moiety or a substituted or unsubstituted $C_1$-$C_6$ alkyl group, wherein 0-2 of the methylene groups of the alkyl group can optionally be replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms;

$R_6$ is selected from the group consisting of H, a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or SR*, when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H, when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*; or $R_6$ and $R_7$, taken together form a 4-, 5-, 6- or 7-membered heterocyclic or non-aromatic heterocyclic ring optionally substituted with halogen, OR*, N(R*)$_2$ or SR*; or NR$_6$, Q and CHR$_7$ together form a substituted or unsubstituted heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of —SO$_2$NR$_6$-Q-CHR$_7$—, —O—, —COO—, and —CONH—;

h=0-70; k=0 or 1; d=0-12; m=0-12; p=0-12;

Z is a N, O or S nucleophile that forms a bond with the linker moiety or enzymatically cleavable oligopeptide; and each R* is independently H or C$_{1-20}$ alkyl.

3. The agent of claim 1, wherein L comprises a moiety selected from the group consisting of an amido bond, amino-polyethylene glycol-carboxylic acid, amino-polyethylene glycol azide, diaminoPEG, cysteic acid, glutamic acid, aminocaproic acid, ethylenediamine, propylenediamine, spermidine, spermine, hexanediamine, and a diamine-amino acid.

4. The agent of claim 1, wherein the biological modifier has a molecular weight from 10 kDa to 35 kDa.

5. The agent of claim 1, wherein the biological modifier is selected from the group consisting of polyethylene glycol, methoxypolyethylene glycol, branched polypropylene glycol, polypropylene glycol, a graft copolymer of poly-lysine and methoxypolyethyleneglycol, a fatty acid, a lipid, and a phospholipid.

6. The agent of claim 1, wherein the biological modifier is selected from the group consisting of an amino acid, a peptide, a carbohydrate, a dextran, a sulfonate, and a polysulfonate.

7. The agent of claim 1, wherein the biological modifier is covalently linked to the enzymatically cleavable peptide at a position that is not between two amino acids covalently linked to a fluorophore or a quencher.

8. The agent of claim 1, wherein the biological modifier is covalently linked to the enzymatically cleavable oligopeptide through an acyl moiety.

9. The agent of claim 1, wherein the biological modifier is covalently linked to the enzymatically cleavable oligopeptide by a 3+2 cycloaddition reaction between an azide moiety chemically linked to the biological modifier and an alkyne moiety chemically linked to an N-terminus of the enzymatically cleavable oligopeptide or wherein the biological modifier is chemically linked to the enzymatically cleavable oligopeptide by a 3+2 cycloaddition reaction between an alkyne moiety chemically linked to the biological modifier and an azide moiety covalently linked to the N-terminus of the enzymatically cleavable oligopeptide.

10. The agent of claim 1, wherein the biological modifier is covalently linked to the enzymatically cleavable oligopeptide by an amide coupling reaction between the biological modifier and the C-terminus of the enzymatically cleavable oligopeptide.

11. The agent of claim 1, wherein the enzymatically cleavable oligopeptide is cleavable by at least one enzyme selected from the group consisting of a cathepsin, a matrix metalloprotease, a peptidase, a carboxypeptidase, a glycosidase, a lipase, a phospholipase, a phosphatase, a phosphodiesterase, a sulfatase, a reductase, and a bacterial enzyme.

12. The agent of claim 1, wherein N is a radioisotopic metal selected from the group consisting of copper, gallium, indium, technetium, yttrium, and lutetium.

13. The agent of claim 1, wherein N is a therapeutic radiopharmaceutical.

* * * * *

UNITED STATES PATENT AND TRADEMARK OFFICE
CERTIFICATE OF CORRECTION

PATENT NO.       : 9,999,687 B2
APPLICATION NO.  : 15/250038
DATED            : June 19, 2018
INVENTOR(S)      : Rajopadhye et al.

Page 1 of 1

It is certified that error appears in the above-identified patent and that said Letters Patent is hereby corrected as shown below:

In Claim 2 at Column 325, Lines 38-48, replace:

"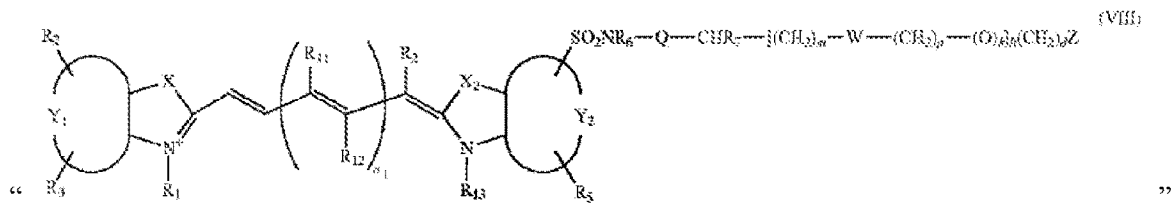"

With:

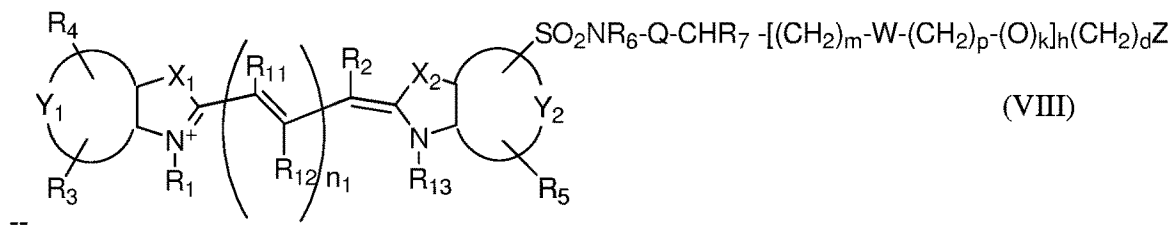

--.

Signed and Sealed this
Twentieth Day of November, 2018

Andrei Iancu
*Director of the United States Patent and Trademark Office*